US012735698B2

(12) United States Patent
Smith et al.

(10) Patent No.: US 12,735,698 B2
(45) **Date of Patent: *Sep. 15, 2026**

(54) MODIFIED GUIDE RNAS

(71) Applicant: Intellia Therapeutics, Inc., Cambridge, MA (US)

(72) Inventors: Amy Madison Rhoden Smith, Durham, NC (US); David V. Morrissey, Winchester, MA (US); Walter Strapps, Dedham, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/256,778

(22) Filed: Jul. 1, 2025

(65) Prior Publication Data

US 2026/0015611 A1 Jan. 15, 2026

Related U.S. Application Data

(60) Continuation of application No. 18/941,127, filed on Nov. 8, 2024, which is a division of application No. 17/900,960, filed on Sep. 1, 2022, now Pat. No. 12,173,284, which is a division of application No. 16/434,512, filed on Jun. 7, 2019, now Pat. No. 11,479,767, which is a continuation of application No. PCT/US2017/065306, filed on Dec. 8, 2017.

(60) Provisional application No. 62/431,756, filed on Dec. 8, 2016.

(51) Int. Cl.
*C12N 15/11* (2006.01)
*C12N 9/22* (2006.01)

(52) U.S. Cl.
CPC ................ *C12N 15/11* (2013.01); *C12N 9/22* (2013.01); *C12N 2310/20* (2017.05); *C12N 2310/315* (2013.01); *C12N 2310/344* (2013.01); *C12N 2310/346* (2013.01); *C12N 2320/51* (2013.01)

(58) Field of Classification Search
CPC ...... C12N 15/11; C12N 9/22; C12N 2310/20; C12N 2310/315; C12N 2310/344; C12N 2310/346; C12N 2320/51; C12N 15/113; C12N 2310/321; C12N 2310/322; C12N 2310/531; C12N 2310/3533; C12N 2310/3521; C12N 2310/3525; A61P 35/00; A61P 43/00
See application file for complete search history.

(56) References Cited

U.S. PATENT DOCUMENTS

| | | | | |
|---|---|---|---|---|
| 2015/0376586 A1 | 12/2015 | May et al. | | |
| 2015/0376628 A1 | 12/2015 | Schoenherr et al. | | |
| 2016/0024524 A1* | 1/2016 | Joung | ................ | C12N 15/1031 435/258.1 |

FOREIGN PATENT DOCUMENTS

| | | | | |
|---|---|---|---|---|
| WO | 2014093712 A1 | 6/2014 | | |
| WO | 2014152432 A2 | 9/2014 | | |
| WO | WO-2016089433 A1 * | 6/2016 | ........... | C12N 15/907 |
| WO | 2016164356 A1 | 10/2016 | | |
| WO | 2017004279 A2 | 1/2017 | | |
| WO | 2017068377 A1 | 4/2017 | | |
| WO | 2017136794 A1 | 8/2017 | | |
| WO | 2017173054 A1 | 10/2017 | | |
| WO | 2017185054 A1 | 10/2017 | | |

OTHER PUBLICATIONS

Briner et al., "Guide RNA Functional Modules Direct Cas9 Activity and Orthogonality", Molecular Cell 56:333-339, 2014.
Finn, J. D. et al. "A Single Administration of CRISPR/Cas9 Lipid Nanoparticles Achieves Robust and Persistent In Vivi Genome Editing" Cell Reports 22, 2227-2235 (2018).
Hendel, Ayal et al. "Chemically modified guide RNAs enhance CRISPR-Cas genome editing in human primary cells." Nature biotechnology vol. 33,9 (2015): 985-989.
International Search Report and Written Opinion for PCT/US2017/065306 dated Apr. 17, 2018.
Latorre, A. et al. "Modified RNAs in CRISPR/Cas9: An Old Trick Works Again" Angew. Chem. Int. Ed. 2016, 55, 3548-3550.
Iizuka et al. "Growth Inhibition of Head and Neck Squamous Cell Carcinoma Cells by sgRNA Targeting the Cyclin D1 mRNA Based on TRUE Gene Silencing" PLoS One, 9(12): e114121, 2014, 1-19.
Ran, F Ann et al. "In vivo genome editing using *Staphylococcus aureus* Cas9." Nature vol. 520,7546 (2015): 186-91.
Ryan, et al. "Improving CRISPR-Cas specificity with chemical modifications in single-guide RNAs" Nucleic Acids Research, 2018, 46(2):792-803 (published online Dec. 4, 2017).
Wang Ming et al., "Efficient delivery of genome-editing proteins using bioreducible lipid nanoparticles", Proceedings National Academy of Sciences PNAS, vol. 113, No. 11, Feb. 29, 2016, p. 2868-2873.
Yin Hao et al., "Therapeutic genome editing by combined viral and non-viral delivery of CRISPR system components in vivo", Nature Biotechnology, vol. 34, No. 3, Feb. 1, 2016, p. 328-333.
Yu, Xin et al. "Improved delivery of Cas9 protein/gRNA complexes using lipofectamine CRISPRMAX." Biotechnology Letters vol. 38,6 (2016): 919-29.

* cited by examiner

*Primary Examiner* — Neil P Hammell
*Assistant Examiner* — Kyle T Rega
(74) *Attorney, Agent, or Firm* — McNeill PLLC

(57) ABSTRACT

This disclosure relates to modified single and dual guide RNAs having improved in vitro and in vivo activity in gene editing methods.

22 Claims, 41 Drawing Sheets

Specification includes a Sequence Listing.

25 nM

| | TR000110 | TR000111 | TR000112 | TR000113 | TR000114 | TR000115 | TR000116 | TR000117 | TR000118 | TR000119 | TR000121 | TR000002 |
|---|---|---|---|---|---|---|---|---|---|---|---|---|
| CR003393 | 54.1 ± 5 | 61.2 ± 3.1 | 56.7 ± 5 | 55.9 ± 4 | 53.8 ± 10.7 | 56.3 ± 10 | 52.7 ± 5.8 | 55.5 ± 7 | 40.7 ± 12.9 | 48.5 ± 8.1 | 51.3 ± 11.4 | |
| CR003394 | 57.7 ± 4.7 | 61.5 ± 8.2 | 64.8 ± 6.4 | 65.4 ± 8.9 | 60.1 ± 2.5 | 61.6 ± 4.6 | 57.3 ± 7.2 | 57.8 ± 8.3 | 38.6 ± 7.9 | 50.9 ± 10.3 | 54.8 ± 8.9 | |
| CR003395 | 52.4 ± 2.4 | 62.8 ± 6.8 | 61.1 ± 7.2 | 62.8 ± 11.1 | 55.9 ± 7.6 | 57 ± 4.9 | 53.4 ± 7.1 | 52.5 ± 8.1 | 38.2 ± 7.5 | 49.7 ± 14.4 | 53.1 ± 11.7 | |
| CR003396 | 56 ± 3.9 | 56.4 ± 7.6 | 58.7 ± 7.3 | 58.1 ± 7.3 | 54.7 ± 4.9 | 58.8 ± 5 | 48.9 ± 2.8 | 52.5 ± 9.7 | 34.3 ± 6 | 48.3 ± 10.3 | 52.4 ± 9.5 | |
| CR003398 | 50.8 ± 10.2 | 56.2 ± 8.2 | 62.5 ± 6.9 | 59.7 ± 8.9 | 56.3 ± 3.4 | 61.2 ± 5 | 53 ± 7.1 | 53.8 ± 9.2 | 29.4 ± 9.3 | 52.2 ± 12.2 | 51.9 ± 15.6 | |
| CR003402 | 42.7 ± 4.5 | 53.3 ± 5.4 | 56.9 ± 11 | 57.4 ± 12.1 | 52.8 ± 9.3 | 55.1 ± 8.5 | 46.1 ± 8.4 | 50.5 ± 8.8 | 17.7 ± 6.7 | 45.2 ± 12 | 52.8 ± 11.3 | |
| CR003403 | 45.8 ± 9.9 | 52.7 ± 8.6 | 59.7 ± 13.9 | 54.8 ± 13.7 | 47.2 ± 12.1 | 50.9 ± 8.4 | 43.4 ± 10.3 | 47 ± 13 | 10.5 ± 5.9 | 44.5 ± 15.2 | 46 ± 19.3 | |
| CR000686 | | | | | | | | | | | | 34.5 ± 6.4 |

2.5 nM

| | TR000110 | TR000111 | TR000112 | TR000113 | TR000114 | TR000115 | TR000116 | TR000117 | TR000118 | TR000119 | TR000121 | TR000002 |
|---|---|---|---|---|---|---|---|---|---|---|---|---|
| CR003393 | 41.8 ± 6.2 | 50.4 ± 3.2 | 40.2 ± 4.7 | 43.4 ± 2 | 40.1 ± 4.8 | 43.1 ± 3.9 | 39.1 ± 4.2 | 43 ± 6 | 15.6 ± 3.1 | 34.9 ± 11.6 | 38.6 ± 2.2 | |
| CR003394 | 45.4 ± 4.7 | 49.6 ± 7.9 | 43.9 ± 6.6 | 46.7 ± 5.6 | 40.4 ± 7.5 | 47.2 ± 6.9 | 46.8 ± 3.1 | 43.9 ± 2.4 | 13.7 ± 1.6 | 28.9 ± 4.3 | 35.9 ± 6.2 | |
| CR003395 | 39 ± 10 | 56 ± 5.1 | 42.2 ± 3.5 | 48.2 ± 3.2 | 36 ± 2.8 | 47.4 ± 7.3 | 44.4 ± 5.9 | 41.6 ± 7 | 12 ± 1.4 | 25.8 ± 1 | 31.4 ± 1.8 | |
| CR003396 | 34.8 ± 2.3 | 46.5 ± 0.4 | 42 ± 4.9 | 42.4 ± 1.8 | 32 ± 4 | 44.4 ± 5.5 | 41.1 ± 7.7 | 40.5 ± 5.1 | 20.7 ± 1.2 | 26 ± 1.2 | 42.4 ± 8.9 | |
| CR003398 | 33.6 ± 3.3 | 47 ± 6.8 | 41.9 ± 2.6 | 41.9 ± 1.1 | 37.1 ± 4.1 | 43.2 ± 9.4 | 40.1 ± 3.9 | 42.9 ± 3.6 | 1.4 ± 0.1 | 34.2 ± 2 | 40.7 ± 7.4 | |
| CR003402 | 31.2 ± 4.7 | 46.4 ± 5 | 38.5 ± 2.8 | 40.7 ± 3.5 | 29.9 ± 1.1 | 42.4 ± 6.6 | 31.7 ± 2.9 | 32.8 ± 4.6 | 7 ± 0.8 | 31.3 ± 2.1 | 46.8 ± 3.8 | |
| CR003403 | 28 ± 4.3 | 38.3 ± 3.3 | 37.5 ± 4.4 | 36.4 ± 2.7 | 31.4 ± 4.6 | 34.6 ± 3.7 | 32.9 ± 4 | 35.8 ± 4.2 | 1.4 ± 0.1 | 34.6 ± 6.1 | 40.7 ± 6.6 | |
| CR000686 | | | | | | | | | | | | 21.7 ± 4.9 |

| | TR000127 | TR000128 | TR000130 | TR000134 | TR000135 | TR000136 | TR000137 | TR000138 | TR000139 | TR000142 | TR000143 | TR000002 |
|---|---|---|---|---|---|---|---|---|---|---|---|---|
| CR003723 | 18 ± 13.8 | 22.8 ± 4.1 | 24 ± 2.6 | 26.9 ± 2.8 | 20.8 ± 5 | 22.2 ± 5.7 | 26.7 ± 5 | 23.6 ± 4.1 | 13.7 ± 2.4 | 22.3 ± 4.4 | 10.8 ± 2.2 | 18.5 ± 1.5 |
| CR003725 | 28.4 ± 1.2 | 29.2 ± 4.2 | 27.9 ± 1.3 | 30.6 ± 3.4 | 26.1 ± 3.8 | 25.9 ± 4.4 | 30 ± 3 | 26.9 ± 2 | 18.5 ± 2.2 | 25.1 ± 0.9 | 23.1 ± 1.7 | |
| CR003726 | 30.4 ± 1.1 | 31.3 ± 3.2 | 30.6 ± 2.9 | 32 ± 2.2 | 29.8 ± 2.5 | 29.9 ± 2.8 | 32.3 ± 1 | 28.7 ± 2.2 | 20.9 ± 2.4 | 27 ± 1.4 | 23.6 ± 2.3 | 24.9 ± 1.1 |
| CR003727 | 31.6 ± 2.1 | 27 ± 2.7 | 29.6 ± 0.8 | 32.1 ± 1.3 | 26.7 ± 1.2 | 27.2 ± 5.2 | 31 ± 2 | 28.1 ± 0.7 | 19.2 ± 0.7 | 26.7 ± 2.1 | 22.5 ± 1.2 | 25.6 ± 3 |
| CR003728 | 34.6 ± 2.4 | 2.4 ± 0.1 | 34.9 ± 2.6 | 37.7 ± 3.1 | 33.1 ± 2.1 | 33.1 ± 4 | 35.4 ± 0.9 | 32.4 ± 2.9 | 25.8 ± 4.8 | 30.7 ± 2.7 | 28.2 ± 2.2 | 28.6 ± 0.7 |
| CR003729 | 34.8 ± 0.9 | 32.3 ± 1.5 | 33.8 ± 1.1 | 34.8 ± 2.5 | 29.8 ± 1.8 | 31.5 ± 3.6 | 32.6 ± 1.7 | 31 ± 1.9 | 25.4 ± 3.7 | 28.6 ± 0.5 | 25.6 ± 1.1 | 27.8 ± 0.6 |
| CR003734 | 27.5 ± 0.3 | 21.5 ± 1.5 | 29.8 ± 1.6 | 29.5 ± 1.6 | 13.7 ± 2.1 | 14.6 ± 1.2 | 31 ± 2.4 | 28 ± 2.5 | 7 ± 1.1 | 25.5 ± 1.3 | 3.4 ± 0.1 | 22.7 ± 2.8 |
| CR000686 | 23 ± 2.8 | 22.4 ± 3.9 | 23.6 ± 6.2 | 26.4 ± 1 | 22.2 ± 2 | 19.5 ± 1.1 | 24.6 ± 3 | 27.4 ± 2.6 | 12.2 ± 1.7 | 22.9 ± 1.8 | 20.2 ± 1.1 | 22.6 ± 3 |

1 nM

| | TR000127 | TR000128 | TR000130 | TR000134 | TR000135 | TR000136 | TR000137 | TR000138 | TR000139 | TR000142 | TR000143 | TR000002 |
|---|---|---|---|---|---|---|---|---|---|---|---|---|
| CR003723 | 18.3 ± 14.1 | 16 ± 12.1 | 25.3 ± 0.8 | 22.5 ± 3.4 | 14.3 ± 10.6 | 17.5 ± 2 | 23.1 ± 3.8 | 21 ± 1.4 | 8.8 ± 1.4 | 18.3 ± 0.7 | 8.3 ± 1.5 | 14.6 ± 0.4 |
| CR003725 | 26.9 ± 1.8 | 25.1 ± 4.1 | 25 ± 2.7 | 24.8 ± 2.3 | 23.1 ± 2.8 | 16.2 ± 12.1 | 17.3 ± 13.1 | 22.5 ± 1 | 15.2 ± 1.7 | 22.7 ± 1.5 | 19.7 ± 3.1 | |
| CR003726 | 16.8 ± 12.9 | 26.4 ± 2 | 23.6 ± 2.6 | 25.2 ± 1.5 | 22.7 ± 3.4 | 20.7 ± 1.5 | 26.6 ± 1.4 | 20.4 ± 0.9 | 13.3 ± 0.3 | 21.6 ± 1.5 | 18.6 ± 0.5 | 17 ± 1 |
| CR003727 | 24.1 ± 3.1 | 20.3 ± 1.4 | 21 ± 1.3 | 23.6 ± 2.6 | 19.7 ± 1.7 | 20.3 ± 1.4 | 15.3 ± 11.3 | 20.2 ± 1.5 | 11.7 ± 1.7 | 20.7 ± 0.7 | 15.1 ± 0.8 | 19.7 ± 4.2 |
| CR003728 | 26.9 ± 0.8 | 2.4 ± 0.1 | 28.2 ± 2.4 | 27.9 ± 0.6 | 26.4 ± 3.2 | 22.9 ± 1.2 | 26.4 ± 1.9 | 24.8 ± 0.5 | 18.8 ± 1.8 | 23.3 ± 1.4 | 20.3 ± 1.1 | 23.4 ± 3.7 |
| CR003729 | 26.3 ± 2.5 | 30.5 ± 4.6 | 28.3 ± 2.7 | 28.6 ± 2 | 25.3 ± 3.1 | 24.6 ± 1.6 | 25 ± 0.3 | 23.7 ± 0.6 | 17.1 ± 1.7 | 21.9 ± 0.5 | 21 ± 2 | 22 ± 2 |
| CR003734 | 18.9 ± 5.3 | 15.2 ± 3 | 21.4 ± 1.7 | 20.1 ± 0.1 | 8.5 ± 1.7 | 7.4 ± 0.9 | 20.4 ± 0.8 | 20.4 ± 1.4 | 3 ± 0.1 | 19.3 ± 0.8 | 2.5 ± 0.3 | 17.3 ± 2.1 |
| CR000686 | 16.2 ± 1 | 17.3 ± 3.4 | 18.3 ± 3.3 | 20.5 ± 5 | 15.4 ± 1.2 | 14.8 ± 3 | 18.9 ± 3.6 | 20.1 ± 1.7 | 7.9 ± 2.3 | 17.5 ± 3.3 | 15.4 ± 1 | 14.1 ± 1.6 |

FIG. 9

| Guide | Average % Editing | Std. Dev. |
|---|---|---|
| *G209 Lot#2* | *44.2* | *4.1* |
| *G209 Lot#4* | *47.5* | *5.3* |
| *G262* | *52.2* | *4.7* |
| *G263* | *60.9* | *3.8* |
| *G264* | *48.9* | *5.8* |
| *G265* | *44.7* | *11.1* |
| *G266* | *47.0* | *7.8* |
| *G267* | *58.9* | *3.1* |

* = Phosphorothioate

End-modified sgRNA
G000209

* = Phosphorothioate

Highly modified sgRNA
G000267

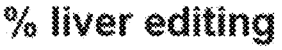
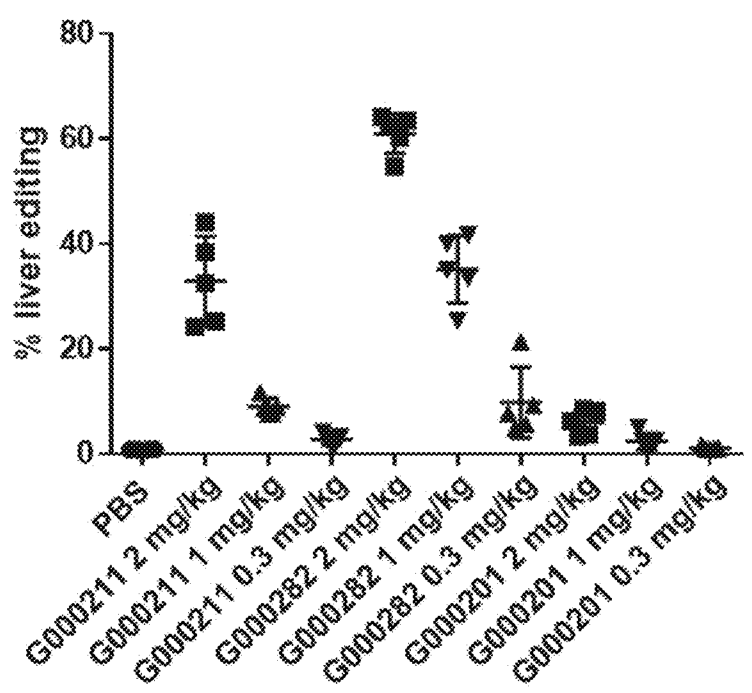
*FIG. 17A*
| | Average % Editing | Std. Dev. |
|---|---|---|
| PBS | 0.8370155 | 0.03184162 |
| G211 2 mg/kg | 32.89082 | 8.520595 |
| G211 1 mg/kg | 9.024511 | 1.640143 |
| G211 0.3 mg/kg | 2.762495 | 0.9668095 |
| G282 2 mg/kg | 60.99886 | 3.792423 |
| G282 1 mg/kg | 35.13641 | 6.434229 |
| G282 0.3 mg/kg | 9.812781 | 6.713302 |
| G284 2 mg/kg | 6.007987 | 2.434861 |
| G284 1 mg/kg | 2.413099 | 1.540902 |
| G284 0.3 mg/kg | 1.130903 | 0.3189707 |
*FIG. 17B*

| | Average % TTR Reduction | Std. Dev. |
|---|---|---|
| PBS | 100.000 | 20.31276 |
| G211 2 mg/kg | 46.73565 | 14.33137 |
| G211 1 mg/kg | 62.66805 | 10.30656 |
| G211 0.3 mg/kg | 68.51203 | 10.40399 |
| G282 2 mg/kg | 9.890765 | 5.288372 |
| G282 1 mg/kg | 39.58118 | 12.35095 |
| G282 0.3 mg/kg | 64.59702 | 10.51861 |
| G284 2 mg/kg | 67.28742 | 10.217 |
| G284 1 mg/kg | 37.76873 | 19.77835 |
| G284 0.3 mg/kg | 30.4822 | 6.612638 |

| Guide | Dose | Average % Editing |
|---|---|---|
| *PBS* | | *2.38* |
| *G269* | *2 MPK* | *28.57* |
| | *1 MPK* | *16.21* |
| | *0.3 MPK* | *3.54* |
| *G283* | *2 MPK* | *56.32* |
| | *1 MPK* | *39.73* |
| | *0.3 MPK* | *8.08* |
| *G285* | *2 MPK* | *4.80* |
| | *1 MPK* | *2.90* |
| | *0.3 MPK* | *2.44* |

dgRNA
CR000686 + TR000002

| Group | Average % Editing | Std. Dev. |
|---|---|---|
| PBS | 0 | 0 |
| G332 1mpk | 34.14 | 9.575 |
| G332 0.5 mpk | 22.08 | 14.13 |
| G333 1 mpk | 29.28 | 18.53 |
| G333 0.5 mpk | 8.801 | 3.082 |
| G336 1 mpk | 67.92 | 8.609 |
| G336 0.5 mpk | 41.72 | 8.277 |
| G338 1 mpk | 56.25 | 8.561 |
| G338 0.5 mpk | 33.48 | 15.63 |
| G339 1 mpk | 58.36 | 9.444 |
| G339 0.5 mpk | 18.23 | 5.654 |
| G342 1 mpk | 35.12 | 16.84 |
| G342 0.5 mpk | 27.94 | 15.83 |
| G347 1 mpk | 6.073 | 1.825 |
| G347 0.5 mpk | 3.399 | 2.13 |
| G348 1 mpk | 5.464 | 2.171 |
| G348 0.5 mpk | 2.333 | 0.448 |
| G350 1 mpk | 52.66 | 12.88 |
| G350 0.5 mpk | 25.27 | 7.695 |
| G351 1 mpk | 54.94 | 16.24 |
| G351 0.5 mpk | 28.52 | 3.014 |
| G282 1 mpk | 71.08 | 3.789 |
| G282 0.5 mpk | 38.6 | 14.45 |

*FIG. 22B*

| Guide | Average % Editing |
| --- | --- |
| TSS | 0.32 |
| G282 | 52.06 |
| G537 | 35.78 |
| G538 | 7.5 |
| G539 | 33.9 |
| G541 | 39.04 |
| G542 | 38.54 |
| G543 | 2.96 |
| G544 | 38.78 |
| G545 | 43.6 |
| G546 | 19.74 |
| G547 | 36.44 |
| G548 | 12.2 |
| G211-42 | 42.04 |
| G349 | 43.48 |

*FIG. 23B*

| GUIDE | EC50 |
|---|---|
| G332 | 11.42 |
| G333 | 13.07 |
| G336 | 8.735 |
| G338 | 11.80 |
| G339 | 8.778 |
| G342 | 11.60 |
| G347 | 26.07 |
| G348 | 83.09 |
| G350 | 10.57 |
| G351 | 8.797 |
| G282 | 10.04 |

*FIG. 24C*

MODIFIED GUIDE RNAS

SEQUENCE LISTING

The instant application contains a Sequence Listing which has been submitted electronically in XML format and is hereby incorporated by reference in its entirety. Said XML copy, created on Dec. 2, 2022, is named 01155-0004-02US_SequenceListing_ST26 and is 509,585 bytes in size.

This application is a Continuation of U.S. application Ser. No. 18/941,127, which was filed on Nov. 8, 2024, which is a Divisional of U.S. application Ser. No. 17/900,960, now U.S. Pat. No. 12,173,284, which was filed on Sep. 1, 2022, which is a Divisional of U.S. application Ser. No. 16/434,512, now U.S. Pat. No. 11,479,767, which was filed on Jun. 7, 2019, which is a Continuation of International Application No. PCT/US2017/065306, which was filed on Dec. 8, 2017, and which claims the benefit of priority to U.S. Provisional Application No. 62/431,756, which was filed on Dec. 8, 2016, all of which are incorporated by reference in their entirety.

This disclosure relates to the field of gene editing using CRISPR/Cas systems, a part of the prokaryotic immune system that recognizes and cuts exogenous genetic elements. The CRISPR/Cas system relies on a single nuclease, termed CRISPR-associated protein 9 (Cas9), which induces site-specific breaks in DNA. Cas9 is guided to specific DNA sequences by small RNA molecules termed guide RNA (gRNA). Guide RNA comprises trRNA (also known as tracrRNA) and crisprRNA (crRNA). The trRNA and crRNA may be contained within a single guide RNA (sgRNA) or in two separate RNA molecules of a dual guide RNA (dgRNA). Cas9 in combination with trRNA and crRNA or an sgRNA is termed the Cas9 ribonucleoprotein complex (RNP).

Oligonucleotides, and in particular RNA, are sometimes degraded in cells and in serum by endonuclease or exonuclease cleavage. Improved methods and compositions for preventing such degradation, improving stability of gRNAs and enhancing gene editing efficiency is desired, especially for therapeutic applications.

SUMMARY

In some embodiments, therapeutic genome editing tools are provided comprising modified guide RNAs. The modified guide RNAs described herein may improve the stability of the guide RNA and the guide RNA/Cas9 complex and improve the activity of Cas9 (e.g., SpyCas9 and equivalents) to cleave target DNA. In some embodiments, the guide RNA is an sgRNA. In some embodiments, the guide RNA is a dgRNA. In some embodiments, the guide RNA is a tracrRNA. In some embodiments, the guide RNA is a crRNA.

The guide RNAs described herein comprise at least one modified nucleotide. Modifications may include 2'-O-methyl (2'-O-Me), 2'-O-(2-methoxyethyl) (2'-O-moe), 2'-fluoro (2'-F), phosphorothioate (PS) bond between nucleotides, G-C substitutions, and inverted abasic linkages between nucleotides and equivalents thereof. Embodiments of the invention include:

In some embodiments, a single guide RNA (sgRNA) is encompassed comprising a 5' end modification and one or more modification in one or more of the upper stem region; the hairpin 1 region; and the hairpin 2 region, wherein the 5' end modification comprises at least two phosphorothioate linkages within the first seven nucleotides at the 5' end of the 5' terminus. In some instances, the modification is a 2'-O-methyl (2'-O-Me) modified nucleotide. In some embodiments, the modification is a 2'-fluoro (2'-F) modified nucleotide.

In some embodiments, the sgRNA comprises modifications at US1 to US12 and/or a modification at H1-1 and/or a modification in H2-1. In some embodiments, the sgRNA comprises modifications at H1-1 to H1-12 and/or H2-1 to H2-15. In some embodiments, the sgRNA comprises one or more modifications in each of the upper stem region, the hairpin 1 region, and the hairpin 2 region. In some embodiments, the sgRNA comprises a modified nucleotide between hairpin 1 and hairpin 2 regions. In some embodiments, the sgRNA comprises a modification in the lower stem region.

In some embodiments, the sgRNA comprises a modification at the 5' terminus and/or the 3' terminus. In some embodiments, the sgRNA comprises a 3' end modification in the 3' terminus. In some embodiments, the sgRNA comprises modifications on at least two of the last four nucleotides at the 3' end of the 3' terminus. In some embodiments, the sgRNA comprises a 5' end modification in the 5' terminus. In some embodiments, the sgRNA comprises modifications on at least two of the first four nucleotides at the 5' end of the 5' terminus. In some embodiments, the sgRNA comprises a 3' end modification in the 3' terminus and a 5' end modification in the 5' terminus. In some embodiments, the sgRNA comprises modifications on at least two of the last four nucleotides at the 3' end of the 3' terminus and on at least two of the first four nucleotides at the 5' end of the 5' terminus. In some instances, these modifications are 2'-O-Me, 2'-F, 2'-O-moe, or phosphorothioate (PS) bonds linking the nucleotides. In some embodiments, the sgRNA comprises PS bonds between at least two of the last four nucleotides at the 3' end of the 3' terminus and/or at least two of the first four nucleotides at the 5' end of the 5' terminus. In some instances, the sgRNA comprises 5' terminus and 3' terminus with more than one modification as described herein, such as, with PS bonds and 2'-O-Me modifications.

In some embodiments, the sgRNA comprises a modification in the bulge region. In some embodiments, 50% of the nucleotides in the bulge region are modified, wherein the modification is 2'-O-Me or 2'-F.

In some embodiments, the sgRNA comprises a modification in the nexus region. In some embodiments, the sgRNA comprises modifications at N15, N16, N17, and/or N18 in the nexus region, wherein the modification is 2'-O-Me or 2'-F. In some instances, N16, N17, and N18 are linked with PS bonds.

In some embodiments, the sgRNA comprises at least the first three nucleotides at the 5' end of the 5' terminus, and the last three nucleotides at the 3' end of the 3' terminus are modified.

In some embodiments, the sgRNA comprises modifications at the 3' terminus and/or 5' terminus. In some instances, the first four nucleotides at the 5' end of the 5' terminus, and the last four nucleotides at the 3' end of the 3' terminus are linked with phosphorothioate (PS) bonds. In some embodiments, the 5' and 3' modification comprises 2'-O-Me or 2'-O-moe. In some embodiments, the 5' and 3' modification comprises 2'-F. In some embodiments, the 5' and/or 3' modification comprises PS bonds linking nucleotides. In some embodiments, the 5' and/or 3' modification comprises one or more of 2'-O-Me, 2'-O-moe, 2'-F, and PS bonds linking nucleotides.

In some embodiments, the sgRNA comprises modifications at the first four nucleotides at the 5' end of the 5' terminus and the last four nucleotides at the 3' end of the 3'terminus. In some instances, these modifications are linking PS bond (i.e., PS bonds that link the first four and last four nucleotides). In some embodiments, the sgRNA further comprises 2'-O-Me modifications at the first three nucleotides at the 5' end of the 5' terminus and the last three nucleotides at the 3' end of the 3' terminus.

In some embodiments, the sgRNA comprises modifications at the first four nucleotides at the 5' end of the 5' terminus and the last four nucleotides at the 3' end of the 3' terminus, wherein the modifications are at least PS bonds linking the four nucleotides, and further wherein the first three nucleotides at the 5' end of the 5' terminus and the last three nucleotides at the 3' end of the 3' terminus comprise 2'-O-Me, 2'-O-moe, or 2'-F modifications.

In some embodiments, the sgRNA comprises modifications LS1, LS6, LS7, LS8, LS11, and LS12, wherein the modification is 2'-O-Me or 2'-F.

In some embodiments, the sgRNA comprises modifications at each of the nucleotides in the bulge region, wherein the modification is 2'-O-Me or 2'-F.

In some embodiments, the sgRNA comprises modifications at each of the nucleotides in the upper stem region, wherein the modification is 2'-O-Me or 2'-F.

In some embodiments, the sgRNA comprises modifications at each of the nucleotides in the hairpin 1 region, wherein the modification is 2'-O-Me or 2'-F.

In some embodiments, the sgRNA comprises modifications at each of the nucleotides in the hairpin 2 region, wherein the modification is 2'-O-Me or 2'-F.

In some embodiments, an sgRNA is encompassed comprising 2'-O-Me modified nucleotides at the following positions:

a. the first three nucleotides at the 5' end of the 5' terminus;
b. LS1, LS6, LS7, LS8, LS11, and/or LS12 in the lower stem region;
c. B1 and/or B2 in the bulge region;
d. each nucleotide in the upper stem region;
e. N16, N17, and/or N18 in the nexus region;
f. each nucleotide in the hairpin 1 region;
g. each nucleotide in the hairpin 2 region; and
h. the last four nucleotides at the 3' end of the 3' terminus.

In some embodiments, B3-B6 are modified with 2'-O-Me. In some instances, the sgRNA further comprising three phosphorothioate (PS) bonds linking the first four nucleotides at the 5' end of the 5' terminus and three PS bonds linking the last four nucleotides at the 3' end of the 3' terminus. In some embodiments, the sgRNA comprises 2'-F modifications at LS9 and LS10. In some embodiments, the sgRNA comprises 2'F modifications at N15, N16, N17, and N18. In some embodiments, the sgRNA comprises 2'F modifications at H2-9, H2-10, H2-11, H2-12, H2-13, H2-14, and H2-15. In some embodiments, the sgRNA comprises 2'F modifications at the second to last, third to last, and fourth to last nucleotides at the 3' end of the 3' terminus.

In some embodiments, an sgRNA is encompassed comprising 2'-F modified nucleotides at the following positions:

a. LS9 and LS10 in the lower stem region;
b. N15, N16, N17, and N18 in the nexus region; and
c. H2-9, H2-10, H2-11, H2-12, H2-13, H2-14, and H2-15 in the hairpin 2 region.

In some embodiments, the sgRNA comprises 2'-F modified nucleotides at the second to last, third to last, and fourth to last nucleotides at the 3' terminus. In some embodiments, the sgRNA comprises three phosphorothioate (PS) bonds linking the first four nucleotides at the 5' end of the 5' terminus and three PS bonds linking the last four nucleotides at the 3' end of the 3' terminus. In some embodiments, the sgRNA comprises 2'-O-Me or 2'-F modified nucleotides at the first three nucleotides at the 5' end of the 5' terminus, and 2'-O-Me or 2'-F modified nucleotides at three of the last four nucleotides at the 3' end of the 3' terminus.

In some embodiments, an sgRNA is encompassed comprising a. 2'-O-Me modified nucleotides at the first three nucleotides at the 5' end of the 5' terminus;
b. Optional 2'-O-Me modified nucleotides at LS1 and/or LS6;
c. 2'-O-Me modified nucleotides at US1-US12;
d. 2'-O-Me modified nucleotides at H1-1-H1-12;
e. Optional 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' end of the 3' terminus; and optionally further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:

a. 2'-O-Me modified nucleotides at the first three nucleotides at the 5' end of the 5' terminus;
b. 2'-F modified nucleotides at LS1-LS6;
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' end of the 3' terminus; and optionally further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:

a. 2'-O-Me modified nucleotides at the first three nucleotides at the 5' terminus;
b. 2'-F modified nucleotides at LS2-LS5;
c. 2'-O-Me modified nucleotides at LS1 and LS6;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-F modified nucleotides at LS9 and LS10;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:

a. 2'-O-Me modified nucleotides at the first three nucleotides at the 5' terminus;
b. 2'-O-Me modified nucleotides at US1-US12;
c. 2'-O-Me modified nucleotides at LS8, LS10, and LS12;
d. 2'-O-F modified nucleotides at LS7, LS9, and LS11;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides at the first three nucleotides at the 5' terminus;
b. 2'-O-Me modified nucleotides at LS1, LS6, LS7, LS8, LS11, and LS12
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus, and optionally further comprising three phosphorothioate (PS) bonds linking the first four nucleotides at the 5' end of the 5' terminus and three PS bonds linking the last four nucleotides at the 3' end of the 3' terminus In some embodiments, a sgRNA is encompassed comprising:

a. 2'-O-Me modified nucleotides at the first three nucleotides at the 5' terminus;
b. 2'-O-Me modified nucleotides at LS1, LS6, LS7, LS8, LS11, and LS12;
c. 2'-F modified nucleotides at LS9 and LS10;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides at the first three nucleotides at the 5' end of the 5' terminus;
b. 2'-O-Me modified nucleotides at US1-US12;
c. 2'-O-Me modified nucleotides at H1-1-H1-12;
d. a 2'-O-Me modified nucleotide between Hairpin 1 and Hairpin 2;
e. 2'-O-Me modified nucleotides at H2-1-H2-8;
f. 2'-F modified nucleotides at H2-9-H2-15;
g. 2'-F modified nucleotides at the second from last, third from last, and fourth from last nucleotide at the 3' terminus; and
h. a 2'-O-Me modified nucleotide at the last nucleotide at the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides at the first three nucleotides at the 5' end of the 5' terminus;
b. 2'-O-Me modified nucleotides at US1-US12;
c. 2'-O-Me modified nucleotides at H1-2, H1-4, H1-6, H1-8, H1-10, and H1-12;
d. 2'-F modified nucleotides at H1-1, H1-3, H1-5, H1-7, H1-9, and H1-11;
e. a 2'-F modified nucleotide between Hairpin 1 and Hairpin 2;
f. 2'-F modified nucleotides at H2-2, H2-4, H2-6, H2-8, H2-10, H2-12; and H2-14;
g. 2'-O-Me modified nucleotides at H2-1, H2-3, H2-5, H2-7, H2-9, H2-11; H2-13, and H2-15;
h. 2'-F modified nucleotides at the second from last, and fourth from last nucleotide at the 3' terminus; and
i. 2'-O-Me modified nucleotide at the third from last and last nucleotide at the 3' end of the 3' terminus, and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:

a. 2'-O-Me modified nucleotides LS8, LS10, LS12, H1-2, H1-4, H1-6, H1-8, H1-10, H1-12, H2-1, H2-3, H2-5, H2-7, H2-9, H2-11, H2-13, and H2-15; and
b. 2'-F modified nucleotides at LS7, LS9, LS11; H1-1, H1-3, H1-5, H1-7, H1-9, H1-11, H1-13, H2-2, H2-4, H2-6, H2-8, H2-10, H2-12, and H2-14, and optionally further comprising three phosphorothioate (PS) bonds linking the first four nucleotides at the 5' end of the 5' terminus and three PS bonds linking the last four nucleotides at the 3' end of the 3' terminus; and optionally further comprising:

c. 2'-O-Me modified nucleotides at the last and third to last nucleotide at the 3' end of the 3' terminus; and/or
d. 2'-F modified nucleotides at the second to last, fourth to last, and/or last nucleotide at the 3' end of the 3' terminus.

In some embodiments, a sgRNA is encompassed comprising the nucleic acids of any of SEQ ID Nos: 228-353, including the modifications of Table 4. In some embodiments, a sgRNA is encompassed comprising any of SEQ ID Nos: 228-332, including the modifications of Table 4. In some embodiments, an sgRNA is encompassed comprising any of SEQ ID Nos: 235-240, 265-285, and 309-329, including the modifications of Table 4. In some embodiments, an sgRNA is encompassed comprising SEQ ID No: 240. In some embodiments, a sgRNA is encompassed comprising SEQ ID No. 240, including the modifications of Table 4. In some embodiments, a sgRNA is encompassed comprising SEQ ID No: 242. In some embodiments, a sgRNA is encompassed comprising SEQ ID No: 358. In additional embodiments, a sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification at each nucleotide of the sgRNA that corresponds to a nucleotide of the reference sequence identifier in Table 4, is identical to or equivalent to the modification shown in the reference sequence identifier in Table 4, optionally further comprising three phosphorothioate (PS) bonds linking the first four nucleotides at the 5' end of the 5' terminus and three PS bonds linking the last four nucleotides at the 3' end of the 3' terminus. In some embodiments, the sgRNA further comprises at least three PS bonds linking the nucleotides in the hairpin 1 region. In some embodiments, the sgRNA further comprises at least three PS bonds linking the nucleotides in the hairpin 2 region. In some embodiments, the sgRNA further comprises at least three PS bonds linking the nucleotides in the upper stem region. In some embodiments, the sgRNA forms a ribonucleoprotein complex with *S. pyogenes* Cas9.

FIGURE LEGENDS

FIG. 4 shows percent editing as measured by NGS of mouse TTR gene following transfection of Neuro2A cells with modified crRNAs and trRNAs together with Cas9 mRNA. Standard deviations follow the value.

Figure 6:
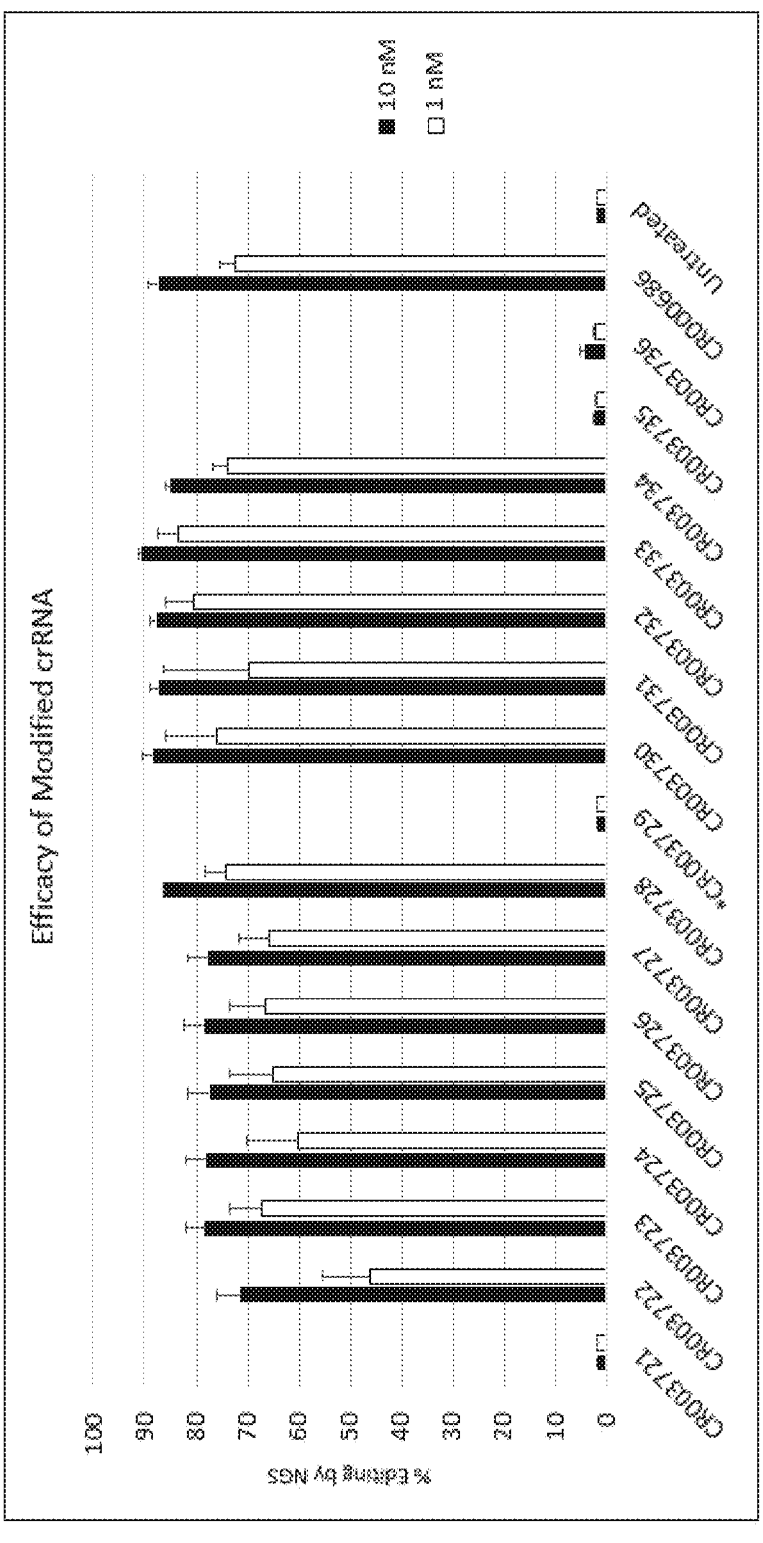

FIG. 6 shows percent editing as measured by NGS of mouse TTR gene following transfection of Neuro2A cells with modified crRNAs and unmodified trRNA (TR000002) together with Cas9 mRNA. The asterisk denotes a dual guide that for technical reasons did not show activity in this experiment. This dual guide was tested again in the experiment represented in FIG. 9, in which it showed editing activity.

Figure 7:
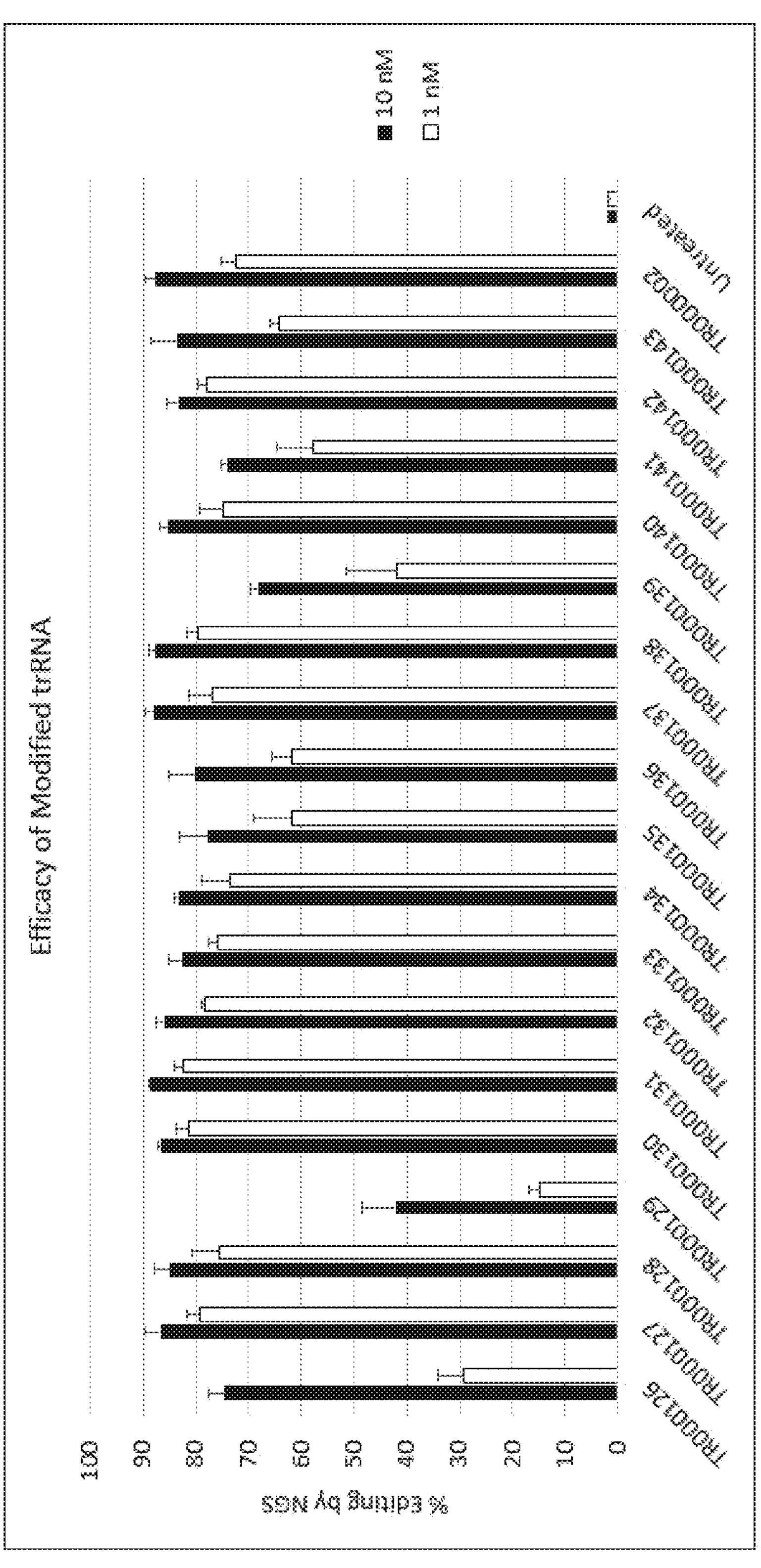

FIG. 7 shows percent editing as measured by NGS of mouse TTR gene following transfection of Neuro2A cells with unmodified crRNA (CR000686) and modified trRNAs together with Cas9 mRNA.

Figure 8:
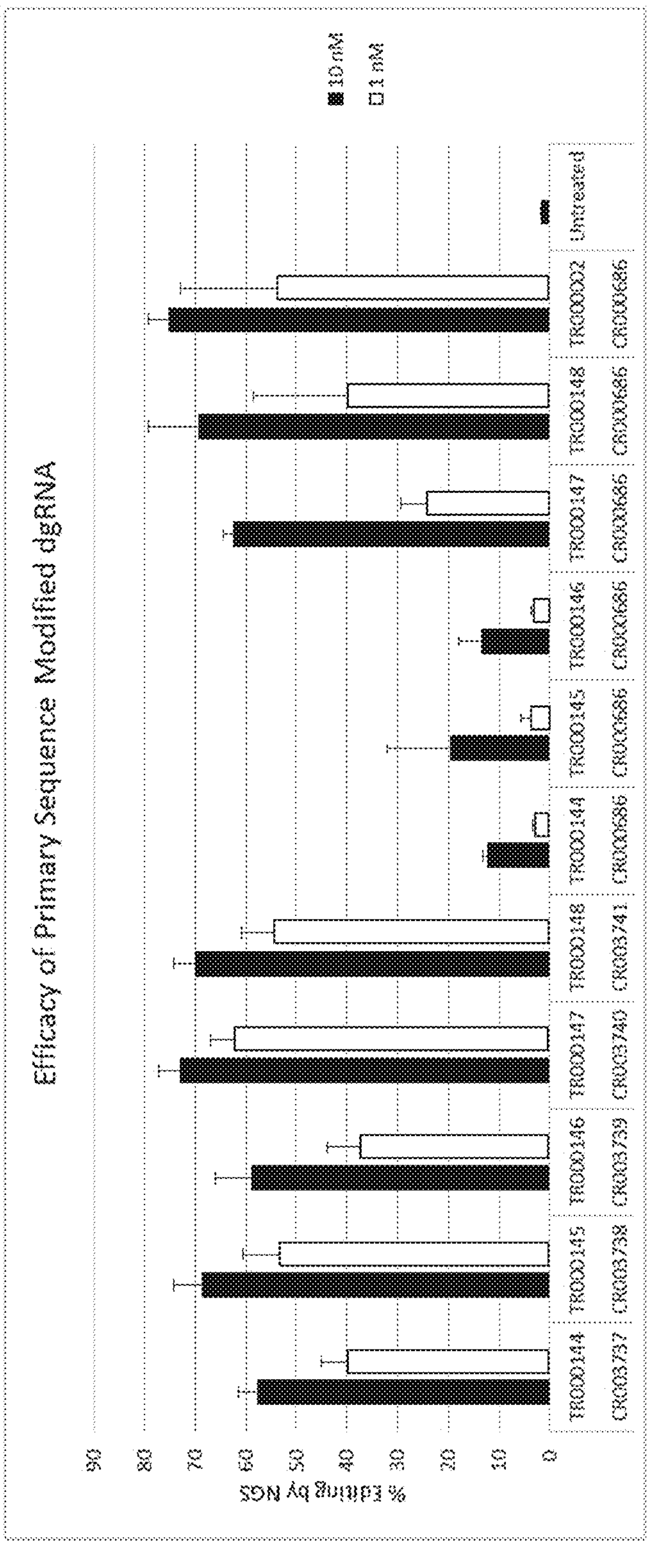

FIG. 8 shows percent editing as measured by NGS of mouse TTR gene following transfection of Neuro2A cells with Cas9 mRNA and crRNA and trRNA pairings with G-C pairings or G-U mismatches not found in the parental sequences.

FIG. 9 shows percent editing as measured by NGS of mouse TTR gene following transfection of Neuro2A cells with modified crRNAs and modified trRNAs together with Cas9 mRNA. Standard deviations follow the value.

Figure 10:
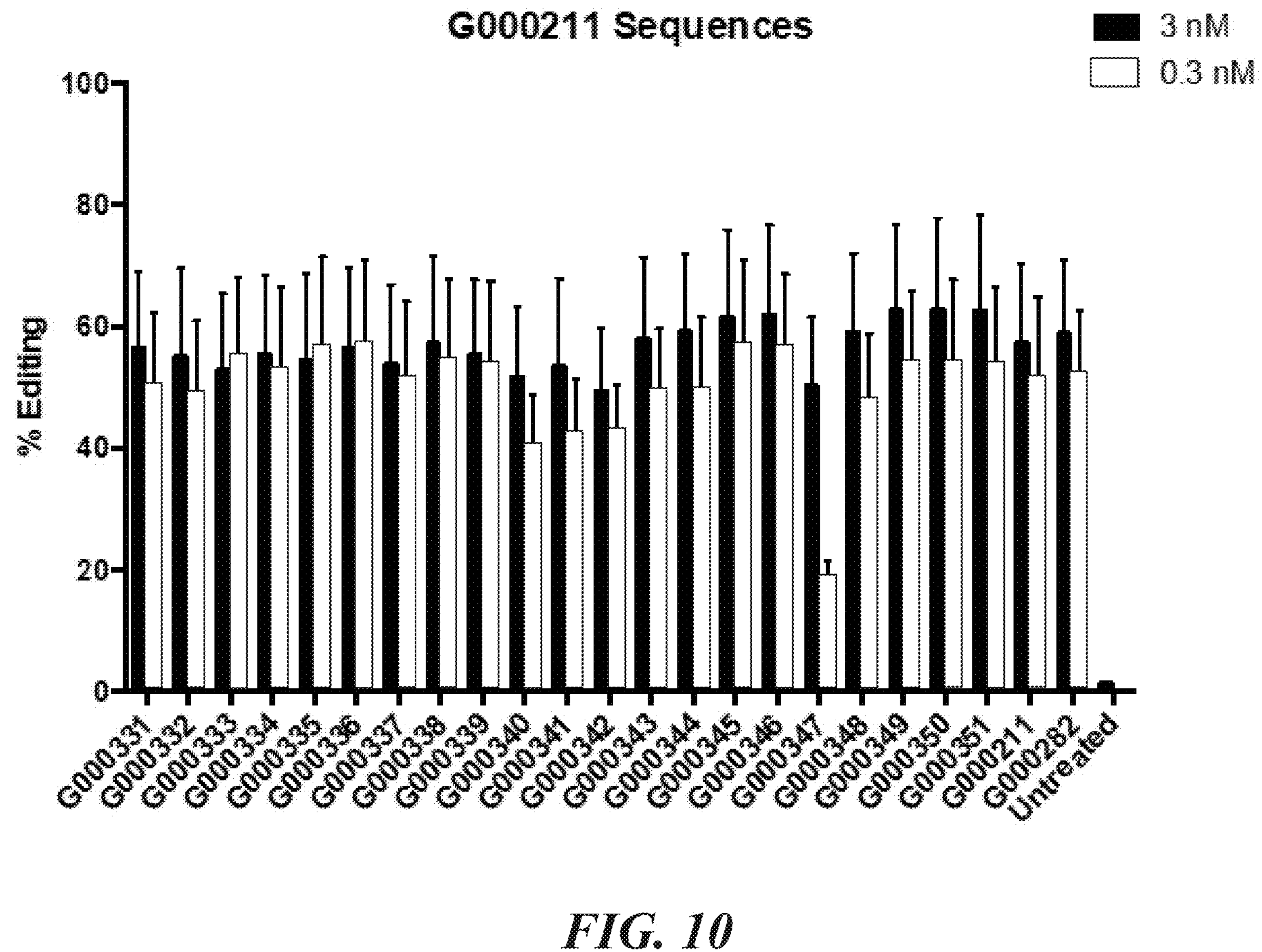

FIG. 10 shows percent editing as measured by NGS of mouse TTR gene following transfection of Neuro2A cells with modified sgRNAs together with Cas9 mRNA.

Figure 11:
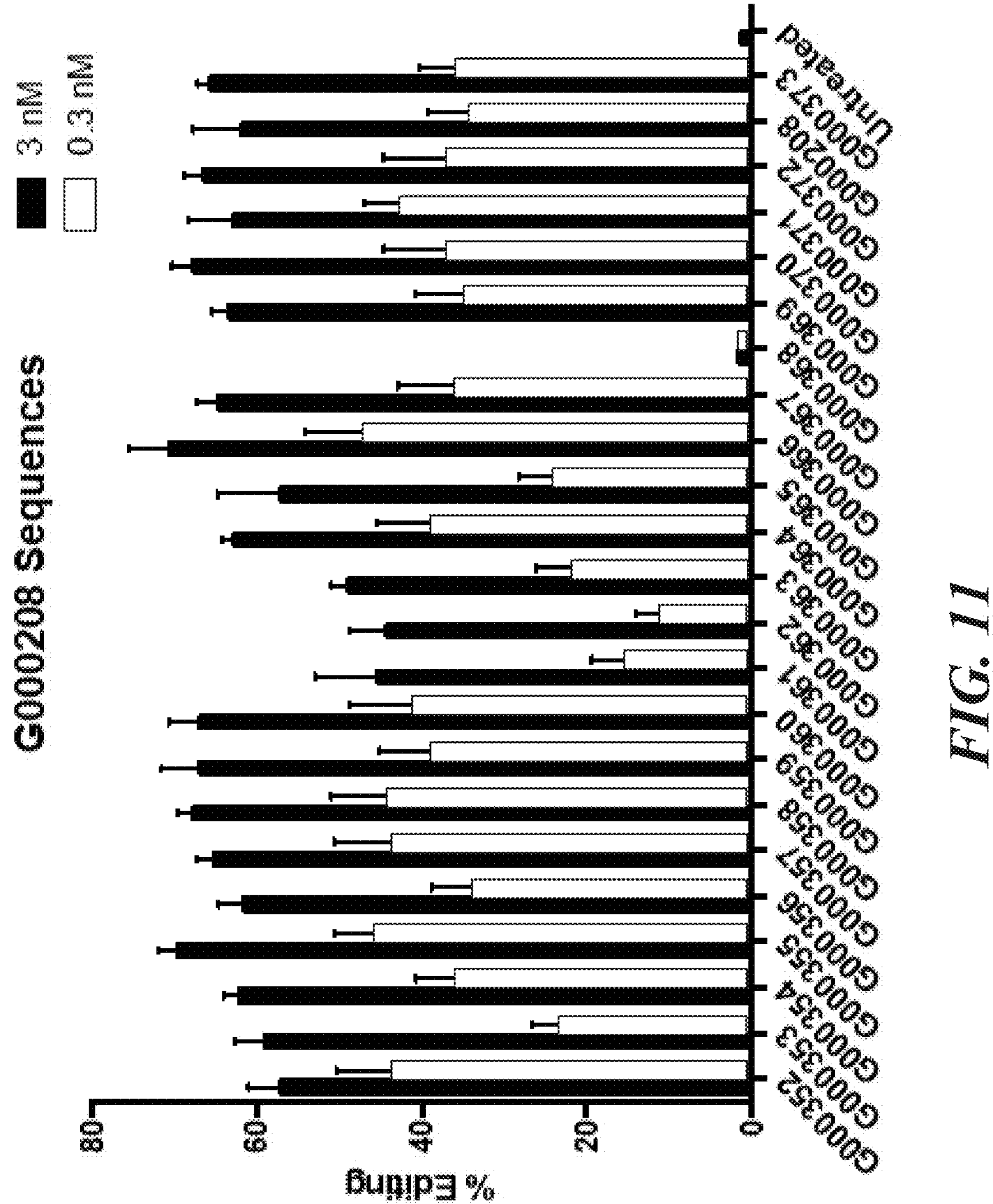

FIG. 11 shows percent editing as measured by NGS of mouse Factor VII (FVII) gene following transfection of Neuro2A cells with modified sgRNAs together with Cas9 mRNA.

Figure 12A:
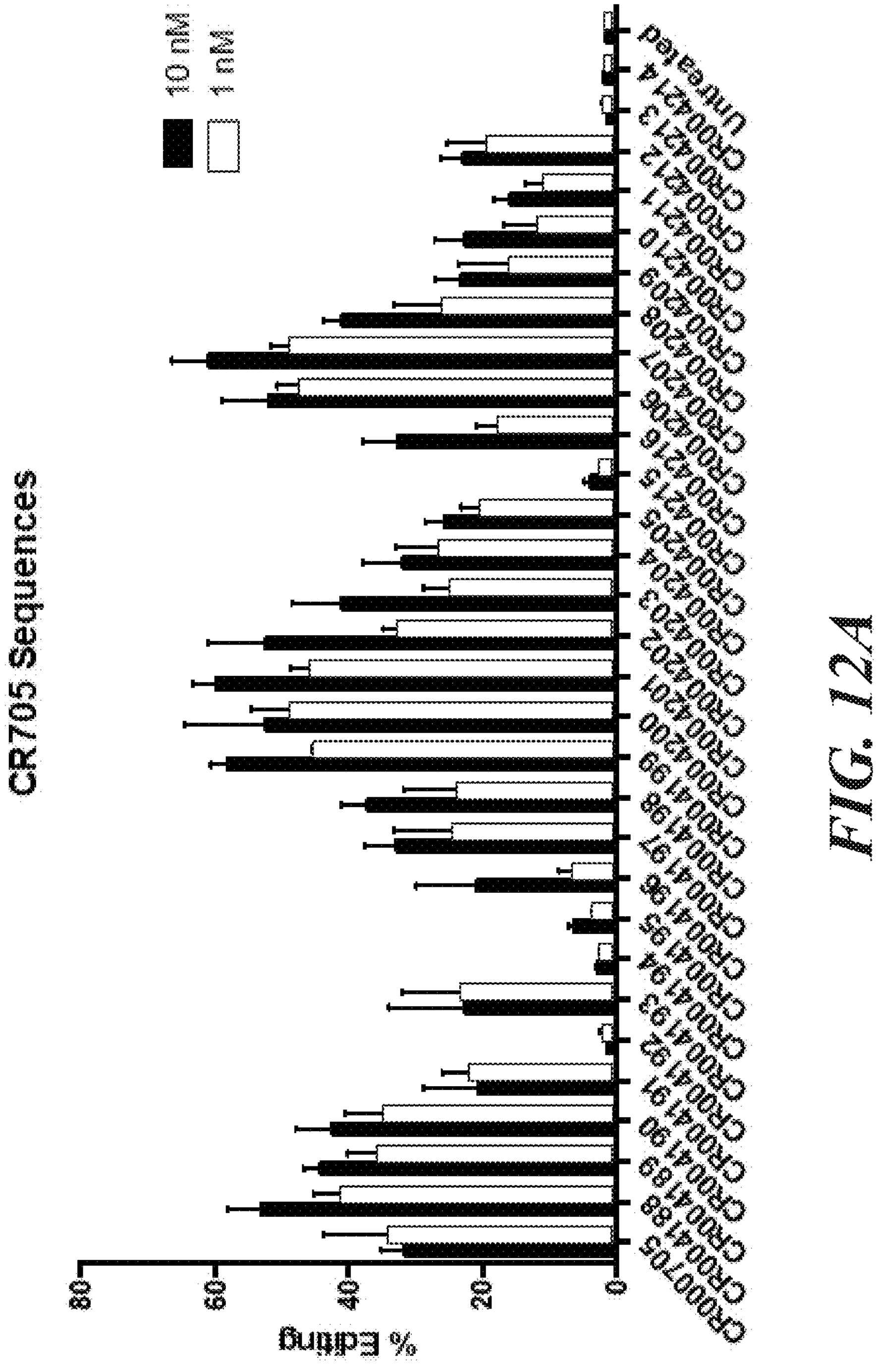
Figure 12B:
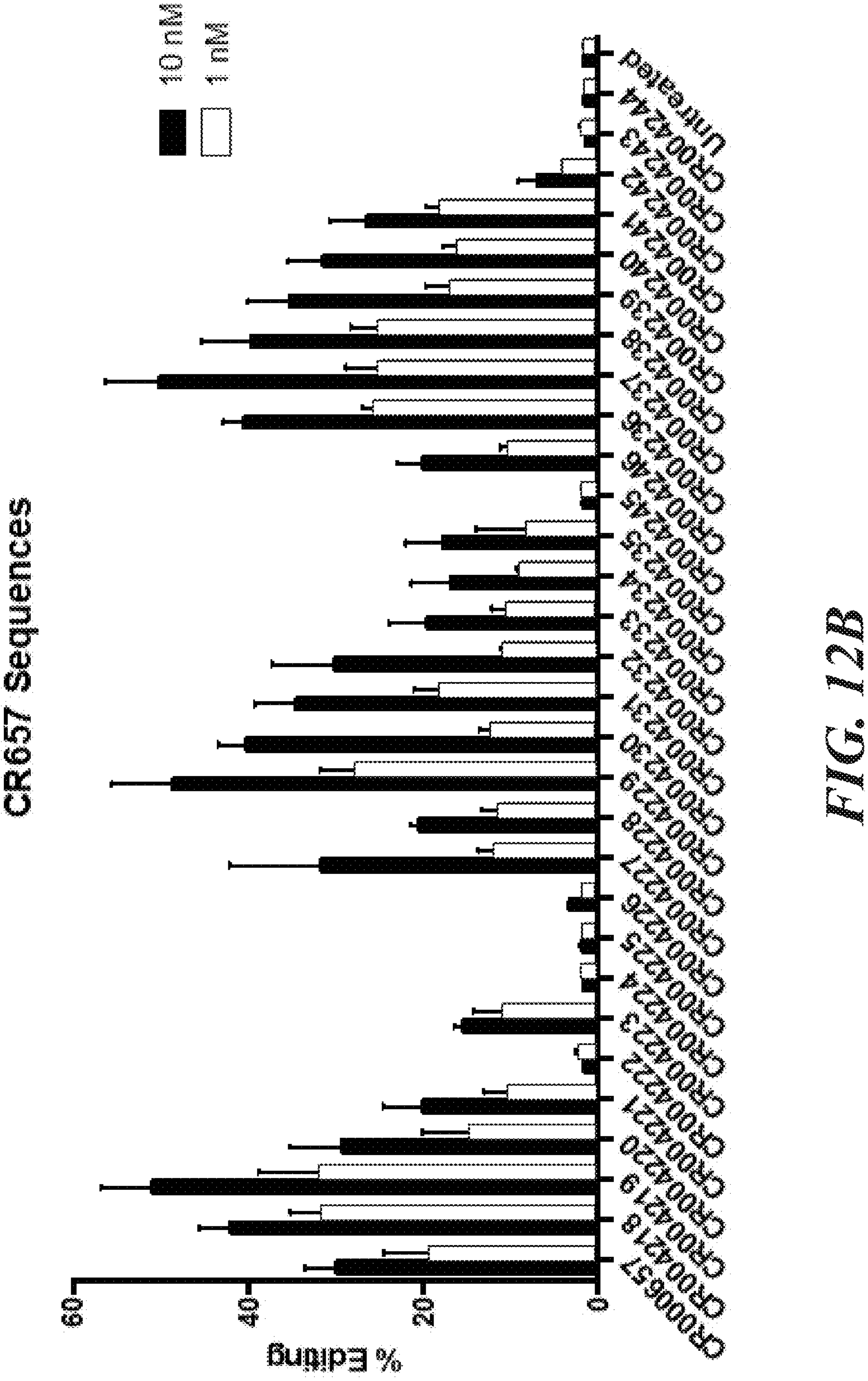

FIGS. 12A and 12B show percent editing as measured by NGS of mouse TTR (FIG. 12A) or FVII (FIG. 12B) following transfection of Neuro2A cells with modified crRNAs and unmodified trRNA together with Cas9 mRNA.

Figure 13A:
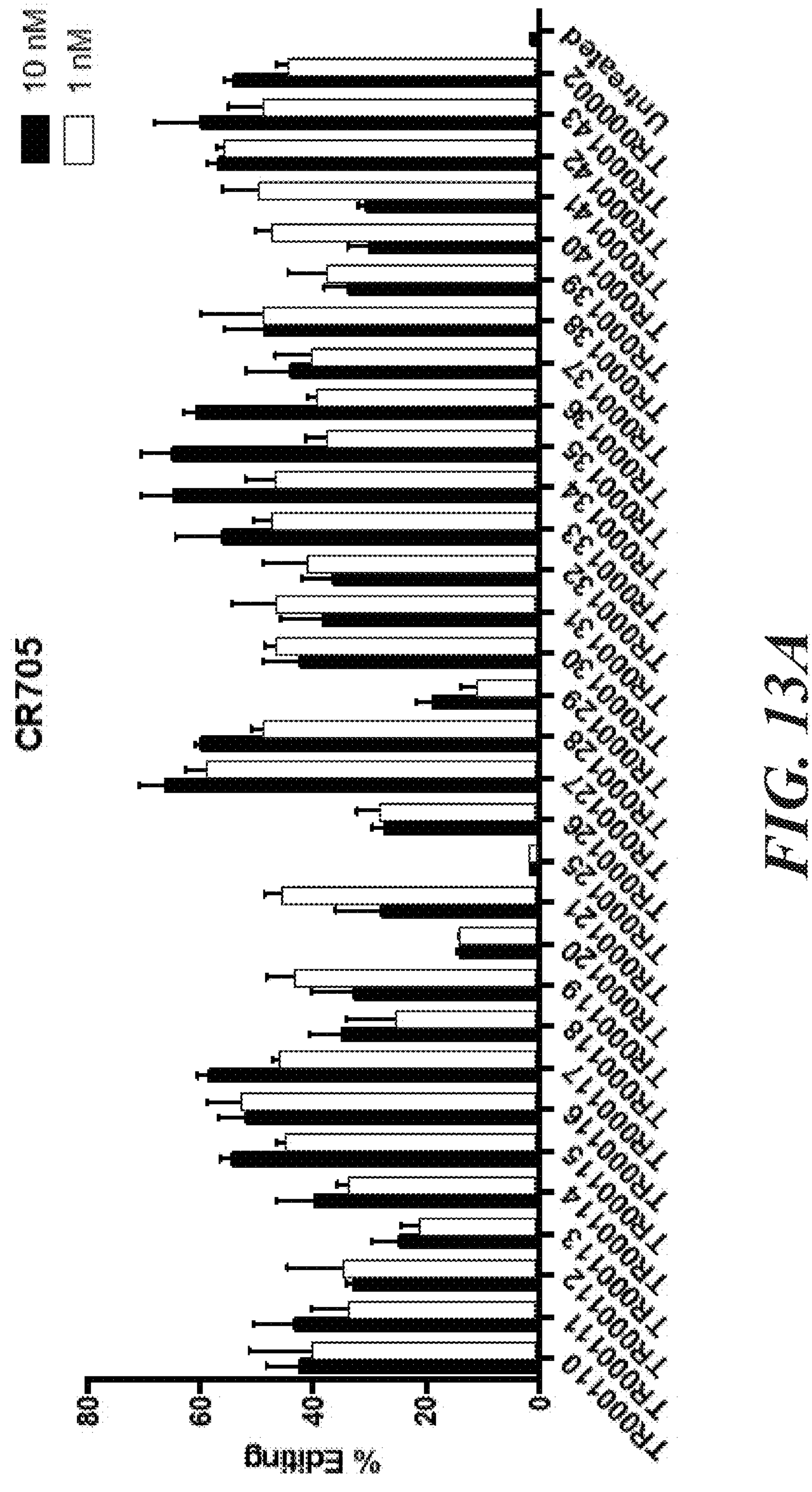
Figure 13B:
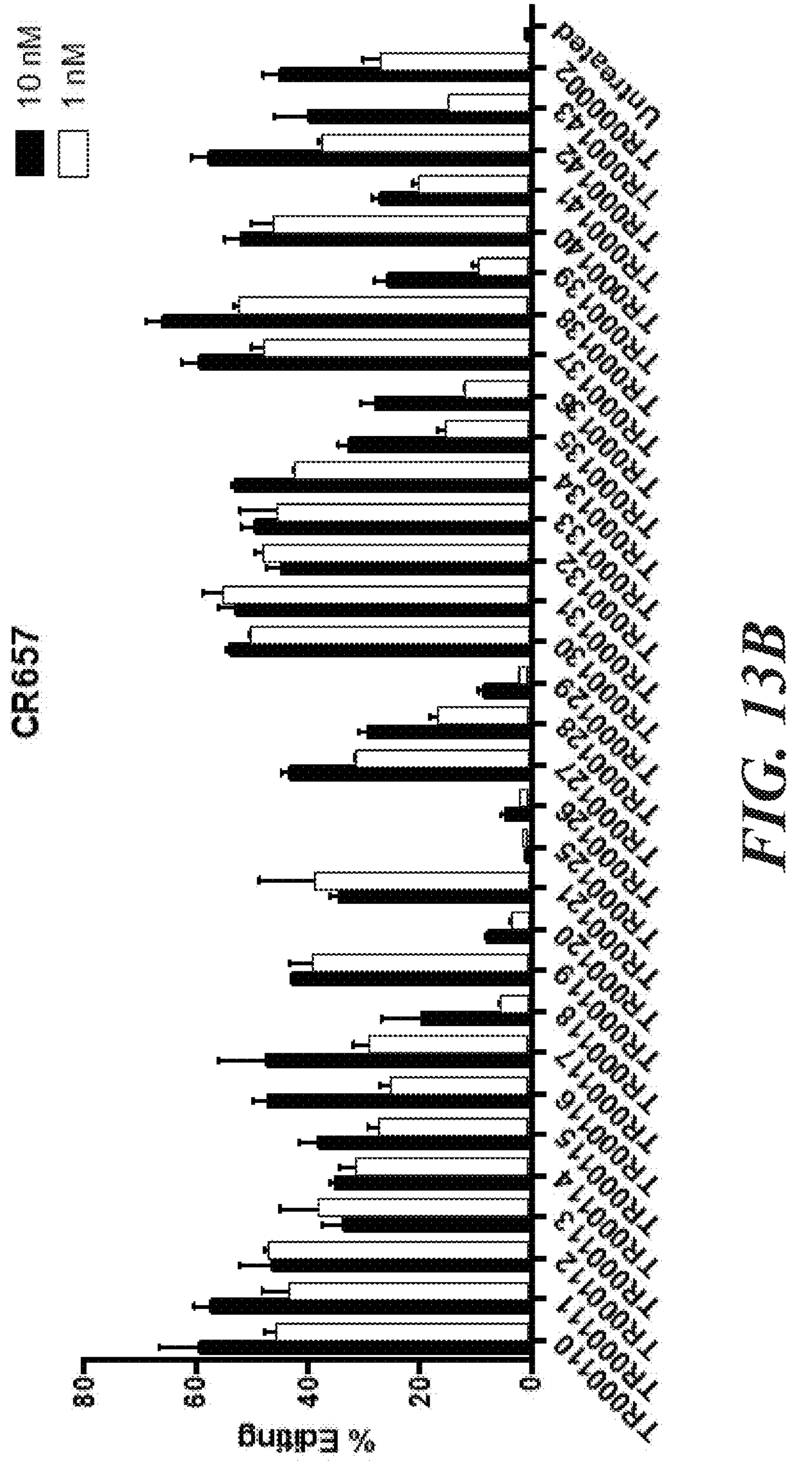
Figure 14A:
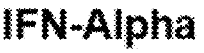
Figure 14A:
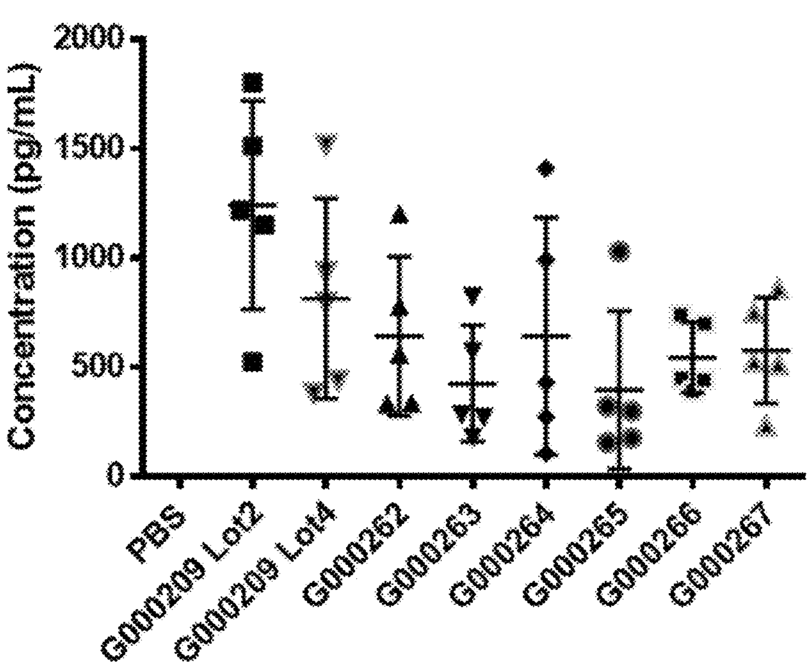
Figure 14B:
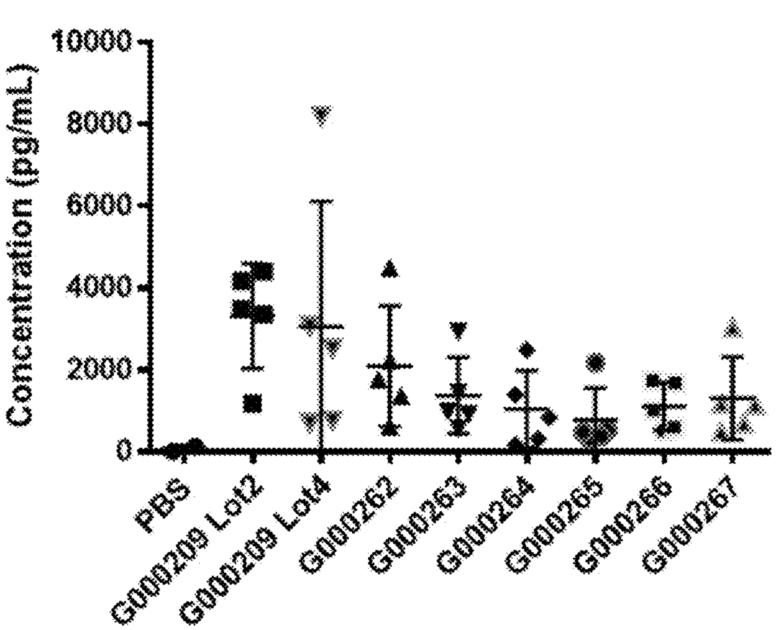
Figure 14C:
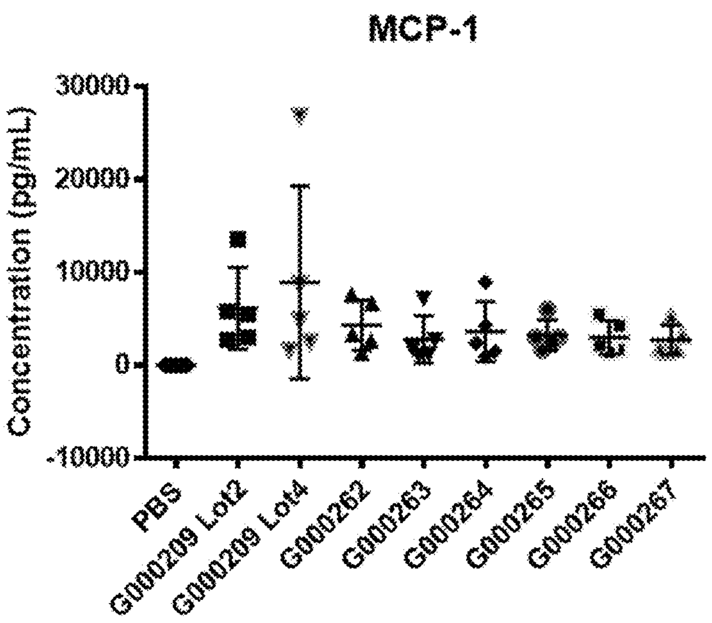
Figure 14D:
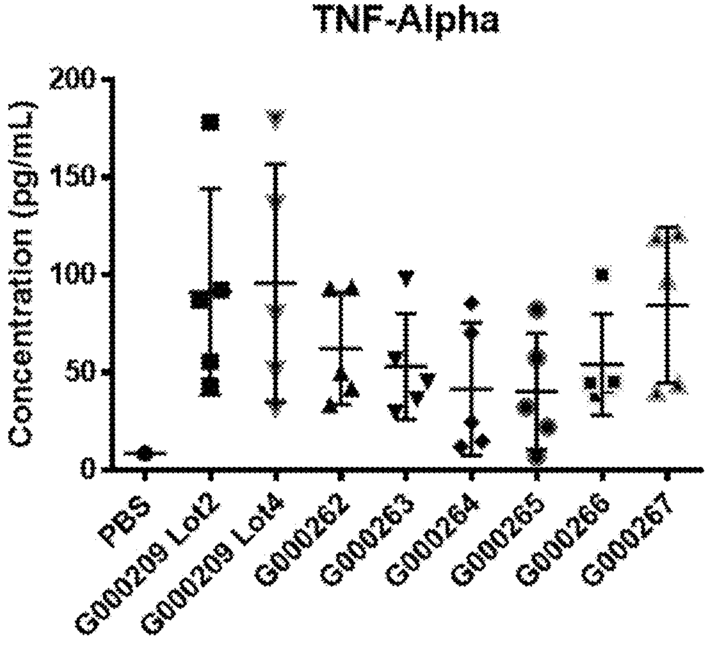

FIGS. 13A and 13B shows percent editing as measured by NGS of mouse TTR (FIG. 13A) or FVII (FIG. 13B) following transfection of Neuro2A cells with modified trRNAs and unmodified crRNA together with Cas9 mRNA.

FIGS. 14A, 14B, 14C, and 14D show interferon alpha (IFN-alpha, 14A), interleukin 6 (IL-6, 14B), monocyte chemotactic protein 1 (MCP-1, 14C), and tumor necrosis factor alpha (TNF-alpha, 14D) levels in serum after in vivo administration of LNPs comprising Cas9 mRNA and sgRNAs.

Figure 15A:
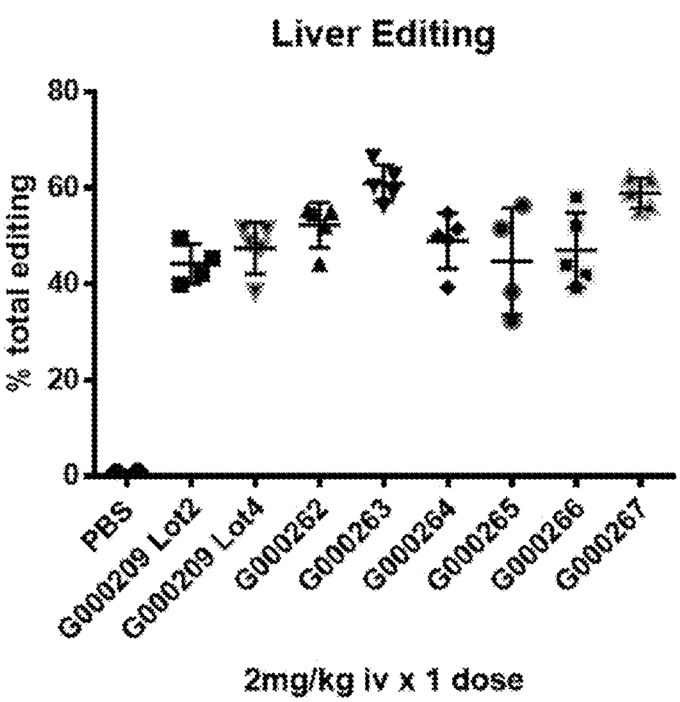
Figure 15B:
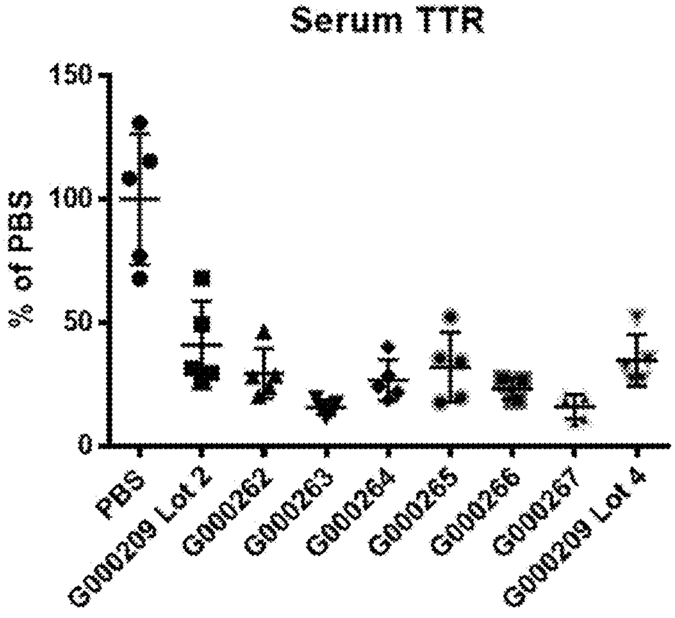
Figures 15C, 15D:
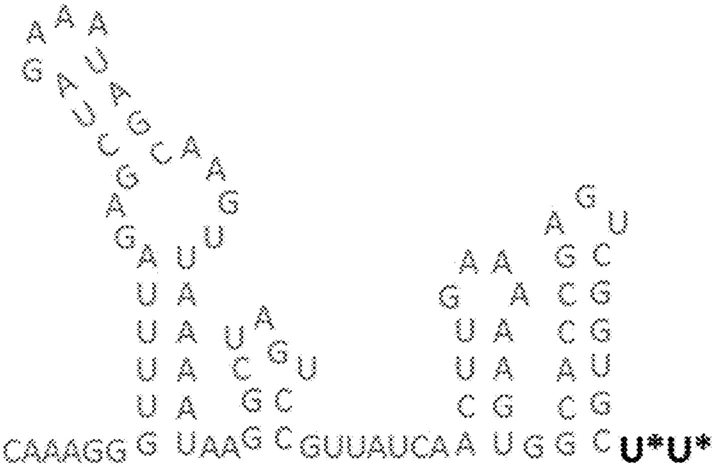
Figure 15E:
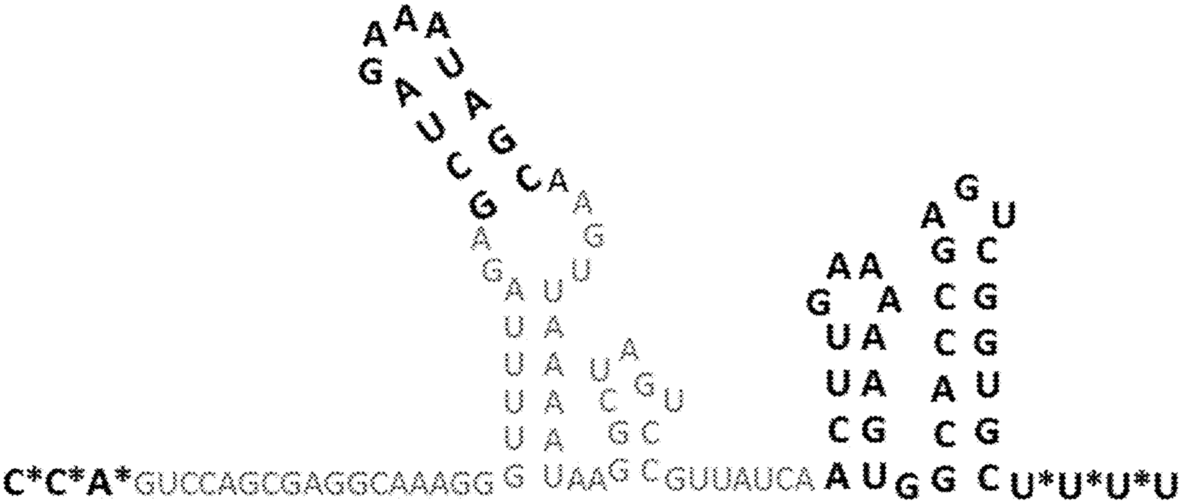
Figure 16A:
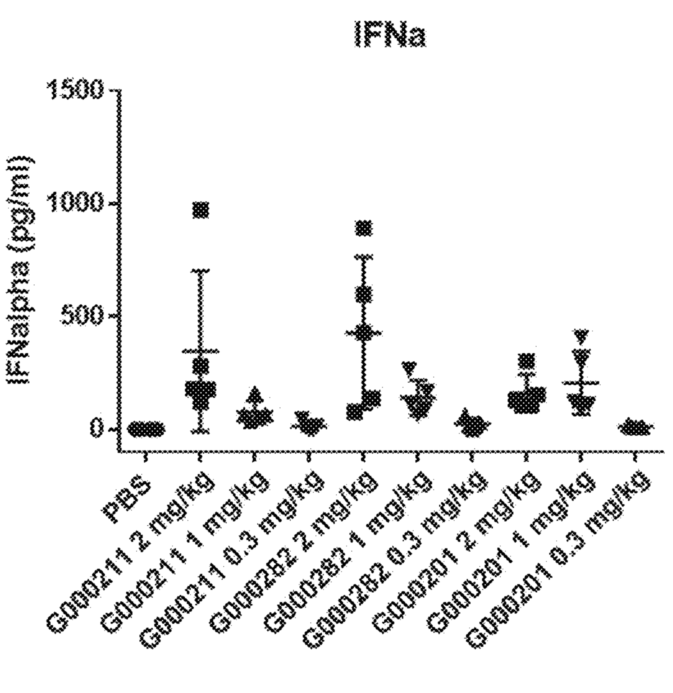
Figure 16B:
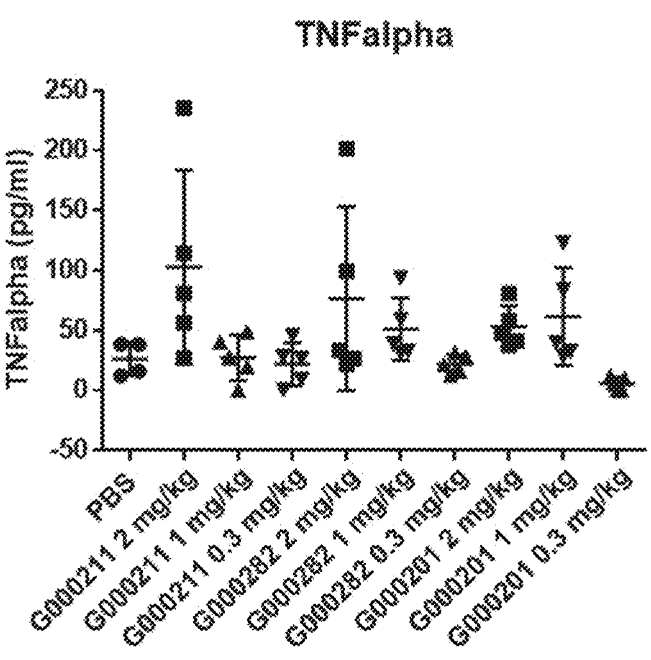
Figure 16C:
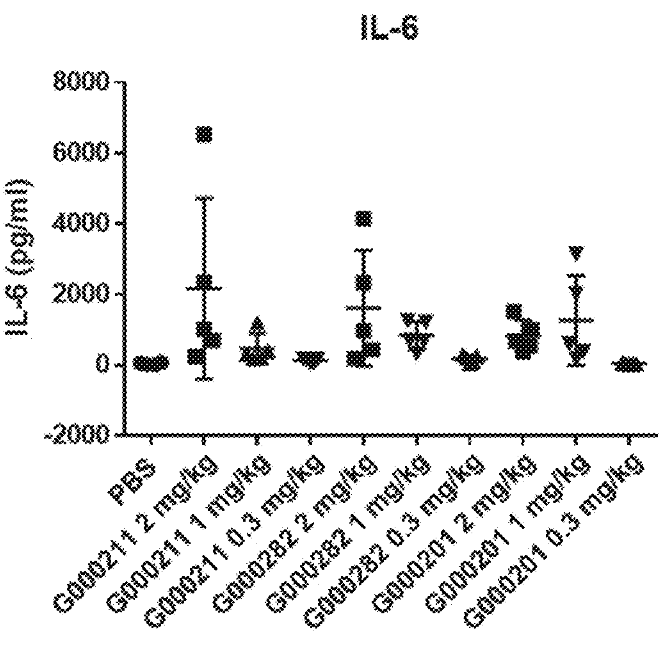
Figure 16D:
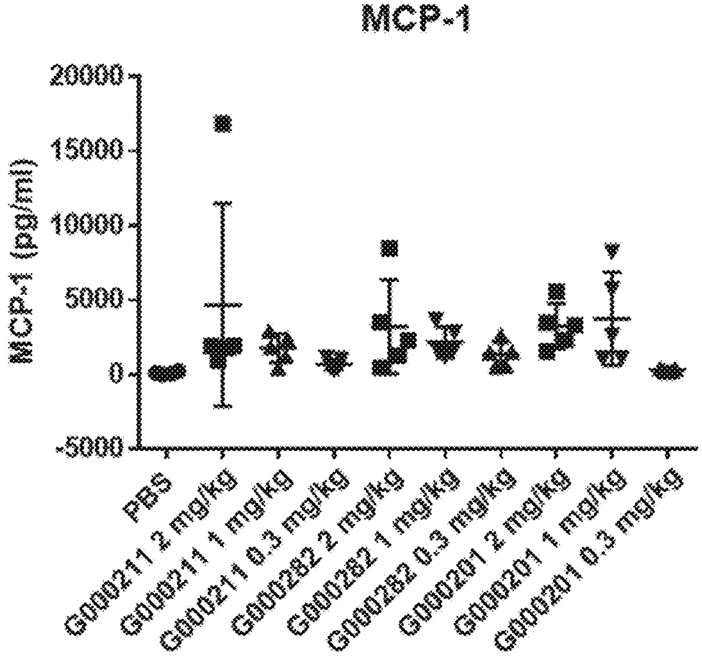

FIGS. 15A, 15B, and 15C show in vivo results following administration of LNPs comprising Cas9 mRNA and sgRNAs. FIG. 15A shows percentage of total editing in liver. FIG. 15B shows serum TTR levels. FIG. 15C shows the mean and standard deviation for the results of FIG. 15A. FIG. 15D summarizes modifications to the G000209 sgRNA (SEQ ID NO: 228). FIG. 15E summarizes modifications to the G000267 sgRNA (SEQ ID NO: 234). In FIGS. 15D and 15E, the nucleotides in bold are 2'-O-Me modified.

FIGS. 16A, 16B, 16C, and 16D show interferon alpha (IFN-alpha, 16A), tumor necrosis factor alpha (TNF-alpha, 16B), interleukin 6 (IL-6, 16C), and monocyte chemotactic protein 1 (MCP-1, 16D) levels in serum after in vivo administration of LNPs comprising Cas9 mRNA and sgRNAs.

Figures 17C, 17D:
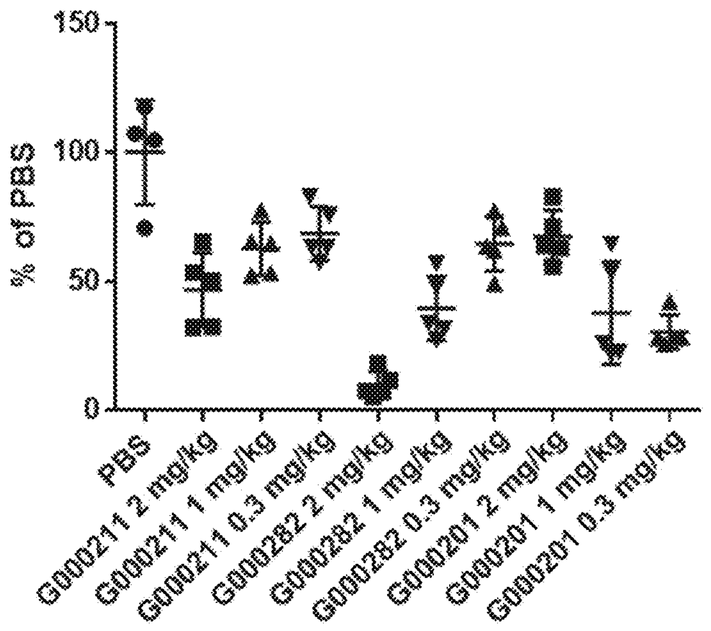

FIGS. 17A, 17B, 17C, and 17D show in vivo results following administration of LNPs comprising Cas9 mRNA and sgRNAs. FIG. 17A shows percentage of total editing in liver. FIG. 17B shows the mean and standard deviation for the results of FIG. 17A. FIG. 17C shows serum TTR levels. FIG. 17D shows the mean and standard deviation for the results of FIG. 17B.

Figure 18A:
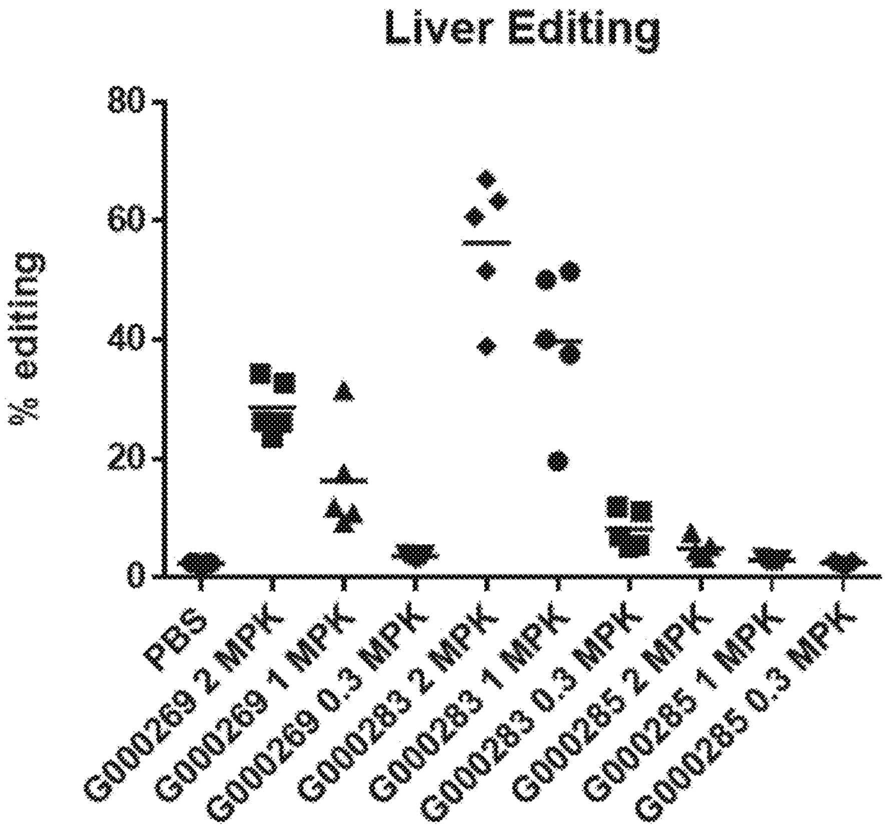
Figures 18B, 18C:
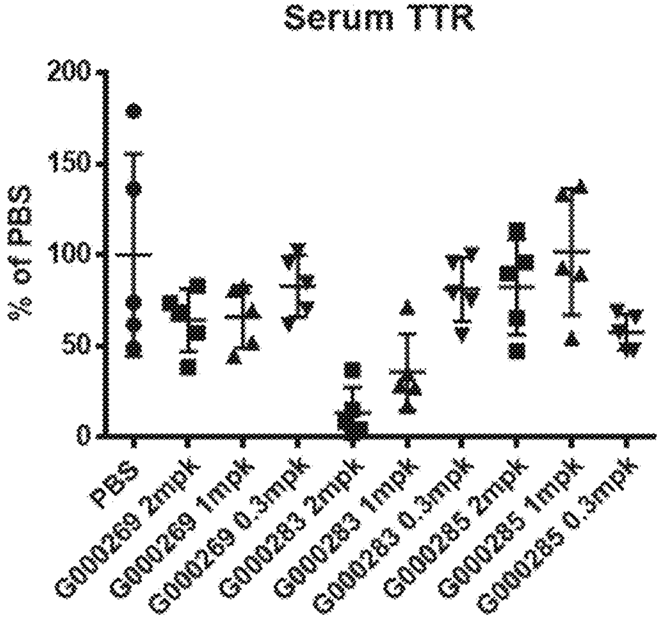
Figure 19A:
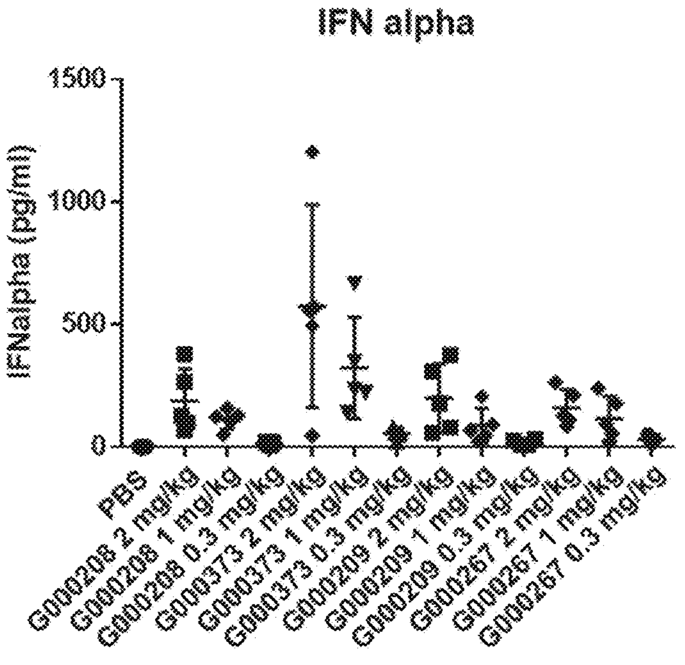
Figure 19B:
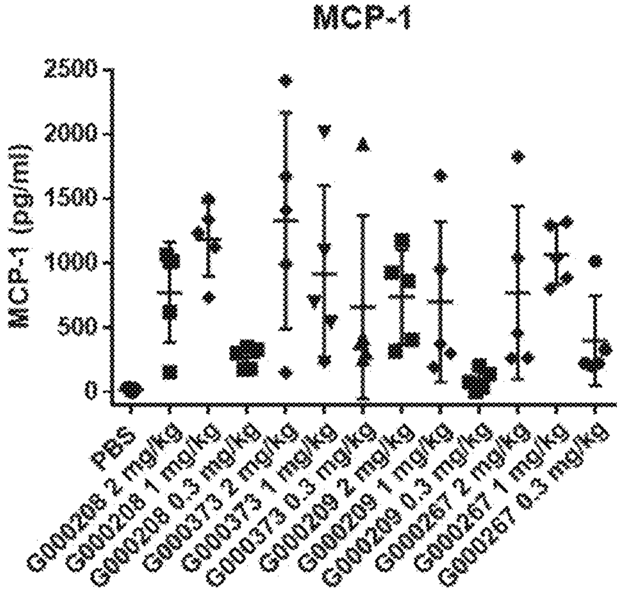
Figure 19C:
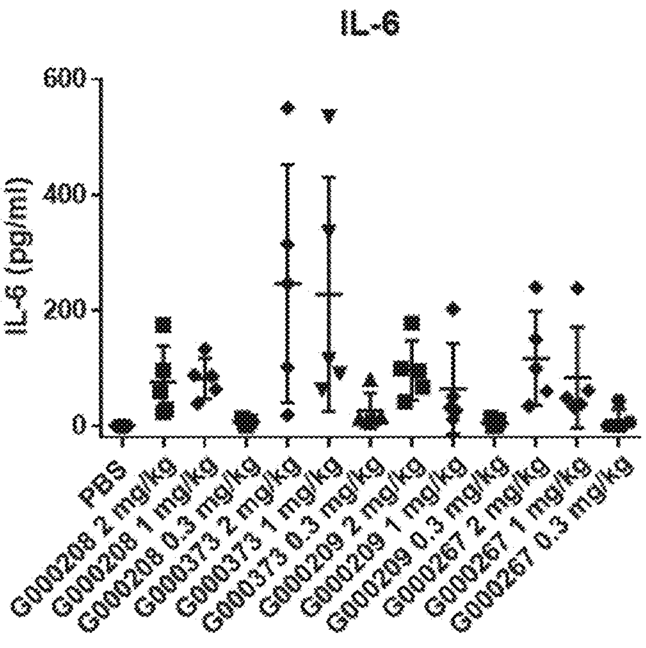
Figure 19D:
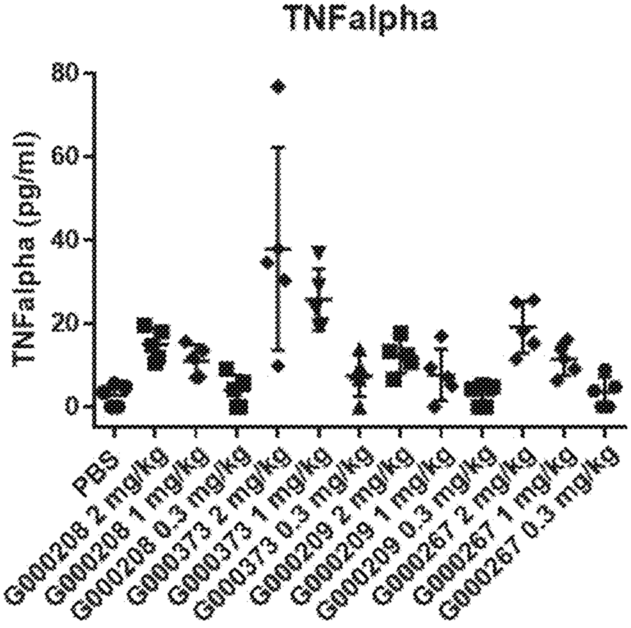

FIGS. 18A, 18B, and 18C show in vivo results following administration of LNPs comprising Cas9 mRNA and sgRNAs. FIG. 18A shows percentage of total editing in liver. FIG. 18B summarizes liver editing data. FIG. 18C shows serum TTR levels. MPK=milligrams per kilogram; BLOD=below level of detection.

FIGS. 19A, 19B, 19C, and 19D show interferon alpha (IFN-alpha, 19A), monocyte chemotactic protein 1 (MCP-1, 19B), interleukin 6 (IL-6, 19C), and tumor necrosis factor alpha (TNF-alpha, 19D) levels in serum after in vivo administration of LNPs comprising Cas9 mRNA and sgRNAs.

Figure 20A:
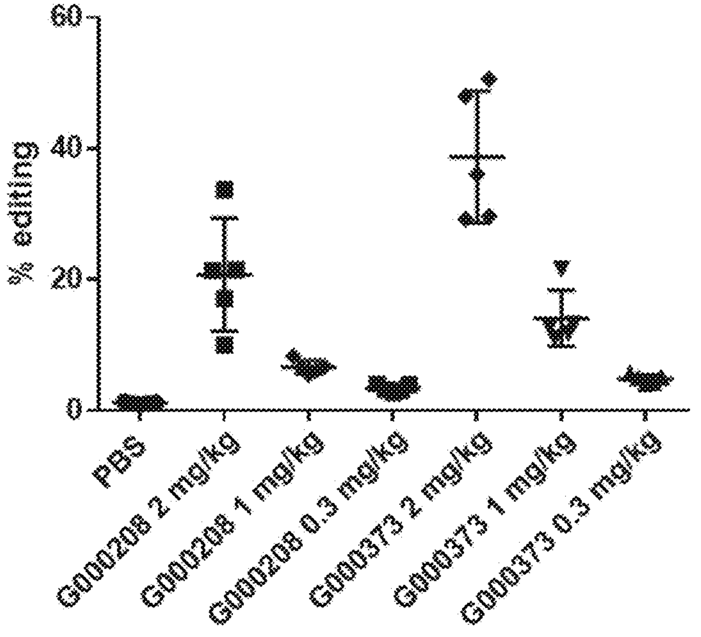
Figure 20B:
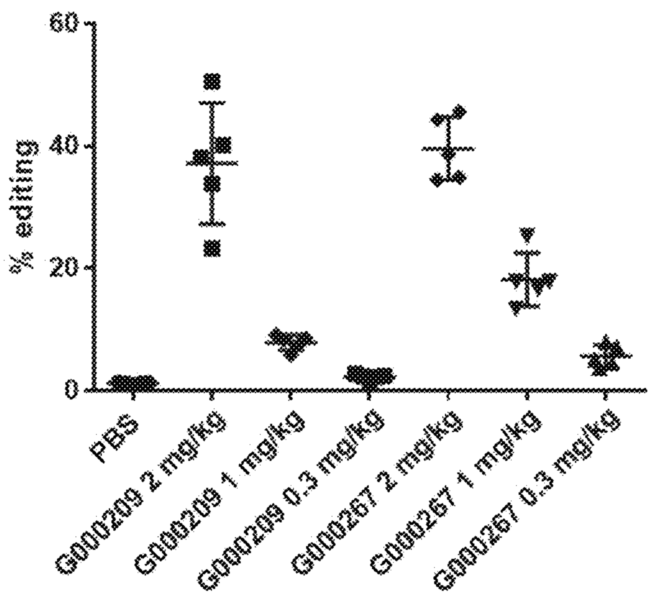

FIGS. 20A and 20B show editing in liver of FVII locus (FIG. 20A) and TTR locus (FIG. 20B) following in vivo administration of LNPs comprising Cas9 mRNA and sgRNAs.

Figure 21A:
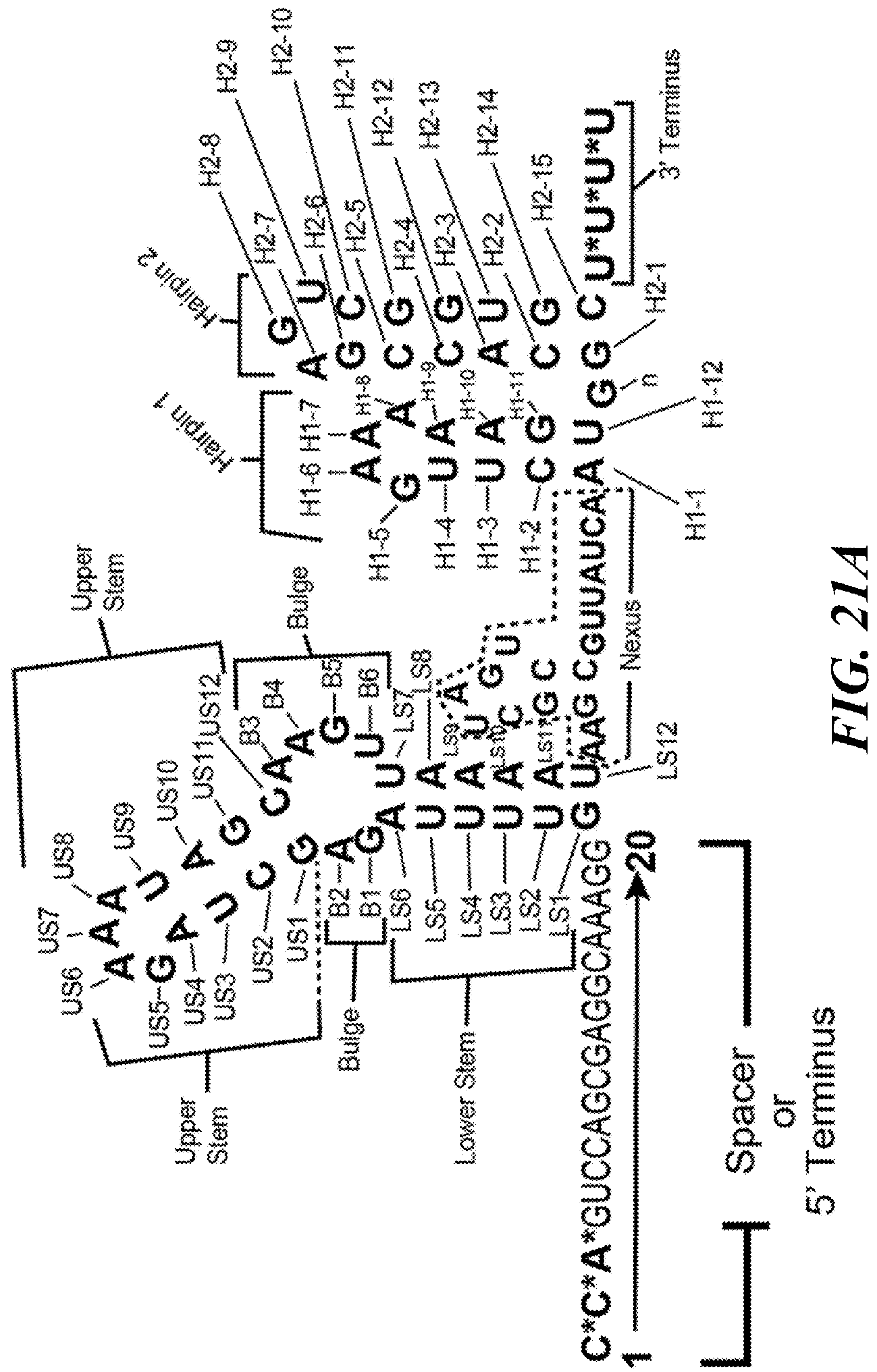
Figure 21B:
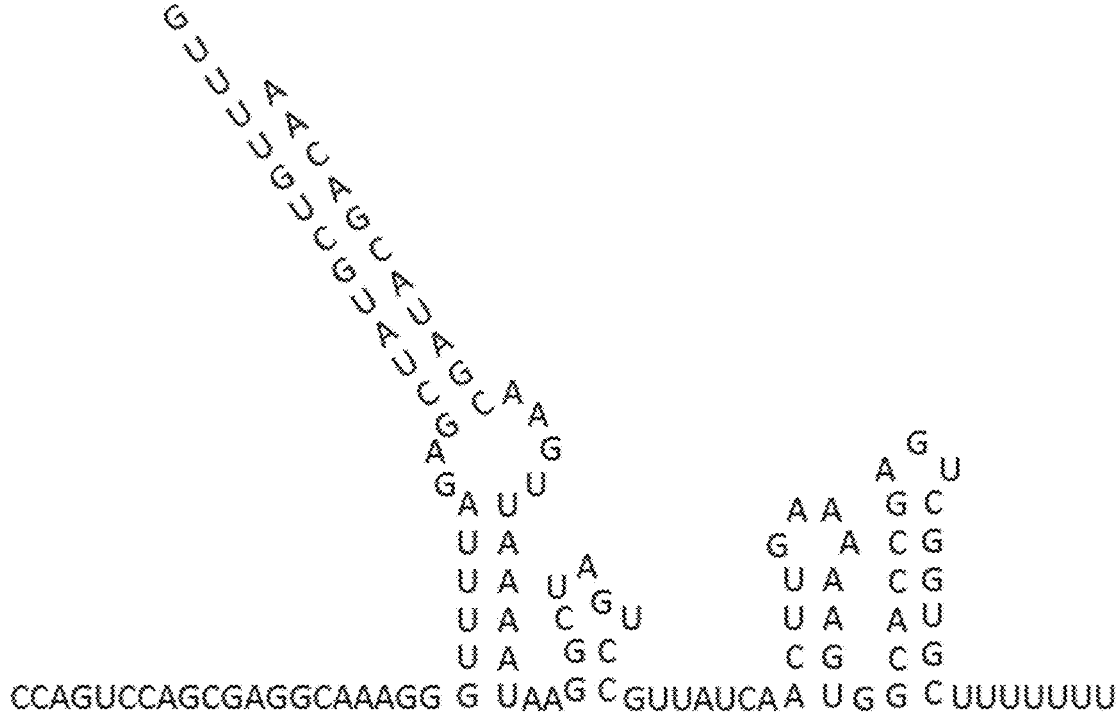
Figure 21C:
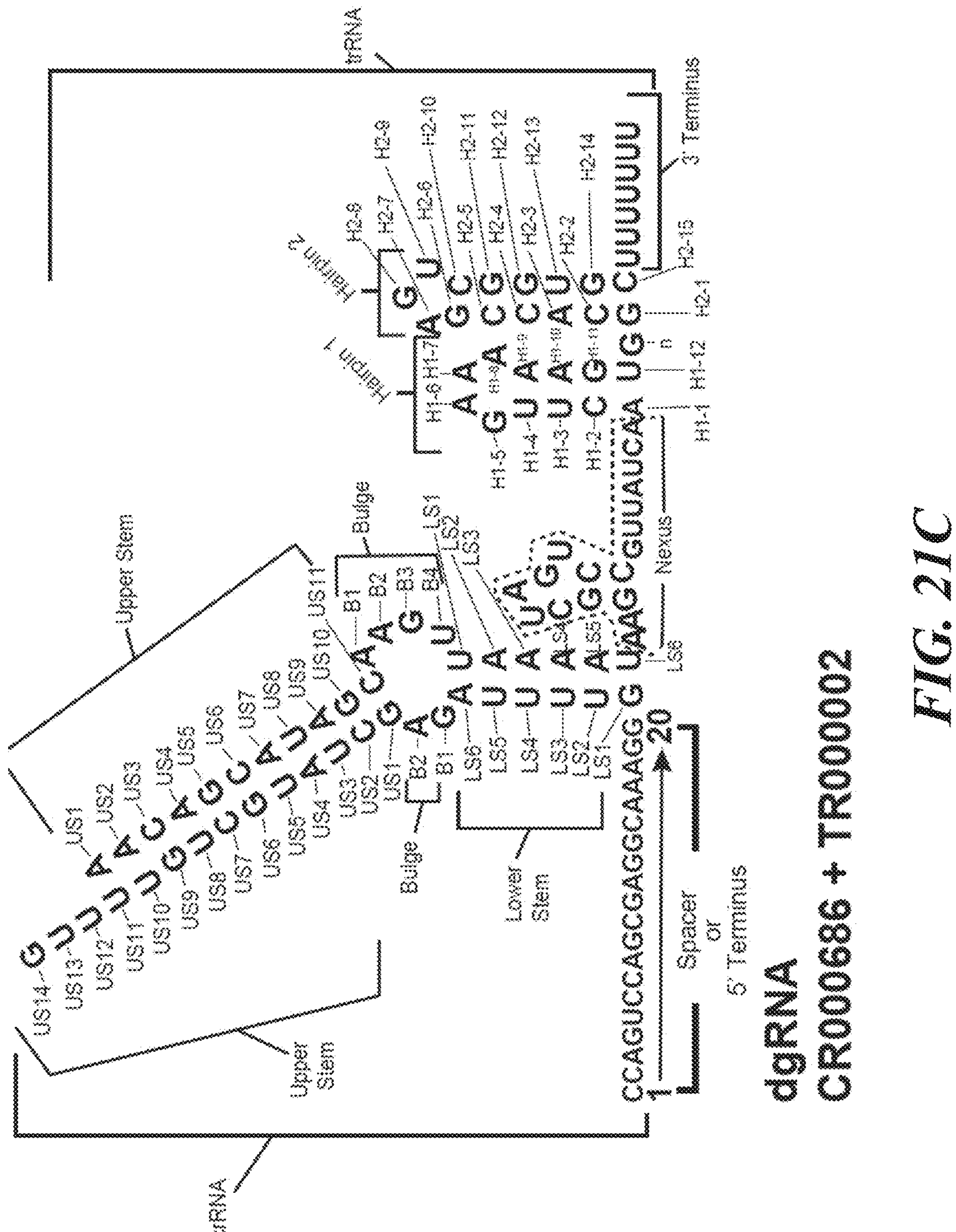

FIGS. 21A, 21B, and 21C show schematics of an annotated sgRNA (SEQ ID NO: 341) (FIG. 21A), non-annotated dgRNA CR000686 (SEQ ID NO: 1) and TR000002 (SEQ ID NO: 188) (FIG. 21B), and annotated dgRNA CR000686 (SEQ ID NO: 1) and TR000002 (SEQ ID NO: 188) (FIG. 21C).

Figure 22A:
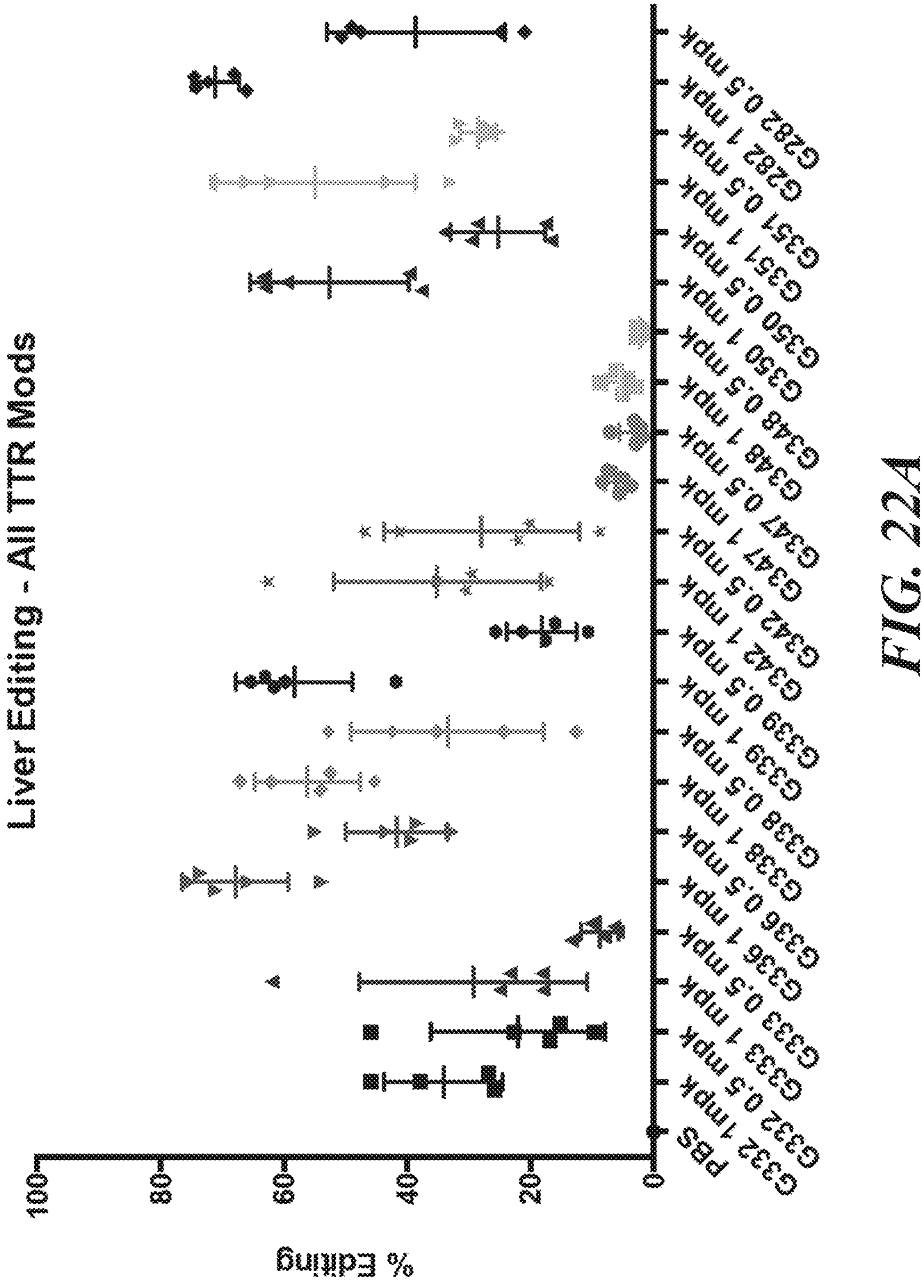
Figure 22C:
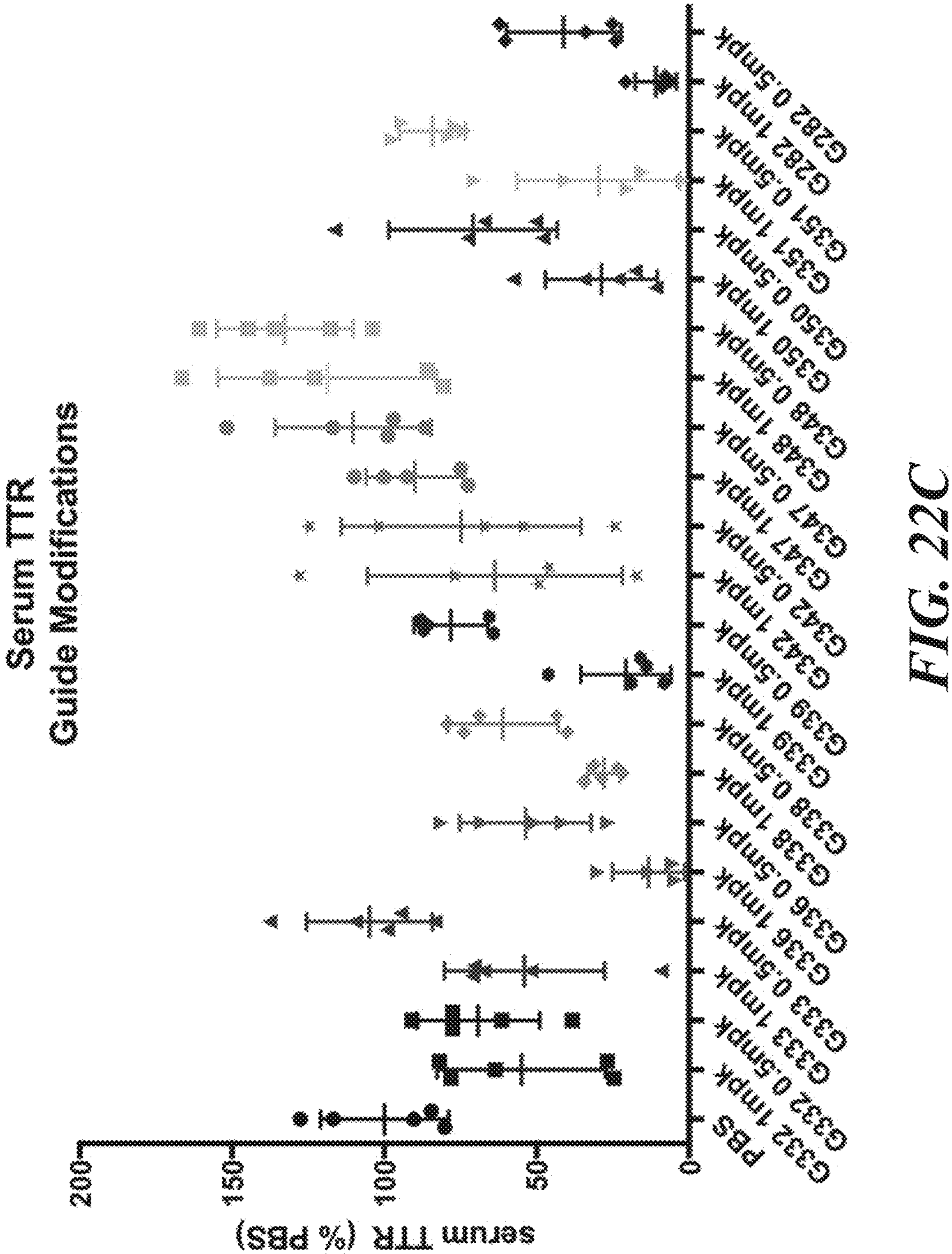

FIGS. 22A, 22B, and 22C show in vivo results following administration of LNPs comprising Cas9 mRNA and sgRNAs. FIG. 22A shows percentage of total editing of TTR locus in liver. FIG. 22B summarizes liver editing data. FIG. 22C shows serum TTR levels.

Figure 23A:
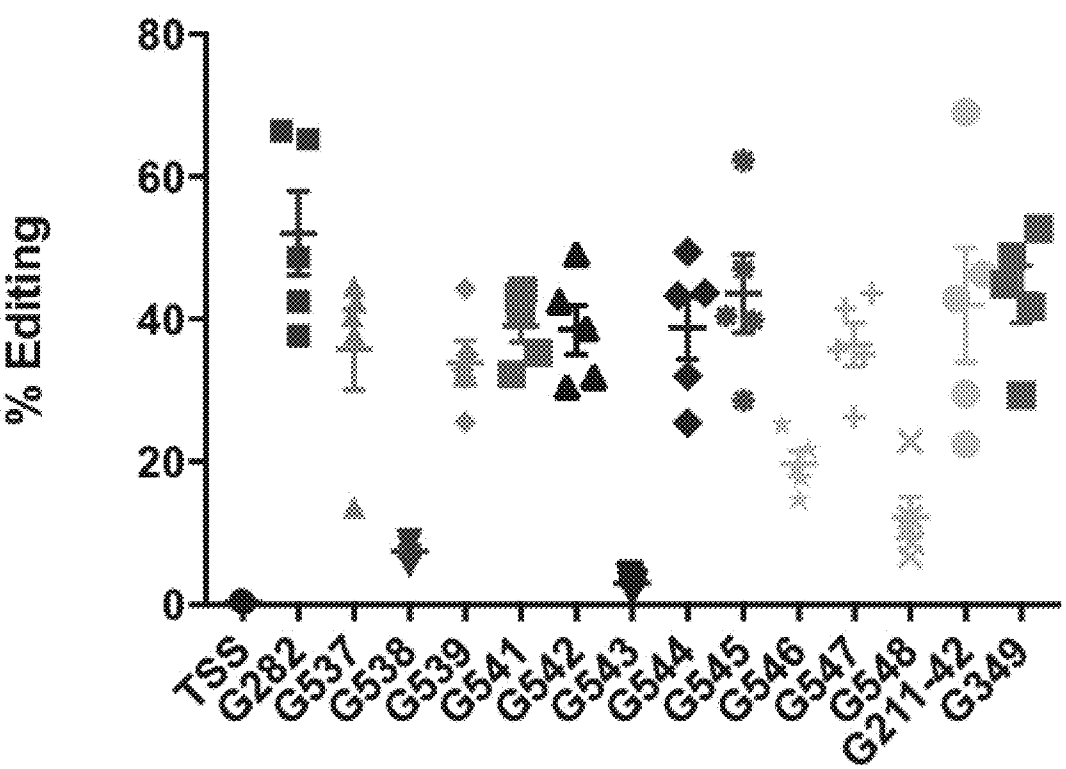
Figure 23C:
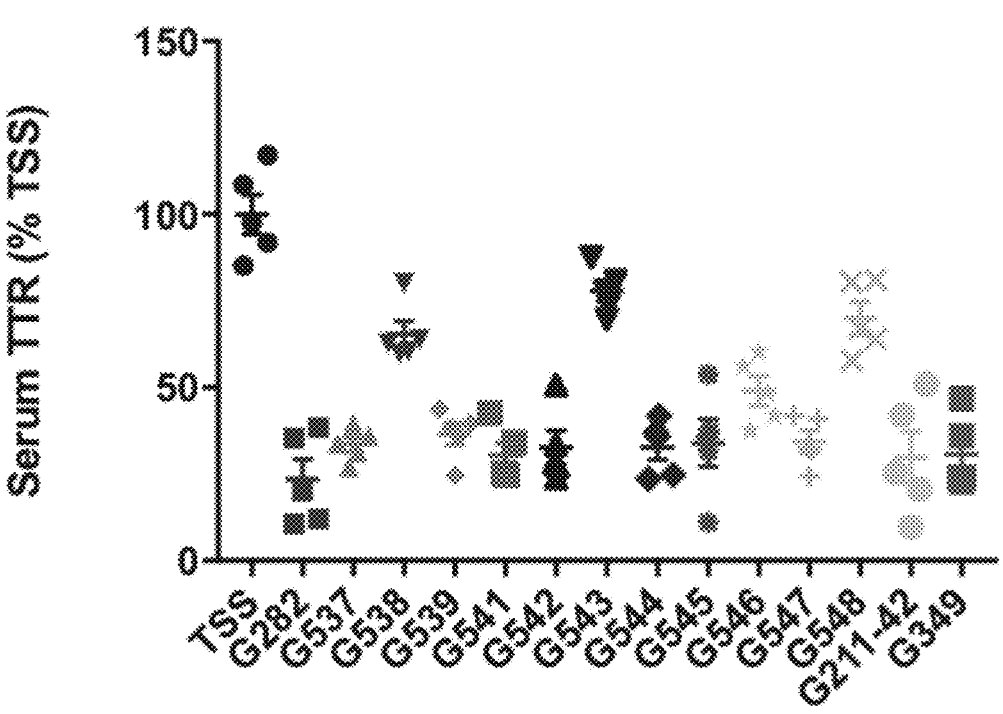

FIGS. 23A, 23B, and 23C show in vivo results following administration of LNPs comprising Cas9 mRNA and sgRNAs. FIG. 23A shows percentage of total editing of TTR locus in liver. FIG. 23B summarizes liver editing data. FIG. 23C shows serum TTR levels.

Figure 24A:
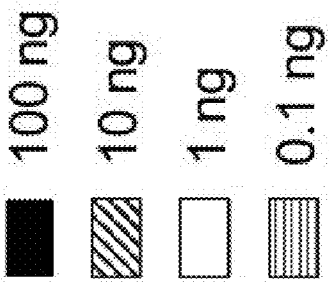
Figure 24A:
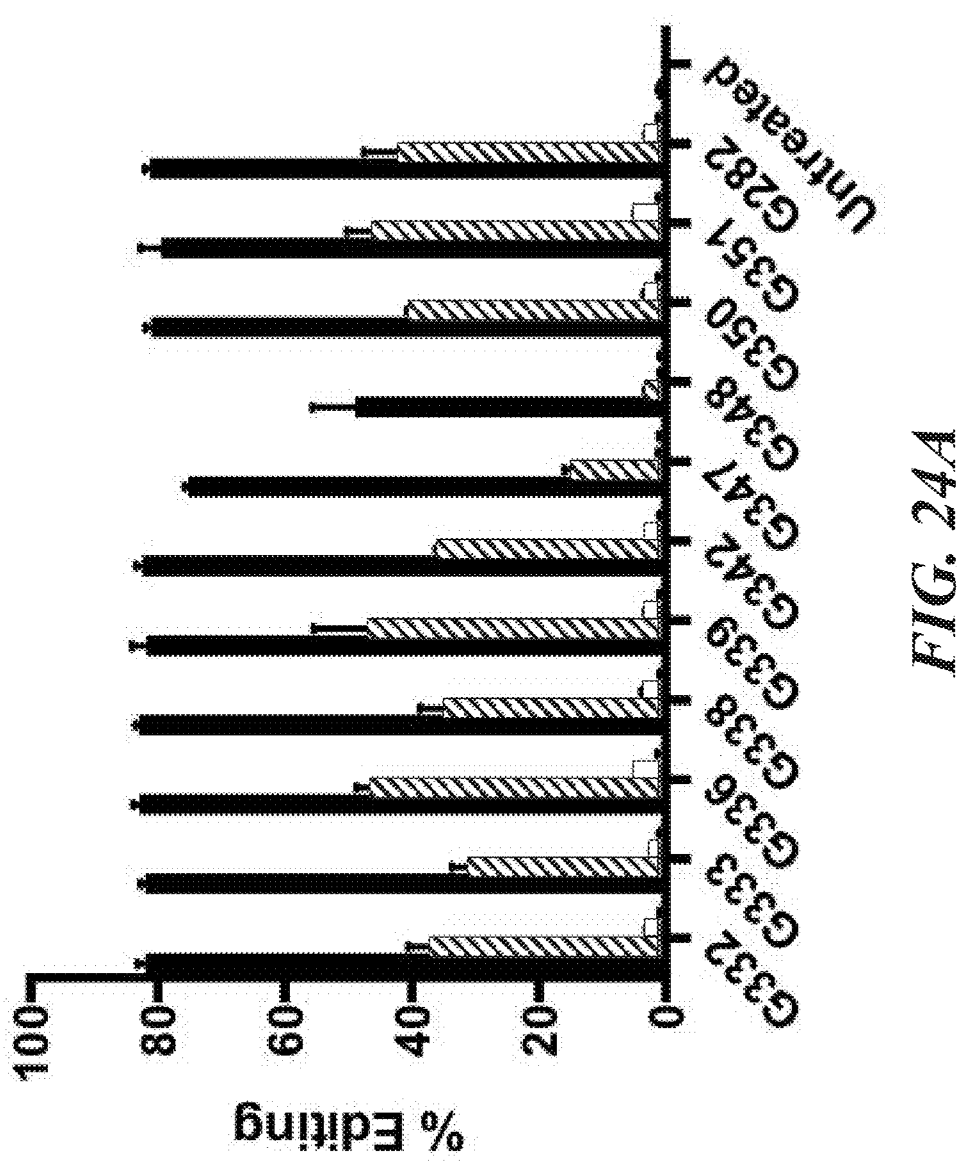
Figure 24B:
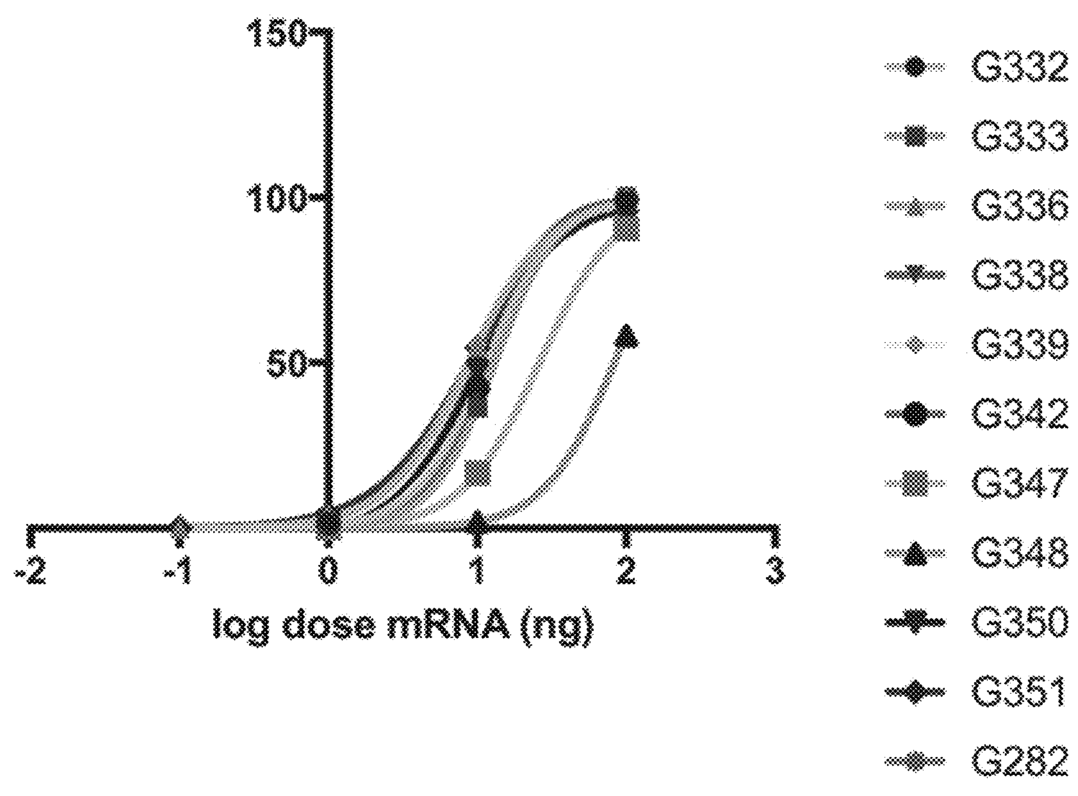

FIGS. 24A, 24B, and 24C show editing in primary mouse hepatocytes following administration of LNPs comprising Cas9 mRNA and sgRNAs. FIG. 24A shows editing percentage of total editing of TTR locus. FIG. 24B shows normalized transforms of editing percentage as a function of mRNA dose used to calculate EC50. FIG. 24C shows EC50 values for the LNPs tested.

DETAILED DESCRIPTION

Provided herein are modified guide RNAs, including dual and single guide RNAs for use in gene editing methods. The modified guides are more stable and show improved in vitro and in vivo efficacy as compared to their non-modified counterparts. Sequences of engineered and tested guide RNAs are shown in Table 4.

TABLE 4

| SEQ ID NO | Name | Alias | Description | Sequence |
|---|---|---|---|---|
| | crRNA | | | |
| 1 | CR000686 | | unmodified | CCAGUCCAGCGAGGCAAAGGGUUUUAGAGCUAUGCUGUUUUG |
| 2 | CR003393 | CR686-1 | upper | CCAGUCCAGCGAGGCAAAGGGUUUUAGAmGmCmUmAmUmGmCmUmGmUmUmUmUmG |
| 3 | CR003394 | CR686-2 | partial upper | CCAGUCCAGCGAGGCAAAGGGUUUUAGAGCUAmUmGmCmUmGmUmUmUmUmG |
| 4 | CR003395 | CR686-3 | partial upper | CCAGUCCAGCGAGGCAAAGGGUUUUAGAGCUAUGCmUmGmUmUmUmUmG |
| 5 | CR003396 | CR686-4 | partial upper | CCAGUCCAGCGAGGCAAAGGGUUUUAGAGCUAUGCUGUmUmUmUmG |
| 6 | CR003397 | CR686-5 | lower | CCAGUCCAGCGAGGCAAAGGmGmUmUmUmUmAGAGCUAUGCUGUUUUG |
| 7 | CR003398 | CR686-6 | lower walk | CCAGUCCAGCGAGGCAAAGGmGUUUUAGAGCUAUGCUGUUUUG |
| 8 | CR003399 | CR686-7 | lower walk | CCAGUCCAGCGAGGCAAAGGGmUUUUAGAGCUAUGCUGUUUUG |
| 9 | CR003400 | CR686-8 | lower walk | CCAGUCCAGCGAGGCAAAGGGUmUUUAGAGCUAUGCUGUUUUG |
| 10 | CR003401 | CR686-9 | lower walk | CCAGUCCAGCGAGGCAAAGGGUUmUUAGAGCUAUGCUGUUUUG |
| 11 | CR003402 | CR686-10 | lower walk | CCAGUCCAGCGAGGCAAAGGGUUUmUAGAGCUAUGCUGUUUUG |
| 12 | CR003403 | CR686-11 | lower walk | CCAGUCCAGCGAGGCAAAGGGUUUUmAGAGCUAUGCUGUUUUG |
| 13 | CR003404 | CR686-12 | partial lower | CCAGUCCAGCGAGGCAAAGGGmUmUmUmUAGAGCUAUGCUGUUUUG |
| 14 | CR003405 | CR686-13 | partial lower | CCAGUCCAGCGAGGCAAAGGGUmUmUUAGAGCUAUGCUGUUUUG |
| 15 | CR003406 | CR686-GC1 | Lower GC | CCAGUCCAGCGAGGCAAAGGGGCGCAGAGCUAUGCUGUUUUG |
| 16 | CR003407 | CR686-GC3 | Upper GC | CCAGUCCAGCGAGGCAAAGGGUUUUAGAGCUAUGCUGGCGCG |
| 17 | CR003408 | CR686-GC5 | Lower Upper GC | CCAGUCCAGCGAGGCAAAGGGGCGCAGAGCUAUGCUGGCGCG |
| 18 | CR003409 | CR686 all OMe | | mCmCmAmGmUmCmCmAmGmCmGmAmGmGmCmAmAmAmGmGmGmUmUmUmUmAmGmAmGmCmUmAmUmGmCmUmGmUmUmUmUmG |
| 19 | CR003393-mod only | | upper | GUUUUAGAmGmCmUmAmUmGmCmUmGmUmUmUmUmG |
| 20 | CR003394-mod only | | partial upper | GUUUUAGAGCUAmUmGmCmUmGmUmUmUmUmG |
| 21 | CR003395-mod only | | partial upper | GUUUUAGAGCUAUGCmUmGmUmUmUmUmG |

TABLE 4-continued

| SEQ ID NO | Name | Alias | Description | Sequence |
|---|---|---|---|---|
| 22 | CR003396-mod only | | partial upper | GUUUUAGAGCUAUGCUGUmUmUmUmG |
| 23 | CR003397-mod only | | lower | mGmUmUmUmUmAGAGCUAUGCUGUUUUG |
| 24 | CR003398-mod only | | lower walk | mGUUUUAGAGCUAUGCUGUUUUG |
| 25 | CR003399-mod only | | lower walk | GmUUUUAGAGCUAUGCUGUUUUG |
| 26 | CR003400-mod only | | lower walk | GUmUUUAGAGCUAUGCUGUUUUG |
| 27 | CR003401-mod only | | lower walk | GUUmUUAGAGCUAUGCUGUUUUG |
| 28 | CR003402-mod only | | lower walk | GUUUmUAGAGCUAUGCUGUUUUG |
| 29 | CR003403-mod only | | lower walk | GUUUUmAGAGCUAUGCUGUUUUG |
| 30 | CR003404-mod only | | partial lower | GmUmUmUmUAGAGCUAUGCUGUUUUG |
| 31 | CR003405-mod only | | partial lower | GUmUmUUAGAGCUAUGCUGUUUUG |
| 32 | CR003721 | CR686-14 | upper and lower | CCAGUCCAGCGAGGCAAAGGmGUUUmUmAGAmGmCmUmAmUmGmC mUmGmUmUmUmUmG |
| 33 | CR003722 | CR686-15 | lower combo | CCAGUCCAGCGAGGCAAAGGmGUUUmUmAGAGCUAUGCUGUUUUG |
| 34 | CR003723 | CR686-16 | upper, lower combo | CCAGUCCAGCGAGGCAAAGGmGUUUUmAGAmGmCmUmAmUmGmCm UmGmUmUmUmUmG |
| 35 | CR003724 | CR686-17 | lower combo | CCAGUCCAGCGAGGCAAAGGmGUUUUmAGAGCUAUGCUGUUUUG |
| 36 | CR003725 | CR686-18 | upper, lower combo | CCAGUCCAGCGAGGCAAAGGmGUUUUAGAmGmCmUmAmUmGmCmU mGmUmUmUmUmG |
| 37 | CR003726 | CR686-19 | nexus walk | CCAGUCCAGCGAGGCAAAGGGUUUUAmGAmGmCmUmAmUmGmCmU mGmUmUmUmUmG |
| 38 | CR003727 | CR686-20 | nexus walk | CCAGUCCAGCGAGGCAAAGGGUUUUAGmAmGmCmUmAmUmGmCmU mGmUmUmUmUmG |
| 39 | CR003728 | CR686-21 | nexus walk | CCAGUCCAGCGAGGCAAAGGGUUUUAfGAmGmCmUmAmUmGmCmUm GmUmUmUmUmG |
| 40 | CR003729 | CR686-22 | nexus walk | CCAGUCCAGCGAGGCAAAGGGUUUUAGfAmGmCmUmAmUmGmCmUm GmUmUmUmUmG |
| 41 | CR003730 | CR686-23 | 2'F lower walk | CCAGUCCAGCGAGGCAAAGGGfUUUUAGAmGmCmUmAmUmGmCmUm GmUmUmUmUmG |
| 42 | CR003731 | CR686-24 | 2'F lower walk | CCAGUCCAGCGAGGCAAAGGGUfUUUAGAmGmCmUmAmUmGmCmUm GmUmUmUmUmG |
| 43 | CR003732 | CR686-25 | 2'F lower walk | CCAGUCCAGCGAGGCAAAGGGUUfUUAGAmGmCmUmAmUmGmCmUm GmUmUmUmUmG |
| 44 | CR003733 | CR686-26 | 2'F lower walk | CCAGUCCAGCGAGGCAAAGGGUUUfUAGAmGmCmUmAmUmGmCmUm GmUmUmUmUmG |
| 45 | CR003734 | CR686-27 | 2'F lower combo | CCAGUCCAGCGAGGCAAAGGfGfUfUfUfUfAGAmGmCmUmAmUmGmCm UmGmUmUmUmUmG |
| 46 | CR003735 | CR686-28 | lower alt | CCAGUCCAGCGAGGCAAAGGfGmUfUmUfUmAGAmGmCmUmAmUmG mCmUmGmUmUmUmUmG |
| 47 | CR003736 | CR686-29 | lower alt | CCAGUCCAGCGAGGCAAAGGmGfUmUfUmUfAGAmGmCmUmAmUmG mCmUmGmUmUmUmUmG |

TABLE 4-continued

| SEQ ID NO | Name | Alias | Description | Sequence |
|---|---|---|---|---|
| 48 | CR003737 | CR686-GC6 | Lower GC | CCAGUCCAGCGAGGCAAAGGGUCUCAGAmGmCmUmAmUmGmCmUmGmUmUmUmUmG |
| 49 | CR003738 | CR686-GC7 | Lower C walk | CCAGUCCAGCGAGGCAAAGGGCUUUAGAmGmCmUmAmUmGmCmUmGmUmUmUmUmG |
| 50 | CR003739 | CR686-GC8 | Lower C walk | CCAGUCCAGCGAGGCAAAGGGUCUUAGAmGmCmUmAmUmGmCmUmGmUmUmUmUmG |
| 51 | CR003740 | CR686-GC9 | Lower C walk | CCAGUCCAGCGAGGCAAAGGGUUCUAGAmGmCmUmAmUmGmCmUmGmUmUmUmUmG |
| 52 | CR003741 | CR686-GC10 | Lower C walk | CCAGUCCAGCGAGGCAAAGGGUUUCAGAmGmCmUmAmUmGmCmUmGmUmUmUmUmG |
| 53 | CR003721-mod only | CR686-14-mod only | upper and lower | mGUUUmUmAGAmGmCmUmAmUmGmCmUmGmUmUmUmUmG |
| 54 | CR003722-mod only | CR686-15-mod only | lower combo | mGUUUmUmAGAGCUAUGCUGUUUUG |
| 55 | CR003723-mod only | CR686-16-mod only | upper, lower combo | mGUUUUmAGAmGmCmUmAmUmGmCmUmGmUmUmUmUmG |
| 56 | CR003724-mod only | CR686-17-mod only | lower combo | mGUUUUmAGAGCUAUGCUGUUUUG |
| 57 | CR003725-mod only | CR686-18-mod only | upper, lower combo | mGUUUUAGAmGmCmUmAmUmGmCmUmGmUmUmUmUmG |
| 58 | CR003726-mod only | CR686-19-mod only | nexus walk | GUUUUAmGAmGmCmUmAmUmGmCmUmGmUmUmUmUmG |
| 59 | CR003727-mod only | CR686-20-mod only | nexus walk | GUUUUAGmAmGmCmUmAmUmGmCmUmGmUmUmUmUmG |
| 60 | CR003728-mod only | CR686-21-mod only | nexus walk | GUUUUAfGAmGmCmUmAmUmGmCmUmGmUmUmUmUmG |
| 61 | CR003729-mod only | CR686-22-mod only | nexus walk | GUUUUAGfAmGmCmUmAmUmGmCmUmGmUmUmUmUmG |
| 62 | CR003730-mod only | CR686-23-mod only | 2'F lower walk | GfUUUUAGAmGmCmUmAmUmGmCmUmGmUmUmUmUmG |
| 63 | CR003731-mod only | CR686-24-mod only | 2'F lower walk | GUfUUUAGAmGmCmUmAmUmGmCmUmGmUmUmUmUmG |
| 64 | CR003732-mod only | CR686-25-mod only | 2'F lower walk | GUUfUUAGAmGmCmUmAmUmGmCmUmGmUmUmUmUmG |
| 65 | CR003733-mod only | CR686-26-mod only | 2'F lower walk | GUUUfUAGAmGmCmUmAmUmGmCmUmGmUmUmUmUmG |
| 66 | CR003734-mod only | CR686-27-mod only | 2'F lower combo | fGfUfUfUfUfAGAmGmCmUmAmUmGmCmUmGmUmUmUmUmG |
| 67 | CR003735-mod only | CR686-28-mod only | lower alt | fGmUfUmUfUmAGAmGmCmUmAmUmGmCmUmGmUmUmUmUmG |
| 68 | CR003736-mod only | CR686-29-mod only | lower alt | mGfUmUfUmUfAGAmGmCmUmAmUmGmCmUmGmUmUmUmUmG |
| 69 | CR003737-mod only | CR686-GC6-mod only | Lower GC | GUCUCAGAmGmCmUmAmUmGmCmUmGmUmUmUmUmG |
| 70 | CR003738-mod only | CR686-GC7-mod only | Lower C walk | GCUUUAGAmGmCmUmAmUmGmCmUmGmUmUmUmUmG |
| 71 | CR003739-mod only | CR686-GC8-mod only | Lower C walk | GUCUUAGAmGmCmUmAmUmGmCmUmGmUmUmUmUmG |
| 72 | CR003740-mod only | CR686-GC9-mod only | Lower C walk | GUUCUAGAmGmCmUmAmUmGmCmUmGmUmUmUmUmG |

TABLE 4-continued

| SEQ ID NO | Name | Alias | Description | Sequence |
|---|---|---|---|---|
| 73 | CR003741-mod only | CR686-GC10-mod only | Lower C walk | GUUUCAGAmGmCmUmAmUmGmCmUmGmUmUmUmUmG |
| 74 | CR000705 | | unmodified | UUACAGCCACGUCUACAGCAGUUUUAGAGCUAUGCUGUUUUG |
| 75 | CR004188 | CR705-1 | upper | UUACAGCCACGUCUACAGCAGUUUUAGAmGmCmUmAmUmGmCmUmGmUmUmUmUmG |
| 76 | CR004189 | CR705-2 | partial upper | UUACAGCCACGUCUACAGCAGUUUUAGAGCUAmUmGmCmUmGmUmUmUmUmG |
| 77 | CR004190 | CR705-3 | partial upper | UUACAGCCACGUCUACAGCAGUUUUAGAGCUAUGCmUmGmUmUmUmUmG |
| 78 | CR004191 | CR705-4 | partial upper | UUACAGCCACGUCUACAGCAGUUUUAGAGCUAUGCUGUmUmUmUmG |
| 79 | CR004192 | CR705-5 | lower | UUACAGCCACGUCUACAGCAmGmUmUmUmUmAGAGCUAUGCUGUUUUG |
| 80 | CR004193 | CR705-6 | lower walk | UUACAGCCACGUCUACAGCAmGUUUUAGAGCUAUGCUGUUUUG |
| 81 | CR004194 | CR705-7 | lower walk | UUACAGCCACGUCUACAGCAGmUUUUAGAGCUAUGCUGUUUUG |
| 82 | CR004195 | CR705-8 | lower walk | UUACAGCCACGUCUACAGCAGUmUUUAGAGCUAUGCUGUUUUG |
| 83 | CR004196 | CR705-9 | lower walk | UUACAGCCACGUCUACAGCAGUUmUUAGAGCUAUGCUGUUUUG |
| 84 | CR004197 | CR705-10 | lower walk | UUACAGCCACGUCUACAGCAGUUUmUAGAGCUAUGCUGUUUUG |
| 85 | CR004198 | CR705-11 | lower walk | UUACAGCCACGUCUACAGCAGUUUUmAGAGCUAUGCUGUUUUG |
| 86 | CR004199 | CR705-14 | upper and lower | UUACAGCCACGUCUACAGCAmGUUUmUmAGAmGmCmUmAmUmGmCmUmGmUmUmUmUmG |
| 87 | CR004200 | CR705-15 | lower combo | UUACAGCCACGUCUACAGCAmGUUUmUmAGAGCUAUGCUGUUUUG |
| 88 | CR004201 | CR705-16 | upper, lower combo | UUACAGCCACGUCUACAGCAmGUUUUmAGAmGmCmUmAmUmGmCmUmGmUmUmUmUmG |
| 89 | CR004202 | CR705-17 | lower combo | UUACAGCCACGUCUACAGCAmGUUUUmAGAGCUAUGCUGUUUUG |
| 90 | CR004203 | CR705-18 | upper, lower combo | UUACAGCCACGUCUACAGCAmGUUUUAGAmGmCmUmAmUmGmCmUmGmUmUmUmUmG |
| 91 | CR004204 | CR705-19 | nexus walk | UUACAGCCACGUCUACAGCAGUUUUAmGAmGmCmUmAmUmGmCmUmGmUmUmUmUmG |
| 92 | CR004205 | CR705-20 | nexus walk | UUACAGCCACGUCUACAGCAGUUUUAGmAmGmCmUmAmUmGmCmUmGmUmUmUmUmG |
| 93 | CR004206 | CR705-21 | nexus walk | UUACAGCCACGUCUACAGCAGUUUUAfGAmGmCmUmAmUmGmCmUmGmUmUmUmUmG |
| 94 | CR004207 | CR705-22 | nexus walk | UUACAGCCACGUCUACAGCAGUUUUAGfAmGmCmUmAmUmGmCmUmGmUmUmUmUmG |
| 95 | CR004208 | CR705-23 | 2'F lower walk | UUACAGCCACGUCUACAGCAGfUUUUAGAmGmCmUmAmUmGmCmUmGmUmUmUmUmG |
| 96 | CR004209 | CR705-24 | 2'F lower walk | UUACAGCCACGUCUACAGCAGUfUUUAGAmGmCmUmAmUmGmCmUmGmUmUmUmUmG |
| 97 | CR004210 | CR705-25 | 2'F lower walk | UUACAGCCACGUCUACAGCAGUUfUUAGAmGmCmUmAmUmGmCmUmGmUmUmUmUmG |
| 98 | CR004211 | CR705-26 | 2'F lower walk | UUACAGCCACGUCUACAGCAGUUUfUAGAmGmCmUmAmUmGmCmUmGmUmUmUmUmG |
| 99 | CR004212 | CR705-27 | 2'F lower combo | UUACAGCCACGUCUACAGCAfGfUfUfUfUfAGAmGmCmUmAmUmGmCmUmGmUmUmUmUmG |
| 100 | CR004213 | CR705-28 | lower alt | UUACAGCCACGUCUACAGCAfGmUfUmUfUmAGAmGmCmUmAmUmGmCmUmGmUmUmUmUmG |
| 101 | CR004214 | CR705-29 | lower alt | UUACAGCCACGUCUACAGCAmGfUmUfUmUfAGAmGmCmUmAmUmGmCmUmGmUmUmUmUmG |

TABLE 4-continued

| SEQ ID NO | Name | Alias | Description | Sequence |
|---|---|---|---|---|
| 102 | CR004215 | CR705-GC1 | Lower GC | UUACAGCCACGUCUACAGCAGGCGCAGAGCUAUGCUGUUUUG |
| 103 | CR004216 | CR705-GC3 | Upper GC | UUACAGCCACGUCUACAGCAGUUUUAGAGCUAUGCUGGCGCG |
| 104 | CR004188-mod only | CR705-1-mod only | upper | GUUUUAGAmGmCmUmAmUmGmCmUmGmUmUmUmUmG |
| 105 | CR004189-mod only | CR705-2-mod only | partial upper | GUUUUAGAGCUAmUmGmCmUmGmUmUmUmUmG |
| 106 | CR004190-mod only | CR705-3-mod only | partial upper | GUUUUAGAGCUAUGCmUmGmUmUmUmUmG |
| 107 | CR004191-mod only | CR705-4-mod only | partial upper | GUUUUAGAGCUAUGCUGUmUmUmUmG |
| 108 | CR004192-mod only | CR705-5-mod only | lower | mGmUmUmUmUmAGAGCUAUGCUGUUUUG |
| 109 | CR004193-mod only | CR705-6-mod only | lower walk | mGUUUUAGAGCUAUGCUGUUUUG |
| 110 | CR004194-mod only | CR705-7-mod only | lower walk | GmUUUUAGAGCUAUGCUGUUUUG |
| 111 | CR004195-mod only-mod only | CR705-8-mod only | lower walk | GUmUUUAGAGCUAUGCUGUUUUG |
| 112 | CR004196-mod only | CR705-9-mod only | lower walk | GUUmUUAGAGCUAUGCUGUUUUG |
| 113 | CR004197-mod only | CR705-10-mod only | lower walk | GUUUmUAGAGCUAUGCUGUUUUG |
| 114 | CR004198-mod only | CR705-11-mod only | lower walk | GUUUUmAGAGCUAUGCUGUUUUG |
| 115 | CR004199-mod only | CR705-14-mod only | upper and lower | mGUUUmUmAGAmGmCmUmAmUmGmCmUmGmUmUmUmUmG |
| 116 | CR004200-mod only | CR705-15-mod only | lower combo | mGUUUmUmAGAGCUAUGCUGUUUUG |
| 117 | CR004201-mod only | CR705-16-mod only | upper, lower combo | mGUUUUmAGAmGmCmUmAmUmGmCmUmGmUmUmUmUmG |
| 118 | CR004202-mod only | CR705-17-mod only | lower combo | mGUUUUmAGAGCUAUGCUGUUUUG |
| 119 | CR004203-mod only | CR705-18-mod only | upper, lower combo | mGUUUUAGAmGmCmUmAmUmGmCmUmGmUmUmUmUmG |
| 120 | CR004204-mod only | CR705-19-mod only | nexus walk | GUUUUAmGAmGmCmUmAmUmGmCmUmGmUmUmUmUmG |
| 121 | CR004205-mod only | CR705-20-mod only | nexus walk | GUUUUAGmAmGmCmUmAmUmGmCmUmGmUmUmUmUmG |
| 122 | CR004206-mod only | CR705-21-mod only | nexus walk | GAmGmCmUmAmUmGmCmUmGmUmUmUmUmG |
| 123 | CR004207-mod only | CR705-22-mod only | nexus walk | GfAmGmCmUmAmUmGmCmUmGmUmUmUmUmG |
| 124 | CR004208-mod only | CR705-23-mod only | 2'F lower walk | GfUUUUAGAmGmCmUmAmUmGmCmUmGmUmUmUmUmG |
| 125 | CR004209-mod only | CR705-24-mod only | 2'F lower walk | GUfUUUAGAmGmCmUmAmUmGmCmUmGmUmUmUmUmG |
| 126 | CR004210-mod only | CR705-25-mod only | 2'F lower walk | GUUfUUAGAmGmCmUmAmUmGmCmUmGmUmUmUmUmG |

TABLE 4-continued

| SEQ ID NO | Name | Alias | Description | Sequence |
|---|---|---|---|---|
| 127 | CR004211-mod only | CR705-26-mod only | 2'F lower walk | GUUUfUAGAmGmCmUmAmUmGmCmUmGmUmUmUmUmG |
| 128 | CR004212-mod only | CR705-27-mod only | 2'F lower combo | fGfUfUfUfUfAGAmGmCmUmAmUmGmCmUmGmUmUmUmUmG |
| 129 | CR004213-mod only | CR705-28-mod only | lower alt | fGmUfUmUfUmAGAmGmCmUmAmUmGmCmUmGmUmUmUmUmG |
| 130 | CR004214-mod only | CR705-29-mod only | lower alt | mGfUmUfUmUfAGAmGmCmUmAmUmGmCmUmGmUmUmUmUmG |
| 131 | CR000657 | | unmodified | CAGGGCUCUUGAAGAUCUCCGUUUUAGAGCUAUGCUGUUUUG |
| 132 | CR004218 | CR657-1 | upper | CAGGGCUCUUGAAGAUCUCCGUUUUAGAmGmCmUmAmUmGmCmUmGmUmUmUmUmG |
| 133 | CR004219 | CR657-2 | partial upper | CAGGGCUCUUGAAGAUCUCCGUUUUAGAGCUAmUmGmCmUmGmUmUmUmUmG |
| 134 | CR004220 | CR657-3 | partial upper | CAGGGCUCUUGAAGAUCUCCGUUUUAGAGCUAUGCmUmGmUmUmUmUmG |
| 135 | CR004221 | CR657-4 | partial upper | CAGGGCUCUUGAAGAUCUCCGUUUUAGAGCUAUGCUGUmUmUmUmG |
| 136 | CR004222 | CR657-5 | lower | CAGGGCUCUUGAAGAUCUCCmGmUmUmUmUmAGAGCUAUGCUGUUUUG |
| 137 | CR004223 | CR657-6 | lower walk | CAGGGCUCUUGAAGAUCUCCmGUUUUAGAGCUAUGCUGUUUUG |
| 138 | CR004224 | CR657-7 | lower walk | CAGGGCUCUUGAAGAUCUCCGmUUUUAGAGCUAUGCUGUUUUG |
| 139 | CR004225 | CR657-8 | lower walk | CAGGGCUCUUGAAGAUCUCCGUmUUUAGAGCUAUGCUGUUUUG |
| 140 | CR004226 | CR657-9 | lower walk | CAGGGCUCUUGAAGAUCUCCGUUmUUAGAGCUAUGCUGUUUUG |
| 141 | CR004227 | CR657-10 | lower walk | CAGGGCUCUUGAAGAUCUCCGUUUmUAGAGCUAUGCUGUUUUG |
| 142 | CR004228 | CR657-11 | lower walk | CAGGGCUCUUGAAGAUCUCCGUUUUmAGAGCUAUGCUGUUUUG |
| 143 | CR004229 | CR657-14 | upper and lower | CAGGGCUCUUGAAGAUCUCCmGUUUmUmAGAmGmCmUmAmUmGmCmUmGmUmUmUmUmG |
| 144 | CR004230 | CR657-15 | lower combo | CAGGGCUCUUGAAGAUCUCCmGUUUmUmAGAGCUAUGCUGUUUUG |
| 145 | CR004231 | CR657-16 | upper, lower combo | CAGGGCUCUUGAAGAUCUCCmGUUUUmAGAmGmCmUmAmUmGmCmUmGmUmUmUmUmG |
| 146 | CR004232 | CR657-17 | lower combo | CAGGGCUCUUGAAGAUCUCCmGUUUUmAGAGCUAUGCUGUUUUG |
| 147 | CR004233 | CR657-18 | upper, lower combo | CAGGGCUCUUGAAGAUCUCCmGUUUUAGAmGmCmUmAmUmGmCmUmGmUmUmUmUmG |
| 148 | CR004234 | CR657-19 | nexus walk | CAGGGCUCUUGAAGAUCUCCGUUUUAmGAmGmCmUmAmUmGmCmUmGmUmUmUmUmG |
| 149 | CR004235 | CR657-20 | nexus walk | CAGGGCUCUUGAAGAUCUCCGUUUUAGmAmGmCmUmAmUmGmCmUmGmUmUmUmUmG |
| 150 | CR004236 | CR657-21 | nexus walk | CAGGGCUCUUGAAGAUCUCCGUUUUAfGAmGmCmUmAmUmGmCmUmGmUmUmUmUmG |
| 151 | CR004237 | CR657-22 | nexus walk | CAGGGCUCUUGAAGAUCUCCGUUUUAGfAmGmCmUmAmUmGmCmUmGmUmUmUmUmG |
| 152 | CR004238 | CR657-23 | 2'F lower walk | CAGGGCUCUUGAAGAUCUCCGfUUUUAGAmGmCmUmAmUmGmCmUmGmUmUmUmUmG |
| 153 | CR004239 | CR657-24 | 2'F lower walk | CAGGGCUCUUGAAGAUCUCCGUfUUUAGAmGmCmUmAmUmGmCmUmGmUmUmUmUmG |
| 154 | CR004240 | CR657-25 | 2'F lower walk | CAGGGCUCUUGAAGAUCUCCGUUfUUAGAmGmCmUmAmUmGmCmUmGmUmUmUmUmG |

TABLE 4-continued

| SEQ ID NO | Name | Alias | Description | Sequence |
|---|---|---|---|---|
| 155 | CR004241 | CR657-26 | 2'F lower walk | CAGGGCUCUUGAAGAUCUCCGUUUfUAGAmGmCmUmAmUmGmCmUmGmUmUmUmUmG |
| 156 | CR004242 | CR657-27 | 2'F lower combo | CAGGGCUCUUGAAGAUCUCCfGfUfUfUfUfAGAmGmCmUmAmUmGmCmUmGmUmUmUmUmG |
| 157 | CR004243 | CR657-28 | lower alt | CAGGGCUCUUGAAGAUCUCCfGmUfUmUfUmAGAmGmCmUmAmUmGmCmUmGmUmUmUmUmG |
| 158 | CR004244 | CR657-29 | lower alt | CAGGGCUCUUGAAGAUCUCCmGfUmUfUmUfAGAmGmCmUmAmUmGmCmUmGmUmUmUmUmG |
| 159 | CR004245 | CR657-GC1 | Lower GC | CAGGGCUCUUGAAGAUCUCCGGCGCAGAGCUAUGCUGUUUUG |
| 160 | CR004246 | CR657-GC3 | Upper GC | CAGGGCUCUUGAAGAUCUCCGUUUUAGAGCUAUGCUGGCGCG |
| 161 | CR004218-mod only | CR657-1-mod only | upper | GUUUUAGAmGmCmUmAmUmGmCmUmGmUmUmUmUmG |
| 162 | CR004219-mod only | CR657-2-mod only | partial upper | GUUUUAGAGCUAmUmGmCmUmGmUmUmUmUmG |
| 163 | CR004220-mod only | CR657-3-mod only | partial upper | GUUUUAGAGCUAUGCmUmGmUmUmUmUmG |
| 164 | CR004221-mod only | CR657-4-mod only | partial upper | GUUUUAGAGCUAUGCUGUmUmUmUmG |
| 165 | CR004222-mod only | CR657-5-mod only | lower | mGmUmUmUmUmAGAGCUAUGCUGUUUUG |
| 166 | CR004223-mod only | CR657-6-mod only | lower walk | mGUUUUAGAGCUAUGCUGUUUUG |
| 167 | CR004224-mod only | CR657-7-mod only | lower walk | GmUUUUAGAGCUAUGCUGUUUUG |
| 168 | CR004225-mod only | CR657-8-mod only | lower walk | GUmUUUAGAGCUAUGCUGUUUUG |
| 169 | CR004226-mod only | CR657-9-mod only | lower walk | GUUmUUAGAGCUAUGCUGUUUUG |
| 170 | CR004227-mod only | CR657-10-mod only | lower walk | GUUUmUAGAGCUAUGCUGUUUUG |
| 171 | CR004228-mod only | CR657-11-mod only | lower walk | GUUUUmAGAGCUAUGCUGUUUUG |
| 172 | CR004229-mod only | CR657-14-mod only | upper and lower | mGUUUmUmAGAmGmCmUmAmUmGmCmUmGmUmUmUmUmG |
| 173 | CR004230-mod only | CR657-15-mod only | lower combo | mGUUUmUmAGAGCUAUGCUGUUUUG |
| 174 | CR004231-mod only | CR657-16-mod only | upper, lower combo | mGUUUUmAGAmGmCmUmAmUmGmCmUmGmUmUmUmUmG |
| 175 | CR004232-mod only | CR657-17-mod only | lower combo | mGUUUUmAGAGCUAUGCUGUUUUG |
| 176 | CR004233-mod only | CR657-18-mod only | upper, lower combo | mGUUUUAGAmGmCmUmAmUmGmCmUmGmUmUmUmUmG |
| 177 | CR004234-mod only | CR657-19-mod only | nexus walk | GUUUUAmGAmGmCmUmAmUmGmCmUmGmUmUmUmUmG |
| 178 | CR004235-mod only | CR657-20-mod only | nexus walk | GUUUUAGmAmGmCmUmAmUmGmCmUmGmUmUmUmUmG |
| 179 | CR004236-mod only | CR657-21-mod only | nexus walk | GUUUUAfGAmGmCmUmAmUmGmCmUmGmUmUmUmUmG |
| 180 | CR004237-mod only | CR657-22-mod only | nexus walk | GUUUUAGfAmGmCmUmAmUmGmCmUmGmUmUmUmUmG |

TABLE 4-continued

| SEQ ID NO | Name | Alias | Description | Sequence |
|---|---|---|---|---|
| 181 | CR004238-mod only | CR657-23-mod only | 2'F lower walk | GfUUUUAGAmGmCmUmAmUmGmCmUmGmUmUmUmUmG |
| 182 | CR004239-mod only | CR657-24-mod only | 2'F lower walk | GUfUUUAGAmGmCmUmAmUmGmCmUmGmUmUmUmUmG |
| 183 | CR004240-mod only | CR657-25-mod only | 2'F lower walk | GUUfUUAGAmGmCmUmAmUmGmCmUmGmUmUmUmUmG |
| 184 | CR004241-mod only | CR657-26-mod only | 2'F lower walk | GUUUfUAGAmGmCmUmAmUmGmCmUmGmUmUmUmUmG |
| 185 | CR004242-mod only | CR657-27-mod only | 2'F lower combo | fGfUfUfUfUfAGAmGmCmUmAmUmGmCmUmGmUmUmUmUmG |
| 186 | CR004243-mod only | CR657-28-mod only | lower alt | fGmUfUmUfUmAGAmGmCmUmAmUmGmCmUmGmUmUmUmUmG |
| 187 | CR004244-mod only | CR657-29-mod only | lower alt | mGfUmUfUmUfAGAmGmCmUmAmUmGmCmUmGmUmUmUmUmG |
| | trRNA | | | |
| 188 | TR000002 | | unmodified | AACAGCAUAGCAAGUUAAAAUAAGGCUAGUCCGUUAUCAACUUGAAAAAGUGGCACCGAGUCGGUGCUUUUUUU |
| 189 | TR000110 | TR2-v2-1 | shortened tail | AACAGCAUAGCAAGUUAAAAUAAGGCUAGUCCGUUAUCAACUUGAAAAAGUGGCACCGAGUCGGUGCUUUU |
| 190 | TR000111 | TR2-v2-2 | Upper, hairpins | mAmAmCmAmGmCmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 191 | TR000112 | TR2-v2-3 | upper only | mAmAmCmAmGmCmAmUmAmGmCAAGUUAAAAUAAGGCUAGUCCGUUAUCAACUUGAAAAAGUGGCACCGAGUCGGUGCUUUU |
| 192 | TR000113 | TR2-v2-4 | hairpin 1 | AACAGCAUAGCAAGUUAAAAUAAGGCUAGUCCGUUAUCAmAmCmUmUmGmAmAmAmAmAmGmUmGGCACCGAGUCGGUGCUUUU |
| 193 | TR000114 | TR2-v2-5 | hairpin 2 | AACAGCAUAGCAAGUUAAAAUAAGGCUAGUCCGUUAUCAACUUGAAAAAGUGmGmCmAmCmCmGmAmGmUmCmGmGmUmGmCmUmUmUmU |
| 194 | TR000115 | TR2-v2-6 | upper, hairpin 2 | mAmAmCmAmGmCmAmUmAmGmCAAGUUAAAAUAAGGCUAGUCCGUUAUCAACUUGAAAAAGUGmGmCmAmCmCmGmAmGmUmCmGmGmUmGmCmUmUmUmU |
| 195 | TR000116 | TR2-v2-7 | both hairpins | AACAGCAUAGCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 196 | TR000117 | TR2-v2-8 | lower walk | AACAGCAUAGCAAGUmUmAAAAUAAGGCUAGUCCGUUAUCAACUUGAAAAAGUGGCACCGAGUCGGUGCUUUU |
| 197 | TR000118 | TR2-v2-9 | lower walk | AACAGCAUAGCAAGUUAmAmAAUAAGGCUAGUCCGUUAUCAACUUGAAAAAGUGGCACCGAGUCGGUGCUUUU |
| 198 | TR000119 | TR2-v2-10 | lower walk | AACAGCAUAGCAAGUUAAAmAmUAAGGCUAGUCCGUUAUCAACUUGAAAAAGUGGCACCGAGUCGGUGCUUUU |
| 199 | TR000120 | TR2-v2-11 | partial nexus | AACAGCAUAGCAAGUUAAAAUAAGGCUAGUCCGmUmUmAUCAACUUGAAAAAGUGGCACCGAGUCGGUGCUUUU |
| 200 | TR000121 | TR2-v2-12 | partial nexus | AACAGCAUAGCAAGUUAAAAUAAGGCUAGUCCGUUAmUmCmAACUUGAAAAAGUGGCACCGAGUCGGUGCUUUU |
| 201 | TR000122 | TR2-GC1 | Lower GC | AACAGCAUAGCAAGUUGCGCUAAGGCUAGUCCGUUAUCAACUUGAAAAAGUGGCACCGAGUCGGUGCUUUU |
| 202 | TR000123 | TR2-GC3 | upper GC | GCCAGCAUAGCAAGUUAAAAUAAGGCUAGUCCGUUAUCAACUUGAAAAAGUGGCACCGAGUCGGUGCUUUU |
| 203 | TR000124 | TR2-GC5 | Lower Upper GC | GCCAGCAUAGCAAGUUGCGCUAAGGCUAGUCCGUUAUCAACUUGAAAAAGUGGCACCGAGUCGGUGCUUUU |

TABLE 4-continued

| SEQ ID NO | Name | Alias | Description | Sequence |
|---|---|---|---|---|
| 204 | TR000125 | TR2 all OMe | | mAmAmCmAmGmCmAmUmAmGmCmAmAmGmUmUmAmAmAmAmU mAmAmGmGmCmUmAmGmUmCmCmGmUmUmAmUmCmAmAmCmU mUmGmAmAmAmAmAmGmUmGmGmCmAmCmCmGmAmGmUmCmG mGmUmGmCmUmUmUmUmUmUmU |
| 205 | TR000126 | TR2-v2-13 | lower | mAmAmCmAmGmCmAmUmAmGmCAAGUmUmAmAmAmAmUAAGGCU AGUCCGUUAUCAmAmCmUmUmGmAmAmAmAmAmGmUmGmGmCmA mCmCmGmAmGmUmCmGmGmUmGmCmUmUmUmU |
| 206 | TR000127 | TR2-v2-14 | lower | mAmAmCmAmGmCmAmUmAmGmCAAGUmUmAAAmAmUAAGGCUAG UCCGUUAUCAmAmCmUmUmGmAmAmAmAmAmGmUmGmGmCmAmC mCmGmAmGmUmCmGmGmUmGmCmUmUmUmU |
| 207 | TR000128 | TR2-v2-15 | lower | mAmAmCmAmGmCmAmUmAmGmCAAGUmUmAfAfAmAmUAAGGCUA GUCCGUUAUCAmAmCmUmUmGmAmAmAmAmAmGmUmGmGmCmAm CmCmGmAmGmUmCmGmGmUmGmCmUmUmUmU |
| 208 | TR000129 | TR2-v2-16 | lower alt | mAmAmCmAmGmCmAmUmAmGmCAAGUmUfAmAfAmAfUAAGGCUAG UCCGUUAUCAmAmCmUmUmGmAmAmAmAmAmGmUmGmGmCmAmC mCmGmAmGmUmCmGmGmUmGmCmUmUmUmU |
| 209 | TR000130 | TR2-v2-17 | lower alt | mAmAmCmAmGmCmAmUmAmGmCAAGUfUmAfAmAfAmUAAGGCUAG UCCGUUAUCAmAmCmUmUmGmAmAmAmAmAmGmUmGmGmCmAmC mCmGmAmGmUmCmGmGmUmGmCmUmUmUmU |
| 210 | TR000131 | TR2-v2-18 | nexus walk | mAmAmCmAmGmCmAmUmAmGmCAAGUUAAAAUAAGGCUAGUCCGUU AUCmAmAmCmUmUmGmAmAmAmAmAmGmUmGmGmCmAmCmCmG mAmGmUmCmGmGmUmGmCmUmUmUmU |
| 211 | TR000132 | TR2-v2-19 | nexus walk | mAmAmCmAmGmCmAmUmAmGmCAAGUUAAAAUAAGGCUAGUCCGUU AUmCAmAmCmUmUmGmAmAmAmAmAmGmUmGmGmCmAmCmCmG mAmGmUmCmGmGmUmGmCmUmUmUmU |
| 212 | TR000133 | TR2-v2-20 | nexus walk | mAmAmCmAmGmCmAmUmAmGmCAAGUUAAAAUAAGGCUAGUCCGUU AmUCAmAmCmUmUmGmAmAmAmAmAmGmUmGmGmCmAmCmCmG mAmGmUmCmGmGmUmGmCmUmUmUmU |
| 213 | TR000134 | TR2-v2-21 | nexus walk | mAmAmCmAmGmCmAmUmAmGmCAAGUUAAAAUAAGGCUAGUCCGUU mAUCAmAmCmUmUmGmAmAmAmAmAmGmUmGmGmCmAmCmCmG mAmGmUmCmGmGmUmGmCmUmUmUmU |
| 214 | TR000135 | TR2-v2-22 | nexus walk | mAmAmCmAmGmCmAmUmAmGmCAAGUUAAAAUAAGGCUAGUCCGU mUAUCAmAmCmUmUmGmAmAmAmAmAmGmUmGmGmCmAmCmCm GmAmGmUmCmGmGmUmGmCmUmUmUmU |
| 215 | TR000136 | TR2-v2-23 | nexus walk | mAmAmCmAmGmCmAmUmAmGmCAAGUUAAAAUAAGGCUAGUCCGm UUAUCAmAmCmUmUmGmAmAmAmAmAmGmUmGmGmCmAmCmCm GmAmGmUmCmGmGmUmGmCmUmUmUmU |
| 216 | TR000137 | TR2-v2-24 | nexus walk | mAmAmCmAmGmCmAmUmAmGmCAAGUUAAAAUAAGGCUAGUCCGUU AUfCfAmAmCmUmUmGmAmAmAmAmAmGmUmGmGmCmAmCmCmG mAmGmUmCmGmGmUmGmCmUmUmUmU |
| 217 | TR000138 | TR2-v2-25 | nexus walk | mAmAmCmAmGmCmAmUmAmGmCAAGUUAAAAUAAGGCUAGUCCGUU fAfUCAmAmCmUmUmGmAmAmAmAmAmGmUmGmGmCmAmCmCmG mAmGmUmCmGmGmUmGmCmUmUmUmU |
| 218 | TR000139 | TR2-v2-26 | nexus walk | mAmAmCmAmGmCmAmUmAmGmCAAGUUAAAAUAAGGCUAGUCCGfUf UAUCAmAmCmUmUmGmAmAmAmAmAmGmUmGmGmCmAmCmCmG mAmGmUmCmGmGmUmGmCmUmUmUmU |
| 219 | TR000140 | TR2-v2-27 | nexus walk | mAmAmCmAmGmCmAmUmAmGmCAAGUUAAAAUAAmGmGmCUAGUC CGUUAUCAmAmCmUmUmGmAmAmAmAmAmGmUmGmGmCmAmCm CmGmAmGmUmCmGmGmUmGmCmUmUmUmU |
| 220 | TR000141 | TR2-v2-28 | nexus walk | mAmAmCmAmGmCmAmUmAmGmCAAGUUAAAAUAAGGCUAGUmCmC mGUUAUCAmAmCmUmUmGmAmAmAmAmAmGmUmGmGmCmAmCm CmGmAmGmUmCmGmGmUmGmCmUmUmUmU |
| 221 | TR000142 | TR2-v2-29 | bulge walk | mAmAmCmAmGmCmAmUmAmGmCmAmAGUUAAAAUAAGGCUAGUCC GUUAUCAmAmCmUmUmGmAmAmAmAmAmGmUmGmGmCmAmCmC mGmAmGmUmCmGmGmUmGmCmUmUmUmU |

TABLE 4-continued

| SEQ ID NO | Name | Alias | Description | Sequence |
|---|---|---|---|---|
| 222 | TR000143 | TR2-v2-30 | bulge walk | mAmAmCmAmGmCmAmUmAmGmCAAmGmUUAAAAUAAGGCUAGUCC GUUAUCAmAmCmUmUmGmAmAmAmAmAmGmUmGmGmCmAmCmC mGmAmGmUmCmGmGmUmGmCmUmUmUmU |
| 223 | TR000144 | TR2-GC6 | Lower GC | AACAGCAUAGCAAGUUGAGAUAAGGCUAGUCCGUUAUCAACUUGAAAAA GUGGCACCGAGUCGGUGCUUUU |
| 224 | TR000145 | TR2-GC7 | Lower GC walk | AACAGCAUAGCAAGUUAAAGUAAGGCUAGUCCGUUAUCAACUUGAAAAA GUGGCACCGAGUCGGUGCUUUU |
| 225 | TR000146 | TR2-GC8 | Lower GC walk | AACAGCAUAGCAAGUUAAGAUAAGGCUAGUCCGUUAUCAACUUGAAAAA GUGGCACCGAGUCGGUGCUUUU |
| 226 | TR000147 | TR2-GC9 | Lower GC walk | AACAGCAUAGCAAGUUAGAAUAAGGCUAGUCCGUUAUCAACUUGAAAAA GUGGCACCGAGUCGGUGCUUUU |
| 227 | TR000148 | TR2-GC10 | Lower GC walk | AACAGCAUAGCAAGUUGAAAUAAGGCUAGUCCGUUAUCAACUUGAAAAA GUGGCACCGAGUCGGUGCUUUU |
| | sgRNA | | | |
| 228 | G000209 | | | mC*mC*mA*GUCCAGCGAGGCAAAGGGUUUUAGAGCUAGAAAUAGCAAG UUAAAAUAAGGCUAGUCCGUUAUCAACUUGAAAAAGUGGCACCGAGUCG GUGCmU*mU*mU*U |
| 229 | G000262 | G209-1 | hairpin 2 | mC*mC*mA*GUCCAGCGAGGCAAAGGGUUUUAGAGCUAGAAAUAGCAAG UUAAAAUAAGGCUAGUCCGUUAUCAACUUGAAAAAGUmGmGmCmAmC mCmGmAmGmUmCmGmGmUmGmCmU*mU*mU*mU |
| 230 | G000263 | G209-2 | hairpins | mC*mC*mA*GUCCAGCGAGGCAAAGGGUUUUAGAGCUAGAAAUAGCAAG UUAAAAUAAGGCUAGUCCGUUAUCAmAmCmUmUmGmAmAmAmAmAm GmUmGmGmCmAmCmCmGmAmGmUmCmGmGmUmGmCmU*mU*mU *mU |
| 231 | G000264 | G209-3 | tetraloop | mC*mC*mA*GUCCAGCGAGGCAAAGGGUUUUAGAGCUAmGmAmAmAU AGCAAGUUAAAAUAAGGCUAGUCCGUUAUCAACUUGAAAAAGUGGCACC GAGUCGGUGCmU*mU*mU*U |
| 232 | G000265 | G209-4 | upper | mC*mC*mA*GUCCAGCGAGGCAAAGGGUUUUAGAmGmCmUmAGAAAm UmAmGmCAAGUUAAAAUAAGGCUAGUCCGUUAUCAACUUGAAAAAGUG GCACCGAGUCGGUGCmU*mU*mU*U |
| 233 | G000266 | G209-5 | upper and loop | mC*mC*mA*GUCCAGCGAGGCAAAGGGUUUUAGAmGmCmUmAmGmA mAmAmUmAmGmCAAGUUAAAAUAAGGCUAGUCCGUUAUCAACUUGAA AAAGUGGCACCGAGUCGGUGCmU*mU*mU*U |
| 234 | G000267 | G209-6 | upper, loop, hairpins | mC*mC*mA*GUCCAGCGAGGCAAAGGGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGmUmCmG mGmUmGmCmU*mU*mU*mU |
| 235 | G000262-mod only | G209-1-mod only | hairpin 2 | GUUUUAGAGCUAGAAAUAGCAAGUUAAAAUAAGGCUAGUCCGUUAUCAA CUUGAAAAAGUmGmGmCmAmCmCmGmAmGmUmCmGmGmUmGmCm U*mU*mU*mU |
| 236 | G000263-mod only | G209-2-mod only | hairpins | GUUUUAGAGCUAGAAAUAGCAAGUUAAAAUAAGGCUAGUCCGUUAUCAm AmCmUmUmGmAmAmAmAmAmGmUmGmGmCmAmCmCmGmAmGm UmCmGmGmUmGmCmU*mU*mU*mU |
| 237 | G000264-mod only | G209-3-mod only | tetraloop | GUUUUAGAGCUAmGmAmAmAUAGCAAGUUAAAAUAAGGCUAGUCCGU UAUCAACUUGAAAAAGUGGCACCGAGUCGGUGCmU*mU*mU*U |
| 238 | G000265-mod only | G209-4-mod only | upper | GUUUUAGAmGmCmUmAGAAAmUmAmGmCAAGUUAAAAUAAGGCUAG UCCGUUAUCAACUUGAAAAAGUGGCACCGAGUCGGUGCmU*mU*mU*U |
| 239 | G000266-mod only | G209-5-mod only | upper and loop | GUUUUAGAmGmCmUmAmGmAmAmAmUmAmGmCAAGUUAAAAUAAG GCUAGUCCGUUAUCAACUUGAAAAAGUGGCACCGAGUCGGUGCmU*mU* mU*U |
| 240 | G000267-mod only | G209-6-mod only | upper, loop, hairpins | GUUUUAGAmGmCmUmAmGmAmAmAmUmAmGmCAAGUUAAAAUAAG GCUAGUCCGUUAUCAmAmCmUmUmGmAmAmAmAmAmGmUmGmGm CmAmCmCmGmAmGmUmCmGmGmUmGmCmU*mU*mU*mU |

TABLE 4-continued

| SEQ ID NO | Name | Alias | Description | Sequence |
|---|---|---|---|---|
| 241 | G000211 | | end mod | mU*mU*mA*CAGCCACGUCUACAGCAGUUUUAGAGCUAGAAAUAGCAAGUUAAAAUAAGGCUAGUCCGUUAUCAACUUGAAAAAGUGGCACCGAGUCGGUGCmU*mU*mU*U |
| 242 | G000282 | | mod6 | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 243 | G000201 | | unmod | UUACAGCCACGUCUACAGCAGUUUUAGAGCUAGAAAUAGCAAGUUAAAAUAAGGCUAGUCCGUUAUCAACUUGAAAAAGUGGCACCGAGUCGGUGCUUUU |
| 244 | G000331 | G211-7 | lower cr | mU*mU*mA*CAGCCACGUCUACAGCAmGUUUUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 245 | G000332 | G211-8 | lower cr | mU*mU*mA*CAGCCACGUCUACAGCAfGfUfUfUfUfAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 246 | G000333 | G211-9 | lower cr | mU*mU*mA*CAGCCACGUCUACAGCAmGfUfUfUfUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 247 | G000334 | G211-10 | lower tr | mU*mU*mA*CAGCCACGUCUACAGCAGUUUUAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 248 | G000335 | G211-11 | lower tr | mU*mU*mA*CAGCCACGUCUACAGCAGUUUUAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 249 | G000336 | G211-12 | lower tr | mU*mU*mA*CAGCCACGUCUACAGCAGUUUUAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 250 | G000337 | G211-13 | lower all | mU*mU*mA*CAGCCACGUCUACAGCAmGUUUUmAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 251 | G000338 | G211-14 | lower all | mU*mU*mA*CAGCCACGUCUACAGCAmGUUUUmAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 252 | G000339 | G211-15 | lower all | mU*mU*mA*CAGCCACGUCUACAGCAmGUUUUmAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 253 | G000340 | G211-16 | lower all | mU*mU*mA*CAGCCACGUCUACAGCAfGfUfUfUfUfAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 254 | G000341 | G211-17 | lower all | mU*mU*mA*CAGCCACGUCUACAGCAfGfUfUfUfUfAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 255 | G000342 | G211-18 | lower all | mU*mU*mA*CAGCCACGUCUACAGCAfGfUfUfUfUfAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 256 | G000343 | G211-19 | Bulge cr | mU*mU*mA*CAGCCACGUCUACAGCAGUUUUAmGmAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 257 | G000344 | G211-20 | Bulge tr | mU*mU*mA*CAGCCACGUCUACAGCAGUUUUAGAmGmCmUmAmGmAmAmAmUmAmGmCmAmAmGmUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 258 | G000345 | G211-21 | nexus | mU*mU*mA*CAGCCACGUCUACAGCAGUUUUAGAmGmCmUmAmGmAmAmAmUmAmGmCAAGUUAAAAUAAGGCUAGUCCGUUfAfUfCfAmAmCmUmUmGmAmAmAmAmAmGmUmGmGmCmAmCmCmGmAmGmUmCmGmGmUmGmCmU*mU*mU*mU |
| 259 | G000346 | G211-22 | nexus | mU*mU*mA*CAGCCACGUCUACAGCAGUUUUAGAmGmCmUmAmGmAmAmAmUmAmGmCAAGUUAAAAUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 260 | G000347 | G211-23 | lower all | mU*mU*mA*CAGCCACGUCUACAGCAfGfUfUfUfUfAmGmAmGmCmUmAmGmAmAmAmUmAmGmCmAmAmGmUmUmAfAfAmAmUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 261 | G000348 | G211-24 | no PS | mUmUmACAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 262 | G000349 | G211-25 | 2 OMe PS | mU*mU*ACAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmU*mU*mU |
| 263 | G000350 | G211-26 | 2'F hairpin | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGfUfCfGfGfUfGfCfU*fU*fU*mU |
| 264 | G000351 | G211-27 | Alt hairpin | mU*mU*mA*CAGCCACGUCUACAGCAGUUUUAGAmGmCmUmAmGmAmAmAmUmAmGmCAAGUUAAAAUAAGGCUAGUCCGUUAUCAfAmCfUmUfGmAfAmAfAmAfGmUfGmGfCmAfCmCfGmAfGmUfCmGfGmUfGmCfU*mU*fU*mU |
| 265 | G000331-mod only | G211-7-mod only | lower cr | mGUUUUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 266 | G000332-mod only | G211-8-mod only | lower cr | fGfUfUfUfUfAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 267 | G000333-mod only | G211-9-mod only | lower cr | mGfUfUfUfUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 268 | G000334-mod only | G211-10-mod only | lower tr | GUUUUAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 269 | G000335-mod only | G211-11-mod only | lower tr | GUUUUAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 270 | G000336-mod only | G211-12-mod only | lower tr | GUUUUAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 271 | G000337-mod only | G211-13-mod only | lower all | mGUUUUmAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 272 | G000338-mod only | G211-14-mod only | lower all | mGUUUUmAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 273 | G000339-mod only | G211-15-mod only | lower all | mGUUUUmAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 274 | G000340-mod only | G211-16-mod only | lower all | fGfUfUfUfUfAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 275 | G000341-mod only | G211-17-mod only | lower all | fGfUfUfUfUfAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 276 | G000342-mod only | G211-18-mod only | lower all | fGfUfUfUfUfAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 277 | G000343-mod only | G211-19-mod only | Bulge cr | GUUUUAmGmAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 278 | G000344-mod only | G211-20-mod only | Bulge tr | GUUUUAGAmGmCmUmAmGmAmAmAmUmAmGmCmAmAmGmUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 279 | G000345-mod only | G211-21-mod only | nexus | GUUUUAGAmGmCmUmAmGmAmAmAmUmAmGmCAAGUUAAAAUAAGGCUAGUCCGUUfAfUfCfAmAmCmUmUmGmAmAmAmAmAmGmUmGmGmCmAmCmCmGmAmGmUmCmGmGmUmGmCmU*mU*mU*mU |
| 280 | G000346-mod only | G211-22-mod only | nexus | GUUUUAGAmGmCmUmAmGmAmAmAmUmAmGmCAAGUUAAAAUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 281 | G000347-mod only | G211-23-mod only | lower all | fGfUfUfUfUfAmGmAmGmCmUmAmGmAmAmAmUmAmGmCmAmAmGmUmUmAfAfAmAmUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 282 | G000348-mod only | G211-24-mod only | no PS | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 283 | G000349-mod only | G211-25-mod only | 2 OMe PS | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmU*mU*mU |
| 284 | G000350-mod only | G211-26-mod only | 2'F hairpin | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGfUfCfGfGfUfGfCfU*fU*fU*mU |
| 285 | G000351-mod only | G211-27-mod only | Alt hairpin | GUUUUAGAmGmCmUmAmGmAmAmAmUmAmGmCAAGUUAAAAUAAGGCUAGUCCGUUAUCAfAmCfUmUfGmAfAmAfAmAfGmUfGmGfCmAfCmCfGmAfGmUfCmGfGmUfGmCfU*mU*fU*mU |
| 286 | G000208 | | end mod | mC*mA*mG*GGCUCUUGAAGAUCUCCGUUUUAGAGCUAGAAAUAGCAAGUUAAAAUAAGGCUAGUCCGUUAUCAACUUGAAAAAGUGGCACCGAGUCGGUGCmU*mU*mU*U |
| 287 | G000373 | | mod6 | mC*mA*mG*GGCUCUUGAAGAUCUCCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 288 | G000352 | G208-7 | lower cr | mC*mA*mG*GGCUCUUGAAGAUCUCCmGUUUUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 289 | G000353 | G208-8 | lower cr | mC*mA*mG*GGCUCUUGAAGAUCUCCfGfUfUfUfUfAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 290 | G000354 | G208-9 | lower cr | mC*mA*mG*GGCUCUUGAAGAUCUCCmGfUfUfUfUmAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 291 | G000355 | G208-10 | lower tr | mC*mA*mG*GGCUCUUGAAGAUCUCCGUUUUAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 292 | G000356 | G208-11 | lower tr | mC*mA*mG*GGCUCUUGAAGAUCUCCGUUUUAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 293 | G000357 | G208-12 | lower tr | mC*mA*mG*GGCUCUUGAAGAUCUCCGUUUUAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 294 | G000358 | G208-13 | lower all | mC*mA*mG*GGCUCUUGAAGAUCUCCmGUUUUmAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 295 | G000359 | G208-14 | lower all | mC*mA*mG*GGCUCUUGAAGAUCUCCmGUUUUmAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 296 | G000360 | G208-15 | lower all | mC*mA*mG*GGCUCUUGAAGAUCUCCmGUUUUmAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 297 | G000361 | G208-16 | lower all | mC*mA*mG*GGCUCUUGAAGAUCUCCfGfUfUfUfUfAGAmGmCmUmAmGmAmAmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 298 | G000362 | G208-17 | lower all | mC*mA*mG*GGCUCUUGAAGAUCUCCfGfUfUfUfUfAGAmGmCmUmAmGmAmAmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 299 | G000363 | G208-18 | lower all | mC*mA*mG*GGCUCUUGAAGAUCUCCfGfUfUfUfUfAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 300 | G000364 | G208-19 | Bulge cr | mC*mA*mG*GGCUCUUGAAGAUCUCCGUUUUAmGmAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 301 | G000365 | G208-20 | Bulge tr | mC*mA*mG*GGCUCUUGAAGAUCUCCGUUUUAGAmGmCmUmAmGmAmAmAmUmAmGmCmAmAmGmUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 302 | G000366 | G208-21 | nexus | mC*mA*mG*GGCUCUUGAAGAUCUCCGUUUUAGAmGmCmUmAmGmAmAmAmUmAmGmCAAGUUAAAAUAAGGCUAGUCCGUUfAfUfCfAmAmCmUmUmGmAmAmAmAmAmGmUmGmGmCmAmCmCmGmAmGmUmCmGmGmUmGmCmU*mU*mU*mU |
| 303 | G000367 | G208-22 | nexus | mC*mA*mG*GGCUCUUGAAGAUCUCCGUUUUAGAmGmCmUmAmGmAmAmAmUmAmGmCAAGUUAAAAUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 304 | G000368 | G208-23 | lower all | mC*mA*mG*GGCUCUUGAAGAUCUCCfGfUfUfUfUfAmGmAmGmCmUm AmGmAmAmAmUmAmGmCmAmAmGmUmUmAfAfAmAmUAAGGCUAG UCCGUUAmUmCmAmAmCmUmUmGmAmAmAmAmAmGmUmGmGmC mAmCmCmGmAmGmUmCmGmGmUmGmCmU*mU*mU*mU |
| 305 | G000369 | G208-24 | no PS | mCmAmGGGCUCUUGAAGAUCUCCGUUUUAGAmGmCmUmAmGmAmA mAmUmAmGmCAAGUUAAAAUAAGGCUAGUCCGUUAUCAmAmCmUmU mGmAmAmAmAmAmGmUmGmGmCmAmCmCmGmAmGmUmCmGmG mUmGmCmUmUmUmU |
| 306 | G000370 | G208-25 | 2 OMe PS | mC*mAG*GGCUCUUGAAGAUCUCCGUUUUAGAmGmCmUmAmGmAmA mAmUmAmGmCAAGUUAAAAUAAGGCUAGUCCGUUAUCAmAmCmUmU mGmAmAmAmAmAmGmUmGmGmCmAmCmCmGmAmGmUmCmGmG mUmGmCmUmU*mU*mU |
| 307 | G000371 | G208-26 | 2'F hairpin | mC*mA*mG*GGCUCUUGAAGAUCUCCGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGfUfCfGfGfU fGfCfU*fU*fU*mU |
| 308 | G000372 | G208-27 | Alt hairpin | mC*mA*mG*GGCUCUUGAAGAUCUCCGUUUUAGAmGmCmUmAmGmA mAmAmUmAmGmCAAGUUAAAAUAAGGCUAGUCCGUUAUCAfAmCfUmU fGmAfAmAfAmAfGmUfGmGfCmAfCmCfGmAfGmUfCmGfGmUfGmCfU* mU*fU*mU |
| 309 | G000352-mod only | G208-7-mod only | lower cr | mGUUUUmAGAmGmCmUmAmGmAmAmAmUmAmGmCAAGUUAAAAU AAGGCUAGUCCGUUAUCAmAmCmUmUmGmAmAmAmAmAmGmUmG mGmCmAmCmCmGmAmGmUmCmGmGmUmGmCmU*mU*mU*mU |
| 310 | G000353-mod only | G208-8-mod only | lower cr | fGfUfUfUfUfAGAmGmCmUmAmGmAmAmAmUmAmGmCAAGUUAAAAU AAGGCUAGUCCGUUAUCAmAmCmUmUmGmAmAmAmAmAmGmUmG mGmCmAmCmCmGmAmGmUmCmGmGmUmGmCmU*mU*mU*mU |
| 311 | G000354-mod only | G208-9-mod only | lower cr | mGfUfUfUfUmAGAmGmCmUmAmGmAmAmAmUmAmGmCAAGUUAAA AUAAGGCUAGUCCGUUAUCAmAmCmUmUmGmAmAmAmAmAmGmUm GmGmCmAmCmCmGmAmGmUmCmGmGmUmGmCmU*mU*mU*mU |
| 312 | G000355-mod only | G208-10-mod only | lower tr | GUUUUAGAmGmCmUmAmGmAmAmAmUmAmGmCAAGUmUmAAAmA mUAAGGCUAGUCCGUUAUCAmAmCmUmUmGmAmAmAmAmAmGmU mGmGmCmAmCmCmGmAmGmUmCmGmGmUmGmCmU*mU*mU*mU |
| 313 | G000356-mod only | G208-11-mod only | lower tr | GUUUUAGAmGmCmUmAmGmAmAmAmUmAmGmCAAGUmUmAfAfAm AmUAAGGCUAGUCCGUUAUCAmAmCmUmUmGmAmAmAmAmAmGmU mGmGmCmAmCmCmGmAmGmUmCmGmGmUmGmCmU*mU*mU*mU |
| 314 | G000357-mod only | G208-12- | lower tr | GUUUUAGAmGmCmUmAmGmAmAmAmUmAmGmCAAGUfUmAfAmAfA mUAAGGCUAGUCCGUUAUCAmAmCmUmUmGmAmAmAmAmAmGmU mGmGmCmAmCmCmGmAmGmUmCmGmGmUmGmCmU*mU*mU*mU |
| 315 | G000358-mod only | G208-13-mod only | lower all | mGUUUUmAGAmGmCmUmAmGmAmAmAmUmAmGmCAAGUmUmAAA mAmUAAGGCUAGUCCGUUAUCAmAmCmUmUmGmAmAmAmAmAmGm UmGmGmCmAmCmCmGmAmGmUmCmGmGmUmGmCmU*mU*mU*m U |
| 316 | G000359-mod only | G208-14-mod only | lower all | mGUUUUmAGAmGmCmUmAmGmAmAmAmUmAmGmCAAGUmUmAfAf AmAmUAAGGCUAGUCCGUUAUCAmAmCmUmUmGmAmAmAmAmAmG mUmGmGmCmAmCmCmGmAmGmUmCmGmGmUmGmCmU*mU*mU* mU |
| 317 | G000360-mod only | G208-15-mod only | lower all | mGUUUUmAGAmGmCmUmAmGmAmAmAmUmAmGmCAAGUfUmAfAm AfAmUAAGGCUAGUCCGUUAUCAmAmCmUmUmGmAmAmAmAmAmG mUmGmGmCmAmCmCmGmAmGmUmCmGmGmUmGmCmU*mU*mU* mU |
| 318 | G000361-mod only | G208-16-mod only | lower all | fGfUfUfUfUfAGAmGmCmUmAmGmAmAmAmUmAmGmCAAGUmUmAA AmAmUAAGGCUAGUCCGUUAUCAmAmCmUmUmGmAmAmAmAmAmG mUmGmGmCmAmCmCmGmAmGmUmCmGmGmUmGmCmU*mU*mU* mU |
| 319 | G000362-mod only | G208-17-mod only | lower all | fGfUfUfUfUfAGAmGmCmUmAmGmAmAmAmUmAmGmCAAGUmUmAfA fAmAmUAAGGCUAGUCCGUUAUCAmAmCmUmUmGmAmAmAmAmAm GmUmGmGmCmAmCmCmGmAmGmUmCmGmGmUmGmCmU*mU*mU *mU |

TABLE 4-continued

| SEQ ID NO | Name | Alias | Description | Sequence |
|---|---|---|---|---|
| 320 | G000363-mod only | G208-18-mod only | lower all | fGfUfUfUfUfAGAmGmCmUmAmGmAmAmAmUmAmGmCAAGUfUmAfAmAfAmUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 321 | G000364-mod only | G208-19-mod only | Bulge cr | GUUUUAmGmAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 322 | G000365-mod only | G208-20-mod only | Bulge tr | GUUUUAGAmGmCmUmAmGmAmAmAmUmAmGmCmAmAmGmUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 323 | G000366-mod only | G208-21-mod only | nexus | GUUUUAGAmGmCmUmAmGmAmAmAmUmAmGmCAAGUUAAAAUAAGGCUAGUCCGUUfAfUfCfAmAmCmUmUmGmAmAmAmAmAmGmUmGmGmCmAmCmCmGmAmGmUmCmGmGmUmGmCmU*mU*mU*mU |
| 324 | G000367-mod only | G208-22-mod only | nexus | GUUUUAGAmGmCmUmAmGmAmAmAmUmAmGmCAAGUUAAAAUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 325 | G000368-mod only | G208-23-mod only | lower all | fGfUfUfUfUfAmGmAmGmCmUmAmGmAmAmAmUmAmGmCmAmAmGmUmUmAfAfAmAmUAAGGCUAGUCCGUUAmUmCmAmAmCmUmUmGmAmAmAmAmAmGmUmGmGmCmAmCmCmGmAmGmUmCmGmGmUmGmCmU*mU*mU*mU |
| 326 | G000369-mod only | G208-24-mod only | no PS | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 327 | G000370-mod only | G208-25-mod only | 2 OMe PS | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmU*mU*mU |
| 328 | G000371-mod only | G208-26-mod only | 2'F hairpin | GUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGfUfCfGfGfUfGfCfU*fU*fU*mU |
| 329 | G000372-mod only | G208-27-mod only | Alt hairpin | GUUUUAGAmGmCmUmAmGmAmAmAmUmAmGmCAAGUUAAAAUAAGGCUAGUCCGUUAUCAfAmCfUmUfGmAfAmAfAmAfGmUfGmGfCmAfCmCfGmAfGmUfCmGfGmUfGmCfU*mU*fU*mU |
| 330 | G000269 | | end mod | mC*mC*mC*AUACUCCUACAGCACCAGUUUUAGAGCUAGAAAUAGCAAGUUAAAAUAAGGCUAGUCCGUUAUCAACUUGAAAAAGUGGCACCGAGUCGGUGCmU*mU*mU*U |
| 331 | G000283 | | mod6 | mC*mC*mC*AUACUCCUACAGCACCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 332 | G000285 | | unmod | CCCAUACUCCUACAGCACCAGUUUUAGAGCUAGAAAUAGCAAGUUAAAAUAAGGCUAGUCCGUUAUCAACUUGAAAAAGUGGCACCGAGUCGGUGCUUUU |
| 342 | G000537 | G211-33 | 5'end 3xOMePS | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmUmUmUmU |
| 343 | G000538 | G211-34 | 3'end 3xOMePS | mUmUmACAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 344 | G000539 | G211-35 | 5xOMePS | mU*mU*mA*mC*mA*GCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmG*mC*mU*mU*mU*mU |
| 345 | G000541 | G211-37 | 3xOMePS+2PS | mU*mU*mA*C*A*GCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmG*mC*mU*mU*mU*mU |

TABLE 4-continued

| SEQ ID NO | Name | Alias | Description | Sequence |
|---|---|---|---|---|
| 346 | G000542 | G211-38 | 3xOMePS+7PS | mU*mU*mA*C*A*G*C*C*A*C*GUCUACAGCAGUUUUAGAmGmCmUm AmGmAmAmAmUmAmGmCAAGUUAAAAUAAGGCUAGUCCGUUAUCA mAmCmUmUmGmAmAmAmAmAmGmUmGmGmCmAmCmCmGmAmG mU*mC*mG*mG*mU*mG*mC*mU*mU*mU*mU |
| 347 | G000543 | G211-39 | invd abasic | (invd)UUACAGCCACGUCUACAGCAGUUUUAGAmGmCmUmAmGmAmA mAmUmAmGmCAAGUUAAAAUAAGGCUAGUCCGUUAUCAmAmCmUm UmGmAmAmAmAmAmGmUmGmGmCmAmCmCmGmAmGmUmCmG mGmUmGmCmUmUmUmU(invd) |
| 348 | G000544 | G211-40 | invd abasic + 3xOMePS | (invd)mU*mU*mA*CAGCCACGUCUACAGCAGUUUUAGAmGmCmUmAm GmAmAmAmUmAmGmCAAGUUAAAAUAAGGCUAGUCCGUUAUCAmA mCmUmUmGmAmAmAmAmAmGmUmGmGmCmAmCmCmGmAmGm UmCmGmGmUmGmCmU*mU*mU*mU(invd) |
| 349 | G000564 | G211-42 | 3xMOE-PS | moeU*moeU*moeA*CAGCCACGUCUACAGCAGUUUUAGAmGmCmUmA mGmAmAmAmUmAmGmCAAGUUAAAAUAAGGCUAGUCCGUUAUCAm AmCmUmUmGmAmAmAmAmAmGmUmGmGmCmAmCmCmGmAmGm UmCmGmGmUmGmCmoeU*moeU*moeU*mU |
| 350 | G000545 | G211-43 | US loop PS | mU*mU*mA*CAGCCACGUCUACAGCAGUUUUAGAmGmCmUmA*mG* mA*mA*mA*mUmAmGmCAAGUUAAAAUAAGGCUAGUCCGUUAUCAm AmCmUmUmGmAmAmAmAmAmGmUmGmGmCmAmCmCmGmAmGm UmCmGmGmUmGmCmU*mU*mU*mU |
| 351 | G000546 | G211-44 | H1 loop PS | mU*mU*mA*CAGCCACGUCUACAGCAGUUUUAGAmGmCmUmAmGmA mAmAmUmAmGmCAAGUUAAAAUAAGGCUAGUCCGUUAUCAmAmCmU mU*mG*mA*mA*mA*mAmAmGmUmGmGmCmAmCmCmGmAmGmU mCmGmGmUmGmCmU*mU*mU*mU |
| 352 | G000547 | G211-45 | H2 loop PS | mU*mU*mA*CAGCCACGUCUACAGCAGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmG*mA*mG*mU* mCmGmGmUmGmCmU*mU*mU*mU |
| 353 | G000548 | G211-46 | all loops PS | mU*mU*mA*CAGCCACGUCUACAGCAGUUUUAGAmGmCmUmA*mG* mA*mA*mA*mUmAmGmCAAGUUAAAAUAAGGCUAGUCCGUUAUCAm AmCmUmU*mG*mA*mA*mA*mAmAmGmUmGmGmCmAmCmCmG* mA*mG*mU*mCmGmGmUmGmCmU*mU*mU*mU |
| 354 | | | Mod6 (with modifications not shown in sequence listing) | mN*mN*mN*NNNNNNNNNNNNNNNNNGUUUUAGAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUm CmGmGmUmGmCmU*mU*mU*mU N = any nucleotide |
| 355 | | | Invariable region only | GUUUUAGAGCUAGAAAUAGCAAGUUAAAAUAAGGCUAGUCCGUUAUCA ACUUGAAAAAGUGGCACCGAGUCGGUGCUUUU |
| 356 | | | Mod6 pattern; invariable region only | GUUUUAGAmGmCmUmAmGmAmAmAmUmAmGmCAAGUUAAAAUAA GGCUAGUCCGUUAUCAmAmCmUmUmGmAmAmAmAmAmGmUmGmG mCmAmCmCmGmAmGmUmCmGmGmUmGmCmU*mU*mU*mU |
| 357 | | | Variable and invariable region | NNNNNNNNNNNNNNNNNNNNGUUUUAGAGCUAGAAAUAGCAAGUUAA AAUAAGGCUAGUCCGUUAUCAACUUGAAAAAGUGGCACCGAGUCGGUGC UUUU |
| 358 | | | Mod6 with modifications shown in sequence listing | mN*mN*mN*NNNNNNNNNNNNNNNNNGUUUUAGAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUm CmGmGmUmGmCmU*mU*mU*mU N = any nucleotide |

"Guide RNA" and "gRNA" are used herein interchangeably to refer collectively to either an sgRNA, a trRNA (also known as tracrRNA), or a crRNA (also known as a CRISPR RNA). The crRNA and trRNA may be associated on one RNA molecule (single guide RNA [sgRNA]) or in two separate RNA molecules (dual guide RNA [dgRNA]). "Guide RNA" or "gRNA" refers to each type.

The trRNA sequences may be naturally-occurring, or the trRNA sequence may include modifications or variations compared to naturally-occurring sequences.

"Editing efficiency" or "editing percentage" or "percent editing" as used herein is the total number of sequence reads with insertions or deletions of nucleotides into the target region of interest over the total number of sequence reads following cleavage by a Cas RNP.

"Hairpin" as used herein describes a loop of nucleic acids that is created when a nucleic acid strand folds and forms base pairs with another section of the same strand. A hairpin may form a structure that comprises a loop or a U-shape. In some embodiments, a hairpin may be comprised of a RNA loop. Hairpins can be formed with two complementary sequences in a single nucleic acid molecule bind together, with a folding or wrinkling of the molecule. In some embodiments, hairpins comprise stem or stem loop structures.

"Regions" as used herein describes conserved groups of nucleic acids. Regions may also be referred to as "modules" or "domains." Regions of a gRNA may perform particular functions, e.g., in directing endonuclease activity of the RNP, for example as described in Briner A E et al., *Molecular Cell* 56:333-339 (2014). Regions of a gRNA are described in Tables 1-3.

"Ribonucleoprotein" (RNP) or "RNP complex" as used herein describes a gRNA, for example, together with a nuclease, such as a Cas protein. In some embodiments, the RNP comprises Cas9 and gRNA.

"Stem loop" as used herein describes a secondary structure of nucleotides that form a base-paired "stem" that ends in a loop of unpaired nucleic acids. A stem may be formed when two regions of the same nucleic acid strand are at least partially complementary in sequence when read in opposite directions. "Loop" as used herein describes a region of nucleotides that do not base pair (i.e., are not complementary) that may cap a stem. A "tetraloop" describes a loop of 4 nucleotides. As used herein, the upper stem of a sgRNA may comprise a tetraloop.

In certain embodiments involving dgRNA, a "stem" region as used herein describes a secondary structure of nucleotides that forms a base-paired region between certain regions of a crRNA and trRNA (e.g., the lower and upper stem regions of each RNA). The "stem" region of a dgRNA may also be referred to in the art as a "flagpole" region.

"Treatment" as used herein covers any administration or application of a therapeutic for disease in a subject, and includes inhibiting the disease, arresting its development, relieving one or more symptoms of the disease, curing the disease, or preventing reoccurrence of one or more symptoms of the disease.

1. Types of Modifications

A. 2'-O-methyl Modifications

Modified sugars are believed to control the puckering of nucleotide sugar rings, a physical property that influences oligonucleotide binding affinity for complementary strands, duplex formation, and interaction with nucleases. Substitutions on sugar rings can therefore alter the confirmation and puckering of these sugars. For example, 2'-O-methyl (2'-O-Me) modifications can increase binding affinity and nuclease stability of oligonucleotides, though as shown in the Examples, the effect of any modification at a given position in an oligonucleotide needs to be empirically determined.

The terms "mA," "mC," "mU," or "mG" may be used to denote a nucleotide that has been modified with 2'-O-Me.

Modification of a ribonucleotide as 2'-O-methyl ribonucleotide can be depicted as follows:

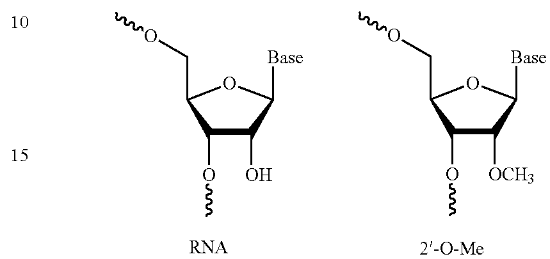

B. 2'-O-(2-methoxyethyl) Modifications

In some embodiments, the modification may be 2'-O-(2-methoxyethyl) (2'-O-moe). Modification of a ribonucleotide as a 2'-O-moe ribonucleotide can be depicted as follows:

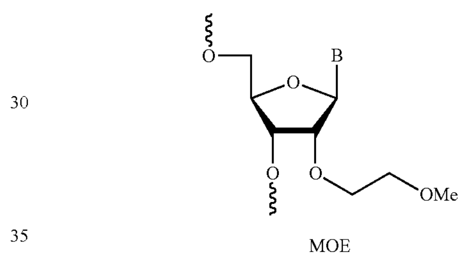

The terms "moeA," "moeC," "moeU," or "moeG" may be used to denote a nucleotide that has been modified with 2'-O-moe.

C. 2'-fluoro Modifications

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fJ," or "fG" may be used to denote a nucleotide that has been substituted with 2'-F.

Substitution of 2'-F can be depicted as follows:

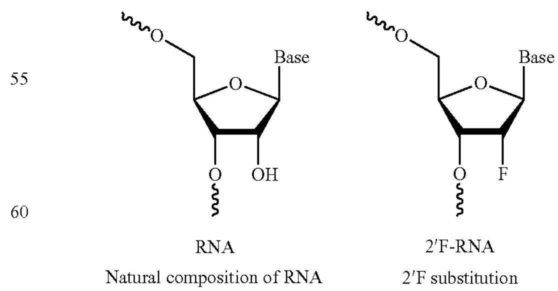

D. Phosphorothioate Modifications

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond. Similarly, the terms "fA*," "fC*," "fU*," or "fG*" may be used to denote a nucleotide that has been substituted with 2'-F and that is linked to the next (e.g., 3') nucleotide with a PS bond. Equivalents of a PS linkage or bond are encompassed by embodiments described herein.

The diagram below shows the substitution of S- into a nonbridging phosphate oxygen, generating a PS bond in lieu of a phosphodiester bond:

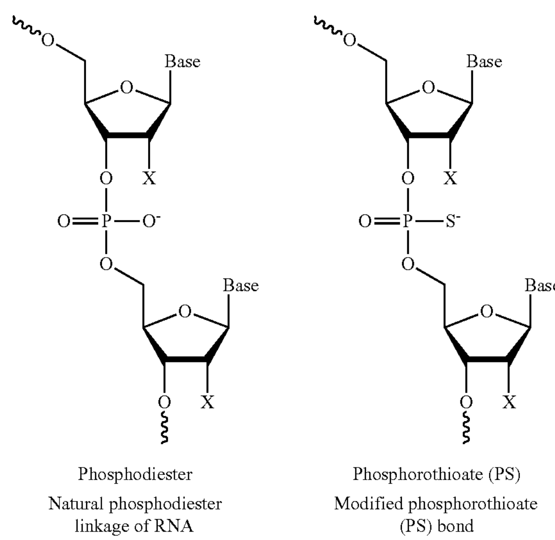

Phosphodiester
Natural phosphodiester linkage of RNA

Phosphorothioate (PS)
Modified phosphorothioate (PS) bond

E. G-C Substitutions

In some embodiments, gRNAs are modified with sequence substitutions that do not comprise chemical modifications. In some embodiments, modified gRNAs are engineered with G-C pairings (e.g., in lower and/or upper stem regions) that are not found in the parental gRNA sequence. In some embodiments, modified gRNAs are engineered with G-U mismatches ("GU wobbles" or mismatch pairings) that are not found in the parental gRNA sequence.

F. Inverted Abasic Modifications

Abasic nucleotides refer to those which lack nitrogenous bases. The figure below depicts an oligonucleotide with an abasic (also known as apurinic) site that lacks a base:

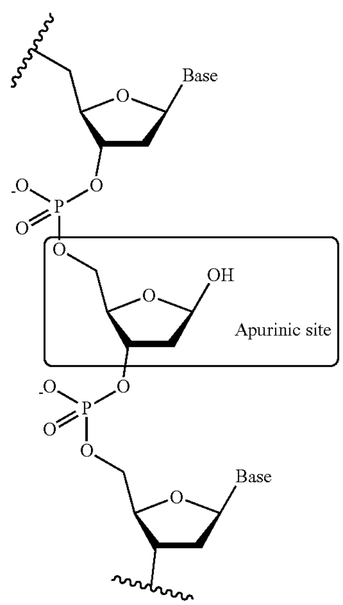

Inverted bases refer to those with linkages that are inverted from the normal 5' to 3' linkage (i.e., either a 5' to 5' linkage or a 3' to 3' linkage). For example:

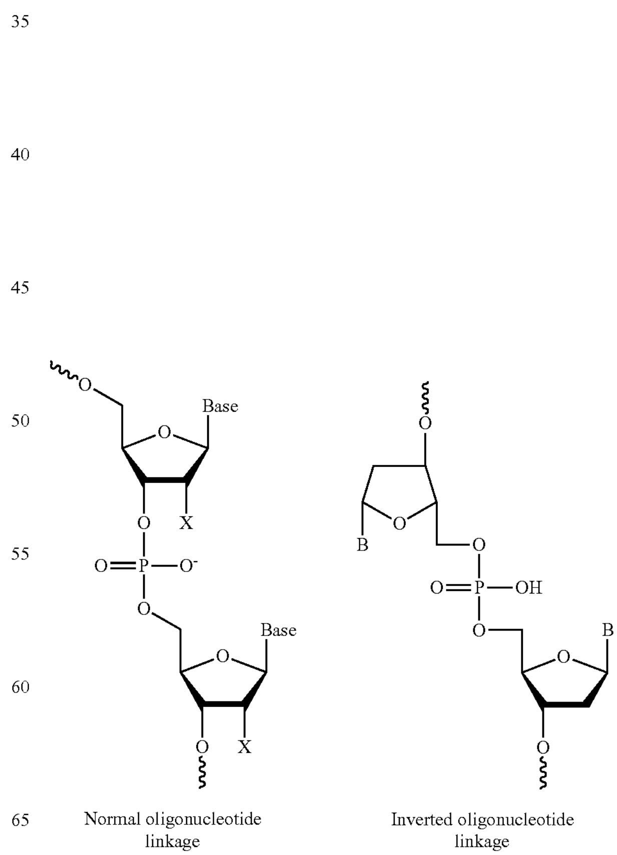

Normal oligonucleotide linkage

Inverted oligonucleotide linkage

-continued

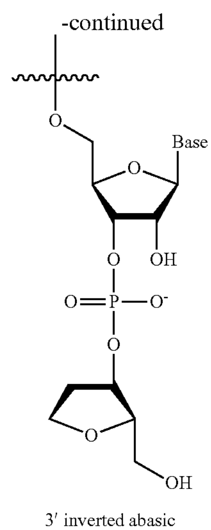

3′ inverted abasic

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap. In this application, the terms "invd" indicates an inverted abasic nucleotide linkage.

The above modifications and their equivalents are included within the scope of the embodiments described herein.

2. Guide RNA Compositions

Compositions comprising guide RNA are encompassed. In some embodiments, the guide RNA comprises a trRNA. In some embodiments, the guide RNA comprises a crRNA. In some embodiments, the guide RNA comprises a crRNA and trRNA. In some embodiments, the guide RNA comprises a crRNA and trRNA on one RNA molecule as a sgRNA. In some embodiments, the guide RNA comprises a crRNA and trRNA on two RNA molecules as a dgRNA. In a dgRNA, the two RNA molecules may associate via base pairing.

In some embodiments, the guide RNA comprises a 5' terminus region. In some embodiments, the guide RNA does not comprise a 5' terminus region. In some embodiments, the 5' terminus region comprises a "spacer" region as described in Briner A E et al., *Molecular Cell* 56: 333-339 (2014) for sgRNA (but applicable herein to all guide RNAs). In some embodiments, the 5' terminus region comprises a 5' end modification. A 5' terminus region with or without a spacer region may be associated with a crRNA, trRNA, sgRNA and/or dgRNA The spacer region is also sometimes referred to herein, and by others, as a "guide region," "guide domain" or "targeting domain." A "target sequence" as used herein refers to a sequence of nucleic acid to which the guide region/domain directs a nuclease for cleavage. In some embodiments, a spyCas9 protein may be directed by a guide region/domain to a target sequence of a target nucleic acid molecule by the nucleotides present in the spacer region. In some embodiments, the guide RNA does not comprise a spacer region.

In some embodiments, the guide RNAs described herein comprise or consist of any of the sequences shown in Table 4. Note, however, that where a sequence shows a guide/spacer region, it should be recognized that the composition may comprise this region or not. Further, guide RNAs are encompassed that comprise the modifications of any of the sequences shown in Table 4, and identified therein by SEQ ID No. That is, the nucleotides may be the same or different, but the modification pattern shown may be the same or similar to a modification pattern of a guide sequence of Table 4. A modification pattern includes the relative position and identity of modifications of the gRNA or a region of the gRNA (e.g. 5' terminus region, lower stem region, bulge region, upper stem region, nexus region, hairpin 1 region, hairpin 2 region, 3' terminus region). In some embodiments, the modification pattern contains at least 50%, 55%, 60%, 70%, 75%, 80%, 85%, 90%, 95%, 96%, 97%, 98%, and 99% of the modifications of any one of the sequences shown in the sequence column of Table 4, or over one or more regions of the sequence. In some embodiments, the modification pattern is at least 50%, 55%, 60%, 70%, 75%, 80%, 85%, 90%, 95%, 96%, 97%, 98%, and 99% identical to the modification pattern of any one of the sequences shown in the sequence column of Table 4. In some embodiments, the modification pattern is at least 50%, 55%, 60%, 70%, 75%, 80%, 85%, 90%, 95%, 96%, 97%, 98%, and 99% identical over one or more regions of the sequence shown in Table 4, e.g., a 5' terminus region, lower stem region, bulge region, upper stem region, nexus region, hairpin 1 region, hairpin 2 region, and/or 3' terminus region. For example, in some embodiments, a guide RNA is encompassed wherein the modification pattern is least 50%, 55%, 60%, 70%, 75%, 80%, 85%, 90%, 95%, 96%, 97%, 98%, and 99% identical to the modification pattern of a sequence over the 5' terminus region. In some embodiments, a guide RNA is encompassed wherein the modification pattern is least 50%, 55%, 60%, 70%, 75%, 80%, 85%, 90%, 95%, 96%, 97%, 98%, and 99% identical over the lower stem. In some embodiments, a guide RNA is encompassed wherein the modification pattern is least 50%, 55%, 60%, 70%, 75%, 80%, 85%, 90%, 95%, 96%, 97%, 98%, and 99% identical over the bulge. In some embodiments, a guide RNA is encompassed wherein the modification pattern is least 50%, 55%, 60%, 70%, 75%, 80%, 85%, 90%, 95%, 96%, 97%, 98%, and 99% identical over the upper stem. In some embodiments, a guide RNA is encompassed wherein the modification pattern is least 50%, 55%, 60%, 70%, 75%, 80%, 85%, 90%, 95%, 96%, 97%, 98%, and 99% identical over the nexus. In some embodiments, a guide RNA is encompassed wherein the modification pattern is least 50%, 55%, 60%, 70%, 75%, 80%, 85%, 90%, 95%, 96%, 97%, 98%, and 99% identical over the hairpin 1. In some embodiments, a guide RNA is encompassed wherein the modification pattern is least 50%, 55%, 60%, 70%, 75%, 80%, 85%, 90%, 95%, 96%, 97%, 98%, and 99% identical over the hairpin 2. In some embodiments, a guide RNA is encompassed wherein the modification pattern is least 50%, 55%, 60%, 70%, 75%, 80%, 85%, 90%, 95%, 96%, 97%, 98%, and 99% identical over the 3' terminus. In some embodiments, the modification pattern differs from the modification pattern of a sequence of Table 4, or a region (e.g. 5' terminus, lower stem, bulge, upper stem, nexus, hairpin 1, hairpin 2, 3' terminus) of such a sequence, at 0, 1, 2, 3, 4, 5, or 6 nucleotides. In some embodiments, the gRNA comprises modifications that differ from the modifications of a sequence of Table 4, at 0, 1, 2, 3, 4, 5, or 6 nucleotides. In some embodiments, the gRNA comprises modifications that differ from modifications of a region (e.g. 5' terminus, lower stem, bulge, upper stem, nexus, hairpin 1, hairpin 2, 3' terminus) of a sequence of Table 4, at 0, 1, 2, 3, 4, 5, or 6 nucleotides.

In some embodiments, the gRNA comprises a 2'-O-methyl (2'-O-Me) modified nucleotide. In some embodiments, the gRNA comprises a 2'-O-(2-methoxyethyl) (2'-O-moe) modified nucleotide. In some embodiments, the gRNA comprises a 2'-fluoro (2'-F) modified nucleotide. In some embodiments, the gRNA comprises a phosphorothioate (PS) bond between nucleotides.

In some embodiments, the gRNA comprises a 5' end modification, a 3' end modification, or 5' and 3' end modifications. In some embodiments, the 5' end modification comprises a phosphorothioate (PS) bond between nucleotides. In some embodiments, the 5' end modification comprises a 2'-O-methyl (2'-O-Me), 2'-O-(2-methoxyethyl) (2'-O-moe), and/or 2'-fluoro (2'-F) modified nucleotide. In some embodiments, the 5' end modification comprises at least one phosphorothioate (PS) bond and one or more of a 2'-O-methyl (2'-O-Me), 2'-O-(2-methoxyethyl) (2'-O-moe), and/or 2'-fluoro (2'-F) modified nucleotide. The end modification may comprise a phosphorothioate (PS), 2'-O-methyl (2'-O-Me), 2'-O-(2-methoxyethyl) (2'-O-moe), and/or 2'-fluoro (2'-F) modification. Equivalent end modifications are also encompassed by embodiments described herein. In some embodiments, the gRNA comprises an end modification in combination with a modification of one or more regions of the gRNA.

A. Compositions of sgRNAs

In some embodiments, the compositions and methods of the invention comprise gRNA comprising a crRNA and trRNA that direct a nuclease such as Cas9 to a target DNA sequence. In some embodiments, the gRNAs described herein may be associated on one RNA molecule (single guide RNA or sgRNA).

In some embodiments, the invention comprises a sgRNA comprising or consisting of any one of the sequences described in SEQ ID Nos: 228-332.

In some embodiments, a sgRNA comprising any one of the modified sequences of SEQ ID Nos: 235-240, 265-285, and 309-329 is provided. In some embodiments, a sgRNA comprising any one of the modified sequences of SEQ ID Nos: 235-240, 265-285, and 309-329, wherein the sgRNA further comprises a 5' "spacer" sequence ("guide sequence") that is complementary to a target sequence, and directs a Cas9 to its target for cleavage is encompassed. In some instances, the invention comprises sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier.

1. Domains of sgRNAs

Briner A E et al., *Molecular Cell* 56:333-339 (2014) describes functional domains of sgRNAs, referred to herein as "domains", including the "spacer" domain responsible for targeting, the "lower stem", the "bulge", "upper stem" (which may include a tetraloop), the "nexus", and the "hairpin 1" and "hairpin 2" domains. See, Briner et al. at page 334, FIG. 1A.

Table 1 and FIG. 21A provide a description of the domains of a sgRNA as used herein. In Table 1, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. In some embodiments, n equals 1.

TABLE 1

Regions of sgRNA (linear view, 5' to 3')

| | LS1-6 | | B1-2 | | US1-12 | | B3-6 | |
|---|---|---|---|---|---|---|---|---|
| 5' terminus (n) | lower stem | n | bulge | n | upper stem | n | bulge | n |

| LS7-12 | | N1-18 | | H1-1 thru H1-12 | | H2-1 thru H2-15 | |
|---|---|---|---|---|---|---|---|
| lower stem | n | nexus | n | hairpin 1 | n | hairpin 2 | 3' terminus |

a) 5' Terminus Region

In some embodiments, the sgRNA comprises nucleotides at the 5' terminus as shown in Table 1. In some embodiments, the 5' terminus of the sgRNA comprises a spacer or guide region that functions to direct a Cas protein to a target nucleotide sequence. In some embodiments, the 5' terminus does not comprise a spacer or guide region. In some embodiments, the 5' terminus comprises a spacer and additional nucleotides that do not function to direct a Cas protein to a target nucleotide region.

In some embodiments, the guide region comprises the first 1-10, 11, 12, 13, 14, 15, 16, 17, 18, 19, or 20 nucleotides at the 5' end of the sgRNA. In some embodiments, the guide region comprises 20 nucleotides. In some embodiments, the guide region may comprise 5, 6, 7, 8, 9, 10, 11, 12, 13, 14, 15, 16, 17, 18, 19, 20, 21, 22, 23, 24, or 25 or more nucleotides. In some embodiments, the guide region may comprise 17 nucleotides. In some embodiments, the guide region may comprise 18 nucleotides. In some embodiments, the guide region may comprise 19 nucleotides.

In some embodiments, the selection of the guide region is determined based on target sequences within the gene of interest for editing. For example, in some embodiments, the sgRNA comprises a guide region that is complementary to target sequences of a gene of interest.

In some embodiments, the target sequence in the gene of interest may be complementary to the guide region of the sgRNA. In some embodiments, the degree of complementarity or identity between a guide region of a sgRNA and its corresponding target sequence in the gene of interest may be about 50%, 55%, 60%, 65%, 70%, 75%, 80%, 85%, 90%, 95%, 96%, 97%, 98%, 99%, or 100%. In some embodiments, the guide region of a sgRNA and the target region of a gene of interest may be 100% complementary or identical. In other embodiments, the guide region of a sgRNA and the target region of a gene of interest may contain at least one mismatch. For example, the guide region of a sgRNA and the target sequence of a gene of interest may contain 1, 2, 3, 4, 5, 6, 7, 8, 9, or 10 mismatches, where the total length of the target sequence is at least about 17, 18, 19, 20 or more base pairs. In some embodiments, the guide region of a sgRNA and the target region of a gene of interest may contain 1-6 mismatches where the guide sequence comprises at least about 17, 18, 19, 20 or more nucleotides. In some embodiments, the guide region of a sgRNA and the target region of a gene of interest may contain 1, 2, 3, 4, 5, or 6 mismatches where the guide sequence comprises about 20 nucleotides. The 5' terminus may comprise nucleotides that are not considered guide regions (i.e., do not function to direct a cas9 protein to a target nucleic acid).

b) Lower Stem

In some embodiments, the sgRNA comprises a lower stem (LS) region that when viewed linearly, is separated by a bulge and upper stem regions. See Table 1.

In some embodiments, the lower stem regions comprise 1-12 nucleotides, e.g. in one embodiment the lower stem regions comprise LS1-LS12. In some embodiments, the lower stem region comprises fewer nucleotides than shown in Table 1 and FIG. 21A. In some embodiments, the lower stem region comprises more nucleotides than shown in Table 1 and FIG. 21A. When the lower stem region comprises fewer or more nucleotides than shown in the schematic of Table 1 and FIG. 21A, the modification pattern, as will be apparent to the skilled artisan, should be maintained.

In some embodiments, the lower stem region has nucleotides that are complementary in nucleic acid sequence when read in opposite directions. In some embodiments, the complementarity in nucleic acid sequence of lower stem leads to a secondary structure of a stem in the sgRNA (e.g., the regions may base pair with one another). In some embodiments, the lower stem regions may not be perfectly complimentary to each other when read in opposite directions.

c) Bulge

In some embodiments, the sgRNA comprises a bulge region comprising six nucleotides, B1-B6. When viewed linearly, the bulge region is separated into two regions. See Table 1. In some embodiments, the bulge region comprises six nucleotides, wherein the first two nucleotides are followed by an upper stem region, followed by the last four nucleotides of the bulge. In some embodiments, the bulge region comprises fewer nucleotides than shown in Table 1 and FIG. 21A. In some embodiments, the bulge region comprises more nucleotides than shown in Table 1 and FIG. 21A. When the bulge region comprises fewer or more nucleotides than shown in the schematic of Table 1 and FIG. 21A, the modification pattern, as will be apparent to the skilled artisan, should be maintained.

In some embodiments, the presence of a bulge results in a directional kink between the upper and lower stem modules in a sgRNA.

d) Upper Stem

In some embodiments, the sgRNA comprises an upper stem region comprising 12 nucleotides. In some embodiments, the upper stem region comprises a loop sequence. In some instances, the loop is a tetraloop (loop consisting of four nucleotides).

In some embodiments, the upper stem region comprises fewer nucleotides than shown in Table 1 and FIG. 21A. In some embodiments, the upper stem region comprises more nucleotides than shown in Table 1 and FIG. 21A. When the upper stem region comprises fewer or more nucleotides than shown in the schematic of Table 1 and FIG. 21A, the modification pattern, as will be apparent to the skilled artisan, should be maintained.

In some embodiments, the upper stem region has nucleotides that are complementary in nucleic acid sequence when read in opposite directions. In some embodiments, the complementarity in nucleic acid sequence of upper stem leads to a secondary structure of a stem in the sgRNA (e.g., the regions may base pair with one another). In some embodiments, the upper stem regions may not be perfectly complimentary to each other when read in opposite directions.

e) Nexus

In some embodiments, the sgRNA comprises a nexus region that is located between the lower stem region and the hairpin 1 region. In some embodiments, the nexus comprises 18 nucleotides. In some embodiments, the nexus region comprises nucleotides N1 through N18 as shown in Table 1 and FIG. 21A.

In some embodiments, the nexus region comprises fewer nucleotides than shown in Table 1 and FIG. 21A. In some embodiments, the nexus region comprises more nucleotides than shown in Table 1 and FIG. 21A. When the nexus region comprises fewer or more nucleotides than shown in the schematic of Table 1 and FIG. 21A, the modification pattern, as will be apparent to the skilled artisan, should be maintained.

In some embodiments, the nexus region has nucleotides that are complementary in nucleic acid sequence when read in opposite directions. In some embodiments, the complementarity in nucleic acid sequence leads to a secondary structure of a stem and/or stem loop in the sgRNA (e.g., certain nucleotides in the nexus region may base pair with one another). In some embodiments, the nexus regions may not be perfectly complimentary to each other when read in opposite directions.

f) Hairpin

In some embodiments, the sgRNA comprises one or more hairpin regions. In some embodiments, the hairpin region is downstream of (e.g., 3' to) the nexus region. In some embodiments, the region of nucleotides immediately downstream of the nexus region is termed “hairpin 1” or “H1”. In some embodiments, the region of nucleotides 3' to hairpin 1 is termed “hairpin 2” or “H2”. In some embodiments, the hairpin region comprises hairpin 1 and hairpin 2. In some embodiments, the sgRNA comprises only hairpin 1 or hairpin 2.

In some embodiments, the hairpin 1 region comprises 12 nucleic acids immediately downstream of the nexus region. In some embodiments, the hairpin 1 region comprises nucleotides H1-1 through H1-12 as shown in Table 1 and FIG. 21A.

In some embodiments, the hairpin 2 region comprises 15 nucleic acids downstream of the hairpin 1 region. In some embodiments, the hairpin 2 region comprises nucleotides H2-1 through H2-15 as shown in Table 1 and FIG. 21A.

In some embodiments, one or more nucleotides is present between the hairpin 1 and the hairpin 2 regions. The one or more nucleotides between the hairpin 1 and hairpin 2 region may be modified or unmodified. In some embodiments, hairpin 1 and hairpin 2 are separated by one nucleotide. In some embodiments, the hairpin regions comprise fewer nucleotides than shown in Table 1 and FIG. 21A. In some embodiments, the hairpin regions comprise more nucleotides than shown in Table 1 and FIG. 21A. When a hairpin region comprises fewer or more nucleotides than shown in the schematic of Table 1 and FIG. 21A, the modification pattern, as will be apparent to the skilled artisan, should be maintained.

In some embodiments, a hairpin region has nucleotides that are complementary in nucleic acid sequence when read in opposite directions. In some embodiments, the hairpin regions may not be perfectly complimentary to each other when read in opposite directions (e.g., the top or loop of the hairpin comprises unpaired nucleotides).

In some embodiments, the sgRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a sgRNA is replaced by 2 nucleotides.

g) 3' Terminus Region

In some embodiments, the sgRNA comprises nucleotides after the hairpin region(s). In some embodiments, the 3' terminus region comprises 1, 2, 3, 4, 5, 6, 7, 8, 9, 10, 15 or 20 or more nucleotides, e.g. that are not associated with the secondary structure of a hairpin. In some embodiments, the 3' terminus region comprises 1, 2, 3, or 4 nucleotides that are not associated with the secondary structure of a hairpin. In some embodiments, the 3' terminus region comprises 4 nucleotides that are not associated with the secondary structure of a hairpin. In some embodiments, the 3' terminus region comprises 1, 2, or 3 nucleotides that are not associated with the secondary structure of a hairpin.

2. Modifications of sgRNAs

In some embodiments, the invention comprises a sgRNA comprising one or more modifications within one or more of the following regions: the nucleotides at the 5' terminus; the lower stem region; the bulge region; the upper stem region; the nexus region; the hairpin 1 region; the hairpin 2 region; and the nucleotides at the 3' terminus.

In some embodiments, the modification comprises a 2'-O-methyl (2'-O-Me) modified nucleotide. In some embodiments, the modification comprises a 2'-O-(2-methoxyethyl) (2'-O-moe) modified nucleotide. In some embodiments, the modification comprises a 2'-fluoro (2'-F) modified nucleotide. In some embodiments, the modification comprises a phosphorothioate (PS) bond between nucleotides.

In some embodiments, the sgRNA comprises modifications at 1, 2, 3, or 4 of the first 4 nucleotides at its 5' end. In some embodiments, the first three or four nucleotides at the 5' terminus, and the last three or four nucleotides at the 3' terminus are modified. In some embodiments, the first four nucleotides at the 5' terminus, and the last four nucleotides at the 3' terminus are linked with phosphorothioate (PS) bonds. In some embodiments, the modification comprises 2'-O-Me. In some embodiments, the modification comprises 2'-F. In some embodiments, the modification comprises 2'-O-moe.

In some embodiments, the sgRNA comprises modifications at 1, 2, 3, or 4 of the first 4 nucleotides at the 5' end. In some embodiments, the sgRNA comprises modifications at 1, 2, 3, or 4 of the first 4 nucleotides at the 3' end. In some embodiments, the first four nucleotides at the 5' terminus and the last four nucleotides at the 3' terminus are linked with a PS bond, and the first three nucleotides at the 5' terminus and the last three nucleotides at the 3' terminus comprise 2'-O-Me or 2'-O-moe modifications.

In some embodiments, the first four nucleotides at the 5' terminus and the last four nucleotides at the 3' terminus are linked with a PS bond, and the first three nucleotides at the 5' terminus and the last three nucleotides at the 3' terminus comprise 2'-F modifications.

In some embodiments, a sgRNA is provided wherein LS1, LS6, LS7, LS8, LS11, and LS12 are modified with 2'-O-Me. In some embodiments, each of the nucleotides in the bulge region of the sgRNA are modified with 2'-O-Me. In some embodiments, each of the nucleotides in the upper stem region of the sgRNA are modified with 2'-O-Me. In some embodiments, N16, N17, and N18 in the nexus region of the sgRNA are modified with 2'-O-Me. In some embodiments, each of the nucleotides in the hairpin 1 region of the sgRNA are modified with 2'-O-Me. In some embodiments, each of the nucleotides in the hairpin 2 region of the sgRNA are modified with 2'-O-Me.

In some embodiments, the sgRNA comprises 2'-O-Me modified nucleotides at the following nucleotides: the first three nucleotides at the 5' terminus; LS1, LS6, LS7, LS8, LS11, and LS12; B1 and B2 in the bulge region; each of the nucleotides in the upper stem region of the sgRNA; N16, N17, and N18 in the nexus region; each of the nucleotides in the hairpin 1 region; each of the nucleotides in the hairpin 2 region; and last four nucleotides at the 3' terminus.

In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me or 2'-F modified nucleic acids at the first three nucleotides at the 5' terminus, and 2'-O-Me or 2'-F modified nucleic acids at the last four nucleotides at the 3' terminus. In some embodiments, LS9 and LS10 are modified with 2'-F. In some embodiments, N15, N16, N17, and N18 are modified with 2'-F. In some embodiments, H2-9, H2-10, H2-11, H2-12, H2-13, HS-14, and H2-15 are modified with 2'-F. In some embodiments, the second to last, third to last, and fourth to last nucleotides at the 3' terminus are modified with 2'-F In some embodiments, a single guide RNA (sgRNA) is provided comprising 2'-F modified nucleic acids at the following nucleotides: LS9 and LS10 in the lower stem region; N15, N16, N17, and N18 in the nexus region; and H2-9, H2-10, H2-11, H2-12, H2-13, HS-14, and H2-15 in the hairpin 2 region. In some embodiments, the sgRNA further comprises 2'-F modified nucleotides at the second to last, third to last, and fourth to last nucleotides at the 3' terminus. In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me or 2'-F modified nucleic acids at the first three nucleotides at the 5' terminus, and 2'-O-Me or 2'-F modified nucleic acids at three of the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1 and LS6; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-F modified nucleotides at LS1-LS6; 2'-O-Me modified nucleotides at US1-US12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-F modified nucleotides at LS2-LS5; 2'-O-Me modified nucleotides at LS1 and LS6; 2'-O-Me modified nucleotides at US1-US12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at LS7, LS8, LS11, and LS12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at LS8, LS10, and LS12; 2'-O-F modified nucleotides at LS7, LS9, and LS11; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1, LS6, LS7, LS8, LS11, and LS12; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1, LS6, LS7, LS8, LS11, and LS12; 2'-F modified nucleotides at LS9 and LS10; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-8; 2'-F modified nucleotides at H2-9-H2-15; 2'-F modified nucleotides at the second from last, third from last, and fourth from last nucleotide at the 3' terminus; and a 2'-O-Me modified nucleotide at the last nucleotide at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at H1-2, H1-4, H1-6, H1-8, H1-10, and H1-12; 2'-F modified nucleotides at H1-1, H1-3, H1-5, H1-7, H1-9, and H1-11; a 2'-F modified nucleotide between Hairpin 1 and Hairpin 2; 2'-F modified nucleotides at H2-2, H2-4, H2-6, H2-8, H2-10, H2-12; and H2-14; 2'-O-Me modified nucleotides at H2-1, H2-3, H2-5, H2-7, H2-9, H2-11; H2-13, and H2-15; 2'-F modified nucleotides at the second from last, and fourth from last nucleotide at the 3' terminus; and 2'-O-Me modified nucleotide at the third from last, and last nucleotide at the 3' terminus. In some embodiments, the sgRNA further comprises three phosphorothioate (PS) bonds linking the first four nucleotides at the 5' terminus and three PS bonds linking the last four nucleotides at the 3' terminus.

Disclosed herein, in some embodiments, is a single guide RNA (sgRNA) comprising 2'-O-Me modifications at nucleotides LS8, LS10, LS12, H1-2, H1-4, H1-6, H1-8, H1-10, H1-12, H2-1, H2-3, H2-5, H2-7, H2-9, H2-11, H2-13, and H2-15; and 2'-F modifications at LS7, LS9, LS11; H1-1, H1-3, H1-5, H1-7, H1-9, H1-11, H1-13, H2-2, H2-4, H2-6, H2-8, H2-10, H2-12, and H2-14. In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me modified nucleotides at the last and third to last nucleotide at the 3' terminus; and 2'-F modified nucleotides at the second to last and third to last nucleotide at the 3' terminus.

Disclosed herein, in some embodiments, is a sgRNA comprising the nucleic acids of any one of SEQ ID Nos: 228-232. Disclosed herein, in some embodiments, is a sgRNA comprising the nucleic acids of any one of SEQ ID Nos: 235-240, 265-285, and 309-329. Disclosed herein, in some embodiments, is a sgRNA comprises nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier. In some embodiments, the sgRNA further comprises three phosphorothioate (PS) bonds linking the first four nucleotides at the 5' terminus and three PS bonds linking the last four nucleotides at the 3' terminus.

In some embodiments, a sgRNA comprising a 5' end modification and one or more modifications in one or more of: the upper stem region; the hairpin 1 region; and the hairpin 2 region is provided, wherein the 5' end modification comprises at least two phosphorothioate linkages within the first seven nucleotides of the 5' terminus.

In some embodiments, a sgRNA comprising a 5' end modification and one or more modifications in one or more of: the upper stem region; the hairpin 1 region; and the hairpin 2 region is provided, wherein the 5' end modification comprises one or more phosphorothioate linkages at the 5' end of the RNA. In some embodiments, one or more phorphorothioate bonds link the 5' terminal nucleotides.

In some embodiments, a sgRNA comprising a 5' end modification and one or more modifications in one or more of: the upper stem region; the hairpin 1 region; and the hairpin 2 region is provided, wherein the 5' end modification comprises one or more phosphorothioate linkages within the first seven nucleotides of the 5' terminus.

In some embodiments, a sgRNA comprising any one of the modified sgRNA sequences of SEQ ID Nos: 228-332 is provided.

In some embodiments, a sgRNA comprising or consisting of any one of the modified sgRNA sequences of SEQ ID Nos: 235-240, 265-285, and 309-329 is provided.

In some embodiments, the invention comprises a sgRNA comprising any one of the modified sequences of SEQ ID Nos: 235-240, 265-285, and 309-329, wherein the sgRNA further comprises a 5' spacer sequence that is at least partially complementary to a target sequence, and directs a Cas9 to its target for cleavage.

In some embodiments, the invention comprises a sgRNA comprising nucleotides having at least 99, 98, 97, 96, 95, 94, 93, 92, 91, 90, 85, 80, 75, or 70% identity to the nucleotides of any one of SEQ ID Nos: 235-240, 265-285, and 309-329, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in in the sequences, but the modification remains unchanged.

In some embodiments, the invention comprises a sgRNA comprising one or more modifications within one or more of the following regions: the nucleotides at the 5' terminus; the lower stem region; the bulge region; the upper stem region; the; the nexus region; the hairpin 1 region; the hairpin 2 region; and the nucleotides at the 3' terminus.

In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the modification comprises an inverted abasic nucleotide.

In some embodiments, a sgRNA is provided comprising 2'-O-Me modified nucleotides at: the first three nucleotides in the 5' terminus; LS1, LS6, LS7, LS8, LS11, and LS12 in the lower stem; B1 and B2 in the bulge region; each of the nucleotides in the upper stem region; N16, N17, and N18 in the nexus region; each of the nucleotides in the hairpin 1 region; one nucleotide between hairpin 1 and hairpin 2; each of the nucleotides in the hairpin 2 region; and the last four nucleotides at the 3' terminus. In one embodiment, the sgRNA further comprises three PS bonds between the first four nucleotides at the 5' terminus and three PS bonds between the last four nucleotides at the 3' terminus.

In some embodiments, a sgRNA is provided comprising 2'-O-Me modified nucleotides at: the first three nucleotides in the 5' terminus; LS1, LS6, LS7, LS8, LS11, and LS12 in the lower stem; B1-B6 in the bulge region; each of the nucleotides in the upper stem region; N16, N17, and N18 in the nexus region; each of the nucleotides in the hairpin 1 region; one nucleotide between hairpin 1 and hairpin 2; each of the nucleotides in the hairpin 2 region; and the last four nucleotides at the 3' terminus. In one embodiment, the sgRNA further comprises three PS bonds between the first four nucleotides at the 5' terminus and three PS bonds between the last four nucleotides at the 3' terminus.

In some embodiments, a sgRNA is provided comprising 2'-F modified nucleotides at: LS9 and LS10 in the lower stem; 15-N18 in the nexus region; H2-9-HS-15 in the hairpin 2 region; and the second to last, third to last, and fourth to last nucleotide in the 3' terminus region.

In some embodiments, a sgRNA is provided comprising 2'-F modified nucleotides at: each nucleotide in the lower stem; 15-N18 in the nexus region; H2-9-HS-15 in the hairpin 2 region; and the second to last, third to last, and fourth to last nucleotide in the 3' terminus region.

In some embodiments, a single guide RNA (sgRNA) is provided comprising 2'-O-Me modified nucleotides at LS8, LS10, LS12, H1-2, H1-4, H1-6, H1-8, H1-10, H1-12, H2-1, H2-3, H2-5, H2-7, H2-9, H2-11, H2-13, H2-15, and the last and third to last nucleotides at the 3' terminus; and 2'-F modifications at LS7, LS9, LS11; H1-1, H1-3, H1-5, H1-7, H1-9, H1-11, H1-13, H2-2, H2-4, H2-6, H2-8, H2-10, H2-12, H2-14, and the second to last and fourth to last nucleotide at the 3' terminus.

Each of the following embodiments are encompassed:

Embodiment 01. A single guide RNA (sgRNA) comprising one or more modifications in one or more of the following regions:
- a. the 5' terminus;
- b. the lower stem region;
- c. the bulge region;
- d. the upper stem region;
- e. the nexus region;
- f. the hairpin 1 region;
- g. the hairpin 2 region; and
- h. the 3' terminus.

Embodiment 02. The sgRNA of embodiment 1, wherein the modification comprises a 2'-O-methyl (2'-O-Me) modified nucleotide.

Embodiment 03. The sgRNA of embodiment 1, wherein the modification comprises a 2'-fluoro (2'-F) modified nucleotide.

Embodiment 04. The sgRNA of embodiment 1, wherein the modification comprises a phosphorothioate (PS) bond between nucleotides.

Embodiment 05. The sgRNA of any one of embodiments 1-3, wherein the first three or four nucleotides at the 5' terminus, and the last three or four nucleotides at the 3' terminus are modified.

Embodiment 06. The sgRNA of any one of embodiments 1-5, wherein the first four nucleotides at the 5' terminus, and the last four nucleotides at the 3' terminus are linked with phosphorothioate (PS) bonds.

Embodiment 07. The sgRNA of embodiment 5, wherein the modification comprises 2'-O-Me.

Embodiment 08. The sgRNA of embodiment 5, wherein the modification comprises 2'-F.

Embodiment 09. The sgRNA of any one of embodiments 1-7, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 10. The sgRNA of any one of embodiments 1-8, wherein the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications.

Embodiment 11. The sgRNA of any one of embodiments 1-10, wherein LS1, LS6, LS7, LS8, LS11, and LS12 are modified with 2'-O-Me.

Embodiment 12. The sgRNA of any one of embodiments 1-11, wherein each of the nucleotides in the bulge region are modified with 2'-O-Me.

Embodiment 13. The sgRNA of any one of embodiments 1-12, wherein each of the nucleotides in the upper stem region are modified with 2'-O-Me.

Embodiment 14. The sgRNA of any one of embodiments 1-13, wherein N16, N17, and N18 in the nexus region are modified with 2'-O-Me.

Embodiment 15. The sgRNA of any one of embodiments 1-14, wherein each of the nucleotides in the hairpin 1 region are modified with 2'-O-Me.

Embodiment 16. The sgRNA of any one of embodiments 1-15, wherein each of the nucleotides in the hairpin 2 region are modified with 2'-O-Me.

Embodiment 17. A single guide RNA (sgRNA) comprising 2'-O-Me modified nucleic acids at the following nucleotides:

a. the first three nucleotides at the 5' terminus;
b. LS1, LS6, LS7, LS8, LS11, and LS12 in the lower stem region;
c. B1 and B2 in the bulge region;
d. each nucleotide in the upper stem region;
e. N16, N17, and N18 in the nexus region;
f. each nucleotide in the hairpin 1 region;
g. each nucleotide in the hairpin 2 region; and
h. the last four nucleotides at the 3' terminus.

Embodiment 18. The sgRNA of embodiment 17, wherein B3-B6 are modified with 2'-O-Me.

Embodiment 19. The sgRNA of embodiment 17, further comprising three phosphorothioate (PS) bonds linking the first four nucleotides at the 5' terminus and three PS bonds linking the last four nucleotides at the 3' terminus.

Embodiment 20. The sgRNA of any one of embodiments 1-10, wherein LS9 and LS10 are modified with 2'-F.

Embodiment 21. The sgRNA of any one of embodiments 1-10 and 20, wherein N15, N16, N17, and N18 are modified with 2'-F.

Embodiment 22. The sgRNA of any one of embodiments 1-10 and 20-21, wherein H2-9, H2-10, H2-11, H2-12, H2-13, H2-14, and H2-15 are modified with 2'-F.

Embodiment 23. The sgRNA of any one of embodiments 1-10 and 21-22, wherein the second to last, third to last, and fourth to last nucleotides at the 3' terminus are modified with 2'-F.

Embodiment 24. A single guide RNA (sgRNA) comprising 2'-F modified nucleotides at the following positions:

a. LS9 and LS10 in the lower stem region;
b. N15, N16, N17, and N18 in the nexus region; and
c. H2-9, H2-10, H2-11, H2-12, H2-13, H2-14, and H2-15 in the hairpin 2 region.

Embodiment 25. The sgRNA of embodiment 24, further comprising 2'-F modified nucleotides at the second to last, third to last, and fourth to last nucleotides at the 3' terminus.

Embodiment 26. The sgRNA of any one of embodiments 24 or 25, further comprising three phosphorothioate (PS) bonds linking the first four nucleotides at the 5' terminus and three PS bonds linking the last four nucleotides at the 3' terminus.

Embodiment 27. The sgRNA of any one of embodiments 24-26, further comprising 2'-O-Me or 2'-F modified nucleotides at the first three nucleotides at the 5' terminus, and 2'-O-Me or 2'-F modified nucleotides at the three of the last four nucleotides at the 3' terminus.

Embodiment 28. A single guide RNA (sgRNA) comprising a. 2'-O-Me modified nucleotides at the first three nucleotides at the 5' terminus;
b. 2'-O-Me modified nucleotides at LS1 and LS6;
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 29. The sgRNA of embodiment 28 further comprising three phosphorothioate (PS) bonds linking the first four nucleotides at the 5' terminus and three PS bonds linking the last four nucleotides at the 3' terminus.

Embodiment 30. A single guide RNA (sgRNA) comprising a. 2'-O-Me modified nucleotides at the first three nucleotides at the 5' terminus;
b. 2'-F modified nucleotides at LS1-LS6;
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 31. The sgRNA of embodiment 30 further comprising three phosphorothioate (PS) bonds linking the first four nucleotides at the 5' terminus and three PS bonds linking the last four nucleotides at the 3' terminus.

Embodiment 32. A single guide RNA (sgRNA) comprising a. 2'-O-Me modified nucleotides at the first three nucleotides at the 5' terminus;
b. 2'-F modified nucleotides at LS2-LS5;
c. 2'-O-Me modified nucleotides at LS1 and LS6;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 33. The sgRNA of embodiment 32 further comprising three phosphorothioate (PS) bonds linking the first four nucleotides at the 5' terminus and three PS bonds linking the last four nucleotides at the 3' terminus.

Embodiment 34. A single guide RNA (sgRNA) comprising a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and g. 2'-O-Me modified nucleotides at the last four nucleotides at the 3' terminus.

Embodiment 35. The sgRNA of embodiment 34 further comprising three phosphorothioate (PS) bonds linking the first four nucleotides at the 5' terminus and three PS bonds linking the last four nucleotides at the 3' terminus.

Embodiment 36. A single guide RNA (sgRNA) comprising a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-F modified nucleotides at LS9 and LS10;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 37. The sgRNA of embodiment 36 further comprising three phosphorothioate (PS) bonds linking the first four nucleotides at the 5' terminus and three PS bonds linking the last four nucleotides at the 3' terminus.

Embodiment 38. A single guide RNA (sgRNA) comprising a. 2'-O-Me modified nucleotides at the first three nucleotides at the 5' terminus;
b. 2'-O-Me modified nucleotides at US1-US12;
c. 2'-O-Me modified nucleotides at LS8, LS10, and LS12;
d. 2'-O-F modified nucleotides at LS7, LS9, and LS11;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 39. The sgRNA of embodiment 32 further comprising three phosphorothioate (PS) bonds linking the first four nucleotides at the 5' terminus and three PS bonds linking the last four nucleotides at the 3' terminus.

Embodiment 40. A single guide RNA (sgRNA) comprising a. 2'-O-Me modified nucleotides at the first three nucleotides at the 5' terminus;
b. 2'-O-Me modified nucleotides at LS1, LS6, LS7, LS8, LS11, and LS12
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 41. The sgRNA of embodiment 40 further comprising three phosphorothioate (PS) bonds linking the first four nucleotides at the 5' terminus and three PS bonds linking the last four nucleotides at the 3' terminus Embodiment 42. A single guide RNA (sgRNA) comprising a. 2'-O-Me modified nucleotides at the first three nucleotides at the 5' terminus;
b. 2'-O-Me modified nucleotides at LS1, LS6, LS7, LS8, LS11, and LS12;
c. 2'-F modified nucleotides at LS9 and LS10;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 43. The sgRNA of embodiment 43 further comprising three phosphorothioate (PS) bonds linking the first four nucleotides at the 5' terminus and three PS bonds linking the last four nucleotides at the 3' terminus.

Embodiment 44. A single guide RNA (sgRNA) comprising a. 2'-O-Me modified nucleotides at the first three nucleotides at the 5' terminus;
b. 2'-O-Me modified nucleotides at US1-US12;
c. 2'-O-Me modified nucleotides at H1-1-H1-12;
d. a 2'-O-Me modified nucleotide between Hairpin 1 and Hairpin 2;
e. 2'-O-Me modified nucleotides at H2-1-H2-8;
f. 2'-F modified nucleotides at H2-9-H2-15;
g. 2'-F modified nucleotides at the second from last, third from last, and fourth from last nucleotide at the 3' terminus; and
h. a 2'-O-Me modified nucleotide at the last nucleotide at the 3' terminus.

Embodiment 45. The sgRNA of embodiment 44 further comprising three phosphorothioate (PS) bonds linking the first four nucleotides at the 5' terminus and three PS bonds linking the last four nucleotides at the 3' terminus.

Embodiment 46. A single guide RNA (sgRNA) comprising a. 2'-O-Me modified nucleotides at the first three nucleotides at the 5' terminus;
b. 2'-O-Me modified nucleotides at US1-US12;
c. 2'-O-Me modified nucleotides at H1-2, H1-4, H1-6, H1-8, H1-10, and H1-12;
d. 2'-F modified nucleotides at H1-1, H1-3, H1-5, H1-7, H1-9, and H1-11;
e. a 2'-F modified nucleotide between Hairpin 1 and Hairpin 2;
f. 2'-F modified nucleotides at H2-2, H2-4, H2-6, H2-8, H2-10, H2-12; and H2-14;
g. 2'-O-Me modified nucleotides at H2-1, H2-3, H2-5, H2-7, H2-9, H2-11; H2-13, and H2-15;
h. 2'-F modified nucleotides at the second from last, and fourth from last nucleotide at the 3' terminus; and
i. 2'-O-Me modified nucleotide at the third from last, and last nucleotide at the 3' terminus.

Embodiment 47. The sgRNA of embodiment 46 further comprising three phosphorothioate (PS) bonds linking the first four nucleotides at the 5' terminus and three PS bonds linking the last four nucleotides at the 3' terminus.

Embodiment 48. A single guide RNA (sgRNA) comprising a. 2'-O-Me modified nucleotides LS8, LS10, LS12, H1-2, H1-4, H1-6, H1-8, H1-10, H1-12, H2-1, H2-3, H2-5, H2-7, H2-9, H2-11, H2-13, and H2-15; and
b. 2'-F modified nucleotides at LS7, LS9, LS11; H1-1, H1-3, H1-5, H1-7, H1-9, H1-11, H1-13, H2-2, H2-4, H2-6, H2-8, H2-10, H2-12, and H2-14.

Embodiment 49. The sgRNA of embodiment 48, further comprising three phosphorothioate (PS) bonds linking the first four nucleotides at the 5' terminus and three PS bonds linking the last four nucleotides at the 3' terminus.

Embodiment 50. The sgRNA of any one of embodiments 48-49, further comprising a. 2'-O-Me modified nucleotides at the last and third to last nucleotide at the 3' terminus; and b. 2'-F modified nucleotides at the second to last and third to last nucleotide at the 3' terminus.

Embodiment 51. A sgRNA comprising the nucleic acids of any one of SEQ ID Nos: 228-332.

Embodiment 52. A sgRNA comprising the nucleic acids of any one of SEQ ID Nos: 235-240, 265-285, and 309-329.

Embodiment 53. A sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier.

Embodiment 54. The sgRNA of any one of embodiments 51-53, further comprising three phosphorothioate (PS) bonds linking the first four nucleotides at the 5' terminus and three PS bonds linking the last four nucleotides at the 3' terminus.

B. Compositions of dgRNAs

In some embodiments, the compositions and methods of the invention comprise gRNA comprising a crRNA and trRNA that direct a nuclease such as Cas9 to a target DNA sequence. In some embodiments, the gRNAs are associated, but on two separate RNA molecules (dual guide RNA or dgRNA).

Table 2 and FIG. 21C provides a description of domains of a crRNA as used herein. The 5' terminus region may comprise a spacer region at or near the 5' terminus of the crRNA and functions to direct a Cas9 to a target region in the DNA, e.g., as described herein. In Table 2, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. Any of the dgRNAs described herein may include an "n" between any domain.

Table 3 and FIG. 21C provide a description of domains of a trRNA as used herein. In Table 3, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. Any of the dgRNAs described herein may include an "n" between any domain.

1. Domains of dgRNAs

As described in Briner 2014, dgRNAs can be developed based on specific functional domains, referred to herein as "domains", including the spacer responsible for targeting, the lower stem, the bulge, the upper stem, the nexus, and the hairpin domains. In dgRNAs, the crRNA comprises some components of the gRNA and the trRNA comprises some components of the gRNA.

Regions of crRNAs are provided in Table 2 and FIG. 21C. Regions of trRNAs are provided in Table 3 and FIG. 21C. FIG. 21C shows a schematic of an exemplary dgRNA.

TABLE 2

| Regions of crRNA (linear view, 5' to 3') | | | | | | |
|---|---|---|---|---|---|---|
| | LS1-6 | | B1-2 | | US1-14 | |
| 5' terminus (n) | lower stem | n | bulge | n | upper stem | 3' terminus |

TABLE 3

| Regions of trRNA (linear view, 5' to 3') | | | | | | | | | | | | | |
|---|---|---|---|---|---|---|---|---|---|---|---|---|---|
| | US1-11 | | B1 -4 | | LS1-6 | | N1-18 | | H1-1 thru H1-12 | | H2-1 thru H2-15 | |
| 5' terminus (n) | upper stem | n | bulge | n | lower stem | n | nexus | n | hairpin 1 | n | hairpin 2 | 3' terminus |

a) 5' Terminus Region

In some embodiments, the dgRNA comprises nucleotides at the 5' terminus of the crRNA and trRNA as shown in Tables 2-3 and FIG. 21C.

In some embodiments, the 5' terminus of the crRNA comprises a spacer or guide region that functions to direct a Cas protein to a target nucleotide sequence. In some embodiments, the 5' terminus does not comprise a spacer or guide region. In some embodiments, the 5' terminus comprises a spacer and additional nucleotides that do not function to direct a Cas protein to a target nucleotide region.

In some embodiments, the guide region comprises the first 1-10, 11, 12, 13, 14, 15, 16, 17, 18, 19, or 20 nucleotides at the 5' end of the crRNA. In some embodiments, the guide region comprises 20 nucleotides. In some embodiments, the guide region may comprise 5, 6, 7, 8, 9, 10, 11, 12, 13, 14, 15, 16, 17, 18, 19, 20, 21, 22, 23, 24, or 25 or more nucleotides. In some embodiments, the guide region may comprise 17 nucleotides. In some embodiments, the guide region may comprise 18 nucleotides. In some embodiments, the guide region may comprise 19 nucleotides.

In some embodiments, the selection of the guide region is determined based on target sequences within the gene of interest for editing. For example, in some embodiments, the crRNA comprises a guide region that is complementary to target sequences of a gene of interest.

In some embodiments, the target sequence in the gene of interest may be complementary to the guide region of the crRNA. In some embodiments, the degree of complementarity or identity between a guide region of a crRNA and its corresponding target sequence in the gene of interest may be about 50%, 55%, 60%, 65%, 70%, 75%, 80%, 85%, 90%, 95%, 96%, 97%, 98%, 99%, or 100%. In some embodiments, the guide region of a crRNA and the target region of a gene of interest may be 100% complementary or identical. In other embodiments, the guide region of a crRNA and the target region of a gene of interest may contain at least one mismatch. For example, the guide region of a crRNA and the target sequence of a gene of interest may contain 1, 2, 3, 4, 5, 6, 7, 8, 9, or 10 mismatches, where the total length of the target sequence is at least about 17, 18, 19, 20 or more base pairs. In some embodiments, the guide region of a crRNA and the target region of a gene of interest may contain 1-6 mismatches where the guide sequence comprises at least about 17, 18, 19, 20 or more nucleotides. In some embodiments, the guide region of a crRNA and the target region of a gene of interest may contain 1, 2, 3, 4, 5, or 6 mismatches where the guide sequence comprises about 20 nucleotides.

In some embodiments, the trRNA comprises a 5' terminus. In some embodiments, the trRNA comprises a 5' terminus which forms, in part, the upper stem of a dgRNA. The 5' terminus of the trRNA is not complementary to a region of the target gene.

b) Lower Stem

In some embodiments, the dgRNA comprises a lower stem (LS) region. The lower stem region comprises a crRNA lower stem region and a trRNA lower stem region that associate as depicted in FIG. 21C. In some embodiments, the lower stem region of the crRNA is at least partially complementary to the lower stem region of the trRNA. In some embodiments, the lower stem region of the crRNA is fully complementary to the lower stem region of the trRNA.

In some embodiments, the lower stem region of the crRNA and trRNA each comprise 6 nucleotides. In some embodiments, the lower stem region of the crRNA and trRNA each comprise fewer nucleotides than shown in Tables 2 and 3 and FIG. 21C. In some embodiments, the lower stem region comprises more nucleotides than shown in Tables 2 and 3 and FIG. 21C. When the lower stem region comprises fewer or more nucleotides than shown in the schematic of Tables 2 and 3 and FIG. 21C, the modification patterns, as will be apparent to the skilled artisan, are maintained. In some embodiments, the number of nucleotides in the lower stem of the crRNA differs from the number of nucleotides in the lower stem of the trRNA.

c) Bulge

In some embodiments, the dgRNA comprises a bulge (B) region. In some embodiments, the crRNA comprises one bulge region and the trRNA comprises one bulge region. In some embodiments, each bulge region comprises 1-4 nucleotides. In some embodiments, the bulge region of the crRNA comprises two nucleotides, and the bulge region of the trRNA comprises four nucleotides.

In some embodiments, the crRNA bulge region is located between the lower stem region and the upper stem region of the crRNA. In some embodiments, the bulge region of the crRNA comprises two nucleotides. In some embodiments, the bulge region of the crRNA comprises nucleotides B1 and B2 as shown Table 2 and FIG. 21C.

In some embodiments, the trRNA bulge region is located between the upper stem region and the lower stem region of the trRNA. In some embodiments, the bulge region of the trRNA comprises four nucleotides. In some embodiments, the bulge region of the trRNA comprises nucleotides B1 through B4 as shown Table 3 and FIG. 21C.

In some embodiments, the presence of a bulge results in a directional kink between the upper and lower stems modules in a dgRNA. The crRNA bulge and trRNA bulge may be partially complementary. The crRNA bulge and trRNA bulge may have no complementary.

In some embodiments, the bulge regions of the crRNA and trRNA comprise more nucleotides than shown in Tables 2 and 3 and FIG. 21C. When the bulge region comprises fewer or more nucleotides than shown in the schematic of Tables 2 and 3 and FIG. 21C, the modification patterns, as will be apparent to the skilled artisan, are maintained. In some embodiments, the number of nucleotides in the bulge of the crRNA differs from the number of nucleotides in the bulge of the trRNA.

d) Upper Stem

In some embodiments, the dgRNA comprises an upper stem (US) region. The upper stem region comprises a crRNA upper stem region and a trRNA upper stem region that associate as depicted in FIG. 21C. In some embodiments, the upper stem region of the crRNA is at least partially complementary to the upper stem region of the trRNA. In some embodiments, the upper stem region of the crRNA is fully complementary to the upper stem region of the trRNA.

In some embodiments, the upper stem region of the crRNA comprises fourteen nucleotides. In some embodiments, the upper stem region of the trRNA comprises eleven nucleotides. In some embodiments, the upper stem regions of the crRNA and trRNA each comprise fewer nucleotides than shown in Tables 2 and 3 and FIG. 21C. In some embodiments, the upper stem regions of the crRNA and trRNA comprise more nucleotides than shown in Tables 2 and 3 and FIG. 21C. When the upper stem region comprises fewer or more nucleotides than shown in the schematic of Tables 2 and 3 and FIG. 21C, the modification patterns, as will be apparent to the skilled artisan, are maintained.

In some embodiments, the upper stem of the crRNA comprises nucleotides US1 through US14 as shown in Table 2 and FIG. 21C.

In some embodiments, the upper stem of the trRNA comprises nucleotides US1 through US11 as shown in Table 3 and FIG. 21C.

e) Nexus

In some embodiments, the dgRNA comprises a trRNA comprising a nexus region. In some embodiments, the nexus is between the lower stem region and the hairpin 1 region of the trRNA. In some embodiments, the nexus is located immediately downstream of the lower stem of the trRNA. In some embodiments, the nexus comprises eighteen nucleotides. In some embodiments, the nexus region of the trRNA comprises nucleotides N1-N18 as shown in Table 3 and FIG. 21C. In some embodiments, the nexus comprises fewer nucleotides than shown in Table 3 and FIG. 21C. In some embodiments, the nexus region of the trRNA comprises more nucleotides than shown in Table 3 and FIG. 21C. When the nexus region comprises fewer or more nucleotides than shown in Table 3 and FIG. 21C, the modification patterns, as will be apparent to the skilled artisan, are maintained.

In some embodiments, the nexus region has nucleotides that are complementary in nucleic acid sequence when read in opposite directions. In some embodiments, the complementarity in nucleic acid sequence leads to a secondary structure of a stem and/or stem loop in the sgRNA (e.g., certain nucleotides in the nexus region may base pair with one another). In some embodiments, the nexus regions may not be perfectly complimentary to each other when read in opposite directions.

f) Hairpin

In some embodiments, the hairpin region of the trRNA is downstream of the nexus region. In some embodiments, the region of nucleotides immediately downstream of the nexus region is termed "hairpin 1." In some embodiments, the region of nucleotides immediately downstream of the hairpin 1 region is termed "hairpin 2." In some embodiments, the hairpin region comprises hairpin 1 and hairpin 2. In some instances, hairpin 1 and hairpin 2 are separated by one or more nucleotide "n." In some embodiments, n=1. In some embodiments, the trRNA comprises only hairpin 1 or hairpin 2.

Replacement of the hairpin 1 region of a trRNA with 2 nucleotides has been shown to allow editing activity of a Cas RNP (see US20150376586, FIG. 16). In some embodiments, the trRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a trRNA is replaced by 2 nucleotides.

In some embodiments, hairpin 1 of the trRNA comprises twelve nucleotides immediately downstream of the nexus region. In some embodiments, the hairpin 1 region of the trRNA comprises nucleotides H1-1 through H1-12 as shown in Table 3 and FIG. 21C.

In some embodiments, non-hairpin nucleotides are present between the hairpin 1 and the hairpin 2 regions of the trRNA. In some embodiments, one to two non-hairpin nucleotides reside between hairpin 1 and hairpin 2.

In some embodiments, hairpin 2 of the trRNA comprises fifteen nucleotides after (3' to) hairpin 1. In some embodiments, the hairpin 2 region of the trRNA comprises nucleotides H2-1 through H2-15 as shown in Table 3 and FIG. 21C. In some embodiments, the hairpin 2 region of the trRNA comprises nucleotides H2-1 through H2-15 as shown in Table 3, and the "n" between hairpin 1 and hairpin 2 is 1 or 2.

In some embodiments, a hairpin region of the trRNA comprises more nucleotides than shown in Table 3 and FIG. 21C. When a hairpin region comprises fewer or more nucleotides than shown in Table 3 and FIG. 21C, the modification patterns, as will be apparent to the skilled artisan, are maintained.

In some embodiments, a hairpin region has nucleotides that are complementary in nucleic acid sequence when read in opposite directions. In some embodiments, the hairpin regions may not be perfectly complimentary to each other when read in opposite directions (e.g., the top or loop of the hairpin comprises unpaired nucleotides).

In some embodiments, the trRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a trRNA is replaced by 2 nucleotides.

g) 3' Terminus

In some embodiments, the dgRNA comprises a trRNA comprising a 3' terminus region comprising additional nucleotides after (3' to) the hairpin region(s). In some embodiments, the 3' terminus region comprises 1, 2, 3, 4, 5, 6, 7, 8, 9, 10, 15 or 20 or more nucleotides that are not associated with the secondary structure of a hairpin. In some embodiments, the 3' terminus region comprises 1, 2, 3, or 4 nucleotides that are not associated with the secondary structure of a hairpin. In some embodiments, the 3' terminus region comprises 4 nucleotides that are not associated with the secondary structure of a hairpin. In some embodiments, the 3' terminus region comprises 1, 2, or 3 nucleotides that are not associated with the secondary structure of a hairpin.

2. Modifications of dgRNAs

In some embodiments, a dgRNA comprises a modified crRNA and an unmodified trRNA. In some embodiments, a dgRNA comprises an unmodified crRNA and a modified trRNA. In some embodiments, both the crRNA and trRNA of a dgRNA comprise modifications.

In some embodiments, the gRNAs described herein are in two separate RNA molecules (dual guide or dgRNA). See, Tables 2, 3, and FIG. 21C.

In some embodiments, the invention comprises a dgRNA comprising or consisting of a) any one of the crRNA sequences of SEQ ID Nos: 1-187; and b) any one of the trRNA sequences described in SEQ ID Nos: 188-227.

In some embodiments, a dgRNA comprising any one of the modified crRNA sequences of 1-187 is provided.

In some embodiments, a dgRNA comprising any one of the modified trRNA sequences of 188-227 is provided.

In some embodiments, a dgRNA comprising any one of the modified crRNA sequences of SEQ ID Nos: 19-31, 53-73, and 104-130 is provided. In some embodiments, the invention comprises a dgRNA comprising any one of the modified sequences of SEQ ID Nos: 19-31, 53-73, and 104-130, wherein the crRNA further comprises a 5' spacer sequence that is at least partially complementary to a target sequence, and directs a Cas9 to its target for cleavage.

In some embodiments, the invention comprises a crRNA comprising any one of the sequences described in SEQ ID Nos: 1-187. In some embodiments, the invention comprises a crRNA comprising or consisting of any one of the sequences described in SEQ ID Nos: 19-31, 53-73, and 104-130. In some embodiments, the invention comprises a crRNA comprising any one of the sequences described in SEQ ID Nos: 19-31, 53-73, and 104-130 and a spacer region.

In some embodiments, the invention comprises a trRNA comprising or consisting of any one of the sequences described in SEQ ID Nos:188-277.

In some embodiments, the invention comprises a crRNA comprising nucleotides having at least 99, 98, 97, 96, 95, 94, 93, 92, 91, 90, 85, 80, 75, or 70% identity to the nucleotides of any one of SEQ ID Nos: 1-187, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in in the sequences, but the modification remains unchanged.

In some embodiments, the invention comprises a trRNA comprising nucleotides having at least 99, 98, 97, 96, 95, 94, 93, 92, 91, 90, 85, 80, 75, or 70% identity to the nucleotides of any one of SEQ ID Nos: 188-277, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in the sequences, but the modification on each nucleotide remains unchanged.

3. crRNAs, trRNAs, and dgRNAs with Modifications

In some embodiments, the crRNA comprises one or more modified nucleotides within one or more of the 5' terminus, lower stem, bulge, upper stem, and 3' terminus.

In some embodiments, the modification comprises 2'-O-Me.

In some embodiments, the modification comprises 2'-F.

In some embodiments, the modification comprises a phosphorothioate (PS) bond linking one or more nucleotides. In some embodiments, the modification is three PS bonds linking the first four nucleotides at the 5' terminus and three PS bonds linking the last four nucleotides at the 3' terminus.

In some embodiments, the modification comprises an inverted abasic nucleotide.

In some embodiments, a crRNA is provided comprising 2'-O-Me modified nucleotides at each nucleotide in the upper stem. In some embodiments, US-1 through US-14 of the crRNA are each modified with 2'-O-Me. In some embodiments, LS1 and LS6 of the crRNA are modified with 2'-O-Me. In some embodiments, LS5 of the crRNA is modified with 2'-O-Me.

In some embodiments, a crRNA comprising 2'-O-Me modified nucleotides at each of the nucleotides in the upper stem, and LS1 and LS6 in the lower stem is provided. In some embodiments, the crRNA further comprises one or more 2'-O-Me or 2'-O-moe modified nucleotides in the 5' and/or 3' terminus region, e.g. in a 5' and/or 3' end modification.

In some embodiments, a crRNA comprising 2'-O-Me modified nucleotides at each of the nucleotides in the upper stem, LS1, LS5, and LS6 in the lower stem is provided. In some embodiments, the crRNA further comprises one or more 2'-O-Me or 2'-O-moe modified nucleotides in the 5' and/or 3' terminus region, e.g. in a 5' and/or 3' end modification.

In some embodiments, the invention comprises a crRNA comprising 2'-F modified nucleotides at LS1, LS2, and LS6 in the lower stem. In some embodiments, the crRNA further comprises 2'-F modified nucleotides at each of B1 and B2 in the bulge region. In some embodiments, the invention comprises a crRNA comprising 2'-F modified nucleotides at LS1, LS2, and LS6 in the lower stem, and at each of B1 and B2 in the bulge region. In some embodiments, the crRNA further comprises one or more 2'-O-Me or 2'-O-moe modified nucleotides in the 5' and/or 3' terminus region, e.g. in a 5' and/or 3' end modification.

In some embodiments, the crRNA comprises 2'-O-Me modified nucleotides at nucleotides LS1 and LS6 in the lower stem region; each of the nucleic acids in the bulge region; and each of the nucleic acids in the upper stem region. In some embodiments, the LS5 nucleotide of the crRNA is also modified with 2'-O-Me. In some embodiments, LS2, LS3, and LS4 of the crRNA are not modified. In some embodiments, the crRNA further comprises one or more 2'-O-Me or 2'-O-moe modified nucleotides in the 5' and/or 3' terminus region, e.g. in a 5' and/or 3' end modification.

In some embodiments, the crRNA comprises 2'-fluoro (2'-F) modified nucleotides at LS1, LS2, and LS6 in the lower stem region, and each of the nucleotides in the bulge region. In some embodiments, the crRNA comprises 2'-fluoro (2'-F) modified nucleotides at LS1, LS2, and LS6 in the lower stem region, and at B2 and B2 in the bulge region. In some embodiments, the crRNA comprises 2'-fluoro (2'-F) modified nucleotides at LS1-LS6 in the lower stem region, and each of the nucleotides in the bulge region. In some embodiments, the crRNA further comprises one or more 2'-O-Me or 2'-O-moe modified nucleotides in the 5' and/or 3' terminus region, e.g. in a 5' and/or 3' end modification.

In some embodiments, the invention comprises a trRNA comprising one or more modified nucleotides within one or more of the following regions: the 5' terminus, the upper stem region; the bulge region; the lower stem region; the nexus region; the hairpin 1 region; the intervening region between the hairpin 1 and hairpin 2 regions; the hairpin 2 region; and the 3' terminus region.

In some embodiments, the modification comprises 2'-O-Me.

In some embodiments, the modification comprises 2'-F.

In some embodiments, the modification comprises a phosphorothioate (PS) bond linking one or more nucleotides. In some embodiments, the modification is three PS bonds linking the first four nucleotides at the 5' terminus and three PS bonds linking the last four nucleotides at the 3' terminus.

In some embodiments, the modification comprises an inverted abasic nucleotide.

In some embodiments, the trRNA comprises 2'-O-Me modified nucleotides at each nucleic acid in the upper stem; B1 and B2 in the bulge region; LS1 and LS2 in the lower stem region; N3, N4, N5, N15, N16, N17, and N18 in the nexus region; each nucleotide in the hairpin 1 region; one nucleotide between the hairpin 1 and hairpin 2 region; and each nucleotide in the hairpin 2 region. In some embodiments, the trRNA further comprises one or more 2'-O-Me or 2'-O-moe modified nucleotides in the 5' and/or 3' terminus region, e.g. in a 5' and/or 3' end modification.

In some embodiments, the trRNA comprises 2'-O-Me modified nucleotides at each nucleic acid in the upper stem; each nucleotide in the bulge region; LS1, LS2, LS5, and LS6 in the lower stem region; N3-N5, N10-N18 in the nexus region; each nucleotide in the hairpin 1 region; one nucleotide between the hairpin 1 and hairpin 2 region; and each nucleotide in the hairpin 2 region. In some embodiments, the crRNA further comprises one or more 2'-O-Me or 2'-O-moe modified nucleotides in the 5' and/or 3' terminus region, e.g. in a 5' and/or 3' end modification.

In some embodiments, the trRNA comprises 2'-F modified nucleotides at N15 through N18 in the nexus region. In some embodiments, the trRNA further comprises one or more 2'-F modified nucleotides in the 5' and/or 3' terminus region, e.g. in a 5' and/or 3' end modification.

In some embodiments, the trRNA comprises 2'-F modified nucleotides at LS4 and LS5 in the lower stem region, and N13-N18 in the nexus region. In some embodiments, the trRNA further comprises one or more 2'-F modified nucleotides in the 5' and/or 3' terminus region, e.g. in a 5' and/or 3' end modification.

In some embodiments, the trRNA comprises 2'-F modified nucleotides at LS1, LS3, and LS5 in the lower stem, and 2'-O-Me modified nucleotides at LS2, LS4, and LS6 in the lower stem.

Disclosed herein, in some embodiments, is a crispr RNA (crRNA) comprising one or more modifications within one or more of the following regions: the first five nucleotides at the 5' terminus; the lower stem region; the bulge region; the upper stem region; and the last five nucleotides at the 3' terminus. In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the first three nucleotides at the 5' terminus, and the last three nucleotides at the 3' terminus are modified. In some embodiments, the first four nucleotides at the 5' terminus, and the last four nucleotides at the 3' terminus are linked with phosphorothioate (PS) bonds. In some embodiments, the modification comprises 2'-O-Me. In some embodiments, the modification comprises 2'-F. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-O-Me modifications. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications. In some embodiments, LS1 and LS6 are modified with 2'-O-Me. In some embodiments, each of the nucleotides in the upper stem region are modified with 2'-O-Me.

In some embodiments, the invention comprises a crispr RNA (crRNA) comprising 2'-O-Me modified nucleic acids at the following nucleotides: LS1 and LS6 in the lower stem region; and each nucleotide in the upper stem region. In some embodiments, the crRNA further comprises three phosphorothioate (PS) bonds linking the first four nucleotides at the 5' terminus and three PS bonds linking the last four nucleotides at the 3' terminus. In some embodiments, the crRNA further comprises 2'-O-Me or 2'-F modified nucleic acids at the first three nucleotides at the 5' terminus, and 2'-O-Me or 2'-F modified nucleic acids at the last three nucleotides at the 3' terminus. In some embodiments, LS1, LS2, and LS6 are modified with 2'-F. In some embodiments, each nucleotide in the bulge region is modified with 2'-F.

Disclosed herein, in some embodiments, is a crispr RNA (crRNA) comprising 2'-F modified nucleic acids at the following nucleotides: LS1, LS2, and LS6 in the lower stem region; and each nucleotide in the bulge region. In some embodiments, the crRNA further comprises three phosphorothioate (PS) bonds linking the first four nucleotides at the 5' terminus and three PS bonds linking the last four nucleotides at the 3' terminus. In some embodiments, the crRNA further comprises 2'-O-Me or 2'-F modified nucleic acids at the first three nucleotides at the 5' terminus, and 2'-O-Me or 2'-F modified nucleic acids at the last three nucleotides at the 3' terminus.

In some embodiments, a crRNA comprising the nucleic acids of any one of SEQ ID Nos: 1-187 is provided. In some embodiments, a crRNA comprising the nucleic acids of any one of SEQ ID Nos: 19-31, 53-73, 104-130, and 161-187 is provided. In some embodiments, a crRNA comprising nucleic acids having at least 99, 98, 97, 96, 95, 94, 93, 92, 91, 90, 85, 80, 75, or 70% identity to the nucleic acids of any one of SEQ ID Nos: 19-31, 53-73, 104-130, and 161-187, wherein the modification pattern is identical to the modification pattern shown in the reference sequence identifier, is provided. In some embodiments, the crRNA further comprises three phosphorothioate (PS) bonds linking the first four nucleotides at the 5' terminus and three PS bonds linking the last four nucleotides at the 3' terminus.

Also encompassed is a tracr RNA (trRNA) comprising one or more modifications within one or more of the following regions: the first five nucleotides at the 5' terminus; the upper stem region; the bulge region; the lower stem region; the nexus region; the hairpin 1 region; the hairpin 2 region; and the last five nucleotides at the 3' terminus. In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the first four nucleotides at the 5' terminus, and the last four nucleotides at the 3' terminus are linked with phosphorothioate (PS) bonds. In some embodiments, the first three nucleotides at the 5' terminus, and the last three nucleotides at the 3' terminus are modified. In some embodiments, the modification comprises 2'-O-Me. In some embodiments, the modification comprises 2'-F. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-O-Me modifications. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications. In some embodiments, each nucleotide in the upper stem region is modified with 2'-O-Me. In some embodiments, B1 and B2 within the bulge region are modified with 2'-O-Me. In some embodiments, N3, N4, N5, N15, N16, N17, and N18 in the nexus region are modified with 2'-O-Me. In some embodiments, each nucleotide in the hairpin 1 region is modified with 2'-O-Me. In some embodiments, each nucleotide in the hairpin 2 region is modified with 2'-O-Me.

In some embodiments, the invention comprises a tracr RNA (trRNA) comprising 2'-O-Me modified nucleic acids at the following nucleotides: each nucleotide in the upper stem; B1 and B2 within the bulge region; N3, N4, N5, N15, N16, N17, and N18 in the nexus region; each nucleotide in the hairpin 1 region; and each nucleotide in the hairpin 2 region. In some embodiments, the trRNA further comprises three phosphorothioate (PS) bonds linking the first four nucleotides at the 5' terminus and three PS bonds linking the last four nucleotides at the 3' terminus. In some embodiments, the trRNA further comprises 2'-O-Me or 2'-F modified nucleotides at the first three nucleotides at the 5' terminus, and 2'-O-Me or 2'-F modified nucleic acids at the last three nucleotides at the 3' terminus. In some embodiments, N15, N16, N17, and N18 are modified with 2'-F. In some embodiments, LS1, LS3, and LS5 are modified with 2'-F, and LS2, LS4, and LS6 are modified with 2'-O-Me. In some embodiments, the trRNA further comprises three phosphorothioate (PS) bonds linking the first four nucleotides at the 5' terminus and three PS bonds linking the last four nucleotides at the 3' terminus. In some embodiments, the trRNA further comprises 2'-O-Me or 2'-F modified nucleic acids at the first three nucleotides at the 5' terminus, and 2'-O-Me or 2'-F modified nucleic acids at the last three nucleotides at the 3' terminus.

In some embodiments, a trRNA comprising the nucleic acids of any one of SEQ ID Nos: 188-227 is provided. In some embodiments, a trRNA comprising nucleic acids having at least 99, 98, 97, 96, 95, 94, 93, 92, 91, 90, 85, 80, 75, or 70% identity to the nucleic acids of any one of SEQ ID Nos: 188-227, wherein the modification pattern is identical to the modification pattern shown in the reference sequence identifier, is provided. In some embodiments, the trRNA further comprises three phosphorothioate (PS) bonds linking the first four nucleotides at the 5' terminus and three PS bonds linking the last four nucleotides at the 3' terminus.

In some instances, a dual guide comprising a crRNA and a trRNA is provided, wherein the crRNA comprises the nucleic acids of any one of SEQ ID Nos: 1-187, and wherein the trRNA comprises the nucleic acids of any one of SEQ ID Nos: 188-227.

A dual guide comprising a crRNA disclosed herein and a trRNA disclosed herein is encompassed, as is a dual guide comprising a crRNA disclosed herein and an unmodified trRNA. In some embodiments, a dual guide comprising an unmodified crRNA and a modified trRNA disclosed herein is provided.

In some embodiments, and of the following are encompassed:

Embodiment 55. A crispr RNA (crRNA) comprising one or more modifications within one or more of the following regions:
- a. the first five nucleotides at the 5' terminus;
- b. the lower stem region;
- c. the bulge region;
- d. the upper stem region; and
- e. the last five nucleotides at the 3' terminus.

Embodiment 56. The crRNA of embodiment 55, wherein the modification comprises a 2'-O-methyl (2'-O-Me) modified nucleotide.

Embodiment 57. The crRNA of embodiment 55, wherein the modification comprises a 2'-fluoro (2'-F) modified nucleotide.

Embodiment 58. The crRNA of embodiment 55, wherein the modification comprises a phosphorothioate (PS) bond between nucleotides.

Embodiment 59. The crRNA of any one of embodiments 55-58, wherein the first three nucleotides at the 5' terminus and the last three nucleotides at the 3' terminus are modified.

Embodiment 60. The crRNA of any one of embodiments 55-58, wherein the first four nucleotides at the 5' terminus, and the last four nucleotides at the 3' terminus are linked with phosphorothioate (PS) bonds.

Embodiment 61. The crRNA of embodiment 59, wherein the modification comprises 2'-O-Me.

Embodiment 62. The crRNA of embodiment 59, wherein the modification comprises 2'-F.

Embodiment 63. The crRNA of any one of embodiments 55-62, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 64. The crRNA of any one of embodiments 55-62, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-F modifications.

Embodiment 65. The crRNA of any one of embodiments 55-60, wherein LS1 and LS6 are modified with 2'-O-Me.

Embodiment 66. The crRNA of any one of embodiments 55-60 and 65, wherein each of the nucleotides in the upper stem region are modified with 2'-O-Me.

Embodiment 67. A crispr RNA (crRNA) comprising 2'-O-Me modified nucleotides at:

a. LS1 and LS6 in the lower stem region; and b. each nucleotide in the upper stem region.

Embodiment 68. The crRNA of embodiment 67, further comprising three phosphorothioate (PS) bonds linking the first four nucleotides at the 5' terminus and three PS bonds linking the last four nucleotides at the 3' terminus.

Embodiment 69. The crRNA of embodiment 67 or 68, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 70. The crRNA of any of embodiments 55-60, wherein LS1, LS2, and LS6 are modified with 2'-F.

Embodiment 71. The crRNA of any of embodiments 55-60 and 70, wherein each nucleotide in the bulge region is modified with 2'-F.

Embodiment 72. A crispr RNA (crRNA) comprising 2'-F modified nucleotides at:

a. LS1, LS2, and LS6 in the lower stem region; and b. each nucleotide in the bulge region.

Embodiment 73. The crRNA of any one of embodiments 70-72, further comprising three phosphorothioate (PS) bonds linking the first four nucleotides at the 5' terminus and three PS bonds linking the last four nucleotides at the 3' terminus.

Embodiment 74. The crRNA of embodiment 72 or 73, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 75. A crRNA comprising the nucleic acids of any one of SEQ ID Nos: 1-187.

Embodiment 76. A crRNA comprising the nucleic acids of any one of SEQ ID Nos: 19-31, 53-73, 104-130, and 161-187.

Embodiment 77. A crRNA comprising nucleic acids having at least 99, 98, 97, 96, 95, 94, 93, 92, 91, 90, 85, 80, 75, or 70% identity to the nucleic acids of any one of SEQ ID Nos: 19-31, 53-73, 104-130, and 161-187, wherein the modification pattern is identical to the modification pattern shown in the reference sequence identifier.

Embodiment 78. The crRNA of any one of embodiments 75-77, further comprising three phosphorothioate (PS) bonds linking the first four nucleotides at the 5' terminus and three PS bonds linking the last four nucleotides at the 3' terminus.

Embodiment 79. A tracr RNA (trRNA) comprising one or more modifications within one or more of the following regions:

a. the first five nucleotides at the 5' terminus;

b. the upper stem region;

c. the bulge region;

d. the lower stem region;

e. the nexus region;

f. the hairpin 1 region;

g. the hairpin 2 region; and h. the last five nucleotides at the 3' terminus.

Embodiment 80. The trRNA of embodiment 79, wherein the modification comprises a 2'-O-methyl (2'-O-Me) modified nucleotide.

Embodiment 81. The trRNA of embodiment 79, wherein the modification comprises a 2'-fluoro (2'-F) modified nucleotide.

Embodiment 82. The trRNA of embodiment 79, wherein the modification comprises a phosphorothioate (PS) bond between nucleotides.

Embodiment 83. The trRNA of any one of embodiments 79-82, wherein the first four nucleotides at the 5' terminus, and the last four nucleotides at the 3' terminus are linked with phosphorothioate (PS) bonds.

Embodiment 84. The trRNA of any one of embodiments 79-82, wherein the first three nucleotides at the 5' terminus, and the last three nucleotides at the 3' terminus are modified.

Embodiment 85. The trRNA of embodiment 84, wherein the modification comprises 2'-O-Me.

Embodiment 86. The trRNA of embodiment 84, wherein the modification comprises 2'-F.

Embodiment 87. The trRNA of any one of embodiments 79-86, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 88. The trRNA of any one of embodiments 79-86, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-F modifications.

Embodiment 89. The trRNA of any one of embodiments 79-84, wherein each nucleotide in the upper stem region is modified with 2'-O-Me.

Embodiment 90. The trRNA of any one of embodiments 79-84 and 89, wherein B1 and B2 within the bulge region are modified with 2'-O-Me.

Embodiment 91. The trRNA of any one of embodiments 79-84 and 89-90, wherein N3, N4, N5, N15, N16, N17, and N18 in the nexus region are modified with 2'-O-Me.

Embodiment 92. The trRNA of any one of embodiments 79-84 and 89-91, wherein each nucleotide in the hairpin 1 region is modified with 2'-O-Me.

Embodiment 93. The trRNA of any one of embodiments 79-84 and 89-92, wherein each nucleotide in the hairpin 2 region is modified with 2'-O-Me.

Embodiment 94. A tracr RNA (trRNA) comprising 2'-O-Me modified nucleotides at:

a. each nucleotide in the upper stem;
b. B1 and B2 within the bulge region;
c. N3, N4, N5, N15, N16, N17, and N18 in the nexus region;
d. each nucleotide in the hairpin 1 region; and
e. each nucleotide in the hairpin 2 region.

Embodiment 95. The trRNA of embodiment 94, further comprising three phosphorothioate (PS) bonds linking the first four nucleotides at the 5' terminus and three PS bonds linking the last four nucleotides at the 3' terminus.

Embodiment 96. The crRNA of embodiment 94 or 95, further comprising 2'-O-Me or 2'-F modified nucleotides at the first three nucleotides at the 5' terminus, and 2'-O-Me or 2'-F modified nucleic acids at the last three nucleotides at the 3' terminus.

Embodiment 97. The trRNA of any of embodiments 79-84, wherein N15, N16, N17, and N18 are modified with 2'-F.

Embodiment 98. The trRNA of any of embodiments 79-84 and 97, wherein LS1, LS3, and LS5 are modified with 2'-F, and LS2, LS4, and LS6 are modified with 2'-O-Me.

Embodiment 99. The trRNA of any one of embodiments 87-98, further comprising three phosphorothioate (PS) bonds linking the first four nucleotides at the 5' terminus and three PS bonds linking the last four nucleotides at the 3' terminus.

Embodiment 100. The trRNA of embodiment 98 or 99, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 101. A trRNA comprising the nucleic acids of any one of SEQ ID Nos: 188-227.

Embodiment 102. A trRNA comprising nucleic acids having at least 99, 98, 97, 96, 95, 94, 93, 92, 91, 90, 85, 80, 75, or 70% identity to the nucleic acids of any one of SEQ ID Nos: 188-227, wherein the modification pattern is identical to the modification pattern shown in the reference sequence identifier.

Embodiment 103. The trRNA of any one of embodiments 101-102, further comprising three phosphorothioate (PS) bonds linking the first four nucleotides at the 5' terminus and three PS bonds linking the last four nucleotides at the 3' terminus.

Embodiment 104. A dual guide comprising a crRNA and a trRNA, wherein the crRNA comprises the nucleotides of any one of SEQ ID Nos: 1-187, and wherein the trRNA comprises the nucleic acids of any one of SEQ ID Nos: 188-227.

Embodiment 105. A dual guide comprising a crRNA of any one of embodiments 55-78 and a trRNA of any one of embodiments 79-103.

Embodiment 106. A dual guide comprising a crRNA of any one of embodiments 55-78 and an unmodified trRNA.

Embodiment 107. A dual guide comprising an unmodified crRNA and a trRNA of any one of embodiments 79-103.

C. Modifications to Terminal Nucleotides

In some embodiments, the 5' or 3' terminal nucleotides of any of the guide RNAs described herein are modified. In some embodiments, the terminal (i.e., last) 1, 2, 3, 4, 5, 6, or 7 nucleotides in 3' terminus region of guide RNA, including, for example, the sgRNA, the dgRNA, the crRNA, trRNA, or both crRNA and trRNA are modified. In some embodiments, the terminal (i.e., last) 1, 2, 3, 4, 5, 6, or 7 nucleotides in 3' terminus region of guide RNA comprise more than one modification. In some embodiments, at least one of the terminal (i.e., last) 1, 2, 3, 4, 5, 6, or 7 nucleotides at the 3' terminus region are modified. In some embodiments, at least two of the terminal (i.e., last) 1, 2, 3, 4, 5, 6, or 7 nucleotides in 3' terminus region are modified. In some embodiments, at least three of the terminal (i.e., last) 1, 2, 3, 4, 5, 6, or 7 nucleotides in 3' terminus region are modified. some embodiments, the modification comprises a PS linkage.

In some embodiments, the 5' end of the 5' terminus region is modified, for example, the first 1, 2, 3, 4, 5, 6, or 7 nucleotides of the sgRNA, the dgRNA, crRNA, trRNA, or both crRNA and trRNA are modified. In some embodiments, the first 1, 2, 3, 4, 5, 6, or 7 nucleotides in 3' terminus region of guide RNA comprise more than one modification. In some embodiments, at least one of the terminal (i.e., first) 1, 2, 3, 4, 5, 6, or 7 nucleotides at the 5' end are modified. In some embodiments, at least two of the terminal 1, 2, 3, 4, 5, 6, or 7 nucleotides at the 5' end are modified. In some embodiments, at least three of the terminal 1, 2, 3, 4, 5, 6, or 7 nucleotides at the 5' end are modified. some embodiments, the modification comprises a PS linkage.

In some embodiments, both the 5' and 3' termini (e.g., ends) of the guide RNA, e.g., sgRNA, dgRNA, crRNA, trRNA, or both crRNA and trRNA are modified. In some embodiments, only the 5' terminus of the guide RNA, e.g., sgRNA, dgRNA, crRNA, trRNA, or both crRNA and trRNA is modified. In some embodiments, only the 3' terminus of the guide RNA, e.g., sgRNA, dgRNA, crRNA, trRNA, or both crRNA and trRNA is modified.

In some embodiments, the gRNA comprises modifications at 1, 2, 3, 4, 5, 6, or 7 of the first 7 nucleotides at a 5' end of the gRNA. In some embodiments, the gRNA comprises modifications at 1, 2, 3, 4, 5, 6, or 7 of the 7 terminal nucleotides at a 3' end. In some embodiments, 2, 3, or 4 of the first 4 nucleotides at the 5' end, and/or 2, 3, or 4 of the terminal 4 nucleotides at the 3' end are modified. In some embodiments, 2, 3, or 4 of the first 4 nucleotides at the 5' end are linked with phosphorothioate (PS) bonds.

In some embodiments, the modification to the 5' terminus and/or 3' terminus comprises a 2'-O-methyl (2'-O-Me) or 2'-O-(2-methoxyethyl) (2'-O-moe) modification to a nucleotide. In some embodiments, the modification comprises a 2'-fluoro (2'-F) modification to a nucleotide. In some embodiments, the modification comprises a phosphorothioate (PS) linkage between nucleotides. In some embodiments, the modification comprises an inverted abasic nucleotide. In some embodiments, the modification comprises a more than one modification selected from 2'-O-Me, 2'-O-moe, 2'-fluoro (2'-F), a phosphorothioate (PS) linkage between nucleotides, and an inverted abasic nucleotide. In some embodiments, an equivalent modification is encompassed.

In some embodiments, the guide RNA, e.g., sgRNA, dgRNA, crRNA, trRNA, or both crRNA and trRNA comprises one or more phosphorothioate (PS) linkages between the first one, two, three, four, five, six, or seven nucleotides at the 5' terminus. In some embodiments, the guide RNA, e.g., sgRNA, dgRNA, crRNA, trRNA, or both crRNA and trRNA comprises one or more PS linkages between the last one, two, three, four, five, six, or seven nucleotides at the 3' terminus. In some embodiments, the guide RNA, e.g., sgRNA, dgRNA, crRNA, trRNA, or both crRNA and trRNA comprises one or more PS linkages between the last one, two, three, four, five, six, or seven nucleotides at both the 5' terminus and the 3' terminus. In some embodiments, in addition to PS linkages, the 5' and 3' terminal nucleotides may comprise 2'-O-Me, 2'-O-moe, or 2'-F modified nucleotides.

In some embodiments, the guide RNA, e.g., sgRNA, dgRNA, crRNA, trRNA, or both crRNA and trRNA comprises modified nucleotides at the 5' and 3' terminus, and modified nucleotides in one or more other regions described in Tables 1-3 and FIG. 21A or 21C.

In some embodiments, the crRNA, trRNA, or both crRNA and trRNA comprises modified nucleotides that are not at the 5' or 3' ends. Specific patterns of modifications are described below and in Table 4.

3. Delivery of gRNAs and Cas Protein

In some embodiments, in addition to the at least one gRNA, the compositions provided herein further comprise a nuclease. In some embodiments, the nuclease is a Cas protein. In some embodiments, the gRNA together with a Cas protein is called a Cas RNP. In some embodiments, the Cas protein is from the Type-II CRISPR/Cas system. In some embodiments, the Cas protein is Cas9. In some embodiments, the Cas9 protein is a wild type Cas9. In some embodiments, the Cas9 protein is derived from the *Streptococcus pyogenes* Cas9 protein, e.g., a *S. pyogenes* Cas9. In some embodiments, the Cas9 protein is not derived from *S. pyogenes*, but functions in the same way as *S. pyogenes* Cas9 such that gRNA that is specific to *S. pyogenes* Cas9 will direct the non-*S. pyogenes* Cas9 to its target site. In some embodiments, the Cas induces a double strand break in target DNA. Equivalents of *S. pyogenes* Cas9 protein are encompassed by the embodiments described herein.

Cas9 encompasses modified and variants thereof. Modified versions of Cas9 having one catalytic domain, either RuvC or HNH, that is inactive are termed "nickases." Nickases cut only one strand on the target DNA, thus creating a single-strand break. A single-strand break may also be known as a "nick." In some embodiments, the compositions and methods comprise nickases. In some embodiments, the compositions and methods comprise a nickase Cas9 that induces a nick rather than a double strand break in the target DNA.

In some embodiments, the Cas protein may be modified to contain only one functional nuclease domain. For example, the Cas protein may be modified such that one of the nuclease domains is mutated or fully or partially deleted to reduce its nucleic acid cleavage activity. In some embodiments, a nickase Cas is used having a RuvC domain with reduced activity. In some embodiments, a nickase Cas is used having an inactive RuvC domain. In some embodiments, a nickase Cas is used having an HNH domain with reduced activity. In some embodiments, a nickase Cas is used having an inactive HNH domain.

In some embodiments, a conserved amino acid within a Cas protein nuclease domain is substituted to reduce or alter nuclease activity. In some embodiments, a Cas protein may comprise an amino acid substitution in the RuvC or RuvC-like nuclease domain. Exemplary amino acid substitutions in the RuvC or RuvC-like nuclease domain include D10A (based on the *S. pyogenes* Cas9 protein). In some embodiments, the Cas protein may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein).

In some embodiments, the RNP complex described herein comprises a nickase and a pair of guide RNAs that are complementary to the sense and antisense strands of the target sequence, respectively. In this embodiment, the guide RNAs direct the nickase to a target sequence and introduce a double stranded break (DSB) by generating a nick on opposite strands of the target sequence (i.e., double nicking). In some embodiments, use of double nicking may improve specificity and reduce off-target effects. In some embodiments, a nickase Cas is used together with two separate guide RNAs targeting opposite strands of DNA to produce a double nick in the target DNA. In some embodiments, a nickase Cas is used together with two separate guide RNAs that are selected to be in close proximity to produce a double nick in the target DNA.

In some embodiments, chimeric Cas proteins are used, where one domain or region of the protein is replaced by a portion of a different protein. In some embodiments, a Cas nuclease domain may be replaced with a domain from a different nuclease such as FokI. In some embodiments, a Cas protein may be a modified nuclease.

In some embodiments, the Cas protein comprises a fusion protein comprising a catalytically inactive Cas9 linked to a heterologous functional domain (see, e.g., WO2014152432). In some embodiments, the catalytically inactive Cas9 is from *S. pyogenes*. In some embodiments, the catalytically inactive Cas9 comprises mutations that inactivate the Cas9. In some embodiments, the heterologous functional domain is a domain that modifies gene expression, histones, or DNA. In some embodiments, the heterologous functional domain is a transcriptional activation domain or a transcriptional repressor domain.

A. PAM

In some embodiments, the target sequence may be adjacent to the PAM. In some embodiments, the PAM may be adjacent to or within 1, 2, 3, or 4, nucleotides of the 3' end of the target sequence. The length and the sequence of the PAM may depend on the Cas protein used. For example, the PAM may be selected from a consensus or a particular PAM sequence for a specific Cas9 protein or Cas9 ortholog, including those disclosed in FIG. 1 of Ran et al., Nature 520:186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG, NAG, NGA, NGAG, NGCG, NNGRRT, TTN, NGGNG, NG, NAAAAN, NNAAAAW, NNNNACA, GNNNCNNA, and NNNNGATT (wherein N is defined as any nucleotide, and W is defined as either A or T, and R is defined as either A or G). In some embodiments, the PAM sequence may be NGG. In some embodiments, the PAM sequence may be NGGNG. In some embodiments, the PAM sequence may be NNAAAAW.

B. Delivery of Modified gRNA

Lipid nanoparticles (LNPs) are a well-known means for delivery of nucleotide and protein cargo, and may be used for delivery of the gRNA, mRNA, Cas9, and RNPs disclosed herein. In some embodiments, the LNPs deliver nucleic acid, protein, or nucleic acid together with protein.

In some embodiments, the invention comprises a method for delivering any one of the gRNAs disclosed herein to a subject, wherein the gRNA is associated with an LNP. In some embodiments, the gRNA/LNP is also associated with a Cas9 or an mRNA encoding Cas9.

In some embodiments, the invention comprises a composition comprising any one of the gRNAs disclosed and an LNP. In some embodiments, the composition further comprises a Cas9 or an mRNA encoding Cas9.

In some embodiments, the LNPs comprise cationic lipids. In some embodiments, the LNPs comprise (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate). In some embodiments, the LNPs comprise molar ratios of a cationic lipid amine to RNA phosphate (N:P) of about 4.5.

In some embodiments, LNPs associated with the gRNAs disclosed herein are for use in preparing a medicament for treating a disease or disorder.

Electroporation is a well-known means for delivery of cargo, and any electroporation methodology may be used for delivery of any one of the gRNAs disclosed herein. In some embodiments, electroporation may be used to deliver any one of the gRNAs disclosed herein and Cas9 or an mRNA encoding Cas9.

In some embodiments, the invention comprises a method for delivering any one of the gRNAs disclosed herein to an ex vivo cell, wherein the gRNA is associated with an LNP or not associated with an LNP. In some embodiments, the gRNA/LNP or gRNA is also associated with a Cas9 or an mRNA encoding Cas9.

4. Methods of Gene Modulation

In some embodiments, the invention comprises a pharmaceutical formulation comprising any one of the gRNAs disclosed herein together with a pharmaceutically acceptable carrier. In some embodiments, the invention comprises a pharmaceutical formulation comprising any one of the gRNAs disclosed herein and an LNP together with a pharmaceutically acceptable carrier. In some embodiments, the invention comprises a pharmaceutical formulation comprising any one of the gRNAs disclosed herein, a Cas9 protein or an mRNA encoding a Cas9 protein, and a LNP together with a pharmaceutically acceptable carrier. In some embodiments, the pharmaceutical formulation is for use in preparing a medicament for treating a disease or disorder. In some embodiments, the invention comprises a method of treating a human patient comprising administering any one of the gRNAs or pharmaceutical formulations described herein.

In some embodiments, the invention comprises a method or use of modifying a target DNA comprising, administering or delivering a Cas protein or Cas mRNA and any one or more of the gRNAs disclosed herein.

In some embodiments, the invention comprises a method or use for modulation of a target gene comprising, administering or delivering a Cas protein or Cas mRNA and any one or more of the gRNAs disclosed herein. In some embodiments, the modulation is editing of the target gene. In some embodiments, the modulation is a change in expression of the protein encoded by the target gene.

In some embodiments, the method or use results in gene editing. In some embodiments, the method or use results in a double-stranded break within the target gene. In some embodiments, the method or use results in formation of indel mutations during non-homologous end joining of the DSB. In some embodiments, the method or use results in an insertion or deletion of nucleotides in a target gene. In some embodiments, the insertion or deletion of nucleotides in a target gene leads to a frameshift mutation or premature stop codon that results in a non-functional protein. In some embodiments, the insertion or deletion of nucleotides in a target gene leads to a knockdown or elimination of target gene expression. In some embodiments, the method or use comprises homology directed repair of a DSB. In some embodiments, the method or use further comprises delivering to the cell a template, wherein at least a part of the template incorporates into a target DNA at or near a double strand break site induced by the Cas protein.

In some embodiments, the method or use results in gene modulation. In some embodiments, the gene modulation is an increase or decrease in gene expression, a change in methylation state of DNA, or modification of a histone subunit. In some embodiments, the method or use results in increased or decreased expression of the protein encoded by the target gene.

In some embodiments, any of the gRNAs disclosed herein may be useful in preparing a medicament for treating a disease or disorder.

A. Measures of Gene Modulation

The efficacy of modified gRNAs can be tested in vitro and in vivo. In some embodiments, the invention comprises one or more of the gRNAs disclosed herein, wherein the gRNA results in gene modulation when provided to a cell together with Cas9. In some embodiments, the efficacy of gRNA can be measured in in vitro or in vivo assays.

1. In Vitro Measurement of Cas Efficacy

In some embodiments, the activity of a Cas RNP comprising a modified sgRNA is compared to the activity of a Cas RNP comprising an unmodified sgRNA.

In some embodiments, the activity of a Cas RNP comprising a dgRNA comprising a modified trRNA is compared to the activity of a Cas RNP comprising a dgRNA comprising an unmodified trRNA.

In some embodiments, the activity of a Cas RNP comprising a dgRNA comprising a modified crRNA is compared to the activity of a Cas RNP comprising a dgRNA comprising an unmodified crRNA.

In some embodiments, the activity of a Cas RNP comprising a dgRNA comprising a modified crRNA and a modified trRNA is compared to the activity of a Cas RNP comprising an unmodified crRNA and an unmodified trRNA.

In some embodiments, the efficiency of a gRNA in increasing or decreasing target protein expression is determined by measuring the amount of target protein. In some embodiments, the invention comprises any one of the gRNAs described herein, wherein the gRNA increases or decreases the amount of protein produced from the targeted gene. In some embodiments, the invention comprises a method of modulating protein expression comprising administering any one of the gRNAs disclosed herein to a subject, wherein the gRNA directs Cas9 to the gene encoding the target protein, and the target protein expression is increased or decreased as compared to a gRNA control that does not target Cas9 to that gene.

In some embodiments, the efficiency of editing with specific gRNAs is determined by the editing present at the target location in the genome following delivery of Cas9 and the gRNA (either sgRNA or dgRNA comprising a crRNA and trRNA). In some embodiments, the efficiency of editing with specific gRNAs is measured by next-generation sequencing. In some embodiments, the editing percentage of the target region of interest is determined. In some embodiments, the total number of sequence reads with insertions or deletions of nucleotides into the target region of interest over the total number of sequence reads is measured following delivery of a gRNA and Cas9. In some embodiments, the invention comprises a method of increasing the efficiency of gene editing comprising, administering or delivering any one of the modified gRNAs described herein to a cell, wherein the percentage of gene editing is increased as compared to a control gRNA that is not similarly modified.

In some embodiments, the efficiency of editing with specific gRNAs is measured by the presence of insertions or deletions of nucleotides introduced by successful gene editing. In some embodiments, the invention comprises a method of creating insertions or deletions of nucleotides in genes comprising, administering or delivering any one of the modified gRNAs described herein to a cell, wherein the nucleotides are inserted or deleted as compared to a control gRNA that is not similarly modified. In some embodiments, activity of a Cas9 and gRNAs is tested in biochemical assays. In some embodiments, activity of a Cas9 and gRNAs is tested in a cell-free cleavage assay. In some embodiments, activity of a Cas9 and gRNAs is tested in Neuro2A cells.

In some embodiments, Cas 9 and sgRNA or dgRNA comprising modified crRNA and/or trRNA shows similar, greater, or reduced activity compared to the unmodified sgRNA or dgRNA comprising unmodified crRNA and trRNA. In some embodiments, Cas9 and modified sgRNA or dgRNA comprising modified crRNA and/or trRNA shows enhanced activity compared to the unmodified sgRNA or dgRNA comprising unmodified crRNA and trRNA.

2. In Vivo Measurement of Cas Efficacy

In some embodiments, the activity of modified gRNAs is measured after in vivo dosing of LNPs comprising modified gRNAs and Cas protein or mRNA encoding Cas protein.

In some embodiments, in vivo efficacy of a gRNA or composition provided herein is determined by editing efficacy measured in DNA extracted from tissue (e.g., liver tissue) after administration of gRNA and Cas9.

3. In Vivo Measurement of Immune System Activation

Modifications to gRNA as disclosed herein may reduce the subject's immune response to in vivo dosing of gRNAs. In some embodiments, activation of the subject's immune response is measured by serum concentrations of cytokine(s) following in vivo dosing of sgRNA or dgRNA comprising trRNA and crRNA together with Cas9 mRNA or protein (e.g., formulated in a LNP). In some embodiments, the cytokine is interferon-alpha (IFN-alpha), interleukin 6 (IL-6), monocyte chemotactic protein 1 (MCP-1), and/or tumor necrosis factor alpha (TNF-alpha). In some embodiments, the invention comprises a method of reducing a subject's immune response to delivery of a gRNA comprising, administering any one of the gRNAs disclosed herein, wherein the gRNA produces a reduced response by the subject's immune system following administration. In some embodiments, the invention comprises a method of reducing activation of the subject's immune system following administration as compared to a control gRNA that is not similarly modified.

In some embodiments, administration of Cas RNP or Cas9 mRNA together with the modified gRNA (e.g., sgRNA or dgRNA) produces lower serum concentration(s) of immune cytokines compared to administration of unmodified sgRNA. In some embodiments, the invention comprises a method of reducing a subject's serum concentration of immune cytokines comprising, administering any one of the gRNAs disclosed herein, wherein the gRNA produces a lower concentration of immune cytokines in a subject's serum as compared to a control gRNA that is not similarly modified.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1—Materials and Methods

A. Synthetic Guide RNA (gRNA)

gRNA in both dual (dgRNA, i.e., crRNA and trRNA) and single guide (sgRNA) format were chemically synthesized by commercial vendors with modified nucleotides and linkages as provided in Table 4.

B. In Vitro Transcription ("IVT") of Cas9 mRNA

Capped and polyadenylated Cas9 mRNA containing N1-methyl pseudo-U was generated by in vitro transcription using a linearized plasmid DNA template and T7 RNA polymerase. Plasmid DNA containing a T7 promoter and a 100 nucleotide (nt) poly(A/T) region was linearized by XbaI and obtained from a commercial manufacturer. The IVT reaction to generate Cas9 modified mRNA was incubated at 37° C. for 4 hours in the following conditions: 50 ng/μL linearized plasmid; 2 mM each of GTP, ATP, CTP, and N1-methyl pseudo-UTP (Trilink); 10 mM ARCA (Trilink); 5 U/μL T7 RNA polymerase (NEB); 1 U/μL Murine RNase inhibitor (NEB); 0.004 U/μL Inorganic *E. coli* pyrophosphatase (NEB); and ix reaction buffer. After the 4 hr incubation, TURBO DNase (ThermoFisher) was added to a final concentration of 0.01 U/μL, and the reaction was incubated for an additional 30 minutes to remove the DNA template. The Cas9 mRNA was purified from enzyme and nucleotides using standard protocols, including silica binding columns such as a MegaClear Transcription Clean-up kit (ThermoFisher) or precipitation steps using LiCl followed by EtOH with NaOAc. The transcript concentration was determined by measuring the light absorbance at 260 nm (Nanodrop), and the transcript was analyzed by capillary electrophoresis by Bioanlayzer (Agilent).

C. Cas9 mRNA and gRNA Transfections in Neuro2A Cells

The mouse cell line Neuro2A was cultured in DMEM media supplemented with 10% fetal bovine serum and was plated at a density of 15,000 cells/well in a 96-well plate 24 hours prior to transfection. On the day of transfection, the media was aspirated from cells and replaced with fresh media. Lipofectamine-2000 (Invitrogen) was diluted 1:50 (v/v) in Opti-MEM (Invitrogen). Cas9 mRNA and single guide RNA were diluted separately in Opti-MEM. For the dual guide format, crRNA and trRNA were diluted together in 1:1 molar ratio in Opti-MEM. Both Cas9 mRNA and gRNA were mixed separately 1:1 (v/v) with diluted Lipofectamine-2000, producing two lipoplexes. After 5 minutes of incubation, lipoplexes were added in succession to cells, for a final concentration of 100 ng Cas9 mRNA/well and 0.4 μL total lipofection reagent. Guides were tested at two dose levels for each experiment, including 25 nM and 2.5 nM, 16.7 nM and 1.67 nM, 10 nM and 1 nM, 8.3 nM and 0.83 nM, and 3 nM and 0.3 nM. For dual guide, this concentration includes equimolar amounts of crRNA and trRNA, such that, for example, 25 nM crRNA and 25 nM trRNA produce 25 nM total dual guide. Cells were lysed 24 hours post transfection, and lysates were used directly in the PCR reaction that was analyzed for editing by NGS.

```
Cas9 mRNA with 1xNLS (SEQ ID NO: 359):
GGGUCCCGCAGUCGGCGUCCAGCGGCUCUGCUUGUUCGUGUGUGUGUCGUUGCAGGCCUU

AUUCGGAUCCAUGGAUAAGAAGUACUCAAUCGGGCUGGAUAUCGGAACUAAUUC

CGUGGGUUGGGCAGUGAUCACGGAUGAAUACAAAGUGCCGUCCAAGAAGUUCAAGGU

CCUGGGGAACACCGAUAGACACAGCAUCAAGAAAAAUCUCAUCGGAGCCCUGCUGUUUGA

CUCCGGCGAAACCGCAGAAGCGACCCGGCUCAAACGUACCGCGAGGCGACGCUA

CACCCGGCGGAAGAAUCGCAUCUGCUAUCUGCAAGAGAUCUUUUCGAACGAAAUGGC

AAAGGUCGACGACAGCUUCUUCCACCGCCUGGAAGAAUCUUUCCUGGUGGAGGAGGA

CAAGAAGCAUGAACGGCAUCCUAUCUUUGGAAACAUCGUCGACGAAGUGGCGUACCA

CGAAAAGUACCCGACCAUCUACCAUCUGCGGAAGAAGUUGGUUGACUCAACUGACAA

GGCCGACCUCAGAUUGAUCUACUUGGCCCUCGCCCAUAUGAUCAAAUUCCGCGGACA

CUUCCUGAUCGAAGGCGAUCUGAACCCUGAUAACUCCGACGUGGAUAAGCUUUUCAU

UCAACUGGUGCAGACCUACAACCAACUGUUCGAAGAAAACCCAAUCAAUGCUAGCGG

CGUCGAUGCCAAGGCCAUCCUGUCCGCCCGGCUGUCGAAGUCGCGGCGCCUCGAAAA

CCUGAUCGCACAGCUGCCGGGAGAGAAAAAGAACGGACUUUUCGGCAACUUGAUCGC

UCUCUCACUGGGACUCACUCCCAAUUUCAAGUCCAAUUUUGACCUGGCCGAGGACGC

GAAGCUGCAACUCUCAAAGGACACCUACGACGACGACUUGGACAAUUUGCUGGCACA

AAUUGGCGAUCAGUACGCGGAUCUGUUCCUUGCCGCUAAGAACCUUUCGGACGCAAU

CUUGCUGUCCGAUAUCCUGCGCGUGAACACCGAAAUAACCAAAGCGCCGCUUAGCGC

CUCGAUGAUUAAGCGGUACGACGAGCAUCACCAGGAUCUCACGCUGCUCAAAGCGCU

CGUGAGACAGCAACUGCCUGAAAAGUACAAGGAGAUCUUCUUCGACCAGUCCAAGAAUGG

GUACGCAGGGUACAUCGAUGGAGGCGCUAGCCAGGAAGAGUUCUAUAAGUUCAU

CAAGCCAAUCCUGGAAAAGAUGGACGGAACCGAAGAACUGCUGGUCAAGCUGAACAG

GGAGGAUCUGCUCCGGAAACAGAGAACCUUUGACAACGGAUCCAUUCCCCACCAGAU

CCAUCUGGGUGAGCUGCACGCCAUCUUGCGGCGCCAGGAGGACUUUUACCCAUUCCU

CAAGGACAACCGGGAAAAGAUCGAGAAAAUUCUGACGUUCCGCAUCCCGUAUUACGU

GGGCCCACUGGCGCGCGGCAAUUCGCGCUUCGCGUGGAUGACUAGAAAAUCAGAGGA

AACCAUCACUCCUUGGAAUUUCGAGGAAGUUGUGGAUAAGGGAGCUUCGGCACAAAG

CUUCAUCGAACGAAUGACCAACUUCGACAAGAAUCUCCCAAACGAGAAGGUGCUUCC

UAAGCACAGCCUCCUUUACGAAUACUUCACUGUCUACAACGAACUGACUAAAGUGAAAUA

CGUUACUGAAGGAAUGAGGAAGCCGGCCUUUCUGUCCGGAGAACAGAAGAAAGC
```

-continued

AAUUGUCGAUCUGCUGUUCAAGACCAACCGCAAGGUGACCGUCAAGCAGCUUAAAGA

GGACUACUUCAAGAAGAUCGAGUGUUUCGACUCAGUGGAAAUCAGCGGGGUGGAGGA

CAGAUUCAACGCUUCGCUGGGAACCUAUCAUGAUCUCCUGAAGAUCAUCAAGGACAA

GGACUUCCUUGACAACGAGGAGAACGAGGACAUCCUGGAAGAUAUCGUCCUGACCUU

GACCCUUUUCGAGGAUCGCGAGAUGAUCGAGGAGAGGCUUAAGACCUACGCUCAUCU

CUUCGACGAUAAGGUCAUGAAACAACUCAAGCGCCGCCGGUACACUGGUUGGGGCCG

CCUCUCCCGCAAGCUGAUCAACGGUAUUCGCGAUAAACAGAGCGGUAAAACUAUCCU

GGAUUUCCUCAAAUCGGAUGGCUUCGCUAAUCGUAACUUCAUGCAAUUGAUCCACGA

CGACAGCCUGACCUUUAAGGAGGACAUCCAAAAAGCACAAGUGUCCGGACAGGGAGACUC

ACUCCAUGAACACAUCGCGAAUCUGGCCGGUUCGCCGGCGAUUAAGAAGGGAAU

UCUGCAAACUGUGAAGGUGGUCGACGAGCUGGUGAAGGUCAUGGGACGGCACAAACC

GGAGAAUAUCGUGAUUGAAAUGGCCCGAGAAAACCAGACUACCCAGAAGGGCCAGAA

AAACUCCCGCGAAAGGAUGAAGCGGAUCGAAGAAGGAAUCAAGGAGCUGGGCAGCCA

GAUCCUGAAAGAGCACCCGGUGGAAAACACGCAGCUGCAGAACGAGAAGCUCUACCU

GUACUAUUUGCAAAAUGGACGGGACAUGUACGUGGACCAAGAGCUGGACAUCAAUCG

GUUGUCUGAUUACGACGUGGACCACAUCGUUCCACAGUCCUUUCUGAAGGAUGACUC

GAUCGAUAACAAGGUGUUGACUCGCAGCGACAAGAACAGAGGGAAGUCAGAUAAUGU

GCCAUCGGAGGAGGUCGUGAAGAAGAUGAAGAAUUACUGGCGGCAGCUCCUGAAUGC

GAAGCUGAUUACCCAGAGAAAGUUUGACAAUCUCACUAAAGCCGAGCGCGGCGGACU

CUCAGAGCUGGAUAAGGCUGGAUUCAUCAAACGGCAGCUGGUCGAGACUCGGCAGAU

UACCAAGCACGUGGCGCAGAUCUUGGACUCCCGCAUGAACACUAAAUACGACGAGAA

CGAUAAGCUCAUCCGGGAAGUGAAGGUGAUUACCCUGAAAAGCAAACUUGUGUCGGA

CUUUCGGAAGGACUUUCAGUUUUACAAAGUGAGAGAAAUCAACAACUACCAUCACGCGCA

UGACGCAUACCUCAACGCUGUGGUCGGUACCGCCCUGAUCAAAAAGUACCCUAA

ACUUGAAUCGGAGUUUGUGUACGGAGACUACAAGGUCUACGACGUGAGGAAGAUGAU

AGCCAAGUCCGAACAGGAAAUCGGGAAAGCAACUGCGAAAUACUUCUUUUACUCAAA

CAUCAUGAACUUUUUCAAGACUGAAAUUACGCUGGCCAAUGGAGAAAUCAGGAAGAG

GCCACUGAUCGAAACUAACGGAGAAACGGGCGAAAUCGUGUGGGACAAGGGCAGGGA

CUUCGCAACUGUUCGCAAAGUGCUCUCUAUGCCGCAAGUCAAUAUUGUGAAGAAAAC

CGAAGUGCAAACCGGCGGAUUUUCAAAGGAAUCGAUCCUCCCAAAGAGAAAUAGCGA

CAAGCUCAUUGCACGCAAGAAAGACUGGGACCCGAAGAAGUACGGAGGAUUCGAUUC

GCCGACUGUCGCAUACUCCGUCCUCGUGGUGGCCAAGGUGGAGAAGGGAAAGAGCAA

AAAGCUCAAAUCCGUCAAAGAGCUGCUGGGGAUUACCAUCAUGGAACGAUCCUCGUU

CGAGAAGAACCCGAUUGAUUUCCUCGAGGCGAAGGGUUACAAGGAGGUGAAGAAGGA

UCUGAUCAUCAAACUCCCCAAGUACUCACUGUUCGAACUGGAAAAUGGUCGGAAGCG

CAUGCUGGCUUCGGCCGGAGAACUCCAAAAAGGAAAUGAGCUGGCCUUGCCUAGCAA

GUACGUCAACUUCCUCUAUCUUGCUUCGCACUACGAAAAACUCAAAGGGUCACCGGA

AGAUAACGAACAGAAGCAGCUUUUCGUGGAGCAGCACAAGCAUUAUCUGGAUGAAAUCAU

CGAACAAAUCUCCGAGUUUUCAAAGCGCGUGAUCCUCGCCGACGCCAACCUCGA

CAAAGUCCUGUCGGCCUACAAUAAGCAUAGAGAUAAGCCGAUCAGAGAACAGGCCGA

-continued

GAACAUUAUCCACUUGUUCACCCUGACUAACCUGGGAGCCCCAGCCGCCUUCAAGUA

CUUCGAUACUACUAUCGAUCGCAAAAGAUACACGUCCACCAAGGAAGUUCUGGACGC

GACCCUGAUCCACCAAAGCAUCACUGGACUCUACGAAACUAGGAUCGAUCUGUCGCA

GCUGGGUGGCGAUGGCGGUGGAUCUCCGAAAAAGAAGAGAAAGGUGUAAUGAGCUAG

CCAUCACAUUUAAAAGCAUCUCAGCCUACCAUGAGAAUAAGAGAAAGAAAAUGAAGA

UCAAUAGCUUAUUCAUCUCUUUUUCUUUUUCGUUGGUGUAAAGCCAACACCCUGUCU

AAAAAACAUAAAUUUCUUUAAUCAUUUUGCCUCUUUUCUCUGUGCUUCAAUUAAUAAAAA

AUGGAAAGAACCUCGAGAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

UCUAG

Cas9 mRNA with 2xNLS and HA tag (SEQ ID NO: 360):
GGGUCCCGCAGUCGGCGUCCAGCGGCUCUGCUUGUUCGUGUGUGUGUCGUUGCAGGCCUU

AUUCGGAUCCAUGGAUAAGAAGUACUCAAUCGGGCUGGAUAUCGGAACUAAUUC

CGUGGGUUGGGCAGUGAUCACGGAUGAAUACAAAGUGCCGUCCAAGAAGUUCAAGGU

CCUGGGGAACACCGAUAGACACAGCAUCAAGAAAAAUCUCAUCGGAGCCCUGCUGUUUGA

CUCCGGCGAAACCGCAGAAGCGACCCGGCUCAAACGUACCGCGAGGCGACGCUA

CACCCGGCGGAAGAAUCGCAUCUGCUAUCUGCAAGAGAUCUUUUCGAACGAAAUGGCAAA

GGUCGACGACAGCUUCUUCCACCGCCUGGAAGAAUCUUUCCUGGUGGAGGAGGA

CAAGAAGCAUGAACGGCAUCCUAUCUUUGGAAACAUCGUCGACGAAGUGGCGUACCA

CGAAAAGUACCCGACCAUCUACCAUCUGCGGAAGAAGUUGGUUGACUCAACUGACAA

GGCCGACCUCAGAUUGAUCUACUUGGCCCUCGCCCAUAUGAUCAAAUUCCGCGGACA

CUUCCUGAUCGAAGGCGAUCUGAACCCUGAUAACUCCGACGUGGAUAAGCUUUUCAU

UCAACUGGUGCAGACCUACAACCAACUGUUCGAAGAAAACCCAAUCAAUGCUAGCGG

CGUCGAUGCCAAGGCCAUCCUGUCCGCCCGGCUGUCGAAGUCGCGGCGCCUCGAAAA

CCUGAUCGCACAGCUGCCGGGAGAGAAAAAGAACGGACUUUUCGGCAACUUGAUCGC

UCUCUCACUGGGACUCACUCCCAAUUUCAAGUCCAAUUUUGACCUGGCCGAGGACGCGAA

GCUGCAACUCUCAAAGGACACCUACGACGACGACUUGGACAAUUUGCUGGCACA

AAUUGGCGAUCAGUACGCGGAUCUGUUCCUUGCCGCUAAGAACCUUUCGGACGCAAU

CUUGCUGUCCGAUAUCCUGCGCGUGAACACCGAAAUAACCAAAGCGCCGCUUAGCGC

CUCGAUGAUUAAGCGGUACGACGAGCAUCACCAGGAUCUCACGCUGCUCAAAGCGCU

CGUGAGACAGCAACUGCCUGAAAAGUACAAGGAGAUCUUCUUCGACCAGUCCAAGAA

UGGGUACGCAGGGUACAUCGAUGGAGGCGCUAGCCAGGAAGAGUUCUAUAAGUUCAUCAA

GCCAAUCCUGGAAAAGAUGGACGGAACCGAAGAACUGCUGGUCAAGCUGAACAG

GGAGGAUCUGCUCCGGAAACAGAGAACCUUUGACAACGGAUCCAUUCCCCACCAGAU

CCAUCUGGGUGAGCUGCACGCCAUCUUGCGGCGCCAGGAGGACUUUUACCCAUUCCU

CAAGGACAACCGGGAAAAGAUCGAGAAAAUUCUGACGUUCCGCAUCCCGUAUUACGU

GGGCCCACUGGCGCGCGGCAAUUCGCGCUUCGCGUGGAUGACUAGAAAAUCAGAGGA

AACCAUCACUCCUUGGAAUUUCGAGGAAGUUGUGGAUAAGGGAGCUUCGGCACAAAG

CUUCAUCGAACGAAUGACCAACUUCGACAAGAAUCUCCCAAACGAGAAGGUGCUUCCUAA

GCACAGCCUCCUUUACGAAUACUUCACUGUCUACAACGAACUGACUAAAGUGAA

AUACGUUACUGAAGGAAUGAGGAAGCCGGCCUUUCUGUCCGGAGAACAGAAGAAAGC

-continued

AAUUGUCGAUCUGCUGUUCAAGACCAACCGCAAGGUGACCGUCAAGCAGCUUAAAGA

GGACUACUUCAAGAAGAUCGAGUGUUUCGACUCAGUGGAAAUCAGCGGGGUGGAGGA

CAGAUUCAACGCUUCGCUGGGAACCUAUCAUGAUCUCCUGAAGAUCAUCAAGGACAA

GGACUUCCUUGACAACGAGGAGAACGAGGACAUCCUGGAAGAUAUCGUCCUGACCUU

GACCCUUUUCGAGGAUCGCGAGAUGAUCGAGGAGAGGCUUAAGACCUACGCUCAUCU

CUUCGACGAUAAGGUCAUGAAACAACUCAAGCGCCGCCGGUACACUGGUUGGGGCCG

CCUCUCCCGCAAGCUGAUCAACGGUAUUCGCGAUAAACAGAGCGGUAAAACUAUCCU

GGAUUUCCUCAAAUCGGAUGGCUUCGCUAAUCGUAACUUCAUGCAAUUGAUCCACGACGA

CAGCCUGACCUUUAAGGAGGACAUCCAAAAAGCACAAGUGUCCGGACAGGGAGA

CUCACUCCAUGAACACAUCGCGAAUCUGGCCGGUUCGCCGGCGAUUAAGAAGGGAAU

UCUGCAAACUGUGAAGGUGGUCGACGAGCUGGUGAAGGUCAUGGGACGGCACAAACC

GGAGAAUAUCGUGAUUGAAAUGGCCCGAGAAAACCAGACUACCCAGAAGGGCCAGAA

AAACUCCCGCGAAAGGAUGAAGCGGAUCGAAGAAGGAAUCAAGGAGCUGGGCAGCCA

GAUCCUGAAAGAGCACCCGGUGGAAAACACGCAGCUGCAGAACGAGAAGCUCUACCU

GUACUAUUUGCAAAAUGGACGGGACAUGUACGUGGACCAAGAGCUGGACAUCAAUCG

GUUGUCUGAUUACGACGUGGACCACAUCGUUCCACAGUCCUUUCUGAAGGAUGACUCGAU

CGAUAACAAGGUGUUGACUCGCAGCGACAAGAACAGAGGGAAGUCAGAUAAUGU

GCCAUCGGAGGAGGUCGUGAAGAAGAUGAAGAAUUACUGGCGGCAGCUCCUGAAUGCGAA

GCUGAUUACCCAGAGAAAGUUUGACAAUCUCACUAAAGCCGAGCGCGGCGGACU

CUCAGAGCUGGAUAAGGCUGGAUUCAUCAAACGGCAGCUGGUCGAGACUCGGCAGAU

UACCAAGCACGUGGCGCAGAUCUUGGACUCCCGCAUGAACACUAAAUACGACGAGAACGA

UAAGCUCAUCCGGGAAGUGAAGGUGAUUACCCUGAAAAGCAAACUUGUGUCGGA

CUUUCGGAAGGACUUUCAGUUUUACAAAGUGAGAGAAAUCAACAACUACCAUCACGC

GCAUGACGCAUACCUCAACGCUGUGGUCGGUACCGCCCUGAUCAAAAAGUACCCUAA

ACUUGAAUCGGAGUUUGUGUACGGAGACUACAAGGUCUACGACGUGAGGAAGAUGAU

AGCCAAGUCCGAACAGGAAAUCGGGAAAGCAACUGCGAAAUACUUCUUUUACUCAAACAU

CAUGAACUUUUUCAAGACUGAAAUUACGCUGGCCAAUGGAGAAAUCAGGAAGAG

GCCACUGAUCGAAACUAACGGAGAAACGGGCGAAAUCGUGUGGGACAAGGGCAGGGA

CUUCGCAACUGUUCGCAAAGUGCUCUCUAUGCCGCAAGUCAAUAUUGUGAAGAAAAC

CGAAGUGCAAACCGGCGGAUUUUCAAAGGAAUCGAUCCUCCCAAAGAGAAAUAGCGACAA

GCUCAUUGCACGCAAGAAAGACUGGGACCCGAAGAAGUACGGAGGAUUCGAUUC

GCCGACUGUCGCAUACUCCGUCCUCGUGGUGGCCAAGGUGGAGAAGGGAAAGAGCAA

AAAGCUCAAAUCCGUCAAAGAGCUGCUGGGGAUUACCAUCAUGGAACGAUCCUCGUU

CGAGAAGAACCCGAUUGAUUUCCUCGAGGCGAAGGGUUACAAGGAGGUGAAGAAGGA

UCUGAUCAUCAAACUCCCCAAGUACUCACUGUUCGAACUGGAAAAUGGUCGGAAGCG

CAUGCUGGCUUCGGCCGGAGAACUCCAAAAAGGAAAUGAGCUGGCCUUGCCUAGCAA

GUACGUCAACUUCCUCUAUCUUGCUUCGCACUACGAAAAACUCAAAGGGUCACCGGA

AGAUAACGAACAGAAGCAGCUUUUCGUGGAGCAGCACAAGCAUUAUCUGGAUGAAAU

CAUCGAACAAAUCUCCGAGUUUUCAAAGCGCGUGAUCCUCGCCGACGCCAACCUCGA

CAAAGUCCUGUCGGCCUACAAUAAGCAUAGAGAUAAGCCGAUCAGAGAACAGGCCGA

GAACAUUAUCCACUUGUUCACCCUGACUAACCUGGGAGCCCCAGCCGCCUUCAAGUACUU

-continued

CGAUACUACUAUCGAUCGCAAAAGAUACACGUCCACCAAGGAAGUUCUGGACGC

GACCCUGAUCCACCAAAGCAUCACUGGACUCUACGAAACUAGGAUCGAUCUGUCGCA

GCUGGGUGGCGAUGGCUCGGCUUACCCAUACGACGUGCCUGACUACGCCUCGCUCGG

AUCGGGCUCCCCCAAAAAGAAACGGAAGGUGGACGGAUCCCCGAAAAAGAAGAGAAA

GGUGGACUCCGGAUGAGAAUUAUGCAGUCUAGCCAUCACAUUUAAAAGCAUCUCAGC

CUACCAUGAGAAUAAGAGAAAGAAAAUGAAGAUCAAUAGCUUAUUCAUCUCUUUUUC

UUUUUCGUUGGUGUAAAGCCAACACCCUGUCUAAAAAACAUAAAUUUCUUUAAUCAU

UUUGCCUCUUUUCUCUGUGCUUCAAUUAAUAAAAAAUGGAAAGAACCUCGAGAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAUCUAG

D. Primary Liver Hepatocytes

Primary mouse liver hepatocytes (PMH) (Gibco) were cultured per the manufacturer's protocol (Invitrogen, protocol Nov. 28, 2012). In brief, the cells were thawed and resuspended in hepatocyte thawing medium with supplements (Gibco, Cat. CM7000) followed by centrifugation at 100 g for 10 minutes. The supernatant was discarded and the pelleted cells resuspended in hepatocyte plating medium plus supplement pack (Invitrogen, Cat. A1217601 and CM3000). Cells were counted and plated on Bio-coat collagen I coated 96-well plates (ThermoFisher, Cat. 877272) at a density of 15,000 cells/well and incubated for 5 hours at 37° C. and 5% CO2 atmosphere to allow for monolayer formation. After 5 hours, the plating media was removed and replaced with supplemented hepatocyte culture medium (Invitrogen, Cat. A1217601 and CM4000) containing LNP formulated Cas9 mRNA and guide RNA plus 3% mouse serum. LNPs were diluted from a starting dose level of 100 ng Cas9 mRNA and approximately 30 nM guide RNA per well, carrying out serial dilutions down to 0.1 ng mRNA and 0.03 nM guide per well. Cells were incubated for approximately 48 hours at 37° C. and 5% CO2 atmosphere before cell lysis and NGS analysis as described herein.

E. Lipid Nanoparticle ("LNP") Formulation

LNPs were formulated with a cationic lipid amine to RNA phosphate (N:P) molar ratio of about 4.5. The lipid nanoparticle components were dissolved in 100% ethanol with the following molar ratios: 45 mol-% (12.7 mM) cationic lipid (e.g., (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate); 44 mol-% (12.4 mM) helper lipid (e.g., cholesterol); 9 mol-% (2.53 mM) neutral lipid (e.g., DSPC); and 2 mol-% (0.563 mM) PEG (e.g., PEG2k-DMG). The RNA cargo were prepared in 25 mM sodium acetate buffer, pH 4.5, resulting in a concentration of RNA cargo of approximately 0.45 mg/mL.

The LNPs were formed by microfluidic mixing of the lipid and RNA solutions using a Precision Nanosystems NanoAssemblr™ Benchtop Instrument, according to the manufacturer's protocol. A 2:1 ratio of aqueous to organic solvent was maintained during mixing using differential flow rates.

LNP Formulation Procedure A: After mixing, the LNPs were collected, diluted in phosphate buffered saline (PBS, approximately 1:1), and then remaining buffer was exchanged into PBS (100-fold excess of sample volume), overnight at 4° C. under gentle stirring using a 10 kDa Slide-a-Lyzer™ G2 Dialysis Cassette (ThermoFisher Scientific). The LNPs were concentrated using 10 kDa Amicon spin filter (centrifugation at 4000 g at 4° C.) to achieve the desired concentration. The resulting mixture was then filtered using a 0.2 μm sterile filter. The resulting filtrate was stored at 2-8° C.

LNP Formulation Procedure B: After mixing, the LNPs were collected, diluted in 50 mM Tris at pH 7.5 (approximately 1:1), and then LNPs were exchanged into 50 mM Tris at pH 7.5 (100-fold excess of sample volume), overnight at 4° C. under gentle stirring using a 10 kDa Slide-a-Lyzer™ G2 Dialysis Cassette (ThermoFisher Scientific). The LNPs were concentrated using 10 kDa Amicon spin filter (centrifugation at 4000 g at 4° C.) to achieve twice the desired concentration. These concentrated LNPs were mixed 1:1 with 50 mM Tris, 90 mM NaCl, 10% sucrose at pH 7.5 (2×TSS). The resulting mixture was then filtered using a 0.2 μM sterile filter. The resulting filtrate was stored at −80° C.

LNP Formulation Procedure C: The RNA cargo were prepared in 25 mM sodium citrate, 100 mM sodium chloride at pH 5 resulting in a concentration of RNA cargo of approximately 0.45 mg/mL. After mixing, the LNPs were collected in water at the ratio of 3:1. The LNPs were incubated for an hour at room temperature and mixed 1:1 with water. Then they were buffer-exchanged into 1×TSS (50 mM Tris, 45 mM NaCl, 5% sucrose at pH 7.5) on PD-10 columns (GE Healthcare), using manufacturer's protocol. The LNPs were concentrated using 10 kDa Amicon spin filter (centrifugation at 4000 g at 4° C.) to achieve the desired concentration. The resulting mixture was then filtered using a 0.2 μm sterile filter. The resulting filtrate was stored at −80° C.

F. Next-Generation Sequencing ("NGS") and Analysis for On-Target Cleavage Efficiency To quantitatively determine the efficiency of editing at the target location in the genome, deep sequencing was utilized to identify the presence of insertions and deletions introduced by gene editing.

PCR primers were designed around the target site (e.g., TTR, FVII), and the genomic area of interest was amplified. Primer sequences are provided below in Table 5.

TABLE 5

| Guide | Gene | Forward Primer (5'-3') | SEQ ID | Reverse Primer (5'-3') | SEQ ID |
|---|---|---|---|---|---|
| For experiments with guides based on CR000686/G000209 targeting domains | TTR | AGTCAATAATCAGAATCAGCAGGT | 333 | AGAAGGCACTTCTTCTTTATCTAAGGT | 337 |
| For experiments with guides based on CR000705/G000211 targeting domains | TTR | GTTTTGTTCCAGAGTCTATCACCG | 334 | ACACGAATAAGAGCAAATGGGAAC | 338 |
| For experiments with guides based on G000269/G000285 targeting domains | TTR | ATTACCAGCTTAGCATCCTGTGAA | 335 | ACACGGTTTATAGAGCAAGAACAC | 339 |
| For experiments with guides based on CR000657/G000208 targeting domains | FVII | AGCACATGAGACCTTCTGTTTCTC | 336 | GACATAGGTGTGACCCTCACAATC | 340 |

Additional PCR was performed according to the manufacturer's protocols (Illumina) to add the necessary chemistry for sequencing. The amplicons were sequenced on an Illumina MiSeq instrument. The reads were aligned to the human reference genome (e.g., hg38) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing") is defined as the total number of sequence reads with insertions or deletions over the total number of sequence reads, including wild type.

G. LNP Delivery in vivo

CD-1 female mice, ranging 6-10 weeks of age were used in each study. Animals were weighed and grouped according to body weight for preparing dosing solutions based on group average weight. LNPs were dosed via the lateral tail vein in a volume of 0.2 mL per animal (approximately 10 mL per kilogram body weight). The animals were observed at approximately 6 hours post dose for adverse effects. Body weight was measured at twenty-four hours post-administration, and animals were euthanized at various time points by exsanguination via cardiac puncture under isoflourane anesthesia. Blood was collected into serum separator tubes or into tubes containing buffered sodium citrate for plasma as described herein. For studies involving in vivo editing, liver tissue was collected from the median lobe from each animal for DNA extraction and analysis.

H. Cytokine Induction Analysis

For this analysis, approximately 50-100 μL of blood was collected by tail vein nick for serum cytokine measurements. Blood was allowed to clot at room temperature for approximately 2 hours, and then centrifuged at 1000×g for 10 minutes before collecting the serum. A Luminex based magnetic bead multiplex assay (Affymetrix ProcartaPlus, catalog number Exp040-00000-801) measuring IL-6, TNF-alpha, IFN-alpha, and MCP-1 was used for cytokine analysis in collected in samples. Kit reagents and standards were prepared as directed in the manufacturer's protocol. 25 μL of mouse serum was added to wells containing 25 μL of the diluted antibody coated magnetic beads. The plate was incubated for 2 hours at room temperature and then washed. Diluted biotin antibody (50 μL) was added to the beads and incubated for 1 hour at room temperature. The beads were washed again before adding 50 μL of diluted streptavidin-PE to each well, followed by incubation for 30 minutes. The beads were washed once again and then suspended in 100 μL of wash buffer and read on the Bio-Plex 200 instrument (Bio-Rad). The data was analyzed using Bioplex Manager ver. 6.1 analysis package with cytokine concentrations calculated off a standard curve using a five parameter logistic curve fit.

I. Genomic DNA Isolation

For the in vivo studies, genomic DNA was extracted from 10 mg of tissue using a bead based extraction kit, MagMAX-96 DNA Multi-Sample Kit (ThermoFisher, Cat #4413020) according to manufacturer's protocol, which includes homogenizing the tissue in lysis buffer (approximately 400 L/10 mg tissue). All DNA samples were normalized to 100 ng/μL concentration for PCR and subsequent NGS analysis, as described herein.

J. Transthyretin (TTR) ELISA Analysis

Blood was collected and the serum was isolated as indicated. The total TTR serum levels were determined using a Mouse Prealbumin (Transthyretin) ELISA Kit (Aviva Systems Biology, Cat. OKIA00111). Kit reagents and standards were prepared according to the manufacture's protocol. Mouse serum was diluted to a final dilution of 10,000-fold with 1× assay diluent. This was done by carrying out two sequential 50-fold dilutions resulting in a 2500-fold dilution. A final 4-fold dilution step was carried out for a total sample dilution of 10,000-fold. Both standard curve dilutions (100 μL each) and diluted serum samples were added to each well of the ELISA plate pre-coated with capture antibody. The plate was incubated at room temperature for 30 minutes before washing. Enzyme-antibody conjugate (100 μL per well) was added for a 20-minute incubation. Unbound antibody conjugate was removed and the plate was washed again before the addition of the chromogenic substrate solution. The plate was incubated for 10 minutes before adding 100 μL of the stop solution, e.g., sulfuric acid (approximately 0.3 M). The plate was read on a SpectraMax M5 plate reader at an absorbance of 450 nm. Serum TTR levels were calculated by SoftMax Pro software ver. 6.4.2 using a four parameter logistic curve fit off the standard curve. Final serum values were adjusted for the assay dilution.

Example 2—Engineering Modified gRNA and In Vitro Testing

Modified gRNAs were designed in the dual guide format (dgRNA), as shown in Table 4. Accordingly, both modified crRNAs and trRNAs were designed and chemically synthesized to allow for the pairing of modified and unmodified components forming dgRNA. These pairings were transfected into Neuro2A cells at concentrations as indicated in the figures and editing efficiency (e.g., percent editing) was measured by NGS, as described in Example 1.

Figure 1:
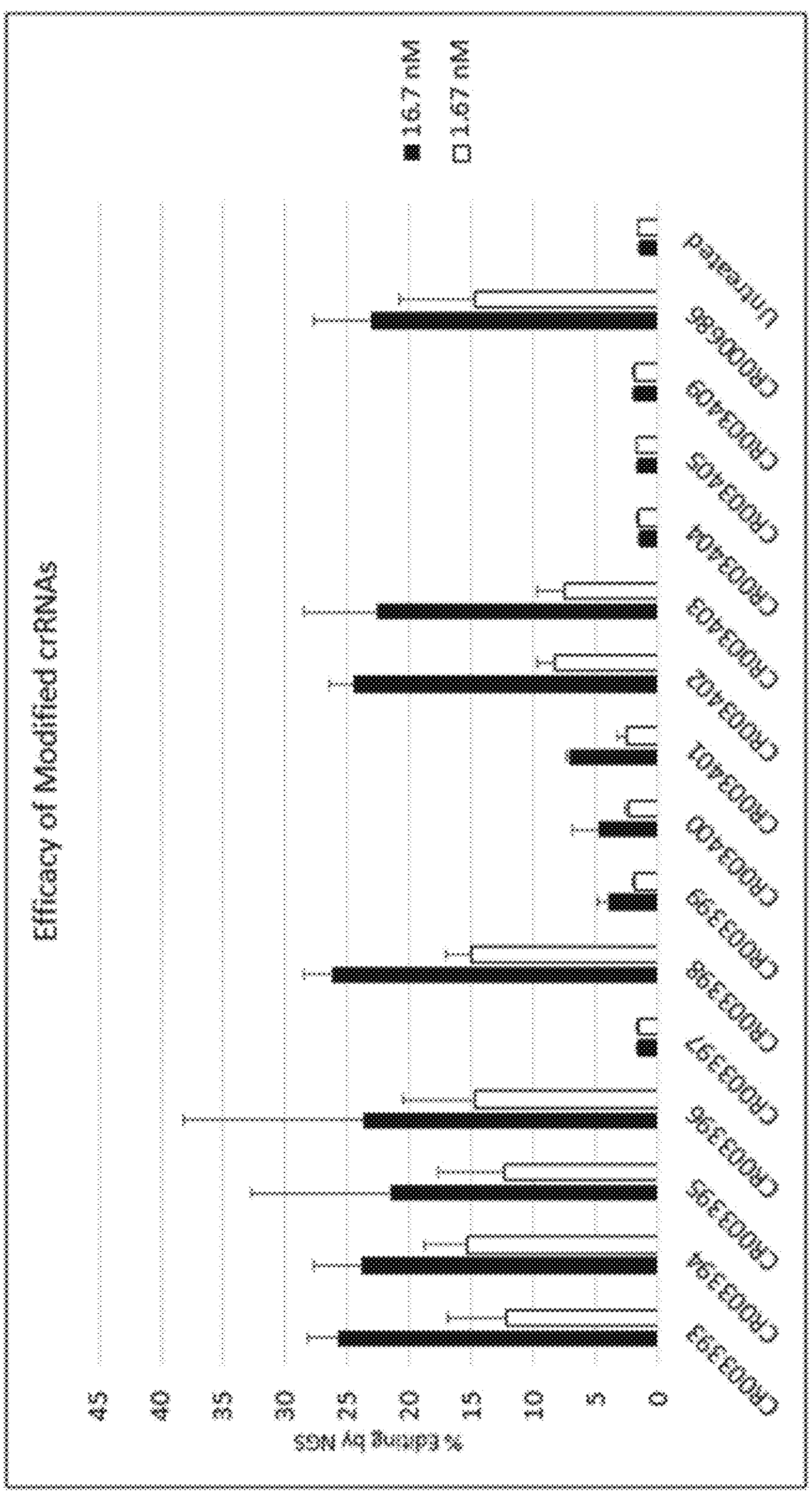
FIG. 1 shows percent editing as measured by next-generation sequence (NGS) of mouse transthyretin (TTR) gene following transfection of Neuro2A cells with modified crRNAs together with Cas9 mRNA and unmodified trRNA (TR000002).

Certain modified crRNAs from Table 4 targeting the mouse TTR gene were transfected with Cas9 mRNA and unmodified trRNA (TR000002). Tested guides included SEQ ID Nos: 1-18. As shown in FIG. 1, some of the modified crRNAs (together with unmodified trRNA) conferred similar or enhanced activity as compared to the unmodified control, while other modified crRNAs decreased activity.

Figure 2:
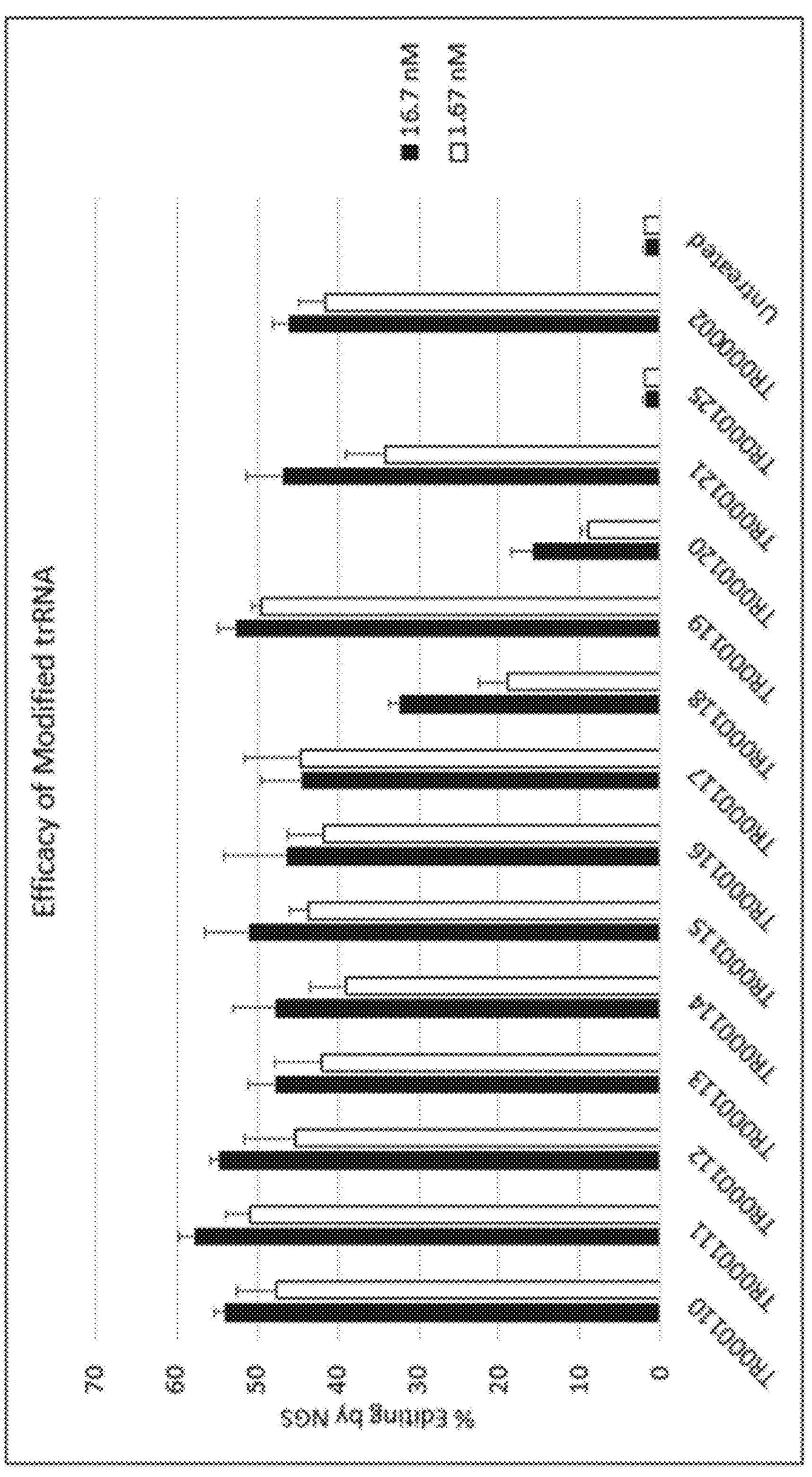
FIG. 2 shows percent editing as measured by NGS of mouse TTR gene following transfection of Neuro2A cells with modified trRNAs together with unmodified crRNA (CR000686) and Cas9 mRNA.

In parallel, modified trRNAs from Table 4 were transfected with Cas9 mRNA along with an unmodified crRNA (CR000686) targeting the same sequence of the mouse TTR gene. Tested guides included SEQ ID Nos: 188-200, and 204. As shown in FIG. 2, many of the modified trRNAs (together with unmodified crRNA) conferred similar or enhanced activity as compared to the unmodified control, while some of the modified trRNAs decreased activity.

Figure 3:
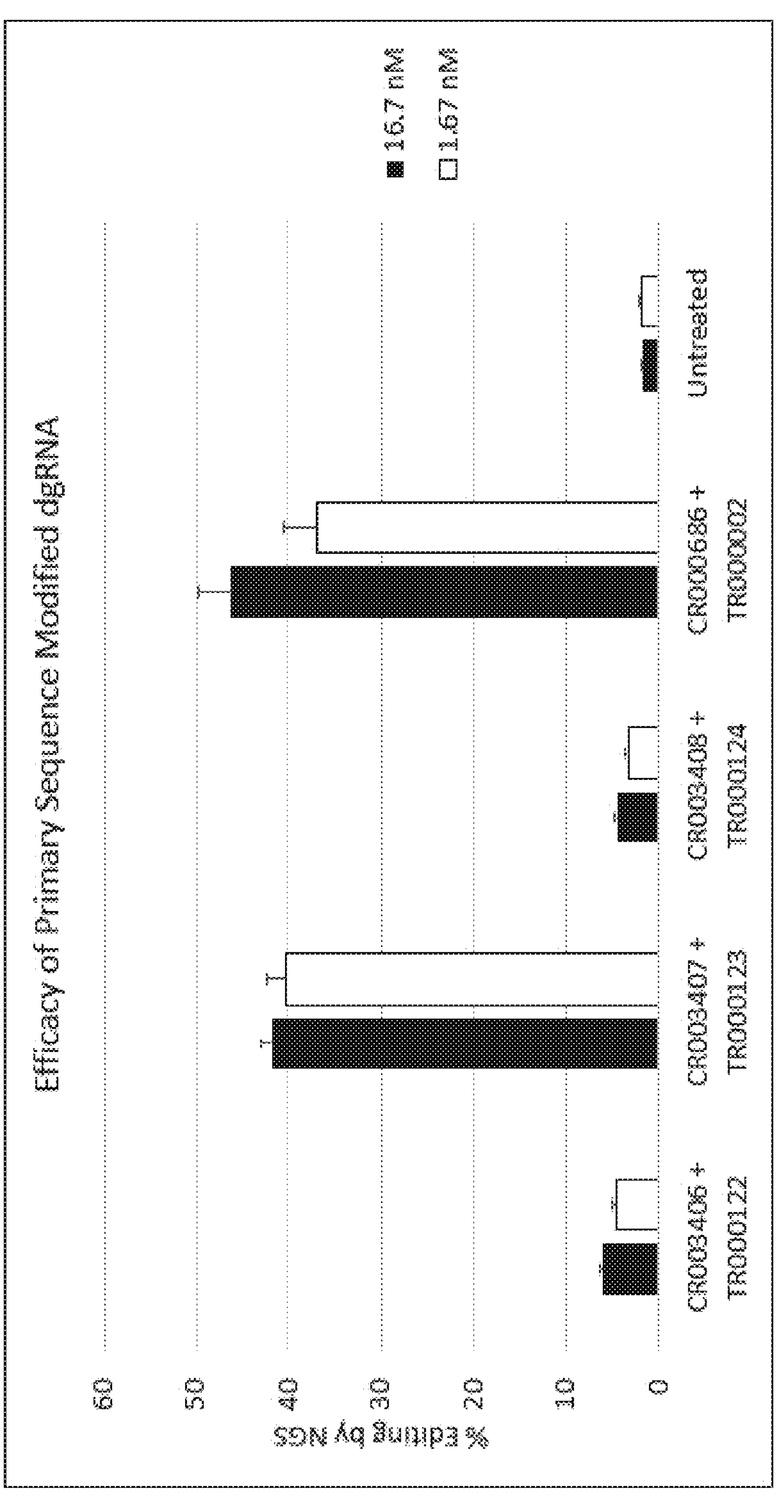
FIG. 3 shows percent editing as measured by NGS of mouse TTR gene following transfection of Neuro2A cells with Cas9 mRNA and crRNAs and trRNAs having G-C pairings not found in parental sequences.

In addition to substituting chemically modified nucleotides, some of the crRNA and trRNA pairings tested were also engineered with sequence substitutions, e.g., resulting in G-C pairings not found in the parental sequences. Tested guides included SEQ ID Nos: 15 and 201; 16 and 202; 1 and 188. As shown in FIG. 3, one such pairing (SEQ ID Nos: 16 and 202) resulted in similar or enhanced activity as compared to the unmodified control, while two of the pairings decreased activity.

Next, pairings of modified crRNAs and modified trRNAs from Table 4 were tested. As shown in FIG. 4, some of the pairings of modified crRNA with modified trRNA conferred similar or enhanced activity as compared to the unmodified controls, while some of the pairings decreased activity. In FIG. 4, the column headings depict different trRNA used in the experiment, and the row headings depict different crRNA used. To determine the combination used in the experiment, you match column to row. TR000002 and CR000686 are the unmodified controls (see lower right cells).

Figure 5:
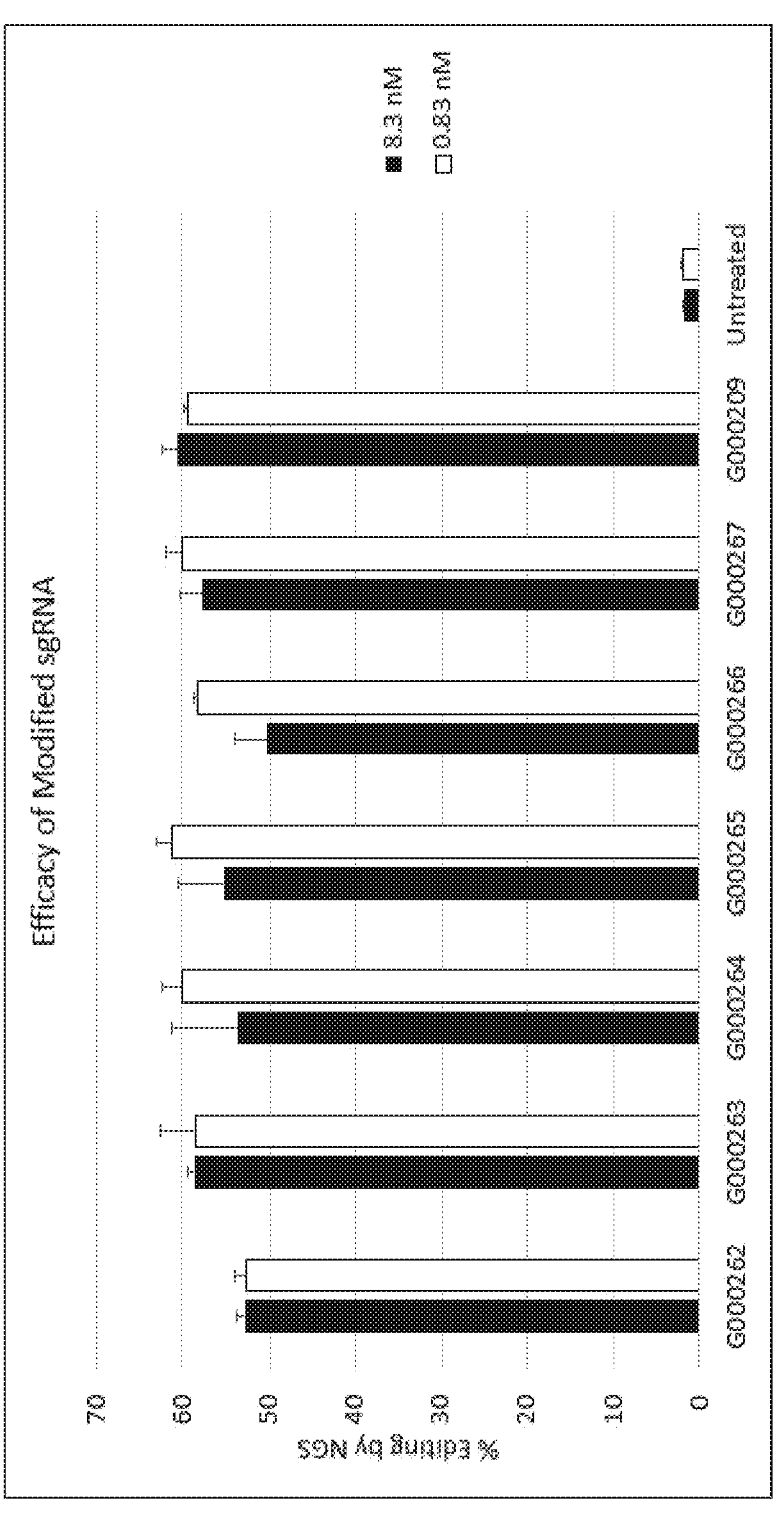
FIG. 5 shows percent editing as measured by NGS of mouse TTR gene following transfection of Neuro2A cells with modified sgRNAs together with Cas9 mRNA.

Based on the dgRNA designs, corresponding single guide RNAs (sgRNAs) were engineered featuring aspects of some of the modified crRNAs and trRNAs, as depicted in Table 4 and FIG. 15D. These sgRNAs, SEQ ID Nos: 228-234, were also tested in Neuro2A cells, and as shown in FIG. 5, each of the modified sgRNAs displayed activities comparable to the controls containing only 5' and 3' end modifications (G0000209; SEQ ID NO: 228).

A similar set of experiments were conducted for additional dgRNAs guides depicted in Table 4 and FIG. 6. Tested guides included SEQ ID Nos: 32-47, and 1. Modified crRNAs also targeting the mouse TTR gene were transfected with Cas9 mRNA and unmodified trRNA (TR000002). As shown in FIG. 6, some of the modified crRNAs (together with unmodified trRNA) conferred similar or enhanced activity as compared to the unmodified control (CR000686), while other modified crRNAs decreased activity.

In parallel, as shown in FIG. 7, modified trRNAs from Table 4 were transfected with Cas9 mRNA along with an unmodified crRNA (CR000686) targeting the same sequence of the mouse TTR gene. Tested guides included SEQ ID Nos: 205-222, and 1. As shown in FIG. 7, many of the modified trRNAs (together with unmodified crRNA) conferred similar or enhanced activity as compared to the unmodified control (TR000002), while some of the modified trRNAs decreased activity.

In addition to substituting chemically modified nucleotides, some of the crRNA and trRNA pairings tested from Table 4 were also engineered with sequence substitutions, e.g., resulting in G-C pairings or G-U mismatches ("GU wobbles") not found in the parental sequences. As shown in FIG. 8, some of the modifications and pairings conferred similar or enhanced activity as compared to the unmodified control, while some (e.g., the "GU wobble" or mismatch pairings) decreased activity. FIG. 8 shows results using trRNA guides shown in SEQ ID Nos: 223-227 and 188 with crRNA guides shown in SEQ ID Nos: 48-52, and 1.

Next, select pairings of the modified crRNAs and modified trRNAs from Table 4 were tested as shown in FIG. 9. Some of the pairings of modified crRNA with modified trRNA conferred similar or enhanced activity as compared to the unmodified controls, while some of the pairings decreased activity. In FIG. 9, the column headings depict different trRNA used in the experiment, and the row headings depict different crRNA used. To determine the combination used in the experiment, you match column to row. Unmodified controls are TR000002, and CR000686.

Some of the modified gRNAs (dgRNAs and sgRNAs) from Table 4 were also tested in a purely biochemical assay (i.e., cell free cleavage assay). Interestingly, many of the modified gRNAs that were largely inactive in the Neuro2A cells were active in the biochemical assay, indicating that such biochemical assays may not be predictive of modified gRNA activity in cells (data not shown).

Example 3. Further Testing of Modified gRNAs to Other Targets

Having established that certain modifications affected gRNA activity, it was next tested whether these modifications would affect the activity when targeting (1) a separate sequence in the same gene or (2) a sequence in a different gene. Accordingly, gRNAs targeting another sequence in the mouse TTR gene as well as a sequence in the mouse Factor-VII (FVII) gene were engineered and synthesized having certain modification patterns tested in Example 2 (see Table 4). These gRNAs were transfected into Neuro2A cells at the concentrations indicated in the figures and editing efficiency (e.g., percent editing) was measured by NGS, as described in Example 1.

Modified crRNAs from Table 4 targeting either the mouse TTR gene (different sequence as targeted in Example 2) or the mouse FVII gene, were transfected with Cas9 mRNA and unmodified trRNA (TR000002). Tested guides included those shown in FIGS. 12A and 12B. Some of the modified crRNAs (together with unmodified trRNA) conferred similar or enhanced activity as compared to the unmodified controls, while other modified crRNAs decreased activity.

In parallel, modified trRNAs from Table 4 were transfected with Cas9 mRNA along with an unmodified crRNA targeting the same sequence of the mouse TTR gene (CR000705; different sequence as targeted in Example 2) or the same sequence as the mouse FVII gene (CR000657). As shown in FIGS. 13A and 13B, many of the modified trRNAs (together with unmodified crRNAs) conferred similar or enhanced activity as compared to the unmodified controls, while some of the modified trRNAs decreased activity. This data shows that certain modification patterns tended to have similar effects over the different sequences.

Based on the dgRNA designs described above, corresponding single guide RNAs (sgRNAs) were engineered featuring aspects of some of the modified crRNAs and trRNAs. See, Table 4. These sgRNAs were also tested in Neuro2A cells. Results are shown in FIG. 10 (mouse TTR) and FIG. 11 (mouse FVII). These experiments show that some modification patterns result in similar effects even when targeting different genes.

Example 4. Testing of Modified gRNA In Vivo

Following the in vitro testing, modified sgRNAs were delivered to animals in six separate studies in order to determine whether the modifications conferred any benefits for editing in vivo.

LNPs were formulated with IVT Cas9 mRNA together with chemically modified sgRNA (targeting TTR or FVII), as described in Example 1. The ratio of mRNA:sgRNA was approximately 1:1, by weight of the RNA components. Unless otherwise indicated, the Cas9 mRNA used in the studies described in this example had the sequence of SEQ ID NO: 360 and the LNPs were formulated using LNP Formulation Procedure A described above.

In one experiment, mice (n=5 per group) were administered a single dose of LNP at 2 mg/kg and blood was collected four hours post dose for serum cytokine analysis. 7 days post dose at necropsy, livers and blood were collected for NGS measurements of editing efficiency and serum TTR analysis, respectively. Each of the sgRNAs in this experiment targeted the same sequence in the TTR gene, the only difference between the sgRNAs being the modifications made to each (See FIGS. 14A-D and 15A-E; Table 4 SEQ ID Nos: 228-234). G000209 (two lots tested) served as the less modified control, having only 2'-O-methyl modifications and phosphorothioate linkages at and between the three terminal nucleotides at both the 5' and 3' termini of the sgRNA, respectively. (See FIG. 15D).

The results shown in FIGS. 14A-D, show that the more heavily modified sgRNAs tended to induce less of a response for each the cytokines assayed, as compared to the less modified G000209 controls. The more heavily modified sgRNAs also conferred larger editing efficiencies in the livers of treated animals, with percent editing reaching ~60% for two of the more heavily modified sgRNAs (e.g., G000263 and G000267) as compared to ~44-47% for the less modified controls (G000209 lots) (FIG. 15A). Importantly, the editing efficiencies correlated with phenotypic changes as serum knockdown of TTR levels were comparable or significantly greater than the less modified controls (See e.g., G000263 and G000267 vs G000209 lots in FIGS. 15A-15B). The differences between the end-modified G000209 and highly-modified G000267 are summarized in FIGS. 15D and 15E (2'-O-Me modified nucleotides are shown in bold, and * represents phosphorothioate linkages).

In another in vivo study, three sgRNAs targeting a separate sequence in the mouse TTR gene were tested. Mice (n=5 per group) were administered a single dose of LNP at 2 mg/kg, 1 mg/kg, or 0.3 mg/kg. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene (a different sequence from what was targeted in the previous in vivo study) with one sgRNA being completely unmodified (G000201 (SEQ ID NO: 243)), another having only end modifications (G000211 (SEQ ID NO: 241)), with 2'-O-methyl modifications and phosphorothioate linkages at and between the three terminal nucleotides at both the 5' and 3' termini of the sgRNA, respectively), and a third sgRNA having the same modification pattern as G000267 in the previous in vivo study (G000282 (SEQ ID NO: 242)).

As shown in FIGS. 16A-16D, each of the sgRNAs resulted in similar responses in a dose dependent manner for each of the cytokines tested. For editing efficiency, the unmodified sgRNA (G000201(SEQ ID NO: 243)) conferred little in vivo editing, while the heavily modified sgRNA (G000282 (SEQ ID NO: 242)) conferred levels reaching ~60% with a dose of 2 mg/kg, which was significantly greater than the levels achieved with the less modified sgRNA (G000211 (SEQ ID NO: 241)) (FIGS. 17A and B). As with the previous in vivo study, the levels of editing correlated with the amount of serum TTR knockdown (FIGS. 17C and D).

A similar study as the second in vivo study was next conducted with another set of three sgRNAs targeting yet a different TTR sequence in the mouse TTR gene (targeting a different sequence then what was targeted in the two previous in vivo studies). Mice (n=5 per group) were administered a single dose of LNP at 2 mg/kg, 1 mg/kg, or 0.3 mg/kg. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene (a different sequence from what was targeted in the previous two in vivo studies) with one sgRNA being completely unmodified (G000285; (SEQ ID NO: 332)), another having only end modifications (G000269 (SEQ ID NO: 330)), with 2'-O-methyl modifications and phosphorothioate linkages at and between the three terminal nucleotides at both the 5' and 3' ends of the sgRNA, respectively), and a third sgRNA having the same modification pattern as G000267 and G000282 in the previous two in vivo studies (G000283 (SEQ ID NO: 331)).

In this study, the unmodified sgRNA (G000285 (SEQ ID NO: 332)) conferred little in vivo editing, while the heavily modified sgRNA (G000283 (SEQ ID NO: 331)) conferred levels reaching ~60% with a dose of 2 mg/kg, which was significantly greater than the levels achieved with the less modified sgRNA (G000269 (SEQ ID NO: 330)) (FIGS. 18A-18B). As with the previous in vivo studies, the levels of editing correlated with the amount of serum TTR knockdown (FIG. 18C).

In a fourth in vivo study, the effects of modifications to gRNAs was evaluated for another gene (FVII). For in-study comparison, two of the sgRNAs tested in the first in vivo study were included (G000209 and G000267). Mice (n=5 per group) were administered a single dose of LNP at 2 mg/kg, 1 mg/kg, or 0.3 mg/kg, and blood was collected four hours post dose for serum cytokine analysis. 6 days post dose at necropsy, livers were collected for NGS measurements of editing efficiency. In this study, each of the sgRNAs targeted the same sequence in the TTR or FVII genes, with one sgRNA for each having only end modifications (G000208 (SEQ ID NO: 286)) for FVII, G000209 for TTR, both having 2'-O-methyl modifications and phosphorothioate linkages at and between the three terminal nucleotides at both the 5' and 3' ends of the sgRNA, respectively), and a second sgRNA having the same modification patterns as G000267, G000282, and G000283 in the previous in vivo studies (G000373 (SEQ ID NO: 287) for FVII; G000267 (SEQ ID NO: 234) for TTR).

As shown in FIGS. 19A-19D, each of the sgRNAs resulted in similar responses in a dose dependent manner for each of the cytokines tested. For editing efficiency, the more heavily modified sgRNA targeting FVII (G000373 (SEQ ID NO: 287)) had an increase in editing efficiency as compared to the less modified version (G000208 (SEQ ID NO: 286)) across each of the doses tested (FIG. 18A). These results were also observed for the sgRNAs targeting TTR (FIGS. 20A-20B).

In another in vivo study, ten additional sgRNAs targeting the same sequence in the mouse TTR gene as G000282 were tested. G000282 was also included in the study for comparative purposes. Mice (n=5 per group) were administered a single dose of LNP at 1 mg/kg or 0.5 mg/kg. The LNPs used in this study were formulated using LNP Formulation Procedure B described above. Seven (7) days post dose at necropsy, livers and blood were collected for NGS measurements of editing efficiency and serum TTR analysis, respectively. In this study, each of the sgRNAs targeted the same sequence in the TTR gene. The modification pattern of each sgRNA tested varied and included 2'-OMe, 2'-F, and PS modifications in the 5' terminus, 3' terminus, hairpin 1, hairpin 2, nexus, lower stem, bulge, and upper stem of the sgRNA. The results of this study are shown in FIGS.

22A-22C, including % editing (FIG. 22A), average editing and standard deviation (FIG. 22B), and serum TTR levels (FIG. 22C). These same sgRNAs were tested in primary mouse hepatocytes as per the methods described herein. The results of this dose response TTR editing study are shown in FIGS. 24A-24C, including % editing (FIG. 24A), dose response curves (FIG. 24B), and EC50 values (FIG. 24C).

In another in vivo study, thirteen sgRNAs targeting the same sequence in the mouse TTR gene as G000282 were tested. G000282 was also included in the study for comparative purposes. Mice (n=5 per group) were administered a single dose of LNP at 1 mg/kg. The LNPs used in this study were formulated using LNP Formulation Procedure C described above. The Cas9 mRNA used in this study had the sequence of SEQ ID NO: 359. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene. The sgRNAs tested include additional 2'-OMe and PS modifications in the 5' terminus, 3' terminus, hairpin 1, hairpin 2, and upper stem of the sgRNA. The results of this study are shown in FIGS. 23A-23C, including % editing (FIG. 23A), average % editing (FIG. 23B), and serum TTR levels (FIG. 23C).

We claim:

1. A single guide RNA (sgRNA) comprising the nucleotide sequence mN*mN*mN*NNNNNNNNNNNNNNNNNGUUUUAG AmGmCmUmAmGmAmAmAmUmA mGmCAAGUUAAAAUAAGGCUAGUCCGUUAUCA-mAmCmUmUmGmAmAmAmAmAm GmUmGmGmC-mAmCmCmGmAmGmUmCmGmGmUm GmCmU*mU*mU*mU, wherein N denotes any one of A, C, G, and U; * denotes a phosphorothioate (PS) linkage; and mN, mA, mC, mG, and mU respectively denote N, A, C, G, and U modified with 2'-O-methyl (2'-O-Me) (SEQ ID NO: 358) of SEQ ID NO: 358.

2. A composition comprising: (a) the sgRNA of claim 1; and (b) a pharmaceutically acceptable excipient or carrier.

3. A composition comprising: (a) the sgRNA of claim 1; and (b) a Cas protein or a mRNA encoding a Cas protein.

4. The composition of claim 3, wherein the Cas protein is a Cas9.

5. The composition of claim 4, wherein the Cas9 is *Streptococcus pyogenes* Cas9.

6. The composition of claim 3, further comprising a lipid nanoparticle (LNP).

7. The composition of claim 3, comprising (a) the sgRNA of claim 1; and (b) a mRNA encoding a *S. pyogenes* Cas9 protein.

8. A method of modifying a target DNA, the method comprising delivering the composition of claim 7 to a cell.

9. A method of modifying a target DNA, the method comprising delivering the composition of claim 3 to a cell.

10. A sgRNA consisting of the nucleotide sequence mN*mN*mN*NNNNNNNNNNNNNNNNNGUUUUAG AmGmCmUmAmGmAmAmAmUmA mGmCAAGUUAAAAUAAGGCUAGUCCGUUAUCA-mAmCmUmUmGmAmAmAmAmAm GmUmGmGmC-mAmCmCmGmAmGmUmCmGmGmUm GmCmU*mU*mU*mU, wherein N denotes any one of A, C, G, and U; * denotes a phosphorothioate (PS) linkage; and mN, mA, mC, mG, and mU respectively denote N, A, C, G, and U modified with 2'-O-methyl (2'-O-Me) (SEQ ID NO: 358) of SEQ ID NO: 358.

11. A composition comprising: (a) the sgRNA of claim 10; and (b) a pharmaceutically acceptable carrier.

12. A composition comprising: (a) the sgRNA of claim 10; and (b) a Cas protein or a mRNA encoding a Cas protein.

13. The composition of claim 12, wherein the Cas protein is a Cas9.

14. The composition of claim 13, wherein the Cas9 is *S. pyogenes* Cas9.

15. The composition of claim 12, further comprising a lipid nanoparticle (LNP).

16. The composition of claim 12, comprising (a) the sgRNA of claim 10; and (b) a mRNA encoding a *S. pyogenes* Cas9 protein.

17. A method of modifying a target DNA, the method comprising delivering the composition of claim 16 to a cell.

18. A method of modifying a target DNA, the method comprising delivering the composition of claim 12 to a cell.

19. A composition comprising: (a) a sgRNA comprising the nucleotide sequence mN*mN*mN*NNNNNNNNNNNNNNNNNGUUUUAG AmGmCmUmAmGmAmAmAmUmA mGmCAAGUUAAAAUAAGGCUAGUCCGUUAUCA-mAmCmUmUmGmAmAmAmAmAm GmUmGmGmC-mAmCmCmGmAmGmUmCmGmGmUm GmCmU*mU*mU*mU, wherein N denotes any one of A, C, G, and U; * denotes a phosphorothioate (PS) linkage; and mN, mA, mC, mG, and mU respectively denote N, A, C, G, and U modified with 2'-O-methyl (2'-O-Me) (SEQ ID NO: 358); (b) a mRNA encoding a *S. pyogenes* Cas9 protein; and (c) a lipid nanoparticle (LNP).

20. A method of modifying a target DNA, the method comprising delivering the composition of claim 19 to a cell.

21. A composition comprising: (a) a sgRNA consisting of the nucleotide sequence mN*mN*mN*NNNNNNNNNNNNNNNNNGUUUUAG AmGmCmUmAmGmAmAmAmUmA mGmCAAGUUAAAAUAAGGCUAGUCCGUUAUCA-mAmCmUmUmGmAmAmAmAmAm GmUmGmGmC-mAmCmCmGmAmGmUmCmGmGmUm GmCmU*mU*mU*mU, wherein N denotes any one of A, C, G, and U; * denotes a phosphorothioate (PS) linkage; and mN, mA, mC, mG, and mU respectively denote N, A, C, G, and U modified with 2'-O-methyl (2'-O-Me) (SEQ ID NO: 358); (b) a mRNA encoding a *S. pyogenes* Cas9 protein; and (c) a lipid nanoparticle (LNP).

22. A method of modifying a target DNA, the method comprising delivering the composition of claim 21 to a cell.

* * * * *

SEQUENCE LISTING

```
Sequence total quantity: 360
SEQ ID NO: 1            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 1
ccagtccagc gaggcaaagg gttttagagc tatgctgttt tg                     42

SEQ ID NO: 2            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 2
ccagtccagc gaggcaaagg gttttagagc tatgctgttt tg                     42

SEQ ID NO: 3            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 3
ccagtccagc gaggcaaagg gttttagagc tatgctgttt tg                     42

SEQ ID NO: 4            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 4
ccagtccagc gaggcaaagg gttttagagc tatgctgttt tg                     42

SEQ ID NO: 5            moltype = RNA  length = 42
```

-continued

```
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 5
ccagtccagc gaggcaaagg gttttagagc tatgctgttt tg                     42

SEQ ID NO: 6            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 6
ccagtccagc gaggcaaagg gttttagagc tatgctgttt tg                     42

SEQ ID NO: 7            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 7
ccagtccagc gaggcaaagg gttttagagc tatgctgttt tg                     42

SEQ ID NO: 8            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 8
ccagtccagc gaggcaaagg gttttagagc tatgctgttt tg                     42

SEQ ID NO: 9            moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 9
ccagtccagc gaggcaaagg gttttagagc tatgctgttt tg                     42

SEQ ID NO: 10           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 10
ccagtccagc gaggcaaagg gttttagagc tatgctgttt tg                     42

SEQ ID NO: 11           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 11
ccagtccagc gaggcaaagg gttttagagc tatgctgttt tg                     42

SEQ ID NO: 12           moltype = RNA  length = 42
FEATURE                 Location/Qualifiers
misc_feature            1..42
```

-continued

```
                        note = source = /note="Description of Artificial Sequence:
                         Synthetic oligonucleotide"
source                  1..42
                        mol_type = other RNA
                        organism = synthetic construct
SEQUENCE: 12
ccagtccagc gaggcaaagg gttttagagc tatgctgttt tg                    42

SEQ ID NO: 13           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 13
ccagtccagc gaggcaaagg gttttagagc tatgctgttt tg                    42

SEQ ID NO: 14           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 14
ccagtccagc gaggcaaagg gttttagagc tatgctgttt tg                    42

SEQ ID NO: 15           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 15
ccagtccagc gaggcaaagg ggcgcagagc tatgctgttt tg                    42

SEQ ID NO: 16           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 16
ccagtccagc gaggcaaagg gttttagagc tatgctggcg cg                    42

SEQ ID NO: 17           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 17
ccagtccagc gaggcaaagg ggcgcagagc tatgctggcg cg                    42

SEQ ID NO: 18           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 18
ccagtccagc gaggcaaagg gttttagagc tatgctgttt tg                    42

SEQ ID NO: 19           moltype = RNA  length = 22
FEATURE                 Location/Qualifiers
misc_feature            1..22
                        note = source = /note="Description of Artificial Sequence:
                         Synthetic oligonucleotide"
```

```
source                  1..22
                        mol_type = other RNA
                        organism = synthetic construct
SEQUENCE: 19
gttttagagc tatgctgttt tg                                          22

SEQ ID NO: 20           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 20
gttttagagc tatgctgttt tg                                          22

SEQ ID NO: 21           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 21
gttttagagc tatgctgttt tg                                          22

SEQ ID NO: 22           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 22
gttttagagc tatgctgttt tg                                          22

SEQ ID NO: 23           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 23
gttttagagc tatgctgttt tg                                          22

SEQ ID NO: 24           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 24
gttttagagc tatgctgttt tg                                          22

SEQ ID NO: 25           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 25
gttttagagc tatgctgttt tg                                          22

SEQ ID NO: 26           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
```

```
                         organism = synthetic construct
SEQUENCE: 26
gttttagagc tatgctgttt tg                                             22

SEQ ID NO: 27            moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 27
gttttagagc tatgctgttt tg                                             22

SEQ ID NO: 28            moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 28
gttttagagc tatgctgttt tg                                             22

SEQ ID NO: 29            moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 29
gttttagagc tatgctgttt tg                                             22

SEQ ID NO: 30            moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 30
gttttagagc tatgctgttt tg                                             22

SEQ ID NO: 31            moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 31
gttttagagc tatgctgttt tg                                             22

SEQ ID NO: 32            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 32
ccagtccagc gaggcaaagg gttttagagc tatgctgttt tg                       42

SEQ ID NO: 33            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 33
```

-continued

```
ccagtccagc gaggcaaagg gttttagagc tatgctgttt tg                    42

SEQ ID NO: 34          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 34
ccagtccagc gaggcaaagg gttttagagc tatgctgttt tg                    42

SEQ ID NO: 35          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 35
ccagtccagc gaggcaaagg gttttagagc tatgctgttt tg                    42

SEQ ID NO: 36          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 36
ccagtccagc gaggcaaagg gttttagagc tatgctgttt tg                    42

SEQ ID NO: 37          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 37
ccagtccagc gaggcaaagg gttttagagc tatgctgttt tg                    42

SEQ ID NO: 38          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 38
ccagtccagc gaggcaaagg gttttagagc tatgctgttt tg                    42

SEQ ID NO: 39          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 39
ccagtccagc gaggcaaagg gttttagagc tatgctgttt tg                    42

SEQ ID NO: 40          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 40
ccagtccagc gaggcaaagg gttttagagc tatgctgttt tg                    42
```

```
SEQ ID NO: 41          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 41
ccagtccagc gaggcaaagg gttttagagc tatgctgttt tg                     42

SEQ ID NO: 42          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 42
ccagtccagc gaggcaaagg gttttagagc tatgctgttt tg                     42

SEQ ID NO: 43          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 43
ccagtccagc gaggcaaagg gttttagagc tatgctgttt tg                     42

SEQ ID NO: 44          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 44
ccagtccagc gaggcaaagg gttttagagc tatgctgttt tg                     42

SEQ ID NO: 45          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 45
ccagtccagc gaggcaaagg gttttagagc tatgctgttt tg                     42

SEQ ID NO: 46          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 46
ccagtccagc gaggcaaagg gttttagagc tatgctgttt tg                     42

SEQ ID NO: 47          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 47
ccagtccagc gaggcaaagg gttttagagc tatgctgttt tg                     42

SEQ ID NO: 48          moltype = RNA  length = 42
FEATURE                Location/Qualifiers
```

```
misc_feature           1..42
                       note = source = /note="Description of Artificial Sequence:
                        Synthetic oligonucleotide"
source                 1..42
                       mol_type = other RNA
                       organism = synthetic construct
SEQUENCE: 48
ccagtccagc gaggcaaagg gtctcagagc tatgctgttt tg                     42

SEQ ID NO: 49          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 49
ccagtccagc gaggcaaagg gctttagagc tatgctgttt tg                     42

SEQ ID NO: 50          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 50
ccagtccagc gaggcaaagg gtcttagagc tatgctgttt tg                     42

SEQ ID NO: 51          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 51
ccagtccagc gaggcaaagg gttctagagc tatgctgttt tg                     42

SEQ ID NO: 52          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 52
ccagtccagc gaggcaaagg gtttcagagc tatgctgttt tg                     42

SEQ ID NO: 53          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 53
gttttagagc tatgctgttt tg                                           22

SEQ ID NO: 54          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 54
gttttagagc tatgctgttt tg                                           22

SEQ ID NO: 55          moltype = RNA  length = 22
FEATURE                Location/Qualifiers
misc_feature           1..22
                       note = source = /note="Description of Artificial Sequence:
```

```
                         Synthetic oligonucleotide"
source                  1..22
                        mol_type = other RNA
                        organism = synthetic construct
SEQUENCE: 55
gttttagagc tatgctgttt tg                                           22

SEQ ID NO: 56           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 56
gttttagagc tatgctgttt tg                                           22

SEQ ID NO: 57           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 57
gttttagagc tatgctgttt tg                                           22

SEQ ID NO: 58           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 58
gttttagagc tatgctgttt tg                                           22

SEQ ID NO: 59           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 59
gttttagagc tatgctgttt tg                                           22

SEQ ID NO: 60           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 60
gttttagagc tatgctgttt tg                                           22

SEQ ID NO: 61           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 61
gttttagagc tatgctgttt tg                                           22

SEQ ID NO: 62           moltype = RNA  length = 22
FEATURE                 Location/Qualifiers
misc_feature            1..22
                        note = source = /note="Description of Artificial Sequence:
                         Synthetic oligonucleotide"
source                  1..22
```

```
                       mol_type = other RNA
                       organism = synthetic construct
SEQUENCE: 62
gttttagagc tatgctgttt tg                                            22

SEQ ID NO: 63          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 63
gttttagagc tatgctgttt tg                                            22

SEQ ID NO: 64          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 64
gttttagagc tatgctgttt tg                                            22

SEQ ID NO: 65          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 65
gttttagagc tatgctgttt tg                                            22

SEQ ID NO: 66          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 66
gttttagagc tatgctgttt tg                                            22

SEQ ID NO: 67          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 67
gttttagagc tatgctgttt tg                                            22

SEQ ID NO: 68          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
SEQUENCE: 68
gttttagagc tatgctgttt tg                                            22

SEQ ID NO: 69          moltype = RNA  length = 22
FEATURE                Location/Qualifiers
misc_feature           1..22
                       note = source = /note="Description of Artificial Sequence:
                        Synthetic oligonucleotide"
source                 1..22
                       mol_type = other RNA
                       organism = synthetic construct
```

-continued

```
SEQUENCE: 69
gtctcagagc tatgctgttt tg                                          22

SEQ ID NO: 70           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 70
gctttagagc tatgctgttt tg                                          22

SEQ ID NO: 71           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 71
gtcttagagc tatgctgttt tg                                          22

SEQ ID NO: 72           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 72
gttctagagc tatgctgttt tg                                          22

SEQ ID NO: 73           moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 73
gtttcagagc tatgctgttt tg                                          22

SEQ ID NO: 74           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 74
ttacagccac gtctacagca gttttagagc tatgctgttt tg                    42

SEQ ID NO: 75           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 75
ttacagccac gtctacagca gttttagagc tatgctgttt tg                    42

SEQ ID NO: 76           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 76
ttacagccac gtctacagca gttttagagc tatgctgttt tg                    42
```

```
SEQ ID NO: 77            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 77
ttacagccac gtctacagca gttttagagc tatgctgttt tg                    42

SEQ ID NO: 78            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 78
ttacagccac gtctacagca gttttagagc tatgctgttt tg                    42

SEQ ID NO: 79            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 79
ttacagccac gtctacagca gttttagagc tatgctgttt tg                    42

SEQ ID NO: 80            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 80
ttacagccac gtctacagca gttttagagc tatgctgttt tg                    42

SEQ ID NO: 81            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 81
ttacagccac gtctacagca gttttagagc tatgctgttt tg                    42

SEQ ID NO: 82            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 82
ttacagccac gtctacagca gttttagagc tatgctgttt tg                    42

SEQ ID NO: 83            moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 83
ttacagccac gtctacagca gttttagagc tatgctgttt tg                    42

SEQ ID NO: 84            moltype = RNA  length = 42
```

-continued

```
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 84
ttacagccac gtctacagca gttttagagc tatgctgttt tg                    42

SEQ ID NO: 85          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 85
ttacagccac gtctacagca gttttagagc tatgctgttt tg                    42

SEQ ID NO: 86          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 86
ttacagccac gtctacagca gttttagagc tatgctgttt tg                    42

SEQ ID NO: 87          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 87
ttacagccac gtctacagca gttttagagc tatgctgttt tg                    42

SEQ ID NO: 88          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 88
ttacagccac gtctacagca gttttagagc tatgctgttt tg                    42

SEQ ID NO: 89          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 89
ttacagccac gtctacagca gttttagagc tatgctgttt tg                    42

SEQ ID NO: 90          moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 90
ttacagccac gtctacagca gttttagagc tatgctgttt tg                    42

SEQ ID NO: 91          moltype = RNA  length = 42
FEATURE                Location/Qualifiers
misc_feature           1..42
```

-continued

```
                        note = source = /note="Description of Artificial Sequence:
                         Synthetic oligonucleotide"
source                  1..42
                        mol_type = other RNA
                        organism = synthetic construct
SEQUENCE: 91
ttacagccac gtctacagca gttttagagc tatgctgttt tg                    42

SEQ ID NO: 92           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 92
ttacagccac gtctacagca gttttagagc tatgctgttt tg                    42

SEQ ID NO: 93           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 93
ttacagccac gtctacagca gttttagagc tatgctgttt tg                    42

SEQ ID NO: 94           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 94
ttacagccac gtctacagca gttttagagc tatgctgttt tg                    42

SEQ ID NO: 95           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 95
ttacagccac gtctacagca gttttagagc tatgctgttt tg                    42

SEQ ID NO: 96           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 96
ttacagccac gtctacagca gttttagagc tatgctgttt tg                    42

SEQ ID NO: 97           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 97
ttacagccac gtctacagca gttttagagc tatgctgttt tg                    42

SEQ ID NO: 98           moltype = RNA  length = 42
FEATURE                 Location/Qualifiers
misc_feature            1..42
                        note = source = /note="Description of Artificial Sequence:
                         Synthetic oligonucleotide"
```

-continued

```
source                  1..42
                        mol_type = other RNA
                        organism = synthetic construct
SEQUENCE: 98
ttacagccac gtctacagca gttttagagc tatgctgttt tg                     42

SEQ ID NO: 99           moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 99
ttacagccac gtctacagca gttttagagc tatgctgttt tg                     42

SEQ ID NO: 100          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 100
ttacagccac gtctacagca gttttagagc tatgctgttt tg                     42

SEQ ID NO: 101          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 101
ttacagccac gtctacagca gttttagagc tatgctgttt tg                     42

SEQ ID NO: 102          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 102
ttacagccac gtctacagca ggcgcagagc tatgctgttt tg                     42

SEQ ID NO: 103          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 103
ttacagccac gtctacagca gttttagagc tatgctggcg cg                     42

SEQ ID NO: 104          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 104
gttttagagc tatgctgttt tg                                           22

SEQ ID NO: 105          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
```

-continued

```
                        organism = synthetic construct
SEQUENCE: 105
gttttagagc tatgctgttt tg                                           22

SEQ ID NO: 106          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 106
gttttagagc tatgctgttt tg                                           22

SEQ ID NO: 107          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 107
gttttagagc tatgctgttt tg                                           22

SEQ ID NO: 108          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 108
gttttagagc tatgctgttt tg                                           22

SEQ ID NO: 109          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 109
gttttagagc tatgctgttt tg                                           22

SEQ ID NO: 110          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 110
gttttagagc tatgctgttt tg                                           22

SEQ ID NO: 111          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 111
gttttagagc tatgctgttt tg                                           22

SEQ ID NO: 112          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 112
```

-continued

```
gttttagagc tatgctgttt tg                                          22

SEQ ID NO: 113          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 113
gttttagagc tatgctgttt tg                                          22

SEQ ID NO: 114          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 114
gttttagagc tatgctgttt tg                                          22

SEQ ID NO: 115          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 115
gttttagagc tatgctgttt tg                                          22

SEQ ID NO: 116          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 116
gttttagagc tatgctgttt tg                                          22

SEQ ID NO: 117          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 117
gttttagagc tatgctgttt tg                                          22

SEQ ID NO: 118          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 118
gttttagagc tatgctgttt tg                                          22

SEQ ID NO: 119          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 119
gttttagagc tatgctgttt tg                                          22
```

-continued

```
SEQ ID NO: 120          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 120
gttttagagc tatgctgttt tg                                             22

SEQ ID NO: 121          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 121
gttttagagc tatgctgttt tg                                             22

SEQ ID NO: 122          moltype = RNA  length = 16
FEATURE                 Location/Qualifiers
misc_feature            1..16
                        note = source = /note="Description of Artificial Sequence:
                         Synthetic oligonucleotide"
source                  1..16
                        mol_type = other RNA
                        organism = synthetic construct
SEQUENCE: 122
gagctatgct gttttg                                                    16

SEQ ID NO: 123          moltype = RNA  length = 16
FEATURE                 Location/Qualifiers
misc_feature            1..16
                        note = source = /note="Description of Artificial Sequence:
                         Synthetic oligonucleotide"
source                  1..16
                        mol_type = other RNA
                        organism = synthetic construct
SEQUENCE: 123
gagctatgct gttttg                                                    16

SEQ ID NO: 124          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 124
gttttagagc tatgctgttt tg                                             22

SEQ ID NO: 125          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 125
gttttagagc tatgctgttt tg                                             22

SEQ ID NO: 126          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 126
gttttagagc tatgctgttt tg                                             22

SEQ ID NO: 127          moltype = RNA  length = 22
FEATURE                 Location/Qualifiers
```

-continued

```
misc_feature          1..22
                      note = source = /note="Description of Artificial Sequence:
                       Synthetic oligonucleotide"
source                1..22
                      mol_type = other RNA
                      organism = synthetic construct
SEQUENCE: 127
gttttagagc tatgctgttt tg                                            22

SEQ ID NO: 128        moltype = RNA  length = 22
FEATURE               Location/Qualifiers
misc_feature          1..22
                      note = source = /note="Description of Artificial Sequence:
                       Synthetic oligonucleotide"
source                1..22
                      mol_type = other RNA
                      organism = synthetic construct
SEQUENCE: 128
gttttagagc tatgctgttt tg                                            22

SEQ ID NO: 129        moltype = RNA  length = 22
FEATURE               Location/Qualifiers
misc_feature          1..22
                      note = source = /note="Description of Artificial Sequence:
                       Synthetic oligonucleotide"
source                1..22
                      mol_type = other RNA
                      organism = synthetic construct
SEQUENCE: 129
gttttagagc tatgctgttt tg                                            22

SEQ ID NO: 130        moltype = RNA  length = 22
FEATURE               Location/Qualifiers
misc_feature          1..22
                      note = source = /note="Description of Artificial Sequence:
                       Synthetic oligonucleotide"
source                1..22
                      mol_type = other RNA
                      organism = synthetic construct
SEQUENCE: 130
gttttagagc tatgctgttt tg                                            22

SEQ ID NO: 131        moltype = RNA  length = 42
FEATURE               Location/Qualifiers
misc_feature          1..42
                      note = source = /note="Description of Artificial Sequence:
                       Synthetic oligonucleotide"
source                1..42
                      mol_type = other RNA
                      organism = synthetic construct
SEQUENCE: 131
cagggctctt gaagatctcc gttttagagc tatgctgttt tg                      42

SEQ ID NO: 132        moltype = RNA  length = 42
FEATURE               Location/Qualifiers
misc_feature          1..42
                      note = source = /note="Description of Artificial Sequence:
                       Synthetic oligonucleotide"
source                1..42
                      mol_type = other RNA
                      organism = synthetic construct
SEQUENCE: 132
cagggctctt gaagatctcc gttttagagc tatgctgttt tg                      42

SEQ ID NO: 133        moltype = RNA  length = 42
FEATURE               Location/Qualifiers
misc_feature          1..42
                      note = source = /note="Description of Artificial Sequence:
                       Synthetic oligonucleotide"
source                1..42
                      mol_type = other RNA
                      organism = synthetic construct
SEQUENCE: 133
cagggctctt gaagatctcc gttttagagc tatgctgttt tg                      42

SEQ ID NO: 134        moltype = RNA  length = 42
FEATURE               Location/Qualifiers
misc_feature          1..42
                      note = source = /note="Description of Artificial Sequence:
```

```
                          Synthetic oligonucleotide"
source                   1..42
                         mol_type = other RNA
                         organism = synthetic construct
SEQUENCE: 134
cagggctctt gaagatctcc gttttagagc tatgctgttt tg                    42

SEQ ID NO: 135           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 135
cagggctctt gaagatctcc gttttagagc tatgctgttt tg                    42

SEQ ID NO: 136           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 136
cagggctctt gaagatctcc gttttagagc tatgctgttt tg                    42

SEQ ID NO: 137           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 137
cagggctctt gaagatctcc gttttagagc tatgctgttt tg                    42

SEQ ID NO: 138           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 138
cagggctctt gaagatctcc gttttagagc tatgctgttt tg                    42

SEQ ID NO: 139           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 139
cagggctctt gaagatctcc gttttagagc tatgctgttt tg                    42

SEQ ID NO: 140           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 140
cagggctctt gaagatctcc gttttagagc tatgctgttt tg                    42

SEQ ID NO: 141           moltype = RNA  length = 42
FEATURE                  Location/Qualifiers
misc_feature             1..42
                         note = source = /note="Description of Artificial Sequence:
                          Synthetic oligonucleotide"
source                   1..42
```

```
                         mol_type = other RNA
                         organism = synthetic construct
SEQUENCE: 141
cagggctctt gaagatctcc gttttagagc tatgctgttt tg                   42

SEQ ID NO: 142           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 142
cagggctctt gaagatctcc gttttagagc tatgctgttt tg                   42

SEQ ID NO: 143           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 143
cagggctctt gaagatctcc gttttagagc tatgctgttt tg                   42

SEQ ID NO: 144           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 144
cagggctctt gaagatctcc gttttagagc tatgctgttt tg                   42

SEQ ID NO: 145           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 145
cagggctctt gaagatctcc gttttagagc tatgctgttt tg                   42

SEQ ID NO: 146           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 146
cagggctctt gaagatctcc gttttagagc tatgctgttt tg                   42

SEQ ID NO: 147           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 147
cagggctctt gaagatctcc gttttagagc tatgctgttt tg                   42

SEQ ID NO: 148           moltype = RNA  length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
```

```
SEQUENCE: 148
cagggctctt gaagatctcc gttttagagc tatgctgttt tg                    42

SEQ ID NO: 149         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 149
cagggctctt gaagatctcc gttttagagc tatgctgttt tg                    42

SEQ ID NO: 150         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 150
cagggctctt gaagatctcc gttttagagc tatgctgttt tg                    42

SEQ ID NO: 151         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 151
cagggctctt gaagatctcc gttttagagc tatgctgttt tg                    42

SEQ ID NO: 152         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 152
cagggctctt gaagatctcc gttttagagc tatgctgttt tg                    42

SEQ ID NO: 153         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 153
cagggctctt gaagatctcc gttttagagc tatgctgttt tg                    42

SEQ ID NO: 154         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 154
cagggctctt gaagatctcc gttttagagc tatgctgttt tg                    42

SEQ ID NO: 155         moltype = RNA  length = 42
FEATURE                Location/Qualifiers
misc_feature           1..42
                       note = source = /note="Description of Artificial Sequence:
                        Synthetic oligonucleotide"
source                 1..42
                       mol_type = other RNA
                       organism = synthetic construct
SEQUENCE: 155
cagggctctt gaagatctcc gttttagagc tatgctgttt tg                    42
```

```
SEQ ID NO: 156          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 156
cagggctctt gaagatctcc gttttagagc tatgctgttt tg                    42

SEQ ID NO: 157          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 157
cagggctctt gaagatctcc gttttagagc tatgctgttt tg                    42

SEQ ID NO: 158          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 158
cagggctctt gaagatctcc gttttagagc tatgctgttt tg                    42

SEQ ID NO: 159          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 159
cagggctctt gaagatctcc ggcgcagagc tatgctgttt tg                    42

SEQ ID NO: 160          moltype = RNA  length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 160
cagggctctt gaagatctcc gttttagagc tatgctggcg cg                    42

SEQ ID NO: 161          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 161
gttttagagc tatgctgttt tg                                          22

SEQ ID NO: 162          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 162
gttttagagc tatgctgttt tg                                          22

SEQ ID NO: 163          moltype = RNA  length = 22
```

-continued

```
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 163
gttttagagc tatgctgttt tg                                            22

SEQ ID NO: 164       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 164
gttttagagc tatgctgttt tg                                            22

SEQ ID NO: 165       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 165
gttttagagc tatgctgttt tg                                            22

SEQ ID NO: 166       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 166
gttttagagc tatgctgttt tg                                            22

SEQ ID NO: 167       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 167
gttttagagc tatgctgttt tg                                            22

SEQ ID NO: 168       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 168
gttttagagc tatgctgttt tg                                            22

SEQ ID NO: 169       moltype = RNA  length = 22
FEATURE              Location/Qualifiers
misc_feature         1..22
                     note = source = /note="Description of Artificial Sequence:
                      Synthetic oligonucleotide"
source               1..22
                     mol_type = other RNA
                     organism = synthetic construct
SEQUENCE: 169
gttttagagc tatgctgttt tg                                            22

SEQ ID NO: 170       moltype = RNA  length = 22
FEATURE              Location/Qualifiers
misc_feature         1..22
```

-continued

```
                          note = source = /note="Description of Artificial Sequence:
                           Synthetic oligonucleotide"
source                    1..22
                          mol_type = other RNA
                          organism = synthetic construct
SEQUENCE: 170
gttttagagc tatgctgttt tg                                            22

SEQ ID NO: 171            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 171
gttttagagc tatgctgttt tg                                            22

SEQ ID NO: 172            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 172
gttttagagc tatgctgttt tg                                            22

SEQ ID NO: 173            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 173
gttttagagc tatgctgttt tg                                            22

SEQ ID NO: 174            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 174
gttttagagc tatgctgttt tg                                            22

SEQ ID NO: 175            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 175
gttttagagc tatgctgttt tg                                            22

SEQ ID NO: 176            moltype = RNA  length = 22
FEATURE                   Location/Qualifiers
misc_feature              1..22
                          note = source = /note="Description of Artificial Sequence:
                           Synthetic oligonucleotide"
source                    1..22
                          mol_type = other RNA
                          organism = synthetic construct
SEQUENCE: 176
gttttagagc tatgctgttt tg                                            22

SEQ ID NO: 177            moltype = RNA  length = 22
FEATURE                   Location/Qualifiers
misc_feature              1..22
                          note = source = /note="Description of Artificial Sequence:
                           Synthetic oligonucleotide"
```

```
source                  1..22
                        mol_type = other RNA
                        organism = synthetic construct
SEQUENCE: 177
gttttagagc tatgctgttt tg                                            22

SEQ ID NO: 178          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 178
gttttagagc tatgctgttt tg                                            22

SEQ ID NO: 179          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 179
gttttagagc tatgctgttt tg                                            22

SEQ ID NO: 180          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 180
gttttagagc tatgctgttt tg                                            22

SEQ ID NO: 181          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 181
gttttagagc tatgctgttt tg                                            22

SEQ ID NO: 182          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 182
gttttagagc tatgctgttt tg                                            22

SEQ ID NO: 183          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
                        organism = synthetic construct
SEQUENCE: 183
gttttagagc tatgctgttt tg                                            22

SEQ ID NO: 184          moltype = RNA  length = 22
FEATURE                 Location/Qualifiers
misc_feature            1..22
                        note = source = /note="Description of Artificial Sequence:
                         Synthetic oligonucleotide"
source                  1..22
                        mol_type = other RNA
```

-continued

```
                         organism = synthetic construct
SEQUENCE: 184
gttttagagc tatgctgttt tg                                           22

SEQ ID NO: 185           moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 185
gttttagagc tatgctgttt tg                                           22

SEQ ID NO: 186           moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 186
gttttagagc tatgctgttt tg                                           22

SEQ ID NO: 187           moltype = RNA  length = 22
FEATURE                  Location/Qualifiers
misc_feature             1..22
                         note = source = /note="Description of Artificial Sequence:
                          Synthetic oligonucleotide"
source                   1..22
                         mol_type = other RNA
                         organism = synthetic construct
SEQUENCE: 187
gttttagagc tatgctgttt tg                                           22

SEQ ID NO: 188           moltype = RNA  length = 74
FEATURE                  Location/Qualifiers
misc_feature             1..74
                         note = source = /note="Description of Artificial Sequence:
                          Synthetic oligonucleotide"
source                   1..74
                         mol_type = other RNA
                         organism = synthetic construct
SEQUENCE: 188
aacagcatag caagttaaaa taaggctagt ccgttatcaa cttgaaaaag tggcaccgag  60
tcggtgcttt tttt                                                    74

SEQ ID NO: 189           moltype = RNA  length = 71
FEATURE                  Location/Qualifiers
misc_feature             1..71
                         note = source = /note="Description of Artificial Sequence:
                          Synthetic oligonucleotide"
source                   1..71
                         mol_type = other RNA
                         organism = synthetic construct
SEQUENCE: 189
aacagcatag caagttaaaa taaggctagt ccgttatcaa cttgaaaaag tggcaccgag  60
tcggtgcttt t                                                       71

SEQ ID NO: 190           moltype = RNA  length = 71
FEATURE                  Location/Qualifiers
misc_feature             1..71
                         note = source = /note="Description of Artificial Sequence:
                          Synthetic oligonucleotide"
source                   1..71
                         mol_type = other RNA
                         organism = synthetic construct
SEQUENCE: 190
aacagcatag caagttaaaa taaggctagt ccgttatcaa cttgaaaaag tggcaccgag  60
tcggtgcttt t                                                       71

SEQ ID NO: 191           moltype = RNA  length = 71
FEATURE                  Location/Qualifiers
misc_feature             1..71
                         note = source = /note="Description of Artificial Sequence:
                          Synthetic oligonucleotide"
source                   1..71
```

```
                        mol_type = other RNA
                        organism = synthetic construct
SEQUENCE: 191
aacagcatag caagttaaaa taaggctagt ccgttatcaa cttgaaaaag tggcaccgag  60
tcggtgcttt t                                                        71

SEQ ID NO: 192          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 192
aacagcatag caagttaaaa taaggctagt ccgttatcaa cttgaaaaag tggcaccgag  60
tcggtgcttt t                                                        71

SEQ ID NO: 193          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 193
aacagcatag caagttaaaa taaggctagt ccgttatcaa cttgaaaaag tggcaccgag  60
tcggtgcttt t                                                        71

SEQ ID NO: 194          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 194
aacagcatag caagttaaaa taaggctagt ccgttatcaa cttgaaaaag tggcaccgag  60
tcggtgcttt t                                                        71

SEQ ID NO: 195          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 195
aacagcatag caagttaaaa taaggctagt ccgttatcaa cttgaaaaag tggcaccgag  60
tcggtgcttt t                                                        71

SEQ ID NO: 196          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 196
aacagcatag caagttaaaa taaggctagt ccgttatcaa cttgaaaaag tggcaccgag  60
tcggtgcttt t                                                        71

SEQ ID NO: 197          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 197
aacagcatag caagttaaaa taaggctagt ccgttatcaa cttgaaaaag tggcaccgag  60
tcggtgcttt t                                                        71

SEQ ID NO: 198          moltype = RNA  length = 71
```

```
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 198
aacagcatag caagttaaaa taaggctagt ccgttatcaa cttgaaaaag tggcaccgag  60
tcggtgcttt t                                                       71

SEQ ID NO: 199         moltype = RNA  length = 71
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 199
aacagcatag caagttaaaa taaggctagt ccgttatcaa cttgaaaaag tggcaccgag  60
tcggtgcttt t                                                       71

SEQ ID NO: 200         moltype = RNA  length = 71
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 200
aacagcatag caagttaaaa taaggctagt ccgttatcaa cttgaaaaag tggcaccgag  60
tcggtgcttt t                                                       71

SEQ ID NO: 201         moltype = RNA  length = 71
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 201
aacagcatag caagttgcgc taaggctagt ccgttatcaa cttgaaaaag tggcaccgag  60
tcggtgcttt t                                                       71

SEQ ID NO: 202         moltype = RNA  length = 71
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 202
gccagcatag caagttaaaa taaggctagt ccgttatcaa cttgaaaaag tggcaccgag  60
tcggtgcttt t                                                       71

SEQ ID NO: 203         moltype = RNA  length = 71
FEATURE                Location/Qualifiers
misc_feature           1..71
                       note = source = /note="Description of Artificial Sequence:
                        Synthetic oligonucleotide"
source                 1..71
                       mol_type = other RNA
                       organism = synthetic construct
SEQUENCE: 203
gccagcatag caagttgcgc taaggctagt ccgttatcaa cttgaaaaag tggcaccgag  60
tcggtgcttt t                                                       71

SEQ ID NO: 204         moltype = RNA  length = 74
FEATURE                Location/Qualifiers
misc_feature           1..74
                       note = source = /note="Description of Artificial Sequence:
                        Synthetic oligonucleotide"
source                 1..74
                       mol_type = other RNA
                       organism = synthetic construct
```

```
SEQUENCE: 204
aacagcatag caagttaaaa taaggctagt ccgttatcaa cttgaaaaag tggcaccgag  60
tcggtgcttt tttt                                                    74

SEQ ID NO: 205          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 205
aacagcatag caagttaaaa taaggctagt ccgttatcaa cttgaaaaag tggcaccgag  60
tcggtgcttt t                                                       71

SEQ ID NO: 206          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 206
aacagcatag caagttaaaa taaggctagt ccgttatcaa cttgaaaaag tggcaccgag  60
tcggtgcttt t                                                       71

SEQ ID NO: 207          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 207
aacagcatag caagttaaaa taaggctagt ccgttatcaa cttgaaaaag tggcaccgag  60
tcggtgcttt t                                                       71

SEQ ID NO: 208          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 208
aacagcatag caagttaaaa taaggctagt ccgttatcaa cttgaaaaag tggcaccgag  60
tcggtgcttt t                                                       71

SEQ ID NO: 209          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 209
aacagcatag caagttaaaa taaggctagt ccgttatcaa cttgaaaaag tggcaccgag  60
tcggtgcttt t                                                       71

SEQ ID NO: 210          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 210
aacagcatag caagttaaaa taaggctagt ccgttatcaa cttgaaaaag tggcaccgag  60
tcggtgcttt t                                                       71

SEQ ID NO: 211          moltype = RNA  length = 71
FEATURE                 Location/Qualifiers
misc_feature            1..71
```

-continued

```
                        note = source = /note="Description of Artificial Sequence:
                         Synthetic oligonucleotide"
source                  1..71
                        mol_type = other RNA
                        organism = synthetic construct
SEQUENCE: 211
aacagcatag caagttaaaa taaggctagt ccgttatcaa cttgaaaaag tggcaccgag  60
tcggtgcttt t                                                       71

SEQ ID NO: 212          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 212
aacagcatag caagttaaaa taaggctagt ccgttatcaa cttgaaaaag tggcaccgag  60
tcggtgcttt t                                                       71

SEQ ID NO: 213          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 213
aacagcatag caagttaaaa taaggctagt ccgttatcaa cttgaaaaag tggcaccgag  60
tcggtgcttt t                                                       71

SEQ ID NO: 214          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 214
aacagcatag caagttaaaa taaggctagt ccgttatcaa cttgaaaaag tggcaccgag  60
tcggtgcttt t                                                       71

SEQ ID NO: 215          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 215
aacagcatag caagttaaaa taaggctagt ccgttatcaa cttgaaaaag tggcaccgag  60
tcggtgcttt t                                                       71

SEQ ID NO: 216          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 216
aacagcatag caagttaaaa taaggctagt ccgttatcaa cttgaaaaag tggcaccgag  60
tcggtgcttt t                                                       71

SEQ ID NO: 217          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 217
aacagcatag caagttaaaa taaggctagt ccgttatcaa cttgaaaaag tggcaccgag  60
```

```
tcggtgcttt t                                                        71

SEQ ID NO: 218          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 218
aacagcatag caagttaaaa taaggctagt ccgttatcaa cttgaaaaag tggcaccgag  60
tcggtgcttt t                                                        71

SEQ ID NO: 219          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 219
aacagcatag caagttaaaa taaggctagt ccgttatcaa cttgaaaaag tggcaccgag  60
tcggtgcttt t                                                        71

SEQ ID NO: 220          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 220
aacagcatag caagttaaaa taaggctagt ccgttatcaa cttgaaaaag tggcaccgag  60
tcggtgcttt t                                                        71

SEQ ID NO: 221          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 221
aacagcatag caagttaaaa taaggctagt ccgttatcaa cttgaaaaag tggcaccgag  60
tcggtgcttt t                                                        71

SEQ ID NO: 222          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 222
aacagcatag caagttaaaa taaggctagt ccgttatcaa cttgaaaaag tggcaccgag  60
tcggtgcttt t                                                        71

SEQ ID NO: 223          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 223
aacagcatag caagttgaga taaggctagt ccgttatcaa cttgaaaaag tggcaccgag  60
tcggtgcttt t                                                        71

SEQ ID NO: 224          moltype = RNA  length = 71
FEATURE                 Location/Qualifiers
misc_feature            1..71
                        note = source = /note="Description of Artificial Sequence:
                         Synthetic oligonucleotide"
```

```
source                  1..71
                        mol_type = other RNA
                        organism = synthetic construct
SEQUENCE: 224
aacagcatag caagttaaag taaggctagt ccgttatcaa cttgaaaaag tggcaccgag  60
tcggtgcttt t                                                       71

SEQ ID NO: 225          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 225
aacagcatag caagttaaga taaggctagt ccgttatcaa cttgaaaaag tggcaccgag  60
tcggtgcttt t                                                       71

SEQ ID NO: 226          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 226
aacagcatag caagttagaa taaggctagt ccgttatcaa cttgaaaaag tggcaccgag  60
tcggtgcttt t                                                       71

SEQ ID NO: 227          moltype = RNA  length = 71
FEATURE                 Location/Qualifiers
misc_feature            1..71
                        note = source = /note="Description of Artificial Sequence:
                         Synthetic oligonucleotide"
source                  1..71
                        mol_type = other RNA
                        organism = synthetic construct
SEQUENCE: 227
aacagcatag caagttgaaa taaggctagt ccgttatcaa cttgaaaaag tggcaccgag  60
tcggtgcttt t                                                       71

SEQ ID NO: 228          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 228
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 229          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 229
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 230          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 230
ccagtccagc gaggcaaagg gttttagagc tagaaatagc aagttaaaat aaggctagtc  60
cgttatcaac ttgaaaaagt ggcaccgagt cggtgctttt                        100
```

```
SEQ ID NO: 231          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 231
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 232          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 232
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 233          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 233
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 234          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 234
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 235          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 235
gttttagagc tagaaatagc aagttaaaat aaggctagtc cgttatcaac ttgaaaaagt  60
ggcaccgagt cggtgctttt                                              80

SEQ ID NO: 236          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 236
gttttagagc tagaaatagc aagttaaaat aaggctagtc cgttatcaac ttgaaaaagt  60
ggcaccgagt cggtgctttt                                              80

SEQ ID NO: 237          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
```

```
                        organism = synthetic construct
SEQUENCE: 237
gttttagagc tagaaatagc aagttaaaat aaggctagtc cgttatcaac ttgaaaaagt  60
ggcaccgagt cggtgctttt                                              80

SEQ ID NO: 238          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 238
gttttagagc tagaaatagc aagttaaaat aaggctagtc cgttatcaac ttgaaaaagt  60
ggcaccgagt cggtgctttt                                              80

SEQ ID NO: 239          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 239
gttttagagc tagaaatagc aagttaaaat aaggctagtc cgttatcaac ttgaaaaagt  60
ggcaccgagt cggtgctttt                                              80

SEQ ID NO: 240          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 240
gttttagagc tagaaatagc aagttaaaat aaggctagtc cgttatcaac ttgaaaaagt  60
ggcaccgagt cggtgctttt                                              80

SEQ ID NO: 241          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 241
ttacagccac gtctacagca gttttagagc tagaaatagc aagttaaaat aaggctagtc  60
cgttatcaac ttgaaaaagt ggcaccgagt cggtgctttt                        100

SEQ ID NO: 242          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 242
ttacagccac gtctacagca gttttagagc tagaaatagc aagttaaaat aaggctagtc  60
cgttatcaac ttgaaaaagt ggcaccgagt cggtgctttt                        100

SEQ ID NO: 243          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 243
ttacagccac gtctacagca gttttagagc tagaaatagc aagttaaaat aaggctagtc  60
cgttatcaac ttgaaaaagt ggcaccgagt cggtgctttt                        100

SEQ ID NO: 244          moltype = RNA  length = 100
FEATURE                 Location/Qualifiers
```

-continued

```
misc_feature            1..100
                        note = source = /note="Description of Artificial Sequence:
                         Synthetic polynucleotide"
source                  1..100
                        mol_type = other RNA
                        organism = synthetic construct
SEQUENCE: 244
ttacagccac gtctacagca gttttagagc tagaaatagc aagttaaaat aaggctagtc  60
cgttatcaac ttgaaaaagt ggcaccgagt cggtgctttt                        100

SEQ ID NO: 245          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 245
ttacagccac gtctacagca gttttagagc tagaaatagc aagttaaaat aaggctagtc  60
cgttatcaac ttgaaaaagt ggcaccgagt cggtgctttt                        100

SEQ ID NO: 246          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 246
ttacagccac gtctacagca gttttagagc tagaaatagc aagttaaaat aaggctagtc  60
cgttatcaac ttgaaaaagt ggcaccgagt cggtgctttt                        100

SEQ ID NO: 247          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 247
ttacagccac gtctacagca gttttagagc tagaaatagc aagttaaaat aaggctagtc  60
cgttatcaac ttgaaaaagt ggcaccgagt cggtgctttt                        100

SEQ ID NO: 248          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 248
ttacagccac gtctacagca gttttagagc tagaaatagc aagttaaaat aaggctagtc  60
cgttatcaac ttgaaaaagt ggcaccgagt cggtgctttt                        100

SEQ ID NO: 249          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 249
ttacagccac gtctacagca gttttagagc tagaaatagc aagttaaaat aaggctagtc  60
cgttatcaac ttgaaaaagt ggcaccgagt cggtgctttt                        100

SEQ ID NO: 250          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 250
```

```
ttacagccac gtctacagca gttttagagc tagaaatagc aagttaaaat aaggctagtc  60
cgttatcaac ttgaaaaagt ggcaccgagt cggtgctttt                        100

SEQ ID NO: 251         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 251
ttacagccac gtctacagca gttttagagc tagaaatagc aagttaaaat aaggctagtc  60
cgttatcaac ttgaaaaagt ggcaccgagt cggtgctttt                        100

SEQ ID NO: 252         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 252
ttacagccac gtctacagca gttttagagc tagaaatagc aagttaaaat aaggctagtc  60
cgttatcaac ttgaaaaagt ggcaccgagt cggtgctttt                        100

SEQ ID NO: 253         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 253
ttacagccac gtctacagca gttttagagc tagaaatagc aagttaaaat aaggctagtc  60
cgttatcaac ttgaaaaagt ggcaccgagt cggtgctttt                        100

SEQ ID NO: 254         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 254
ttacagccac gtctacagca gttttagagc tagaaatagc aagttaaaat aaggctagtc  60
cgttatcaac ttgaaaaagt ggcaccgagt cggtgctttt                        100

SEQ ID NO: 255         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 255
ttacagccac gtctacagca gttttagagc tagaaatagc aagttaaaat aaggctagtc  60
cgttatcaac ttgaaaaagt ggcaccgagt cggtgctttt                        100

SEQ ID NO: 256         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 256
ttacagccac gtctacagca gttttagagc tagaaatagc aagttaaaat aaggctagtc  60
cgttatcaac ttgaaaaagt ggcaccgagt cggtgctttt                        100

SEQ ID NO: 257         moltype = RNA  length = 100
FEATURE                Location/Qualifiers
misc_feature           1..100
                       note = source = /note="Description of Artificial Sequence:
```

```
                         Synthetic polynucleotide"
source                  1..100
                        mol_type = other RNA
                        organism = synthetic construct
SEQUENCE: 257
ttacagccac gtctacagca gttttagagc tagaaatagc aagttaaaat aaggctagtc  60
cgttatcaac ttgaaaaagt ggcaccgagt cggtgctttt                        100

SEQ ID NO: 258          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 258
ttacagccac gtctacagca gttttagagc tagaaatagc aagttaaaat aaggctagtc  60
cgttatcaac ttgaaaaagt ggcaccgagt cggtgctttt                        100

SEQ ID NO: 259          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 259
ttacagccac gtctacagca gttttagagc tagaaatagc aagttaaaat aaggctagtc  60
cgttatcaac ttgaaaaagt ggcaccgagt cggtgctttt                        100

SEQ ID NO: 260          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 260
ttacagccac gtctacagca gttttagagc tagaaatagc aagttaaaat aaggctagtc  60
cgttatcaac ttgaaaaagt ggcaccgagt cggtgctttt                        100

SEQ ID NO: 261          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 261
ttacagccac gtctacagca gttttagagc tagaaatagc aagttaaaat aaggctagtc  60
cgttatcaac ttgaaaaagt ggcaccgagt cggtgctttt                        100

SEQ ID NO: 262          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 262
ttacagccac gtctacagca gttttagagc tagaaatagc aagttaaaat aaggctagtc  60
cgttatcaac ttgaaaaagt ggcaccgagt cggtgctttt                        100

SEQ ID NO: 263          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 263
ttacagccac gtctacagca gttttagagc tagaaatagc aagttaaaat aaggctagtc  60
cgttatcaac ttgaaaaagt ggcaccgagt cggtgctttt                        100
```

```
SEQ ID NO: 264          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 264
ttacagccac gtctacagca gttttagagc tagaaatagc aagttaaaat aaggctagtc  60
cgttatcaac ttgaaaaagt ggcaccgagt cggtgctttt                        100

SEQ ID NO: 265          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 265
gttttagagc tagaaatagc aagttaaaat aaggctagtc cgttatcaac ttgaaaaagt  60
ggcaccgagt cggtgctttt                                              80

SEQ ID NO: 266          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 266
gttttagagc tagaaatagc aagttaaaat aaggctagtc cgttatcaac ttgaaaaagt  60
ggcaccgagt cggtgctttt                                              80

SEQ ID NO: 267          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 267
gttttagagc tagaaatagc aagttaaaat aaggctagtc cgttatcaac ttgaaaaagt  60
ggcaccgagt cggtgctttt                                              80

SEQ ID NO: 268          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 268
gttttagagc tagaaatagc aagttaaaat aaggctagtc cgttatcaac ttgaaaaagt  60
ggcaccgagt cggtgctttt                                              80

SEQ ID NO: 269          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 269
gttttagagc tagaaatagc aagttaaaat aaggctagtc cgttatcaac ttgaaaaagt  60
ggcaccgagt cggtgctttt                                              80

SEQ ID NO: 270          moltype = RNA  length = 80
FEATURE                 Location/Qualifiers
misc_feature            1..80
                        note = source = /note="Description of Artificial Sequence:
                         Synthetic oligonucleotide"
source                  1..80
```

-continued

```
                        mol_type = other RNA
                        organism = synthetic construct
SEQUENCE: 270
gttttagagc tagaaatagc aagttaaaat aaggctagtc cgttatcaac ttgaaaaagt  60
ggcaccgagt cggtgctttt                                              80

SEQ ID NO: 271          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 271
gttttagagc tagaaatagc aagttaaaat aaggctagtc cgttatcaac ttgaaaaagt  60
ggcaccgagt cggtgctttt                                              80

SEQ ID NO: 272          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 272
gttttagagc tagaaatagc aagttaaaat aaggctagtc cgttatcaac ttgaaaaagt  60
ggcaccgagt cggtgctttt                                              80

SEQ ID NO: 273          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 273
gttttagagc tagaaatagc aagttaaaat aaggctagtc cgttatcaac ttgaaaaagt  60
ggcaccgagt cggtgctttt                                              80

SEQ ID NO: 274          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 274
gttttagagc tagaaatagc aagttaaaat aaggctagtc cgttatcaac ttgaaaaagt  60
ggcaccgagt cggtgctttt                                              80

SEQ ID NO: 275          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 275
gttttagagc tagaaatagc aagttaaaat aaggctagtc cgttatcaac ttgaaaaagt  60
ggcaccgagt cggtgctttt                                              80

SEQ ID NO: 276          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 276
gttttagagc tagaaatagc aagttaaaat aaggctagtc cgttatcaac ttgaaaaagt  60
ggcaccgagt cggtgctttt                                              80

SEQ ID NO: 277          moltype = RNA  length = 80
```

-continued

```
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 277
gttttagagc tagaaatagc aagttaaaat aaggctagtc cgttatcaac ttgaaaaagt  60
ggcaccgagt cggtgctttt                                              80

SEQ ID NO: 278          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 278
gttttagagc tagaaatagc aagttaaaat aaggctagtc cgttatcaac ttgaaaaagt  60
ggcaccgagt cggtgctttt                                              80

SEQ ID NO: 279          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 279
gttttagagc tagaaatagc aagttaaaat aaggctagtc cgttatcaac ttgaaaaagt  60
ggcaccgagt cggtgctttt                                              80

SEQ ID NO: 280          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 280
gttttagagc tagaaatagc aagttaaaat aaggctagtc cgttatcaac ttgaaaaagt  60
ggcaccgagt cggtgctttt                                              80

SEQ ID NO: 281          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 281
gttttagagc tagaaatagc aagttaaaat aaggctagtc cgttatcaac ttgaaaaagt  60
ggcaccgagt cggtgctttt                                              80

SEQ ID NO: 282          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 282
gttttagagc tagaaatagc aagttaaaat aaggctagtc cgttatcaac ttgaaaaagt  60
ggcaccgagt cggtgctttt                                              80

SEQ ID NO: 283          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
```

-continued

```
SEQUENCE: 283
gttttagagc tagaaatagc aagttaaaat aaggctagtc cgttatcaac ttgaaaaagt  60
ggcaccgagt cggtgctttt                                              80

SEQ ID NO: 284         moltype = RNA  length = 80
FEATURE                Location/Qualifiers
misc_feature           1..80
                       note = source = /note="Description of Artificial Sequence:
                        Synthetic oligonucleotide"
source                 1..80
                       mol_type = other RNA
                       organism = synthetic construct
SEQUENCE: 284
gttttagagc tagaaatagc aagttaaaat aaggctagtc cgttatcaac ttgaaaaagt  60
ggcaccgagt cggtgctttt                                              80

SEQ ID NO: 285         moltype = RNA  length = 80
FEATURE                Location/Qualifiers
misc_feature           1..80
                       note = source = /note="Description of Artificial Sequence:
                        Synthetic oligonucleotide"
source                 1..80
                       mol_type = other RNA
                       organism = synthetic construct
SEQUENCE: 285
gttttagagc tagaaatagc aagttaaaat aaggctagtc cgttatcaac ttgaaaaagt  60
ggcaccgagt cggtgctttt                                              80

SEQ ID NO: 286         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 286
cagggctctt gaagatctcc gttttagagc tagaaatagc aagttaaaat aaggctagtc  60
cgttatcaac ttgaaaaagt ggcaccgagt cggtgctttt                        100

SEQ ID NO: 287         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 287
cagggctctt gaagatctcc gttttagagc tagaaatagc aagttaaaat aaggctagtc  60
cgttatcaac ttgaaaaagt ggcaccgagt cggtgctttt                        100

SEQ ID NO: 288         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 288
cagggctctt gaagatctcc gttttagagc tagaaatagc aagttaaaat aaggctagtc  60
cgttatcaac ttgaaaaagt ggcaccgagt cggtgctttt                        100

SEQ ID NO: 289         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 289
cagggctctt gaagatctcc gttttagagc tagaaatagc aagttaaaat aaggctagtc  60
cgttatcaac ttgaaaaagt ggcaccgagt cggtgctttt                        100

SEQ ID NO: 290         moltype = RNA  length = 100
FEATURE                Location/Qualifiers
misc_feature           1..100
```

```
                        note = source = /note="Description of Artificial Sequence:
                         Synthetic polynucleotide"
source                  1..100
                        mol_type = other RNA
                        organism = synthetic construct
SEQUENCE: 290
cagggctctt gaagatctcc gttttagagc tagaaatagc aagttaaaat aaggctagtc  60
cgttatcaac ttgaaaaagt ggcaccgagt cggtgctttt                        100

SEQ ID NO: 291          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 291
cagggctctt gaagatctcc gttttagagc tagaaatagc aagttaaaat aaggctagtc  60
cgttatcaac ttgaaaaagt ggcaccgagt cggtgctttt                        100

SEQ ID NO: 292          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 292
cagggctctt gaagatctcc gttttagagc tagaaatagc aagttaaaat aaggctagtc  60
cgttatcaac ttgaaaaagt ggcaccgagt cggtgctttt                        100

SEQ ID NO: 293          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 293
cagggctctt gaagatctcc gttttagagc tagaaatagc aagttaaaat aaggctagtc  60
cgttatcaac ttgaaaaagt ggcaccgagt cggtgctttt                        100

SEQ ID NO: 294          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 294
cagggctctt gaagatctcc gttttagagc tagaaatagc aagttaaaat aaggctagtc  60
cgttatcaac ttgaaaaagt ggcaccgagt cggtgctttt                        100

SEQ ID NO: 295          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 295
cagggctctt gaagatctcc gttttagagc tagaaatagc aagttaaaat aaggctagtc  60
cgttatcaac ttgaaaaagt ggcaccgagt cggtgctttt                        100

SEQ ID NO: 296          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 296
cagggctctt gaagatctcc gttttagagc tagaaatagc aagttaaaat aaggctagtc  60
```

-continued

```
cgttatcaac ttgaaaaagt ggcaccgagt cggtgctttt                          100

SEQ ID NO: 297         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 297
cagggctctt gaagatctcc gttttagagc tagaaatagc aagttaaaat aaggctagtc  60
cgttatcaac ttgaaaaagt ggcaccgagt cggtgctttt                          100

SEQ ID NO: 298         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 298
cagggctctt gaagatctcc gttttagagc tagaaatagc aagttaaaat aaggctagtc  60
cgttatcaac ttgaaaaagt ggcaccgagt cggtgctttt                          100

SEQ ID NO: 299         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 299
cagggctctt gaagatctcc gttttagagc tagaaatagc aagttaaaat aaggctagtc  60
cgttatcaac ttgaaaaagt ggcaccgagt cggtgctttt                          100

SEQ ID NO: 300         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 300
cagggctctt gaagatctcc gttttagagc tagaaatagc aagttaaaat aaggctagtc  60
cgttatcaac ttgaaaaagt ggcaccgagt cggtgctttt                          100

SEQ ID NO: 301         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 301
cagggctctt gaagatctcc gttttagagc tagaaatagc aagttaaaat aaggctagtc  60
cgttatcaac ttgaaaaagt ggcaccgagt cggtgctttt                          100

SEQ ID NO: 302         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 302
cagggctctt gaagatctcc gttttagagc tagaaatagc aagttaaaat aaggctagtc  60
cgttatcaac ttgaaaaagt ggcaccgagt cggtgctttt                          100

SEQ ID NO: 303         moltype = RNA  length = 100
FEATURE                Location/Qualifiers
misc_feature           1..100
                       note = source = /note="Description of Artificial Sequence:
                        Synthetic polynucleotide"
```

```
source                  1..100
                        mol_type = other RNA
                        organism = synthetic construct
SEQUENCE: 303
cagggctctt gaagatctcc gttttagagc tagaaatagc aagttaaaat aaggctagtc  60
cgttatcaac ttgaaaaagt ggcaccgagt cggtgctttt                        100

SEQ ID NO: 304          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 304
cagggctctt gaagatctcc gttttagagc tagaaatagc aagttaaaat aaggctagtc  60
cgttatcaac ttgaaaaagt ggcaccgagt cggtgctttt                        100

SEQ ID NO: 305          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 305
cagggctctt gaagatctcc gttttagagc tagaaatagc aagttaaaat aaggctagtc  60
cgttatcaac ttgaaaaagt ggcaccgagt cggtgctttt                        100

SEQ ID NO: 306          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 306
cagggctctt gaagatctcc gttttagagc tagaaatagc aagttaaaat aaggctagtc  60
cgttatcaac ttgaaaaagt ggcaccgagt cggtgctttt                        100

SEQ ID NO: 307          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 307
cagggctctt gaagatctcc gttttagagc tagaaatagc aagttaaaat aaggctagtc  60
cgttatcaac ttgaaaaagt ggcaccgagt cggtgctttt                        100

SEQ ID NO: 308          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 308
cagggctctt gaagatctcc gttttagagc tagaaatagc aagttaaaat aaggctagtc  60
cgttatcaac ttgaaaaagt ggcaccgagt cggtgctttt                        100

SEQ ID NO: 309          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 309
gttttagagc tagaaatagc aagttaaaat aaggctagtc cgttatcaac ttgaaaaagt  60
ggcaccgagt cggtgctttt                                              80
```

```
SEQ ID NO: 310          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 310
gttttagagc tagaaatagc aagttaaaat aaggctagtc cgttatcaac ttgaaaaagt  60
ggcaccgagt cggtgctttt                                              80

SEQ ID NO: 311          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 311
gttttagagc tagaaatagc aagttaaaat aaggctagtc cgttatcaac ttgaaaaagt  60
ggcaccgagt cggtgctttt                                              80

SEQ ID NO: 312          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 312
gttttagagc tagaaatagc aagttaaaat aaggctagtc cgttatcaac ttgaaaaagt  60
ggcaccgagt cggtgctttt                                              80

SEQ ID NO: 313          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 313
gttttagagc tagaaatagc aagttaaaat aaggctagtc cgttatcaac ttgaaaaagt  60
ggcaccgagt cggtgctttt                                              80

SEQ ID NO: 314          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 314
gttttagagc tagaaatagc aagttaaaat aaggctagtc cgttatcaac ttgaaaaagt  60
ggcaccgagt cggtgctttt                                              80

SEQ ID NO: 315          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 315
gttttagagc tagaaatagc aagttaaaat aaggctagtc cgttatcaac ttgaaaaagt  60
ggcaccgagt cggtgctttt                                              80

SEQ ID NO: 316          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
```

```
                         organism = synthetic construct
SEQUENCE: 316
gttttagagc tagaaatagc aagttaaaat aaggctagtc cgttatcaac ttgaaaaagt  60
ggcaccgagt cggtgctttt                                               80

SEQ ID NO: 317           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 317
gttttagagc tagaaatagc aagttaaaat aaggctagtc cgttatcaac ttgaaaaagt  60
ggcaccgagt cggtgctttt                                               80

SEQ ID NO: 318           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 318
gttttagagc tagaaatagc aagttaaaat aaggctagtc cgttatcaac ttgaaaaagt  60
ggcaccgagt cggtgctttt                                               80

SEQ ID NO: 319           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 319
gttttagagc tagaaatagc aagttaaaat aaggctagtc cgttatcaac ttgaaaaagt  60
ggcaccgagt cggtgctttt                                               80

SEQ ID NO: 320           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 320
gttttagagc tagaaatagc aagttaaaat aaggctagtc cgttatcaac ttgaaaaagt  60
ggcaccgagt cggtgctttt                                               80

SEQ ID NO: 321           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 321
gttttagagc tagaaatagc aagttaaaat aaggctagtc cgttatcaac ttgaaaaagt  60
ggcaccgagt cggtgctttt                                               80

SEQ ID NO: 322           moltype = RNA  length = 80
FEATURE                  Location/Qualifiers
misc_feature             1..80
                         note = source = /note="Description of Artificial Sequence:
                          Synthetic oligonucleotide"
source                   1..80
                         mol_type = other RNA
                         organism = synthetic construct
SEQUENCE: 322
gttttagagc tagaaatagc aagttaaaat aaggctagtc cgttatcaac ttgaaaaagt  60
ggcaccgagt cggtgctttt                                               80

SEQ ID NO: 323           moltype = RNA  length = 80
FEATURE                  Location/Qualifiers
```

```
misc_feature            1..80
                        note = source = /note="Description of Artificial Sequence:
                         Synthetic oligonucleotide"
source                  1..80
                        mol_type = other RNA
                        organism = synthetic construct
SEQUENCE: 323
gttttagagc tagaaatagc aagttaaaat aaggctagtc cgttatcaac ttgaaaaagt  60
ggcaccgagt cggtgctttt                                              80

SEQ ID NO: 324          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 324
gttttagagc tagaaatagc aagttaaaat aaggctagtc cgttatcaac ttgaaaaagt  60
ggcaccgagt cggtgctttt                                              80

SEQ ID NO: 325          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 325
gttttagagc tagaaatagc aagttaaaat aaggctagtc cgttatcaac ttgaaaaagt  60
ggcaccgagt cggtgctttt                                              80

SEQ ID NO: 326          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 326
gttttagagc tagaaatagc aagttaaaat aaggctagtc cgttatcaac ttgaaaaagt  60
ggcaccgagt cggtgctttt                                              80

SEQ ID NO: 327          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 327
gttttagagc tagaaatagc aagttaaaat aaggctagtc cgttatcaac ttgaaaaagt  60
ggcaccgagt cggtgctttt                                              80

SEQ ID NO: 328          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 328
gttttagagc tagaaatagc aagttaaaat aaggctagtc cgttatcaac ttgaaaaagt  60
ggcaccgagt cggtgctttt                                              80

SEQ ID NO: 329          moltype = RNA  length = 80
FEATURE                 Location/Qualifiers
misc_feature            1..80
                        note = source = /note="Description of Artificial Sequence:
                         Synthetic oligonucleotide"
source                  1..80
                        mol_type = other RNA
                        organism = synthetic construct
SEQUENCE: 329
```

```
gttttagagc tagaaatagc aagttaaaat aaggctagtc cgttatcaac ttgaaaaagt  60
ggcaccgagt cggtgctttt                                              80

SEQ ID NO: 330          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 330
cccatactcc tacagcacca gttttagagc tagaaatagc aagttaaaat aaggctagtc  60
cgttatcaac ttgaaaaagt ggcaccgagt cggtgctttt                        100

SEQ ID NO: 331          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 331
cccatactcc tacagcacca gttttagagc tagaaatagc aagttaaaat aaggctagtc  60
cgttatcaac ttgaaaaagt ggcaccgagt cggtgctttt                        100

SEQ ID NO: 332          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 332
cccatactcc tacagcacca gttttagagc tagaaatagc aagttaaaat aaggctagtc  60
cgttatcaac ttgaaaaagt ggcaccgagt cggtgctttt                        100

SEQ ID NO: 333          moltype = DNA  length = 24
FEATURE                 Location/Qualifiers
misc_feature            1..24
                        note = source = /note="Description of Artificial Sequence:
                         Synthetic primer"
source                  1..24
                        mol_type = other DNA
                        organism = synthetic construct
SEQUENCE: 333
agtcaataat cagaatcagc aggt                                         24

SEQ ID NO: 334          moltype = DNA  length = 24
FEATURE                 Location/Qualifiers
misc_feature            1..24
                        note = source = /note="Description of Artificial Sequence:
                         Synthetic primer"
source                  1..24
                        mol_type = other DNA
                        organism = synthetic construct
SEQUENCE: 334
gttttgttcc agagtctatc accg                                         24

SEQ ID NO: 335          moltype = DNA  length = 24
FEATURE                 Location/Qualifiers
misc_feature            1..24
                        note = source = /note="Description of Artificial Sequence:
                         Synthetic primer"
source                  1..24
                        mol_type = other DNA
                        organism = synthetic construct
SEQUENCE: 335
attaccagct tagcatcctg tgaa                                         24

SEQ ID NO: 336          moltype = DNA  length = 24
FEATURE                 Location/Qualifiers
misc_feature            1..24
                        note = source = /note="Description of Artificial Sequence:
                         Synthetic primer"
source                  1..24
                        mol_type = other DNA
```

```
                         organism = synthetic construct
SEQUENCE: 336
agcacatgag accttctgtt tctc                                        24

SEQ ID NO: 337           moltype = DNA  length = 27
FEATURE                  Location/Qualifiers
misc_feature             1..27
                         note = source = /note="Description of Artificial Sequence:
                          Synthetic primer"
source                   1..27
                         mol_type = other DNA
                         organism = synthetic construct
SEQUENCE: 337
agaaggcact tcttctttat ctaaggt                                     27

SEQ ID NO: 338           moltype = DNA  length = 24
FEATURE                  Location/Qualifiers
misc_feature             1..24
                         note = source = /note="Description of Artificial Sequence:
                          Synthetic primer"
source                   1..24
                         mol_type = other DNA
                         organism = synthetic construct
SEQUENCE: 338
acacgaataa gagcaaatgg gaac                                        24

SEQ ID NO: 339           moltype = DNA  length = 24
FEATURE                  Location/Qualifiers
misc_feature             1..24
                         note = source = /note="Description of Artificial Sequence:
                          Synthetic primer"
source                   1..24
                         mol_type = other DNA
                         organism = synthetic construct
SEQUENCE: 339
acacggttta tagagcaaga acac                                        24

SEQ ID NO: 340           moltype = DNA  length = 24
FEATURE                  Location/Qualifiers
misc_feature             1..24
                         note = source = /note="Description of Artificial Sequence:
                          Synthetic primer"
source                   1..24
                         mol_type = other DNA
                         organism = synthetic construct
SEQUENCE: 340
gacataggtg tgaccctcac aatc                                        24

SEQ ID NO: 341           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 341
ccagtccagc gaggcaaagg gttttagagc tagaaatagc aagttaaaat aaggctagtc  60
cgttatcaac ttgaaaaagt ggcaccgagt cggtgctttt                       100

SEQ ID NO: 342           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 342
ttacagccac gtctacagca gttttagagc tagaaatagc aagttaaaat aaggctagtc  60
cgttatcaac ttgaaaaagt ggcaccgagt cggtgctttt                       100

SEQ ID NO: 343           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
```

-continued

```
                         organism = synthetic construct
SEQUENCE: 343
ttacagccac gtctacagca gttttagagc tagaaatagc aagttaaaat aaggctagtc  60
cgttatcaac ttgaaaaagt ggcaccgagt cggtgctttt                       100

SEQ ID NO: 344           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 344
ttacagccac gtctacagca gttttagagc tagaaatagc aagttaaaat aaggctagtc  60
cgttatcaac ttgaaaaagt ggcaccgagt cggtgctttt                       100

SEQ ID NO: 345           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 345
ttacagccac gtctacagca gttttagagc tagaaatagc aagttaaaat aaggctagtc  60
cgttatcaac ttgaaaaagt ggcaccgagt cggtgctttt                       100

SEQ ID NO: 346           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 346
ttacagccac gtctacagca gttttagagc tagaaatagc aagttaaaat aaggctagtc  60
cgttatcaac ttgaaaaagt ggcaccgagt cggtgctttt                       100

SEQ ID NO: 347           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 347
ttacagccac gtctacagca gttttagagc tagaaatagc aagttaaaat aaggctagtc  60
cgttatcaac ttgaaaaagt ggcaccgagt cggtgctttt                       100

SEQ ID NO: 348           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 348
ttacagccac gtctacagca gttttagagc tagaaatagc aagttaaaat aaggctagtc  60
cgttatcaac ttgaaaaagt ggcaccgagt cggtgctttt                       100

SEQ ID NO: 349           moltype = RNA  length = 100
FEATURE                  Location/Qualifiers
misc_feature             1..100
                         note = source = /note="Description of Artificial Sequence:
                          Synthetic polynucleotide"
source                   1..100
                         mol_type = other RNA
                         organism = synthetic construct
SEQUENCE: 349
ttacagccac gtctacagca gttttagagc tagaaatagc aagttaaaat aaggctagtc  60
cgttatcaac ttgaaaaagt ggcaccgagt cggtgctttt                       100

SEQ ID NO: 350           moltype = RNA  length = 100
FEATURE                  Location/Qualifiers
```

```
misc_feature           1..100
                       note = source = /note="Description of Artificial Sequence:
                        Synthetic polynucleotide"
source                 1..100
                       mol_type = other RNA
                       organism = synthetic construct
SEQUENCE: 350
ttacagccac gtctacagca gttttagagc tagaaatagc aagttaaaat aaggctagtc  60
cgttatcaac ttgaaaaagt ggcaccgagt cggtgctttt                         100

SEQ ID NO: 351         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 351
ttacagccac gtctacagca gttttagagc tagaaatagc aagttaaaat aaggctagtc  60
cgttatcaac ttgaaaaagt ggcaccgagt cggtgctttt                         100

SEQ ID NO: 352         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 352
ttacagccac gtctacagca gttttagagc tagaaatagc aagttaaaat aaggctagtc  60
cgttatcaac ttgaaaaagt ggcaccgagt cggtgctttt                         100

SEQ ID NO: 353         moltype = RNA  length = 100
FEATURE                Location/Qualifiers
misc_feature           1..100
                       note = source = /note="Description of Artificial Sequence:
                        Synthetic polynucleotide"
source                 1..100
                       mol_type = other RNA
                       organism = synthetic construct
SEQUENCE: 353
ttacagccac gtctacagca gttttagagc tagaaatagc aagttaaaat aaggctagtc  60
cgttatcaac ttgaaaaagt ggcaccgagt cggtgctttt                         100

SEQ ID NO: 354         moltype = RNA  length = 100
FEATURE                Location/Qualifiers
variation              1..20
                       note = n = any nucleotide
misc_feature           1..100
                       note = source = /note="Description of Artificial Sequence:
                        Synthetic polynucleotide"
source                 1..100
                       mol_type = other RNA
                       organism = synthetic construct
SEQUENCE: 354
nnnnnnnnnn nnnnnnnnnn gttttagagc tagaaatagc aagttaaaat aaggctagtc  60
cgttatcaac ttgaaaaagt ggcaccgagt cggtgctttt                         100

SEQ ID NO: 355         moltype = RNA  length = 80
FEATURE                Location/Qualifiers
misc_feature           1..80
                       note = source = /note="Description of Artificial Sequence:
                        Synthetic polynucleotide"
source                 1..80
                       mol_type = other RNA
                       organism = synthetic construct
SEQUENCE: 355
gttttagagc tagaaatagc aagttaaaat aaggctagtc cgttatcaac ttgaaaaagt  60
ggcaccgagt cggtgctttt                                               80

SEQ ID NO: 356         moltype = RNA  length = 80
FEATURE                Location/Qualifiers
misc_feature           1..80
                       note = source = /note="Description of Artificial Sequence:
                        Synthetic polynucleotide"
source                 1..80
                       mol_type = other RNA
```

```
                        organism = synthetic construct
SEQUENCE: 356
gttttagagc tagaaatagc aagttaaaat aaggctagtc cgttatcaac ttgaaaaagt  60
ggcaccgagt cggtgctttt                                               80

SEQ ID NO: 357          moltype = RNA  length = 100
FEATURE                 Location/Qualifiers
misc_feature            1..100
                        note = source = /note="Description of Artificial Sequence:
                         Synthetic polynucleotide"
source                  1..100
                        mol_type = other RNA
                        organism = synthetic construct
SEQUENCE: 357
nnnnnnnnnn nnnnnnnnnn gttttagagc tagaaatagc aagttaaaat aaggctagtc  60
cgttatcaac ttgaaaaagt ggcaccgagt cggtgctttt                         100

SEQ ID NO: 358          moltype = RNA  length = 100
FEATURE                 Location/Qualifiers
variation               1..20
                        note = n = any nucleotide
modified_base           1..3
                        mod_base = OTHER
                        note = 2'-O-Me modified nucleotides
modified_base           1..2
                        mod_base = OTHER
                        note = Phosphorothioate linkage
modified_base           2..3
                        mod_base = OTHER
                        note = Phosphorothioate linkage
modified_base           3..4
                        mod_base = OTHER
                        note = Phosphorothioate linkage
modified_base           29..40
                        mod_base = OTHER
                        note = 2'-O-Me modified nucleotides
modified_base           69..100
                        mod_base = OTHER
                        note = 2'-O-Me modified nucleotides
modified_base           97..98
                        mod_base = OTHER
                        note = Phosphorothioate linkage
modified_base           98..99
                        mod_base = OTHER
                        note = Phosphorothioate linkage
modified_base           99..100
                        mod_base = OTHER
                        note = Phosphorothioate linkage
misc_feature            1..100
                        note = source = /note="Description of Artificial Sequence:
                         Synthetic polynucleotide"
source                  1..100
                        mol_type = other RNA
                        organism = synthetic construct
SEQUENCE: 358
nnnnnnnnnn nnnnnnnnnn gttttagagc tagaaatagc aagttaaaat aaggctagtc  60
cgttatcaac ttgaaaaagt ggcaccgagt cggtgctttt                         100

SEQ ID NO: 359          moltype = RNA  length = 4514
FEATURE                 Location/Qualifiers
misc_feature            1..4514
                        note = source = /note="Description of Artificial Sequence:
                         mRNA transcript"
source                  1..4514
                        mol_type = other RNA
                        organism = synthetic construct
SEQUENCE: 359
gggtcccgca gtcggcgtcc agcggctctg cttgttcgtg tgtgtgtcgt tgcaggcctt  60
attcggatcc atggataaga agtactcaat cgggctggat atcggaacta attccgtggg  120
ttgggcagtg atcacggatg aatacaaagt gccgtccaag aagttcaagg tcctggggaa  180
caccgataga cacagcatca agaaaaatct catcggagcc ctgctgtttg actccggcga  240
aaccgcagaa gcgacccggc tcaaacgtac cgcgaggcga cgctacaccc ggcggaagaa  300
tcgcatctgc tatctgcaag agatcttttc gaacgaaatg gcaaaggtcg acgacagctt  360
cttccaccgc ctggaagaat ctttcctggt ggaggaggac aagaagcatg aacggcatcc  420
tatctttgga aacatcgtcg acgaagtggc gtaccacgaa aagtacccga ccatctacca  480
tctgcggaag aagttggttg actcaactga caaggccgac ctcagattga tctacttggc  540
cctcgcccat atgatcaaat tccgcggaca cttcctgatc gaaggcgatc tgaaccctga  600
taactccgac gtggataagc ttttcattca actggtgcag acctacaacc aactgttcga  660
agaaaaccca atcaatgcta gcggcgtcga tgccaaggcc atcctgtccg cccggctgtc  720
```

```
gaagtcgcgg cgcctcgaaa acctgatcgc acagctgccg ggagagaaaa agaacggact  780
tttcggcaac ttgatcgctc tctcactggg actcactccc aatttcaagt ccaattttga  840
cctggccgag gacgcgaagc tgcaactctc aaaggacacc tacgacgacg acttggacaa  900
tttgctggca caaattggcg atcagtacgc ggatctgttc cttgccgcta agaacctttc  960
ggacgcaatc ttgctgtccg atatcctgcg cgtgaacacc gaaataacca aagcgccgct  1020
tagcgcctcg atgattaagc ggtacgacga gcatcaccag gatctcacgc tgctcaaagc  1080
gctcgtgaga cagcaactgc ctgaaaagta caaggagatc ttcttcgacc agtccaagaa  1140
tgggtacgca gggtacatcg atggaggcgc tagccaggaa gagttctata agttcatcaa  1200
gccaatcctg gaaaagatgg acggaaccga agaactgctg gtcaagctga acagggagga  1260
tctgctccgg aaacagagaa cctttgacaa cggatccatt ccccaccaga tccatctggg  1320
tgagctgcac gccatcttgc ggcgccagga ggacttttac ccattcctca aggacaaccg  1380
ggaaaagatc gagaaaattc tgacgttccg catcccgtat tacgtgggcc cactggcgcg  1440
cggcaattcg cgcttcgcgt ggatgactag aaaatcagag gaaaccatca ctccttggaa  1500
tttcgaggaa gttgtggata agggagcttc ggcacaaagc ttcatcgaac gaatgaccaa  1560
cttcgacaag aatctcccaa acgagaaggt gcttcctaag cacagcctcc tttacgaata  1620
cttcactgtc tacaacgaac tgactaaagt gaaatacgtt actgaaggaa tgaggaagcc  1680
ggcctttctg tccggagaac agaagaaagc aattgtcgat ctgctgttca agaccaaccg  1740
caaggtgacc gtcaagcagc ttaaagagga ctacttcaag aagatcgagt gtttcgactc  1800
agtggaaatc agcggggtgg aggacagatt caacgcttcg ctgggaacct atcatgatct  1860
cctgaagatc atcaaggaca aggacttcct tgacaacgag gagaacgagg acatcctgga  1920
agatatcgtc ctgaccttga ccctttcga ggatcgcgag atgatcgagg agaggcttaa  1980
gacctacgct catctcttcg acgataaggt catgaaacaa ctcaagcgcc gccggtacac  2040
tggttggggc cgcctctccc gcaagctgat caacggtatt cgcgataaac agagcggtaa  2100
aactatcctg gatttcctca aatcggatgg cttcgctaat cgtaacttca tgcaattgat  2160
ccacgacgac agcctgacct ttaaggagga catccaaaaa gcacaagtgt ccggacaggg  2220
agactcactc catgaacaca tcgcgaatct ggccggttcg ccggcgatta agaagggaat  2280
tctgcaaact gtgaaggtgg tcgacgagct ggtgaaggtc atgggacggc acaaaccgga  2340
gaatatcgtg attgaaatgg cccgagaaaa ccagactacc cagaagggcc agaaaaactc  2400
ccgcgaaagg atgaagcgga tcgaagaagg aatcaaggag ctgggcagcc agatcctgaa  2460
agagcacccg gtggaaaaca cgcagctgca gaacgagaag ctctacctgt actatttgca  2520
aaatggacgg gacatgtacg tggaccaaga gctggacatc aatcggttgt ctgattacga  2580
cgtggaccac atcgttccac agtcctttct gaaggatgac tcgatcgata acaaggtgtt  2640
gactcgcagc gacaagaaca gagggaagtc agataatgtg ccatcggagg aggtcgtgaa  2700
gaagatgaag aattactggc ggcagctcct gaatgcgaag ctgattaccc agagaaagtt  2760
tgacaatctc actaaagccg agcgcggcgg actctcagag ctggataagg ctggattcat  2820
caaacggcag ctggtcgaga ctcggcagat taccaagcac gtggcgcaga tcttggactc  2880
ccgcatgaac actaaatacg acgagaacga taagctcatc cgggaagtga aggtgattac  2940
cctgaaaagc aaacttgtgt cggactttcg gaaggacttt cagttttaca aagtgagaga  3000
aatcaacaac taccatcacg cgcatgacgc atacctcaac gctgtggtcg gtaccgccct  3060
gatcaaaaag taccctaaac ttgaatcgga gtttgtgtac ggagactaca aggtctacga  3120
cgtgaggaag atgatagcca agtccgaaca ggaaatcggg aaagcaactg cgaaatactt  3180
cttttactca aacatcatga actttttcaa gactgaaatt acgctggcca atggagaaat  3240
caggaagagg ccactgatcg aaactaacgg agaaacgggc gaaatcgtgt gggacaaggg  3300
cagggacttc gcaactgttc gcaaagtgct ctctatgccg caagtcaata ttgtgaagaa  3360
aaccgaagtg caaaccggcg gattttcaaa ggaatcgatc ctcccaaaga gaaatagcga  3420
caagctcatt gcacgcaaga aagactggga cccgaagaag tacggaggat tcgattcgcc  3480
gactgtcgca tactccgtcc tcgtggtggc caaggtggag aagggaaaga gcaaaaagct  3540
caaatccgtc aaagagctgc tggggattac catcatggaa cgatcctcgt tcgagaagaa  3600
cccgattgat ttcctcgagg cgaagggtta caaggaggtg aagaaggatc tgatcatcaa  3660
actccccaag tactcactgt tcgaactgga aaatggtcgg aagcgcatgc tggcttcggc  3720
cggagaactc caaaaaggaa atgagctggc cttgcctagc aagtacgtca acttcctcta  3780
tcttgcttcg cactacgaaa aactcaaagg gtcaccggaa gataacgaac agaagcagct  3840
tttcgtggag cagcacaagc attatctgga tgaaatcatc gaacaaatct ccgagttttc  3900
aaagcgcgtg atcctcgccg acgccaacct cgacaaagtc ctgtcggcct acaataagca  3960
tagagataag ccgatcagag aacaggccga gaacattatc cacttgttca ccctgactaa  4020
cctgggagcc ccagccgcct tcaagtactt cgatactact atcgatcgca aaagatacac  4080
gtccaccaag gaagttctgg acgcgaccct gatccaccaa agcatcactg gactctacga  4140
aactaggatc gatctgtcgc agctgggtgg cgatggcggt ggatctccga aaaagaagag  4200
aaaggtgtaa tgagctagcc atcacattta aaagcatctc agcctaccat gagaataaga  4260
gaaagaaaat gaagatcaat agcttattca tctcttttc tttttcgttg gtgtaaagcc  4320
aacaccctgt ctaaaaaaca taaatttctt taatcatttt gcctcttttc tctgtgcttc  4380
aattaataaa aaatggaaag aacctcgaga aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaat ctag                                                    4514
```

```
SEQ ID NO: 360          moltype = RNA  length = 4603
FEATURE                 Location/Qualifiers
misc_feature            1..4603
                        note = source = /note="Description of Artificial Sequence:
                         mRNA transcript"
source                  1..4603
                        mol_type = other RNA
                        organism = synthetic construct
SEQUENCE: 360
gggtcccgca gtcggcgtcc agcggctctg cttgttcgtg tgtgtgtcgt tgcaggcctt  60
attcggatcc atggataaga agtactcaat cgggctggat atcggaacta attccgtggg  120
ttgggcagtg atcacggatg aatacaaagt gccgtccaag aagttcaagg tcctggggaa  180
caccgataga cacagcatca agaaaaatct catcggagcc ctgctgtttg actccggcga  240
aaccgcagaa gcgacccggc tcaaacgtac cgcgaggcga cgctacaccc ggcggaagaa  300
```

-continued

```
tcgcatctgc tatctgcaag agatcttttc gaacgaaatg gcaaaggtcg acgacagctt  360
cttccaccgc ctggaagaat ctttcctggt ggaggaggac aagaagcatg aacggcatcc  420
tatctttgga aacatcgtcg acgaagtggc gtaccacgaa aagtacccga ccatctacca  480
tctgcggaag aagttggttg actcaactga caaggccgac ctcagattga tctacttggc  540
cctcgcccat atgatcaaat tccgcggaca cttcctgatc gaaggcgatc tgaaccctga  600
taactccgac gtggataagc ttttcattca actggtgcag acctacaacc aactgttcga  660
agaaaaccca atcaatgcta gcggcgtcga tgccaaggcc atcctgtccg cccggctgtc  720
gaagtcgcgg cgcctcgaaa acctgatcgc acagctgccg ggagagaaaa agaacggact  780
tttcggcaac ttgatcgctc tctcactggg actcactccc aatttcaagt ccaattttga  840
cctggccgag gacgcgaagc tgcaactctc aaaggacacc tacgacgacg acttggacaa  900
tttgctggca caaattggcg atcagtacgc ggatctgttc cttgccgcta agaacctttc  960
ggacgcaatc ttgctgtccg atatcctgcg cgtgaacacc gaaataacca aagcgccgct  1020
tagcgcctcg atgattaagc ggtacgacga gcatcaccag gatctcacgc tgctcaaagc  1080
gctcgtgaga cagcaactgc ctgaaaagta caaggagatc ttcttcgacc agtccaagaa  1140
tgggtacgca gggtacatcg atggaggcgc tagccaggaa gagttctata agttcatcaa  1200
gccaatcctg gaaaagatgg acggaaccga agaactgctg gtcaagctga acagggagga  1260
tctgctccgg aaacagagaa cctttgacaa cggatccatt ccccaccaga tccatctggg  1320
tgagctgcac gccatcttgc ggcgccagga ggacttttac ccattcctca aggacaaccg  1380
ggaaaagatc gagaaaattc tgacgttccg catcccgtat tacgtgggcc cactggcgcg  1440
cggcaattcg cgcttcgcgt ggatgactag aaaatcagag gaaaccatca ctccttggaa  1500
tttcgaggaa gttgtggata agggagcttc ggcacaaagc ttcatcgaac gaatgaccaa  1560
cttcgacaag aatctcccaa acgagaaggt gcttcctaag cacagcctcc tttacgaata  1620
cttcactgtc tacaacgaac tgactaaagt gaaatacgtt actgaaggaa tgaggaagcc  1680
ggcctttctg tccggagaac agaagaaagc aattgtcgat ctgctgttca agaccaaccg  1740
caaggtgacc gtcaagcagc ttaaagagga ctacttcaag aagatcgagt gtttcgactc  1800
agtggaaatc agcggggtgg aggacagatt caacgcttcg ctgggaacct atcatgatct  1860
cctgaagatc atcaaggaca aggacttcct tgacaacgag gagaacgagg acatcctgga  1920
agatatcgtc ctgaccttga ccctttttcga ggatcgcgag atgatcgagg agaggcttaa  1980
gacctacgct catctcttcg acgataaggt catgaaacaa ctcaagcgcc gccggtacac  2040
tggttggggc cgcctctccc gcaagctgat caacggtatt cgcgataaac agagcggtaa  2100
aactatcctg gatttcctca aatcggatgg cttcgctaat cgtaacttca tgcaattgat  2160
ccacgacgac agcctgacct ttaaggagga catccaaaaa gcacaagtgt ccggacaggg  2220
agactcactc catgaacaca tcgcgaatct ggccggttcg ccggcgatta agaagggaat  2280
tctgcaaact gtgaaggtgg tcgacgagct ggtgaaggtc atgggacggc acaaaccgga  2340
gaatatcgtg attgaaatgg cccgagaaaa ccagactacc cagaagggcc agaaaaactc  2400
ccgcgaaagg atgaagcgga tcgaagaagg aatcaaggag ctgggcagcc agatcctgaa  2460
agagcacccg gtggaaaaca cgcagctgca gaacgagaag ctctacctgt actatttgca  2520
aaatggacgg gacatgtacg tggaccaaga gctggacatc aatcggttgt ctgattacga  2580
cgtggaccac atcgttccac agtcctttct gaaggatgac tcgatcgata acaaggtgtt  2640
gactcgcagc gacaagaaca gagggaagtc agataatgtg ccatcggagg aggtcgtgaa  2700
gaagatgaag aattactggc ggcagctcct gaatgcgaag ctgattaccc agagaaagtt  2760
tgacaatctc actaaagccg agcgcggcgg actctcagag ctggataagg ctggattcat  2820
caaacggcag ctggtcgaga ctcggcagat taccaagcac gtggcgcaga tcttggactc  2880
ccgcatgaac actaaatacg acgagaacga taagctcatc cgggaagtga aggtgattac  2940
cctgaaaagc aaacttgtgt cggactttcg gaaggacttt cagttttaca aagtgagaga  3000
aatcaacaac taccatcacg cgcatgacgc atacctcaac gctgtggtcg gtaccgccct  3060
gatcaaaaag taccctaaac ttgaatcgga gtttgtgtac ggagactaca aggtctacga  3120
cgtgaggaag atgatagcca agtccgaaca ggaaatcggg aaagcaactg cgaaatactt  3180
cttttactca aacatcatga actttttcaa gactgaaatt acgctggcca atggagaaat  3240
caggaagagg ccactgatcg aaactaacgg agaaacgggc gaaatcgtgt gggacaaggg  3300
cagggacttc gcaactgttc gcaaagtgct ctctatgccg caagtcaata ttgtgaagaa  3360
aaccgaagtg caaaccggcg gattttcaaa ggaatcgatc ctcccaaaga gaaatagcga  3420
caagctcatt gcacgcaaga aagactggga cccgaagaag tacggaggat tcgattcgcc  3480
gactgtcgca tactccgtcc tcgtggtggc caaggtggag aagggaaaga gcaaaaagct  3540
caaatccgtc aaagagctgc tggggattac catcatggaa cgatcctcgt tcgagaagaa  3600
cccgattgat ttcctcgagg cgaagggtta caaggaggtg aagaaggatc tgatcatcaa  3660
actccccaag tactcactgt tcgaactgga aaatggtcgg aagcgcatgc tggcttcggc  3720
cggagaactc caaaaaggaa atgagctggc cttgcctagc aagtacgtca acttcctcta  3780
tcttgcttcg cactacgaaa aactcaaagg gtcaccggaa gataacgaac agaagcagct  3840
tttcgtggag cagcacaagc attatctgga tgaaatcatc gaacaaatct ccgagttttc  3900
aaagcgcgtg atcctcgccg acgccaacct cgacaaagtc ctgtcggcct acaataagca  3960
tagagataag ccgatcagag aacaggccga gaacattatc cacttgttca ccctgactaa  4020
cctgggagcc ccagccgcct tcaagtactt cgatactact atcgatcgca aaagatacac  4080
gtccaccaag gaagttctgg acgcgaccct gatccaccaa agcatcactg gactctacga  4140
aactaggatc gatctgtcgc agctgggtgg cgatggctcg gcttacccat acgacgtgcc  4200
tgactacgcc tcgctcggat cgggctcccc caaaaagaaa cggaaggtgg acggatcccc  4260
gaaaaagaag agaaaggtgg actccggatg agaattatgc agtctagcca tcacatttaa  4320
aagcatctca gcctaccatg agaataagag aaagaaaatg aagatcaata gcttattcat  4380
ctctttttct tttcgttgg tgtaaagcca acaccctgtc taaaaaacat aaatttcttt  4440
aatcattttg cctcttttct ctgtgcttca attaataaaa aatggaaaga acctcgagaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaatc tag                   4603
```